US009234198B1

(12) United States Patent
Sazani et al.

(10) Patent No.: US 9,234,198 B1
(45) Date of Patent: Jan. 12, 2016

(54) MULTIPLE EXON SKIPPING COMPOSITIONS FOR DMD

(71) Applicant: Sarepta Therapeutics, Inc., Cambridge, MA (US)

(72) Inventors: Peter Sazani, Bothell, WA (US); Ryszard Kole, Bellevue, WA (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 0 days.

(21) Appl. No.: 14/852,257

(22) Filed: Sep. 11, 2015

Related U.S. Application Data

(60) Continuation of application No. 14/523,610, filed on Oct. 24, 2014, which is a division of application No. 12/605,276, filed on Oct. 23, 2009, now Pat. No. 8,871,918.

(60) Provisional application No. 61/108,416, filed on Oct. 24, 2008.

(51) Int. Cl.
*C12N 15/113* (2010.01)
*C12N 15/11* (2006.01)

(52) U.S. Cl.
CPC ............ *C12N 15/113* (2013.01); *C12N 15/111* (2013.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 5,034,506 A | 7/1991 | Summerton et al. | |
| 5,138,045 A | 8/1992 | Cook et al. | |
| 5,142,047 A | 8/1992 | Summerton et al. | |
| 5,149,797 A | 9/1992 | Pederson et al. | |
| 5,166,315 A | 11/1992 | Summerton et al. | |
| 5,185,444 A | 2/1993 | Summerton et al. | |
| 5,190,931 A | 3/1993 | Inouye | |
| 5,217,866 A | 6/1993 | Summerton et al. | |
| 5,506,337 A | 4/1996 | Summerton et al. | |
| 5,521,063 A | 5/1996 | Summerton et al. | |
| 5,627,274 A | 5/1997 | Kole et al. | |
| 5,665,593 A | 9/1997 | Kole et al. | |
| 5,698,685 A | 12/1997 | Summerton et al. | |
| 5,869,252 A | 2/1999 | Bouma et al. | |
| 5,892,023 A | 4/1999 | Pirotzky et al. | |
| 5,916,808 A | 6/1999 | Kole et al. | |
| 5,976,879 A | 11/1999 | Kole et al. | |
| 6,153,436 A | 11/2000 | Hermonat et al. | |
| 6,210,892 B1 | 4/2001 | Bennett et al. | |
| 6,312,900 B1 | 11/2001 | Dean et al. | |
| 6,391,636 B1 | 5/2002 | Monia | |
| 6,451,991 B1 | 9/2002 | Martin et al. | |
| 6,653,466 B2 | 11/2003 | Matsuo | |
| 6,653,467 B1 | 11/2003 | Matsuo et al. | |
| 6,656,732 B1 | 12/2003 | Bennett et al. | |
| 6,727,355 B2 | 4/2004 | Matsuo et al. | |
| 6,784,291 B2 | 8/2004 | Iversen et al. | |
| 6,806,084 B1 | 10/2004 | Debs et al. | |
| 7,001,761 B2 | 2/2006 | Xiao | |
| 7,070,807 B2 | 7/2006 | Mixson | |
| 7,163,695 B2 | 1/2007 | Mixson | |
| 7,250,289 B2 | 7/2007 | Zhou | |
| 7,314,750 B2 | 1/2008 | Zhou | |
| 7,468,418 B2 | 12/2008 | Iversen et al. | |
| 7,534,879 B2 | 5/2009 | van Deutekom | |
| 7,655,785 B1 | 2/2010 | Bentwich | |
| 7,655,788 B2 | 2/2010 | Khvorova et al. | |
| 7,807,816 B2 | 10/2010 | Wilton et al. | |
| 7,902,160 B2 | 3/2011 | Matsuo et al. | |
| 7,960,541 B2 | 6/2011 | Wilton et al. | |
| 7,973,015 B2 | 7/2011 | van Ommen et al. | |
| 8,084,601 B2 | 12/2011 | Popplewell et al. | |
| 8,232,384 B2 | 7/2012 | Wilton et al. | |
| 8,324,371 B2 | 12/2012 | Popplewell et al. | |
| 8,361,979 B2 | 1/2013 | Aartsma-Rus et al. | |
| 8,450,474 B2 | 5/2013 | Wilton et al. | |
| 8,455,634 B2 | 6/2013 | Wilton et al. | |
| 8,455,635 B2 | 6/2013 | Wilton et al. | |
| 8,455,636 B2 | 6/2013 | Wilton et al. | |
| 8,461,325 B2 | 6/2013 | Popplewell et al. | |
| 8,476,423 B2 | 7/2013 | Wilton et al. | |
| 8,486,907 B2 | 7/2013 | Wilton et al. | |
| 8,501,703 B2 | 8/2013 | Bennett et al. | |
| 8,501,704 B2 | 8/2013 | Mourich et al. | |
| 8,524,676 B2 | 9/2013 | Stein et al. | |
| 8,524,880 B2 | 9/2013 | Wilton et al. | |

(Continued)

FOREIGN PATENT DOCUMENTS

| | | |
|---|---|---|
| AU | 2003284638 A1 | 6/2004 |
| AU | 780517 B2 | 3/2005 |

(Continued)

OTHER PUBLICATIONS

List of Publications for Matthew J. A. Wood, M.D., D. Phil., 11 pages, (Exhibit No. 2124 filed in interferences 106,007 and 106,008 on Feb. 17, 2015.

Liu, Hong-Xiang et al., "Identification of functional exonic splicing enhancer motifs recognized by individual SR proteins," Genes & Development, vol. 12:1998-2012 (1998).

Lu et al, "Massive Idiosyncratic Exon Skipping Corrects the Nonsense Mutation in Dystrophic Mouse Muscle and Produces Functional Revertant Fibers by Clonal Expansion," The Journal of Cell Biology, vol. 148(5):985-995, Mar. 6, 2000 ("Lu et al.") (Exhibit No. 1082 filed in interferences 106008, 106007 on Dec. 23, 2014).

Lu, Qi Long et al., "Functional amounts of dystrophin produced by skipping the mutated exon in the mdx dystrophic mouse," Nature Medicine, vol. 9(8):1009-1014 (2003).

(Continued)

*Primary Examiner* — Jennifer Pitrak McDonald
(74) *Attorney, Agent, or Firm* — Nelson Mullins Riley & Scarborough LLP; Amy E. Mandragouras, Esq.; Erika L. Wallace

(57) ABSTRACT

Provided are antisense molecules capable of binding to a selected target site in the human dystrophin gene to induce exon skipping, and methods of use thereof to treat muscular dystrophy.

8 Claims, 39 Drawing Sheets

(56) References Cited

U.S. PATENT DOCUMENTS

| | | |
|---|---|---|
| 8,536,147 B2 | 9/2013 | Weller et al. |
| 8,552,172 B2 | 10/2013 | Popplewell et al. |
| 8,592,386 B2 | 11/2013 | Mourich et al. |
| 8,618,270 B2 | 12/2013 | Iversen et al. |
| 8,624,019 B2 | 1/2014 | Matsuo et al. |
| 8,637,483 B2 | 1/2014 | Wilton et al. |
| 8,697,858 B2 | 4/2014 | Iversen |
| 8,741,863 B2 | 6/2014 | Moulton et al. |
| 8,759,307 B2 | 6/2014 | Stein et al. |
| 8,759,507 B2 | 6/2014 | Van Deutekom |
| 8,779,128 B2 | 7/2014 | Hanson et al. |
| 8,785,407 B2 | 7/2014 | Stein et al. |
| 8,785,410 B2 | 7/2014 | Iversen et al. |
| 8,835,402 B2 | 9/2014 | Kole et al. |
| 8,865,883 B2 | 10/2014 | Sazani et al. |
| 8,871,918 B2 | 10/2014 | Sazani et al. |
| 8,877,725 B2 | 11/2014 | Iversen et al. |
| 8,895,722 B2 | 11/2014 | Iversen et al. |
| 8,906,872 B2 | 12/2014 | Iversen et al. |
| 9,018,368 B2 | 4/2015 | Wilton et al. |
| 9,024,007 B2 | 5/2015 | Wilton et al. |
| 9,035,040 B2 | 5/2015 | Wilton et al. |
| 2001/0056077 A1 | 12/2001 | Matsuo |
| 2002/0049173 A1 | 4/2002 | Bennett et al. |
| 2002/0055481 A1 | 5/2002 | Matsuo et al. |
| 2002/0110819 A1 | 8/2002 | Weller et al. |
| 2002/0156235 A1 | 10/2002 | Manoharan et al. |
| 2003/0166588 A1 | 9/2003 | Iversen et al. |
| 2003/0224353 A1 | 12/2003 | Stein et al. |
| 2003/0235845 A1 | 12/2003 | van Ommen et al. |
| 2004/0248833 A1 | 12/2004 | Emanuele et al. |
| 2004/0254137 A1 | 12/2004 | Ackermann et al. |
| 2005/0026164 A1 | 2/2005 | Zhou |
| 2005/0048495 A1 | 3/2005 | Baker et al. |
| 2005/0153935 A1 | 7/2005 | Iversen et al. |
| 2006/0099616 A1 | 5/2006 | van Ommen et al. |
| 2006/0147952 A1 | 7/2006 | van Ommen et al. |
| 2006/0148740 A1 | 7/2006 | Platenburg |
| 2006/0287268 A1 | 12/2006 | Iversen et al. |
| 2007/0037165 A1 | 2/2007 | Venter et al. |
| 2007/0082861 A1 | 4/2007 | Matsuo et al. |
| 2008/0194463 A1 | 8/2008 | Weller et al. |
| 2008/0200409 A1 | 8/2008 | Wilson et al. |
| 2008/0209581 A1 | 8/2008 | van Ommen et al. |
| 2009/0076246 A1 | 3/2009 | van Deutekom |
| 2009/0082547 A1 | 3/2009 | Iversen et al. |
| 2009/0088562 A1 | 4/2009 | Weller et al. |
| 2009/0099066 A1 | 4/2009 | Moulton et al. |
| 2009/0228998 A1 | 9/2009 | van Ommen et al. |
| 2009/0269755 A1 | 10/2009 | Aartsma-Rus et al. |
| 2009/0312532 A1 | 12/2009 | Van Deutekom et al. |
| 2010/0016215 A1 | 1/2010 | Moulton et al. |
| 2010/0130591 A1 | 5/2010 | Sazani et al. |
| 2010/0168212 A1 | 7/2010 | Popplewell et al. |
| 2011/0015253 A1 | 1/2011 | Wilton et al. |
| 2011/0015258 A1 | 1/2011 | Wilton et al. |
| 2011/0046203 A1 | 2/2011 | Wilton et al. |
| 2011/0046360 A1 | 2/2011 | Matsuo et al. |
| 2011/0110960 A1 | 5/2011 | Platenburg |
| 2011/0263682 A1 | 10/2011 | De Kimpe et al. |
| 2011/0263686 A1 | 10/2011 | Wilton et al. |
| 2011/0281787 A1 | 11/2011 | Lu et al. |
| 2011/0294753 A1 | 12/2011 | De Kimpe et al. |
| 2011/0312086 A1 | 12/2011 | Van Deutekom |
| 2012/0022134 A1 | 1/2012 | De Kimpe et al. |
| 2012/0022144 A1 | 1/2012 | Wilton et al. |
| 2012/0022145 A1 | 1/2012 | Wilton et al. |
| 2012/0029057 A1 | 2/2012 | Wilton et al. |
| 2012/0029058 A1 | 2/2012 | Wilton et al. |
| 2012/0029059 A1 | 2/2012 | Wilton et al. |
| 2012/0029060 A1 | 2/2012 | Wilton et al. |
| 2012/0041050 A1 | 2/2012 | Wilton et al. |
| 2012/0046342 A1 | 2/2012 | Van Deutekom et al. |
| 2012/0059042 A1 | 3/2012 | Platenburg et al. |
| 2012/0065169 A1 | 3/2012 | Hanson et al. |
| 2012/0065244 A1 | 3/2012 | Popplewell et al. |
| 2012/0108652 A1 | 5/2012 | Popplewell et al. |
| 2012/0108653 A1 | 5/2012 | Popplewell et al. |
| 2012/0115150 A1 | 5/2012 | Bozzoni et al. |
| 2012/0122801 A1 | 5/2012 | Platenburg |
| 2012/0149756 A1 | 6/2012 | Schumperli et al. |
| 2012/0172415 A1 | 7/2012 | Voit et al. |
| 2012/0202752 A1 | 8/2012 | Lu |
| 2012/0289457 A1 | 11/2012 | Hanson |
| 2013/0072671 A1 | 3/2013 | Van Deutekom |
| 2013/0090465 A1 | 4/2013 | Matsuo et al. |
| 2013/0116310 A1 | 5/2013 | Wilton et al. |
| 2013/0197220 A1 | 8/2013 | Ueda |
| 2013/0211062 A1 | 8/2013 | Watanabe et al. |
| 2013/0217755 A1 | 8/2013 | Wilton et al. |
| 2013/0253033 A1 | 9/2013 | Wilton et al. |
| 2013/0253180 A1 | 9/2013 | Wilton et al. |
| 2013/0274313 A1 | 10/2013 | Wilton et al. |
| 2013/0289096 A1 | 10/2013 | Popplewell et al. |
| 2013/0302806 A1 | 11/2013 | Van Deutekom |
| 2013/0331438 A1 | 12/2013 | Wilton et al. |
| 2014/0057964 A1 | 2/2014 | Popplewell et al. |
| 2014/0080896 A1 | 3/2014 | Nelson et al. |
| 2014/0080898 A1 | 3/2014 | Wilton et al. |
| 2014/0094500 A1 | 4/2014 | Sazani et al. |
| 2014/0113955 A1 | 4/2014 | De Kimpe et al. |
| 2014/0128592 A1 | 5/2014 | De Kimpe et al. |
| 2014/0155587 A1 | 6/2014 | Wilton et al. |
| 2014/0213635 A1 | 7/2014 | Van Deutekom |
| 2014/0221458 A1 | 8/2014 | De Kimpe et al. |
| 2014/0243515 A1 | 8/2014 | Wilton et al. |
| 2014/0243516 A1 | 8/2014 | Wilton et al. |
| 2014/0275212 A1 | 9/2014 | van Deutekom |
| 2014/0296323 A1 | 10/2014 | Leumann et al. |
| 2014/0315862 A1 | 10/2014 | Kaye |
| 2014/0315977 A1 | 10/2014 | Bestwick et al. |
| 2014/0316123 A1 | 10/2014 | Matsuo et al. |
| 2014/0323544 A1 | 10/2014 | Bestwick et al. |
| 2014/0329762 A1 | 11/2014 | Kaye |
| 2014/0329881 A1 | 11/2014 | Bestwick et al. |
| 2014/0343266 A1 | 11/2014 | Watanabe et al. |
| 2014/0350067 A1 | 11/2014 | Wilton et al. |
| 2014/0350076 A1 | 11/2014 | van Deutekom |
| 2014/0357698 A1 | 12/2014 | Van Deutekom et al. |
| 2014/0357855 A1 | 12/2014 | Van Deutekom et al. |
| 2015/0045413 A1 | 2/2015 | De Visser et al. |
| 2015/0057330 A1 | 2/2015 | Wilton et al. |
| 2015/0152415 A1 | 6/2015 | Sazani et al. |

FOREIGN PATENT DOCUMENTS

| | | |
|---|---|---|
| CA | 2507125 A1 | 6/2004 |
| EP | 1054058 A1 | 11/2000 |
| EP | 1160318 A2 | 12/2001 |
| EP | 1191097 A1 | 3/2002 |
| EP | 1191098 A2 | 3/2002 |
| EP | 1495769 A1 | 1/2005 |
| EP | 1544297 A2 | 6/2005 |
| EP | 1568769 A1 | 8/2005 |
| EP | 1619249 A1 | 1/2006 |
| EP | 1191098 B9 | 6/2006 |
| EP | 1766010 A1 | 3/2007 |
| EP | 1857548 A1 | 11/2007 |
| EP | 1495769 B1 | 2/2008 |
| EP | 1160318 B1 | 5/2008 |
| EP | 1619249 B1 | 9/2008 |
| EP | 1544297 B1 | 9/2009 |
| EP | 2119783 A1 | 11/2009 |
| EP | 2135948 A2 | 12/2009 |
| EP | 2206781 A2 | 7/2010 |
| EP | 2258863 A1 | 12/2010 |
| EP | 2284264 A1 | 2/2011 |
| EP | 2374885 A2 | 10/2011 |
| EP | 2386636 A2 | 11/2011 |
| EP | 2392660 A2 | 12/2011 |
| EP | 2500430 A2 | 9/2012 |
| EP | 2530153 A1 | 12/2012 |
| EP | 2530154 A1 | 12/2012 |
| EP | 2530155 A1 | 12/2012 |

(56) References Cited

FOREIGN PATENT DOCUMENTS

| | | |
|---|---|---|
| EP | 2530156 A1 | 12/2012 |
| EP | 2581448 A1 | 4/2013 |
| EP | 2594640 A1 | 5/2013 |
| EP | 2594641 A1 | 5/2013 |
| EP | 2594642 A1 | 5/2013 |
| EP | 2602322 A1 | 6/2013 |
| EP | 2607484 A1 | 6/2013 |
| EP | 2612917 A1 | 7/2013 |
| EP | 2614827 A2 | 7/2013 |
| EP | 2623507 A1 | 8/2013 |
| EP | 2636740 A1 | 9/2013 |
| EP | 2636741 A1 | 9/2013 |
| EP | 2636742 A1 | 9/2013 |
| EP | 2435582 B1 | 10/2013 |
| EP | 1606407 B1 | 12/2013 |
| EP | 2435583 B1 | 7/2014 |
| EP | 2488165 B1 | 7/2014 |
| EP | 2135948 B1 | 9/2014 |
| EP | 2799548 A2 | 11/2014 |
| EP | 2801618 A1 | 11/2014 |
| JP | 2000-325085 A | 11/2000 |
| JP | 2002-010790 A | 1/2002 |
| JP | 2002-529499 A | 9/2002 |
| JP | 2002-325582 A | 11/2002 |
| JP | 2002-340857 A | 11/2002 |
| JP | 2004-509622 A | 4/2004 |
| JP | 2010-268815 A | 12/2010 |
| JP | 2011-101655 A | 5/2011 |
| JP | 04777777 B2 | 9/2011 |
| JP | 2011-200235 A | 10/2011 |
| JP | 04846965 B2 | 12/2011 |
| JP | 5138722 B2 | 2/2013 |
| JP | 5378423 B2 | 10/2013 |
| JP | 2014-054250 A | 3/2014 |
| JP | 2014-111638 A | 6/2014 |
| JP | 2014-138589 A | 7/2014 |
| WO | 93/20227 A1 | 10/1993 |
| WO | 94/02595 A1 | 2/1994 |
| WO | 94/26887 A1 | 11/1994 |
| WO | 96/10391 A1 | 4/1996 |
| WO | 96/10392 A1 | 4/1996 |
| WO | 97/30067 A1 | 8/1997 |
| WO | 97/34638 A1 | 9/1997 |
| WO | 00/15780 A1 | 3/2000 |
| WO | 00/44897 A1 | 8/2000 |
| WO | 00/78341 A1 | 12/2000 |
| WO | 01/49775 A2 | 7/2001 |
| WO | 01/72765 A1 | 10/2001 |
| WO | 01/83503 A2 | 11/2001 |
| WO | 01/83740 A2 | 11/2001 |
| WO | 02/18656 A2 | 3/2002 |
| WO | 02/24906 A1 | 3/2002 |
| WO | 02/29406 A1 | 4/2002 |
| WO | 03/053341 A2 | 7/2003 |
| WO | 2004/048570 A2 | 6/2004 |
| WO | 2004/083446 A2 | 9/2004 |
| WO | 2004083432 A1 | 9/2004 |
| WO | 2005/115479 A2 | 12/2005 |
| WO | 2006/000057 A1 | 1/2006 |
| WO | 2006/021724 A2 | 3/2006 |
| WO | 2006/112705 A2 | 10/2006 |
| WO | 2007/058894 A2 | 5/2007 |
| WO | 2007/133812 A2 | 11/2007 |
| WO | 2007/135105 A1 | 11/2007 |
| WO | 2008/036127 A2 | 3/2008 |
| WO | 2009/054725 A2 | 4/2009 |
| WO | 2009/101399 A1 | 8/2009 |
| WO | 2009/139203 A2 | 11/2009 |
| WO | 2010/048586 A1 | 4/2010 |
| WO | 2010/050801 A1 | 5/2010 |
| WO | 2010/050802 A2 | 5/2010 |
| WO | 2010/115993 A1 | 10/2010 |
| WO | 2010/123369 A1 | 10/2010 |
| WO | 2010/136415 A1 | 12/2010 |
| WO | 2010/136417 A1 | 12/2010 |
| WO | 2010/150231 A1 | 12/2010 |
| WO | 2011/024077 A2 | 3/2011 |
| WO | 2011/045747 A1 | 4/2011 |
| WO | 2011/057350 A1 | 5/2011 |
| WO | 2011/143008 A1 | 11/2011 |
| WO | 2012/001941 A1 | 1/2012 |
| WO | 2012/029986 A1 | 3/2012 |
| WO | 2012/043730 A1 | 4/2012 |
| WO | 2012/109296 A1 | 8/2012 |
| WO | 2012/150960 A1 | 11/2012 |
| WO | 2013/033407 A2 | 3/2013 |
| WO | 2013/053928 A1 | 4/2013 |
| WO | 2013/100190 A1 | 7/2013 |
| WO | 2013/112053 A1 | 8/2013 |
| WO | 2014/007620 A2 | 1/2014 |
| WO | 2014/15322 A1 | 1/2014 |
| WO | 2014/100714 A1 | 6/2014 |
| WO | 2014/144978 A2 | 9/2014 |
| WO | 2014/153220 A2 | 9/2014 |
| WO | 2014/153240 A2 | 9/2014 |

OTHER PUBLICATIONS

Lu, Qi-long et al., "What Can We Learn From Clinical Trials of Exon Skipping for DMD?" Molecular Therapy—Nucleic Acids, vol. 3:e152, doi:10.1038/mtna.2014.6, 4 pages (2014).

Lyophilisation of Oligonucleotides, pp. 2, Exhibit No. 1133 filed in Interferences 106,007 and 106,008 on Feb. 17, 2015.

Mann, Christopher J. et al., "Antisense-induced exon skipping and synthesis of dystrophin in the mdx mouse," PNAS, vol. 98(1):42-47 (2001).

Mann, Christopher J. et al., "Improved antisense oligonucleotide induced exon skipping in the mdx mouse model of muscular dystrophy," The Journal of Gene Medicine, vol. 4:644-654 (2002).

Mannino, Raphael J. et al., "Liposome Mediated Gene Transfer," BioTechniques, vol. 6(7):682-690 (1988).

Manual of Patent Examining Procedure 2308.02 (6th ed., rev. 3, Jul. 1997), (University of Western Australia Exhibit 2143, filed Apr. 3, 2015 in Interferences 106007, 106008, and 106013, pp. 1-2).

Manzur A, et al.,. "Glucocorticoid corticosteroids for Duchenne muscular dystrophy," Cochrane Database Syst Rev. 2004;(2):CD003725.

Marshall, N.B. et al., "Arginine-rich cell-penetrating peptides facilitate delivery of antisense oligomers into murine leukocytes and alter pre-mRNA splicing," Journal of Immunological Methods, vol. 325:114-126 (2007).

Mathews et al., "Expanded Sequence Dependence of Thermodynamic Parameters Improves Prediction of RNA Secondary Structure," J. Mol. Biol. 288:911-940 (1999), (University of Western Australia Exhibit 2131, filed Apr. 3, 2015 in Interferences 106007, 106008, and 106013, pp. 1-31).

Mathews et al., "Expanded Sequence Dependence of Thermodynamic Parameters Improves Prediction of RNA Secondary Structure," J. Mol. Biol., vol. 288, pp. 911-940 (1999), Exhibit No. 1212 filed in Interferences 106,007 and 106,008 on Feb. 17, 2015.

Matsuo, Masafumi et al., "Exon Skipping during Splicing of Dystrophin mRNA Precursor due to an Intraexon Deletion in the Dystrophin Gene of Duchenne Muscular Dystrophy Kobe," J. Clin. Invest., vol. 87:2127-2131 (1991).

Matsuo, Masafumi et al., "Treatment of Duchenne Muscular Dystrophy with Oligonucleotides against an Exonic Splicing Enhancer Sequence," Basic Appl. Myol., vol. 13(6):281-285 (2003).

Matsuo, Masafumi, "Duchenne and Becker Muscular Dystrophy: From Gene Diagnosis to Molecular Therapy," IUBMB Life, vol. 53:147-152 (2002).

Matsuo, Masafumi, "Duchenne/Becker muscular dystrophy: from molecular diagnosis to gene therapy," Brain & Development, vol. 18:167-172 (1996).

Matteucci, Mark, "Structural modifications toward improved antisense oligonucleotides," Perspectives in Drug Discovery and Design, vol. 4:1-16 (1996).

Mazzone E, et al. "Functional changes in Duchenne muscular dystrophy: a 12-month longitudinal cohort study," Neurology 2011;77(3):250-6.

McCarville, M. Beth et al., "Rhabdomyosarcoma in Pediatric Patients: The Good, the Bad, and the Unusual," AJR, vol. 176:1563-1569 (2001) (Exhibit No. 1034 filed in interferences 106008, 106007 on Nov. 18, 2014).

(56) References Cited

OTHER PUBLICATIONS

McClorey, G. et al., "Antisense oligonucleotide-induced exon skipping restores dystrophin expression in vitro in a canine model of DMD," Gene Therapy, vol. 13:1373-1381 (2006).

McClorey, G. et al., "Induced dystrophin exon skipping in human muscle explants," Neuromuscular Disorders, vol. 16:583-590 (2006).

McClorey, Graham et al., "Splicing intervention for Duchenne muscular dystrophy," Current Opinion in Pharmacology, vol. 5:529-534 (2005).

McDonald CM, et al., "Profiles of Neuromuscular Diseases, Duchenne muscular dystrophy," Am J Phys Med Rehabil 1995;74:S70-S92.

McDonald CM, et al., "The 6-minute walk test as a new outcome measure in Duchenne muscular dystrophy," Muscle Nerve 2010;41:500-10.

McDonald CM, et al., "The 6-minute walk test in Duchenne/Becker muscular dystrophy: longitudinal observations," Muscle Nerve 2010;42: 966-74.

Mendell JR et al., "Evidence-based path to newborn screening for Duchenne muscular Dystrophy," Ann Neurol 2012;71:304-13.

Mendell JR, et al., "Dystrophin immunity revealed by gene therapy in Duchenne muscular dystrophy," N Engl J Med 2010;363:1429-37.

Mendell JR, et al., "Randomized, double-blind six-month trial of prednisone in Duchenne's muscular dystrophy," N Engl J Med 1989;320:1592-97.

Mendell, Jerry R. et al., "Eteplirsen for the Treatment of Duchenne Muscular Dystrophy," Ann. Neurol., vol. 74:637-647 (2013) (Exhibit No. 2058 filed in interferences 106008, 106013, 106007 on Nov. 18, 2014).

Mendell, Jerry R. et al., "Eteplirsen in Duchenne Muscular Dystrophy (DMD): 144 Week Update on Six-Minute Walk Test (6MWT) and Safety," slideshow, presented at the 19th International Congress of the World Muscle Society, 17 pages (2014) (Exhibit No. 2059 filed in interferences 106008, 106013, 106007 on Nov. 18, 2014).

Mendell, Jerry R. et al., "Gene therapy for muscular dystrophy: Lessons learned and path forward," Neuroscience Letters, vol. 527:90-99 (2012).

Merlini L, et al., "Early corticosteroid treatment in 4 Duchenne muscular dystrophy patients: 14-year follow-up," Muscle Nerve 2012;45:796-802.

Mfold illustrations for Exon 51 and Exon 53 with varying amounts of intron sequence, (University of Western Australia Exhibit 2132, filed Apr. 3, 2015 in Interferences 106007, 106008, and 106013, pp. 1-2).

Mitrpant, Chalermchai et al., "Rational Design of Antisense Oligomers to Induce Dystrophin Exon Skipping," Molecular Therapy, vol. 17(8):1418-1426 (2009).

Monaco, Anthony P. et al., "An Explanation for the Phenotypic Differences between Patients Bearing Partial Deletions of the DMD Locus," Genomics, vol. 2:90-95 (1988).

Morcos, Paul A., "Gene switching: analyzing a broad range of mutations using steric block antisense oligonucleotides," Methods in Enzymology, vol. 313:174-189 (1999).

Moulton, H.M., "Compound and Method for Treating Myotonic Dystrophy," U.S. Appl. No. 12/493,140, 82 pages, filed Jun. 26, 2009.

Moulton, Hong M. et al., "Morpholinos and their peptide conjugates: Therapeutic promise and challenge for Duchenne muscular dystrophy," Biochimica et Biophysica Acta, vol. 1798:2296-2303 (2010).

Muntoni F, et al., "Dystrophin and mutations: one gene, several proteins, multiple phenotypes," Lancet Neurol. 2003;2:731-40.

Muntoni, Francesco et al., "128th ENMC International Workshop on 'Preclinical optimization and Phase I/II Clinical Trials Using Antisense Oligonucleotides in Duchenne Muscular Dystrophy' Oct. 22-24, 2004, Naarden, The Netherlands," Neuromuscular Disorders, vol. 15:450-457 (2005) (Exhibit No. 2025 filed in interferences 106008, 106013, 106007 on Nov. 18, 2014).

Muntoni, Francesco et al., "149th ENMC International Workshop and 1st TREAT-NMD Workshop on: 'Planning Phase I/II Clinical trials using Systemically Delivered Antisense Oligonucleotides in Duchenne Muscular Dystrophy,'" Neuromuscular Disorders, vol. 18:268-275 (2008).

Nelson, David L. et al., "Nucleotides and Nucleic Acids," Lehninger Principles of Biochemistry, 3rd Edition, Chapter 10, pp. 325-328 and glossary p. G-11, Worth Publishers, New York (2000).

Nguyen TM, et. Al., "Use of Epitope libraries to identify exon-specific monoclonal antibodies for characterization of altered dystrophins in muscular dystrophy," Am J Hum Genet 1993;52:1057-66.

Oberbauer, "Renal uptake of an 18-mer phosphorothioate oligonucleotide," Kidney Int'l, vol. 48, pp. 1226-1232 (1995), Exhibit No. 1191 filed in Interferences 106,007 and 106,008 on Feb. 17, 2015.

Oligonucleotide Cleavage and Deprotection Laboratory Notebook Entry, pp. 1, Exhibit No. 1138 filed in Interferences 106,007 and 106,008 on Feb. 16, 2015.

Oligonucleotide diagrams, 5 pages (Exhibit No. 1053 filed in interferences 106008, 106007 on Nov. 18, 2014).

Partial European Search Report for Application No. 10004274.6, 6 pages, dated Oct. 2, 2012.

Partial European Search Report for Application No. 12162995.0, 6 pages, dated Oct. 2, 2012.

*University of Western Australia v. Academisch Ziekenhuis Leiden*, Academisch Ziekenhuis Leiden Opposition 1 (35 U.S.C. § 112(a)), 93 pages, Patent Interference No. 106,007, (Doc 392), dated Feb. 17, 2015.

*University of Western Australia v. Academisch Ziekenhuis Leiden*, Academisch Ziekenhuis Leiden Opposition 1 (Standing Order ¶ 203.1 and 37 C.F.R. § 41.202(a) and (e)), 20 pages, Patent Interference No. 106,013, (Doc 148), dated Feb. 17, 2015.

*University of Western Australia v. Academisch Ziekenhuis Leiden*, Academisch Ziekenhuis Leiden Opposition 2 (Indefiniteness), 31 pages, Patent Interference No. 106,007, (Doc 396), dated Feb. 17, 2015.

*University of Western Australia v. Academisch Ziekenhuis Leiden*, Academisch Ziekenhuis Leiden Opposition 2 (Indefiniteness), 32 pages, Patent Interference No. 106,008, (Doc 401), dated Feb. 17, 2015.

*University of Western Australia v. Academisch Ziekenhuis Leiden*, Academisch Ziekenhuis Leiden Opposition 3 (35 U.S.C. §135(b)), 44 pages, Patent Interference No. 106,008, (Doc 397), dated Feb. 17, 2015.

*University of Western Australia v. Academisch Ziekenhuis Leiden*, Academisch Ziekenhuis Leiden Opposition 3 (Standing Order § 203.1 and 37 C.F.R. § 41.202(a) and (e)), 20 pages, Patent Interference No. 106,007, (Doc 389), dated Feb. 17, 2015.

*University of Western Australia v. Academisch Ziekenhuis Leiden*, Academisch Ziekenhuis Leiden Reply 1 (For Judgment that UWA'a Claims are Unpatentable Under 35 U.S.C. §§ 102 and 103), dated Apr. 3, 2015, filed in Patent Interference No. 106008, pp. 1-17 (Doc 431).

*University of Western Australia v. Academisch Ziekenhuis Leiden*, Academisch Ziekenhuis Leiden Reply 1 (For Judgment that UWA's Claims are Unpatentable Under 35 U.S.C. §§ 102 and 103), dated Apr. 3, 2015, filed in Patent Interference No. 106007, pp. 1-17 (Doc 424).

*University of Western Australia v. Academisch Ziekenhuis Leiden*, Academisch Ziekenhuis Leiden Reply 2 (To Deny the Benefit of AU 2004903474), dated Apr. 3, 2015, filed in Patent Interference No. 106007, pp. 1-11(Doc 425).

*University of Western Australia v. Academisch Ziekenhuis Leiden*, Academisch Ziekenhuis Leiden Reply 2 (To Deny the Benefit of AU 2004903474), dated Apr. 3, 2015, filed in Patent Interference No. 106008, pp. 1-12 (Doc 432).

*University of Western Australia v. Academisch Ziekenhuis Leiden*, Academisch Ziekenhuis Leiden Reply 3 (For Judgment of Unpatentability based on Myriad) dated Apr. 3, 2015, filed in Patent Interference No. 106007, pp. 1-12 (Doc 426).

*University of Western Australia v. Academisch Ziekenhuis Leiden*, Academisch Ziekenhuis Leiden Reply 3 (For Judgment of Unpatentability based on Myriad) dated Apr. 3, 2015, filed in Patent Interference No. 106008, pp. 1-13 (Doc 433).

(56) References Cited

OTHER PUBLICATIONS

*University of Western Australia* v. *Academisch Ziekenhuis Leiden*, Academisch Ziekenhuis Leiden Reply 4 (In Support of Responsive Motion 4 to Add Two New Claims) dated Apr. 3, 2015, filed in Patent Interference No. 106007, pp. 1-17 (Doc 427).
*University of Western Australia* v. *Academisch Ziekenhuis Leiden*, Academisch Ziekenhuis Leiden Reply 4 (In Support of Responsive Motion 4 to Add Two New Claims) dated Apr. 3, 2015, filed in Patent Interference No. 106008, pp. 1-17 (Doc 434).
*University of Western Australia* v. *Academisch Ziekenhuis Leiden*, Academisch Ziekenhuis Leiden Request for Oral Argument, filed in Patent Interference No. 106,007, Apr. 10, 2015, pp. 1-3 (Doc 454).
*University of Western Australia* v. *Academisch Ziekenhuis Leiden*, Academisch Ziekenhuis Leiden Request for Oral Argument, filed in Patent Interference No. 106,008, Apr. 10, 2015, pp. 1-3 (Doc 462).
*University of Western Australia* v. *Academisch Ziekenhuis Leiden*, Academisch Ziekenhuis Leiden Responsive Motion 4 (To Add Two New Claims), 57 pages, Patent Interference No. 106,008, (Doc 245), dated Dec. 23, 2014.
*University of Western Australia* v. *Academisch Ziekenhuis Leiden*, Academisch Ziekenhuis Leiden Responsive Motion 4 (To Add Two New Claims), 65 pages, Patent Interference No. 106,007, (Doc 241), dated Dec. 23, 2014.
*University of Western Australia* v. *Academisch Ziekenhuis Leiden*, Academisch Ziekenhuis Leiden Statement Regarding Oral Argument, filed in Patent Interference No. 106,013, Apr. 10, 2015, pp. 1-3 (Doc 189).
*University of Western Australia* v. *Academisch Ziekenhuis Leiden*, Academisch Ziekenhuis Leiden's List of Exhibits as of May 5, 2015, filed in Patent Interference No. 106,007, May 5, 2015, pp. 1-18 (Doc 466).
*University of Western Australia* v. *Academisch Ziekenhuis Leiden*, Academisch Ziekenhuis Leiden's List of Exhibits as of May 5, 2015, filed in Patent Interference No. 106,008, May 5, 2015, pp. 1-18 (Doc 474).
*University of Western Australia* v. *Academisch Ziekenhuis Leiden*, Academisch Ziekenhuis Leiden's Opposition 4 (To Not Exclude Evidence), filed in Patent Interference No. 106,007, May 5, 2015, pp. 1-22 (Doc 465).
*University of Western Australia* v. *Academisch Ziekenhuis Leiden*, Academisch Ziekenhuis Leiden's Opposition 4 (To Not Exclude Evidence), filed in Patent Interference No. 106,008, May 5, 2015, pp. 1-21 (Doc 473).
*University of Western Australia* v. *Academisch Ziekenhuis Leiden*, Academisch Ziekenhuis Leiden's Second Supplemental Notice of Real Party in Interest, filed in Patent Interference No. 106,007, May 28, 2015, pp. 1-3, (Doc 468).
*University of Western Australia* v. *Academisch Ziekenhuis Leiden*, Academisch Ziekenhuis Leiden's Second Supplemental Notice of Real Party in Interest, filed in Patent Interference No. 106,008, May 28, 2015, pp. 1-3, (Doc 476).
*University of Western Australia* v. Academisch Ziekenhuis Leiden, Academisch Ziekenhuis Leiden's Second Supplemental Notice of Real Party in Interest, filed in Patent Interference No. 106013, May 28, 2015, pp. 1-3, (Doc 191).
*University of Western Australia* v. *Academisch Ziekenhuis Leiden*, Academish Ziekenhuis Leiden Supplemental Notice of Real Party in Interest, pp. 3, Doc 149, Patent Interference No. 106,013 dated Feb. 23, 2015.
*University of Western Australia* v. *Academisch Ziekenhuis Leiden*, Academish Ziekenhuis Leiden Supplemental Notice of Real Party in Interest, pp. 3, Doc 413, Patent Interference No. 106,007 dated Feb. 23, 2015.
*University of Western Australia* v. *Academisch Ziekenhuis Leiden*, Academish Ziekenhuis Leiden Supplemental Notice of Real Party in Interest, pp. 3, Doc 421, Patent Interference No. 106,0008 dated Feb. 23, 2015.

*University of Western Australia* v. *Academisch Ziekenhuis Leiden*, Amendment and Response, U.S. Appl. No. 11/233,495, Filed Jan. 22, 2014, 8 pages, (Exhibit No. 2117 filed in interferences 106,007 and 106, 008, on Feb. 17, 2015.
*University of Western Australia* v. *Academisch Ziekenhuis Leiden*, AZL Annotated Claims, Patent Interference No. 106,007, 15 pages, dated Aug. 15, 2014 9 (Doc 15).
*University of Western Australia* v. *Academisch Ziekenhuis Leiden*, AZL Annotated Claims, Patent Interference No. 106,008, 14 pages, dated Aug. 21, 2014 (Doc 14).
*University of Western Australia* v. *Academisch Ziekenhuis Leiden*, AZL Annotaed Claims, Patent Interference No. 106,103, 14 pages, dated Oct. 27, 2014 (Doc 16).
*University of Western Australia* v. *Academisch Ziekenhuis Leiden*, AZL Clean Claims and Sequence, filed in Patent Interference No. 106,013, 5 pages, dated Oct. 15, 2014 (Doc 12).
*University of Western Australia* v. *Academisch Ziekenhuis Leiden*, AZL Corrected Notice of Related Proceedings, Patent Interference No. 106,007, 3 pages, dated Aug. 1, 2014 (Doc 13).
*University of Western Australia* v. *Academisch Ziekenhuis Leiden*, AZL Exhibit List, 10 pages, Patent Interference No. 106,007 dated Dec. 23, 2014 (Doc 240).
*University of Western Australia* v. *Academisch Ziekenhuis Leiden*, AZL Exhibit List, 10 pages, Patent Interference No. 106,008, dated Dec. 23, 2014 (Doc 244).
*University of Western Australia* v. *Academisch Ziekenhuis Leiden*, AZL List of Exhibits, 9 pages, Patent Interference No. 106,007, dated Nov. 18, 2014 (Doc 209).
*University of Western Australia* v. *Academisch Ziekenhuis Leiden*, Azl List of Exhibits, as of Nov. 18, 2014, 9 pages, Patent Interference No. 106,008, dated Nov. 18, 2014 (Doc 212).
*University of Western Australia* v. *Academisch Ziekenhuis Leiden*, AZL List of Proposed Motions, Patent Interference No. 106,007, 6 pages, dated Sep. 10, 2014 (Doc 16).
*University of Western Australia* v. *Academisch Ziekenhuis Leiden*, AZL List of Proposed Motions, Patent Interference No. 106,008, 8 pages, dated Sep. 10, 2014 (Doc 15).
*University of Western Australia* v. *Academisch Ziekenhuis Leiden*, AZL Motion 1 (For Judgment that UWA's Claims are Unpatentable Under 35 U.S.C. sections 102 and 103), 69 pages, Patent Interference No. 106,007, dated Nov. 18, 2014 (Doc 181).
*University of Western Australia* v. *Academisch Ziekenhuis Leiden*, AZL Motion 1 (For Judgment that UWA's Claims are Unpatentable Under 35 U.S.C. sections 102 and 103), 69 pages, Patent Interference No. 106,008, dated Nov. 18, 2014 (Doc 184).
*University of Western Australia* v. *Academisch Ziekenhuis Leiden*, AZL Motion 2 (To Deny UWA the Benefit of AU 2004903474), 23 pages, Patent Interference No. 106,007, dated Nov. 18, 2014 (Doc 26).
*University of Western Australia* v. *Academisch Ziekenhuis Leiden*, AZL Motion 2 (To Deny UWA the Benefit of AU 2004903474), 24 pages, Patent Interference No. 106,008, dated Nov. 18, 2014 (Doc 29).
*University of Western Australia* v. *Academisch Ziekenhuis Leiden*, AZL Motion 3 (For Judgment of Unpatentability based on Myriad) 20 pages, Patent Interference No. 106,008, dated Nov. 18, 2014 (Doc 30).
*University of Western Australia* v. *Academisch Ziekenhuis Leiden*, AZL Motion 3 (For Judgment of Unpatentability based on Myriad), 19 pages, Patent Interference No. 106,007, dated Nov. 18, 2014 (Doc 27).
*University of Western Australia* v. *Academisch Ziekenhuis Leiden*, AZL Notice of Related Proceedings, Patent Interference No. 106,007, 3 pages, dated Jul. 31, 2014 (Doc 6).
*University of Western Australia* v. *Academisch Ziekenhuis Leiden*, AZL Notice of Related Proceedings, Patent Interference No. 106,008, 3 pages, dated Aug. 5, 2014 (Doc 7).
*University of Western Australia* v. *Academisch Ziekenhuis Leiden*, AZL Notice of Related Proceedings, Patent Interference No. 106,013, 3 pages, dated Oct. 15, 2014 (Doc 11).
US Terminal Disclaimer for U.S. Appl. No. 14/198,992, 1 page, dated Jul. 15, 2014 (Exhibit No. 2096 filed in interferences 106008, 106013, 106007 on Nov. 18, 2014).

(56) References Cited

OTHER PUBLICATIONS

US Terminal Disclaimer for U.S. Appl. No. 14/248,279, 1 page, dated Aug. 7, 2014 (Exhibit No. 2109 filed in interferences 106008, 106013, 106007 on Nov. 18, 2014).
US Track One Request, Application as-filed, and Application Data Sheet for U.S. Appl. No. 14/248,279, 68 pages, dated Apr. 8, 2014 (Exhibit No. 2108 filed in interferences 106008, 106013, 106007 on Nov. 18, 2014).
US Transmittal, application as-filed, and Preliminary Amendment for U.S. Appl. No. 11/570,691, 102 pages, dated Dec. 15, 2006 (Exhibit No. 2103 filed in interferences 106008, 106013, 106007 on Nov. 18, 2014).
US Transmittal, application as-filed, and Preliminary Amendment for U.S. Appl. No. 13/270,992, 101 pages, dated Oct. 11, 2011 (Exhibit No. 2098 filed in interferences 106008, 106013, 106007 on Nov. 18, 2014).
US Transmittal, application as-filed, and Preliminary Amendment for U.S. Appl. No. 13/271,080, 115 pages, dated Oct. 11, 2011 (Exhibit No. 2111 filed in interferences 106008, 106013, 106007 on Nov. 18, 2014).
US Updated Filing Receipt for U.S. Appl. No. 13/550,210, 3 pages, dated Dec. 11, 2012 (Exhibit No. 2044 filed in interferences 106008, 106013, 106007 on Nov. 18, 2014).
USPTO "2014 Procedure for Subject Matter Eligibility Analysis of Claims Reciting or Involving . . . Natural Products" ("the March Guidance"), 19 pages, (Exhibit No. 2118 filed in interferences 106,007 and 106,008 on Feb. 17, 2015.
USPTO Written Description Training Materials, Revised Mar. 25, 2008, Example 12, 6 pages, (Exhibit No. 1068 filed in interferences 106008, 106007 on Dec. 23, 2014).
UWA Clean Claims and Sequence, as filed in Interference No. 106,007 on Aug. 1, 2014 (Paper 12), 8 pages, (Exhibit No. 2126 filed in interferences 106,007 and 106,008 on Feb. 17, 2015.
UWA Clean Claims and Sequence, as filed in Interference No. 106,007 on Aug. 7, 2014 (Paper 12), 8 pages, (Exhibit No. 2127 filed in interferences 106,007 and 106,008 on Feb. 17, 2015.
UWA Motion 1 (For Judgment Under 35 § 112(a)) from Int. No. 106,007 (PN210), 40 Pages, Exhibit No. 1005 filed in Interference 106,013 on Feb. 17, 2015.
UWA Motion 1 (For Judgment Under 35 § 112(a)) from Int. No. 106,008 (Doc 213), pp. 38, Exhibit No. 1004 filed in Interference 106,013 on Feb. 17, 2015.
UWA submission of teleconference transcript , 28 pages, dated Dec. 12, 2014 (Exhibit No. 2114 filed in interferences 106008 and 106007 on Dec. 12, 2014).
Valorization Memorandum published by the Dutch Federation of University Medical Centers in Mar. 2009, (University of Western Australia Exhibit 2140, filed Apr. 3, 2015 in Interferences 106007, 106008, and 106013, pp. 1-33).
Van Deutekom et al., "Antisense-induced exon skipping restores dystrophin expression in DMD patient derived muscle cells," Human Molecular Genetics vol. 10, No. 15: 1547-1554 (2001) (Exhibit No. 1084 filed in interferences 106008, 106007 on Dec. 23, 2014).
van Deutekom et al., "Local Dystrophin Restoration with Antisense Oligonucleotide PRO051," N. Engl. J. Med., vol. 357, No. 26, pp. 2677-2686 (Dec. 2007), Exhibit No. 1213 filed in Interferences 106,007 and 106,008 on Feb. 17, 2015.
Van Deutekom, Judith C. T. et al., "Advances in Duchenne Muscular Dystrophy Gene Therapy," Nature Reviews Genetics, vol. 4(10):774-783 (2003).
Van Ommen 2002 PCT (WO 02/24906 Al), 43 pages,(Exhibit No. 1071 filed in interferences 106008, 106007 on Dec. 23, 2014).
van Putten M, et al., The Effects of Low Levels of Dystrophin on Mouse Muscle Function and Pathology. PLoS ONE 2012;7:e31937, 13 pages.
Van Vliet, Laura et al., "Assessment of the Feasibility of Exon 45-55 Multiexon Skipping for Duchenne Muscular Dystrophy", BMC Medical Genetics, vol. 9(1):105 (2008).

Verma, Sandeep et al., "Modified Oligonucleotides: Synthesis and Strategy for Users," Annu. Rev. Biochem., vol. 67:99-134 (1998) (Exhibit No. 1040 filed in interferences 106008, 106007 on Nov. 18, 2014).
Voit, Thomas et al., "Safety and efficacy of drisapersen for the treatment of Duchenne muscular dystrophy (DEMAND II)): an exploratory, randomised, placebo-controlled phase 2 study," Lancet Neurol., vol. 13:987-996 (2014) (Exhibit No. 2037 filed in interferences 106008, 106013, 106007 on Nov. 18, 2014).
Volloch, Vladimir et al., "Inhibition of Pre-mRNA Splicing by Antisense RNA in Vitro: Effect of RNA Containing Sequences Complementary to Exons," Biochemical and Biophysical Research Communications, vol. 179 (3):1593-1599 (1991).
Wahlestedt et al., "Potent and nontoxic antisense oligonucleotides containing locked nucleic acids," PNAS, vol. 97, No. 10, pp. 5633-5638 (May 2000), Exhibit No. 1201 filed in Interferences 106,007 and 106,008 on Feb. 17, 2015.
Wang et al., "In Vitro evaluation of novel antisense oligonucleotides is predictive of in vivo exon skipping activity for Duchenne muscular dystrophy," J. Gene Medicine, vol. 12, pp. 354-364 (Mar. 2010), Exhibit No. 1115 filed in interferences 106,007 and 106,008 on Feb. 17, 2015.
Wang, Chen-Yen et al., "pH-sensitive immunoliposomes mediate target-cell-specific delivery and controlled expression of a foreign gene in mouse," Proc. Natl. Acad. Sci. USA, vol. 84:7851-7855 (1987).
Watakabe, Akiya et al., "The role of exon sequences in splice site selection," Genes & Development, vol. 7:407-418 (1993).
Watanabe et al., "Plasma Protein Binding of an Antisense Oligonucleotide Targeting Human ICAM-1 (ISIS 2302)," Oligonucleotides, vol. 16, pp. 169-180 (2006), Exhibit No. 1197 filed in Interferences 106,007 and 106,008 on Feb. 17, 2015.
Wijnaendts, L.C.D. et al., "Prognostic importance of DNA flow cytometric variables in rhabdomyosarcomas," J. Clin. Pathol., vol. 46:948-952 (1993) (Exhibit No. 1041 filed in interferences 106008, 106007 on Nov. 18, 2014).
Wilton et al. (2007) "Antisense Oligonucleotide-induced Exon Skipping Across the Human Dystrophin Gene Transcript," Molecular Therapy 15(7):1288-1296, 10 pages, (Exhibit No. 2121 filed in interferences 106,007 and 106,008 on Feb. 17, 2015.
Wilton, Stephen D. et al., "Antisense oligonucleotides in the treatment of Duchenne muscular dystrophy: where are we now?" Neuromuscular Disorders, vol. 15:399-402 (2005).
Wilton, Stephen D. et al., "Specific removal of the nonsense mutation from the mdx dystriphin mRNA using antisense oligonucleotides," Neuromuscular Disorders, vol. 9:330-338 (1999).
WO 2002/24906 A1 of AZL, (University of Western Australia Exhibit 2134, filed Apr. 3, 2015 in Interferences 106007, 106008, and 106013, pp. 1-43.).
WO 2004/083432 (the published AZL PCT Application, "Van Ommen"), pp. 71, Exhibit No. 1003 filed in Interference 106,013 on Feb. 17, 2015.
WO 2013/112053 A1, (University of Western Australia Exhibit 2130, filed Apr. 3, 2015 in Interferences 106007, 106008, and 106013, pp. 1-177).
Wolff, Jon A. et al., "Direct Gene Transfer into Mouse Muscle in Vivo," Science, vol. 247:1465-1468 (1990).
Wong, Marisa L. et al., "Real-time PCR for mRNA quantitation," BioTechniques, vol. 39:75-85 (2005) (Exhibit No. 1066 filed in interferences 106008, 106007 on Nov. 18, 2014).
Wood, "Toward an Oligonucleotide Therapy for Duchenne Muscular Dystrophy: A Complex Development Challenge," Science Translational Medicine, vol. 2, No. 25, pp. 1-6 (Mar. 2010), Exhibit No. 1116 filed in interferences 106,007 and 106,008 on Feb. 17, 2015,Doc 335.
Written Opinion for Application No. PCT/AU2010/001520, 6 pages, dated Jan. 21, 2011.
Wu, B. et al., "Dose-dependent restoration of dystrophin expression in cardiac muscle of dystrophic mice by systemically delivered morpholino," Gene Therapy, vol. 17:132-140 (2010).
Wu, Bo et al., "Effective rescue of dystrophin improves cardiac function in dystrophin-deficient mice by a modified morpholino oligomer," PNAS, vol. 105(39):14814-14819 (2008).

(56) References Cited

OTHER PUBLICATIONS

Wu, Bo et al., "Targeted Skipping of Human Dystrophin Exons in Transgenic Mouse Model Systemically for Antisense Drug Development," PLoS One, vol. 6(5):e19906, 11 pages (2011).

Wu, George Y. et al., "Receptor-mediated Gene Delivery and Expression in Vivo," The Journal of Biological Chemistry, vol. 263(29):14621-14624 (1988).

Wu, George Y. et al., "Receptor-mediated in Vitro Gene Transformation by a Soluble DNA Carrier System," The Journal of Biological Chemistry, vol. 262(10):4429-4432 (1987).

Wyatt et al. "Site-specific cross-linking of mammalian U5 snRNP to the 5' splice site before the first step of pre-mRNA splicing," Genes & Development, vol. 6, pp. 2542-2553 (1992), Exhibit No. 1198 filed in Interferences 106,007 and 106,008 on Feb. 17, 2015.

Yin et al., "A fusion peptide directs enhanced systemic dystrophin exon skipping and functional restoration in dystrophin-deficient mdx mice," Human Mol. Gen., vol. 18, No. 22, pp. 4405-4414 (2009), Exhibit No. 1200 filed in Interferences 106,007 and 106,008 on Feb. 17, 2015.

Yin et al., "Cell Penetrating peptide-conjugated antisense oligonucleotides restore systemic muscle and cardiac dystrophin expression and function," Human Mol. Gen., vol. 17, No. 24, pp. 3909-3918 (2008), Exhibit No. 1199 filed in Interferences 106,007 and 106,008 on Feb. 17, 2015.

Yin et al., "Functional Rescue of Dystrophin-deficient mdx Mice by a ChimericPeptide-PMO," Mol. Therapy, vol. 18, No. 10, pp. 1822-1829 (Oct. 2010), Exhibit No. 1117 filed in interferences 106,007 and 106,008 on Feb. 17, 2015.

Yokota et al., "Efficacy of Systematic Morpholino Exon-Skipping in Duchenne Dystrophy Dogs," American Neurological Assoc., vol. 65, No. 6, pp. 667-676 (Jun. 2009), Exhibit No. 1214 filed in Interferences 106,007 and 106,008 on Feb. 17, 2015.

*Zoltek Corp. v. U.S.*, 95 Fed. Cl. 681 (2011), 23 pages, (Academisch Ziekenhuis Leiden Exhibit 1236, filed May 5, 2015 in Interference 106007 and 106008).

Herschlag, Daniel et al., "Contributions of 2' Hydroxyl Groups of the RNA Substrate to Binding and Catalysis by the Tetrahymena Ribozyme: An Energetic Picture of an Active Site Composed of RNA," Biochemistry, vol. 32:8299-8311(1993) (Exhibit No. 1031 filed in interferences 106008, 106007 on Nov. 18, 2014).

Hoffman EP, et al., "Characterization of dystrophin in muscle-biopsy specimens from patients with Duchenne's or Becker's muscular dystrophy" N Engl J Med 1988;318:1363-68.

Hoffman EP, et al., "Restoring dystrophin expression in Duchenne muscular dystrophy muscle: Progress in exon skipping and stop codon read through," Am J Path 2011;179:12-22.

Hudziak, Robert M. et al., "Antiproliferative Effects of Steric Blocking Phosphorodiamidate Morpholino Antisense Agents Directed against c-myc," Antisense & Nucleic Acid Drug Development, vol. 10:163-176 (2000) (Exhibit No. 1032 filed in interferences 106008, 106007 on Nov. 18, 2014).

Hudziak, Robert M. et al., "Resistance of Morpholino Phosphorodiamidate Oligomers to Enzymatic Degradation," Antisense & Nucleic Acid Drug Development, vol. 6:267-272 (1996).

Hussey, Nicole D. et al., "Analysis of five Duchenne muscular dystrophy exons and gender determination using conventional duplex polymerase chain reaction on single cells," Molecular Human Reproduction, vol. 5(11):1089-1094 (1999).

Interim Guidance on Patent Subject Matter Eligibility ("the December Guidance," 16 pages,(Exhibit No. 2119 filed in interferences 106,007 and 106,008 on Feb. 17, 2015.

International Patent Application No. PCT/AU2000/00693 ("Wraight"), published as WO 00/78341 on Dec. 28, 2000, 201 pages, (Exhibit No. 2125 filed in interferences 106,007 and 106,008 on Feb. 17, 2015.

International Preliminary Report on Patentability and Written Opinion for Application No. PCT/US2009/061960, 8 pages, dated Apr. 26, 2011.

International Preliminary Report on Patentability for Application No. PCT/AU2005/000943, 8 pages, dated Dec. 28, 2006.

International Preliminary Report on Patentability, PCT/US2013/077216, dated Jun. 23, 2015, pp. 1-7.

International Preliminary Report on Patentability, PCT/US2014/029610, dated Jul. 1, 2015, pp. 1-122.

International Search Report and Written Opinion of the International Searching Authority issued in International Patent Application No. PCT/US2013/077216, 5 pages, dated Mar. 27, 2014.

International Search Report and Written Opinion of the International Searching Authority issued in International Patent Application No. PCT/US2014/029610, 6 pages, dated Sep. 18, 2014.

International Search Report and Written Opinion of the International Searching Authority issued in International Patent Application No. PCT/US2014/029689, 8 pages, dated Oct. 21, 2014.

International Search Report and Written Opinion of the International Searching Authority issued in International Patent Application No. PCT/US2014/029766, 8 pages, dated Oct. 21, 2014.

International Search Report for Application No. PCT/AU2005/000943, 5 pages, dated Oct. 20, 2005.

International Search Report for Application No. PCT/US01/14410, 5 pages, dated Mar. 6, 2002.

International Search Report for Application No. PCT/US2009/061960, 9 pages, dated Apr. 6, 2010.

Invitation to pay fees and Partial International Search Report issued by the International Search Authority in International Patent Application No. PCT/US2014/029689, 8 pages, dated Jul. 29, 2014.

ISIS Pharmaceuticals website, 2 pages, http://www.isispharm.com/Pipeline/Therapeutic-Areas/Other.htm (2014) (Exhibit No. 2021 filed in interferences 106008, 106013, 106007 on Nov. 18, 2014).

Iversen, Patrick L. et al., "Efficacy of Antisense Morpholino Oligomer Targeted to c-myc in Prostate Cancer Xenograft Murine Model and a Phase I Safety Study in Humans," Clinical Cancer Research, vol. 9:2510-2519 (2003).

Jarver, Peter et al., "A Chemical View of Oligonucleotides for Exon Skipping and Related Drug Applications," Nucleic Acid Therapeutics, vol. 24(1):37-47 (2014) (Exhibit No. 2061 filed in interferences 106008, 106013, 106007 on Nov. 18, 2014).

Jason, Tracey L.H. et al., "Toxicology of antisense therapeutics," Toxicology and Applied Pharmacology, vol. 201:66-83 (2004) (Exhibit No. 2027 filed in interferences 106008, 106013, 106007 on Nov. 18, 2014).

Jearawiriyapaisarn, Natee et al., "Long-term improvement in mdx cardiomyopathy after therapy with peptide-conjugated morpholino oligomers," Cardiovascular Research, vol. 85:444-453 (2010).

Jearawiriyapaisarn, Natee et al., "Sustained Dystrophin Expression Induced by Peptide-conjugated Morpholino Oligomers in the Muscles of mdx Mice," Mol. Ther., vol. 16(9):1624-1629 (2008).

Job Posting by Sarepta for "Scientist II, Muscle Biology" (2 pages), (Academisch Ziekenhuis Leiden Exhibit 1233, filed Apr. 3, 2015 in Interference 106007 and 106008).

Jones, Simon S. et al., "The Protection of Uracil and Guanine Residues in Oligonucleotide Synthesis," Tetrahedron Letters, vol. 22(47):4755-4758 (1981).

Karlen, Yann et al., "Statistical significance of quantitative PCR," BMC Bioinformatics, 8:131, 16 pages (2007) (Exhibit No. 1033 filed in interferences 106008, 106007 on Nov. 18, 2014).

Karras, James G. et al., "Deletion of Individual Exons and Induction of Soluble Murine Interleukin-5 Receptor-alpha Chain Expression through Antisense Oligonucleotide-Mediated Redirection of Pre-mRNA splicing," Molecular Pharmacology, vol. 58:380-387 (2000).

Kaye, Ed, "Results of the Eteplirsen Phase 2b and Phase 2b Extension Study in Duchenne Muscular Dystrophy," 8th Annual Meeting of the Oligonucleotide Therapeutics Society, Session 9: Advances in Oligonucleotide Clinical Development II, p. 48 (2012).

Kinali, Maria et al., "Local restoration of dystrophin expression with the morpholino oligomer AVI-4658 in Duchenne muscular dystrophy: a single-blind, placebo-controlled, dose-escalation, proof-of-concept study," Lancet Neurol., vol. 8:918-928 (2009).

King et al., "A Dictionary of Genetics," Oxford University Press, 4th Ed. (1990), Exhibit No. 1189 filed in Interferences 106,007 and 106,008 on Feb. 17, 2015.

(56) References Cited

OTHER PUBLICATIONS

Koenig, M. et al., "The Complete Sequence of Dystrophin Predicts a Rod-Shaped Cytoskeleton Protein," Cell, vol. 53:219-228 (1988) (Exhibit No. 1010 filed in interferences 106008, 106007 on Nov. 18, 2014).
Koenig, M. et al., "The Molecular Basis for Duchenne versus Becker Muscular Dystrophy: Correlation of Severity with Type of Deletion," Am. J. Hum. Genet, vol. 45:498-506 (1989) (Exhibit No. 1011 filed in interferences 106008, 106007 on Nov. 18, 2014).
Kohler M, et al., "Quality of life, physical disability and respiratory impairment in Duchenne muscular dystrophy," Am J Respir Crit Care Med 2005;172:1032-6.
Koshkin, Alexei A. et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron, vol. 54:3607-3630 (1998) (Exhibit No. 2007 filed in interferences 106008, 106013, 106007 on Nov. 18, 2014).
Kurreck J., "Antisense Technologies: Improvement Through Novel Chemical Modifications", European Journal of Biochemistry, vol. 270(8):1628-1644 (2003).
Lab-on-a-Chip Data, pp. 28, Exhibit No. 1185 filed in Interferences 106,007 and 106,008 on Feb. 16, 2015.
Laboratory Notebook Entry (Exon 51 Experiments): RT-PCR Analysis of 8036 Cells, pp. 2, Exhibit No. 1179 filed in Interferences 106,007 and 106,008 on Feb. 16, 2015.
Laboratory Notebook Entry (Exon 51 Experiments): RT-PCR Analysis of KM155.C25 Cells, pp. 2, Exhibit No. 1178 filed in Interferences 106,007 and 106,008 on Feb. 16, 2015.
Laboratory Notebook Entry (Exon 51 Experiments): Transfection of 8036 Cells, pp. 1, Exhibit No. 1172 filed in Interferences 106,007 and 106,008 on Feb. 16, 2015.
Laboratory Notebook Entry (Exon 51 Experiments): Transfection of KM155.C25 Cells, pp. 1, Exhibit No. 1171 filed in Interferences 106,007 and 106,008 on Feb. 16, 2015.
Laboratory Notebook Entry (Exon 53 Experiments): RT-PCR Analysis of KM155.C25 Cells, pp. 2, Exhibit No. 1180 filed in Interferences 106,007 and 106,008 on Feb. 16, 2015.
Laboratory Notebook Entry (Exon 53 Experiments): RT-PCR Analysis of R1809 Cells, pp. 2, Exhibit No. 1181 filed in Interferences 106,007 and 106,008 on Feb. 16, 2015.
Laboratory Notebook Entry (Exon 53 Experiments): Transfection of KM155.C25 Cells, pp. 1, Exhibit No. 1173 filed in Interferences 106,007 and 106,008 on Feb. 16, 2015.
Laboratory Notebook Entry (Exon 53 Experiments): Transfection of R1809 Cells, pp. 1, Exhibit No. 1174 filed in Interferences 106,007 and 106,008 on Feb. 16, 2015.
Laboratory Notebook Entry: General RNA recovery, 1 Page, Exhibit No. 1176 filed in Interferences 106,007 and 106,008 on Feb. 16, 2015.
Laboratory Notebook Entry: Lab-on-a-Chip Analysis, pp. 3, Exhibit No. 1184 filed in Interferences 106,007 and 106,008 on Feb. 16, 2015.
Larsen et al., "Antisense properties of peptide nucleic acid," Biochim. Et Biophys. Acta, vol. 1489, pp. 159-166 (1999), Exhibit No. 1190 filed in Interferences 106,007 and 106,008 on Feb. 17, 2015.
AON PS229 (h53AON1) HPLC Chromatograph pp. 2, Exhibit No. 1140 filed in Interferences 106,007 and 106,008 on Feb. 16, 2015.
AON PS229 (h53AON1) HPLC Method Report, pp. 3, Exhibit No. 1139 filed in Interferences 106,007 and 106,008 on Feb. 16, 2015.
AON PS229 (h53AON1) Mass Spectrometry Data, pp. 3, Exhibit No. 1142 filed in Interferences 106,007 and 106,008 on Feb. 16, 2015.
AON PS229 (h53AON1) Synthesis Laboratory Notebook Entry, pp. 1, Exhibit No. 1137 filed in Interferences 106,007 and 106,008 on Feb. 16, 2015.
AON PS229L (h53AON229L) Certificate of Analysis, pp. 1, Exhibit No. 1129 filed in Interferences 106,007 and 106,008 on Feb. 17, 2015.
AON PS43 (h51AON1) Certificate of Analysis, pp. 1, Exhibit No. 1134 filed in Interferences 106,007 and 106,008 on Feb. 16, 2015.
AON PS43 (h51AON1) HPLC Chromatogram, pp. 1, Exhibit No. 1131 filed in Interferences 106,007 and 106,008 on Feb. 17, 2015.
AON PS43 (h51AON1) HPLC Method Report, pp. 4, Exhibit No. 1130 filed in Interferences 106,007 and 106,008 on Feb. 17, 2015.
AON PS43 (h51AON1) Mass Spectrometry Data, pp. 3, Exhibit No. 1135 filed in Interferences 106,007 and 106,008 on Feb. 16, 2015.
AON PS43 (h51AON1) UPLC-UV Data, pp. 2, Exhibit No. 1136 filed in Interferences 106,007 and 106,008 on Feb. 16, 2015.
AONs PS1958, PS1959, PS1960, PS1961, PS1962, PS1963, PS1964, PS1965, PS1966, and PS1967 HPLC Method Report, pp. 3, Exhibit No. 1143 filed in Interferences 106,007 and 106,008 on Feb. 16, 2015.
Applicant-Initiated Interview Summary dated Apr. 8, 2013 in U.S. Appl. No. 13/094,548, (University of Western Australia Exhibit 2144, filed Apr. 3, 2015 in Interferences 106007, 106008, and 106013, pp. 1-11).
Arechavala-Gomeza V, et al., "Immunohistological intensity measurements as a tool to assess sarcolemma-associated protein expression," Neuropathol Appl Neurobiol 2010;36: 265-74.
Arechavala-Gomeza, V. et al., "Comparative Analysis of Antisense Oligonucleotide Sequences for Targeted Skipping of Exon 51 During Dystrophin Pre-mRNA Splicing in Human Muscle," Human Gene Therapy, vol. 18:798-810 (2007).
Arora, Vikram et al., "c-Myc Antisense Limits Rat Liver Regeneration and Indicates Role for c-Myc in Regulating Cytochrome P-450 3A Activity," The Journal of Pharmacology and Experimental Therapeutics, vol. 292(3):921-928 (2000).
*Asetek Danmark A/S v. CMI USA, Inc.*, 2014 WL 5990699, N.D. Cal. 2014, 8 pages, (Academisch Ziekenhuis Leiden Exhibit 1237, filed May 5, 2015 in Interference 106007 and 106008).
Asvadi, Parisa et al., "Expression and functional analysis of recombinant scFv and diabody fragments with specificity for human RhD," Journal of Molecular Recognition, vol. 15:321-330 (2002).
Australian Application No. 2004903474, 36 pages, dated Jul. 22, 2005 (Exhibit No. 1004 filed in interferences 106008, 106007 on Nov. 18, 2014).
AVI BioPharma, Inc., "Exon 51 Sequence of Dystrophin," Document D19 as filed in Opposition of European Patent EP1619249, filed Jun. 23, 2009, 7 pages.
AZL's PCT/NL03/00214 (the as-filed AZL PCT Application) Exhibit No. 1006, filed in Interference No. 106,007, 64 pages, Dec. 23, 2014.
AZL's U.S. Appl. No. 14/295,311 and claims, as-filed Jun. 3, 2014 ("the '311 Application") (Exhibit No. 1077 filed in interferences 106008, 106007 on Dec. 23, 2014).
Azofeifa J, et al., "X-chromosome methylation in manifesting and healthy carriers of dystrophinopathies: concordance of activation ratios among first degree female relatives and skewed inactivation as cause of the affected phenotypes," Hum Genet 1995;96:167-176.
Beaucage, S.L. et al., "Deoxynucleoside Phosphoramidites—A New Class of Key Intermediates for Deoxypolynucleotide Synthesis," Tetrahedron Letters, vol. 22(20):1859-1862 (1981).
Bellare, Priya et al., "A role for ubiquitin in the spliceosome assembly pathway," Nature Structural & Molecular Biology, vol. 15(5):444-451 (2008) (Exhibit No. 1057 filed in interferences 106008, 106007 on Nov. 18, 2014).
Bellare, Priya et al., "Ubiquitin binding by a variant Jab1/MPN domain in the essential pre-mRNA splicing factor Prp8p," RNA, vol. 12:292-302 (2006) (Exhibit No. 1056 filed in interferences 106008,106007 on Nov. 18, 2014).
Bennett, C. Frank et al., "RNA Targeting Therapeutics: Molecular Mechanisms of Antisense Oligonucleotides as a Therapeutic Platform," Annu. Rev. Pharmacol. Toxicol., vol. 50:259-293 (2010) (Exhibit No. 1025 filed in interferences 106008, 106007 on Nov. 18, 2014).
Berge, Stephen M. et al., "Pharmaceutical Salts," Journal of Pharmaceutical Sciences, vol. 66(1):1-18 (1977).
Bestas et al., "Design and Application of Bispecific Splice Switching Oligonucleotides," Nuc. Acid Therap., vol. 24, No. 1, pp. 13-24 (2014), Exhibit No. 1120 filed in interferences 106,007 and 106,008 on Feb. 17, 2015.

(56) References Cited

OTHER PUBLICATIONS

Braasch, Dwaine A. et al., "Locked nucleic acid (LNA): fine-tuning the recognition of DNA and RNA," Chemistry & Biology, vol. 8:1-7 (2001) (Exhibit No. 2009 filed in interferences 106008, 106013, 106007 on Nov. 18, 2014).
Braasch, Dwaine A. et al., "Novel Antisense and Peptide Nucleic Acid Strategies for Controlling Gene Expression," Biochemistry, vol. 41(14):4503-4510 (2002) (Exhibit No. 2006 filed in interferences 106008, 106013, 106007 on Nov. 18, 2014).
Bremmer-Bout, Mattie et al., "Targeted Exon Skipping in Transgenic hDMD Mice: A Model for Direct Preclinical Screening of Human-Specific Antisense Oligonucleotides," Molecular Therapy, vol. 10(2):232-240 (2004) (Exhibit No. 2024 filed in interferences 106008, 106013, 106007 on Nov. 18, 2014).
Brooke MH, et al., "Clinical investigation in Duchenne dystrophy: 2. Determination of the "power" of therapeutic trials based on the natural history," Muscle Nerve. 1983;6:91-103.
Brown, Susan C. et al., "Dystrophic phenotype induced in vitro by antibody blockade of muscle alpha-dystroglycan-laminin interaction," Journal of Cell Science, vol. 112:209-216 (1999).
Bushby K, et al. "Diagnosis and management of Duchenne muscular dystrophy, part 1: diagnosis, and pharmacological and psychosocial management," Lancet Neurol 2010;9:77-93.
Bushby KM, et al., "The clinical, genetic and dystrophin characteristics of Becker muscular dystrophy," II. Correlation of phenotype with genetic and protein abnormalities. J Neurol 1993;240: 105-112.
Bushby KM, et al., "The clinical, genetic and dystrophin characteristics of Becker muscular dystrophy," I. Natural history. J Neurol 1993;240:98-104.
Canonico, A.E. et al., "Expression of a CMV Promoter Drive Human alpha-1 Antitrypsin Gene in Cultured Lung Endothelial Cells and in the Lungs of Rabbits," Clinical Research, vol. 39(2):219A (1991).
Cirak, Sebahattin et al., "Exon skipping and dystrophin restoration in patients with Duchenne muscular dystrophy after systemic phosphorodiamidate morpholino oligomer treatment: an open-label, phase 2, dose-escalation study," Lancet, vol. 378(9791):595-605 (2011).
Claim Chart U.S. Appl. No. 11/233,495, pp. 57, Exhibit No. 1216 filed in Interferences 106,007 and 106,008 on Feb. 17, 2015.
Claim Chart U.S. Appl. No. 13/550,210, pp. 45, Exhibit No. 1217 filed in Interferences 106,007 and 106,008 on Feb. 17, 2015.
Claim Chart, U.S. Pat. No. 7,807,816, 14 pages (Exhibit No. 1063 filed in interferences 106008, 106007 on Nov. 18, 2014).
Claim Chart, U.S. Pat. No. 7,960,541, 17 pages (Exhibit No. 1064 filed in interferences 106008, 106007 on Nov. 18, 2014).
Claim Chart, U.S. Pat. No. 8,455,636, 32 pages (Exhibit No. 1062 filed in interferences 106008, 106007 on Nov. 18, 2014).
Claim Comparison Chart—Claims 11 and 29 in U.S. Appl. No. 13/550,210, pp. 1, Exhibit No. 1226 filed in Interferences 106,007 and 106,008 on Feb. 17, 2015.
Claim Comparison Chart U.S. Appl. No. 13/550,210 vs U.S. Appl. No. 11/233,495, pp. 12, Exhibit No. 1218 filed in Interferences 106,007 and 106,008 on Feb. 17, 2015.
Claim Comparison Chart U.S. Appl. No. 13/550,210 vs U.S. Appl. No. 12/198,007, pp. 1, Exhibit No. 1219 filed in Interferences 106,007 and 106,008 on Feb. 17, 2015.
Claims from U.S. Appl. No. 11/233,495, 6 pages, dated Sep. 21, 2005 (Exhibit No. 2068 filed in interferences 106008, 106013, 106007 on Nov. 18, 2014).
Classification Excerpts from USPC System, 21 pages, (Academisch Ziekenhuis Leiden Exhibit 1234, filed May 5, 2015 in Interference 106,007 and 106008).
Collins, C.A. et al., "Duchenne's muscular dystrophy: animal models used to investigate pathogenesis and develop therapeutic strategies," Int. J. Exp. Pathol., vol. 84(4):165-172 (2003).
Confirmation of Dystrophin Exon 48 to 50 Deletion in Cell Line 8036 Laboratory Notebook Entry, pp. 3, Exhibit No. 1167 filed in Interferences 106,007 and 106,008 on Feb. 16, 2015.
Exon 51 Internal Sequence Schematic, pp. 1, Exhibit No. 1224 filed in Interferences 106,007 and 106,008 on Feb. 17, 2015.
Exon 53 Internal Sequence Schematic, pp. 1, Exhibit No. 1225 filed in Interferences 106,007 and 106,008 on Feb. 17, 2015.
Fairclough et al., "Therapy for Duchenne muscular dystrophy: renewed optimism from genetic approaches," Nature Reviews, vol. 14, pp. 373-378 (Jun. 2013), Exhibit No. 1112 filed in interferences 106,007 and 106,008 on Feb. 17, 2015.
Fall, Abbie M. et al., "Induction of revertant fibres in the mdx mouse using antisense oligonucleotides," Genetic Vaccines and Therapy, vol. 4:3, doi:10.1186/1479-0556-4-3, 12 pages (2006).
Federal Register, vol. 58, No. 183, pp. 49432-49434, Sep. 23, 1993 (6 pages); [Cited as: 58 FR 49432-01, 1993 WL 371451 (F.R.)], Exhibit No. 1221 filed in Interferences 106,007 and 106,008 on Feb. 17, 2015.
Federal Register, vol. 69, No. 155, pp. 49960-50020 dated Aug. 12, 2004 (62 pages), Exhibit No. 1220 filed in Interferences 106,007 and 106,008 on Feb. 17, 2015.
File Excerpt from AZL U.S. Appl. No. 11/233,495: Amendment After Non-Final Office Action, as-filed Nov. 1, 2010 (Exhibit No. 1085 filed in interferences 106008, 106007 on Dec. 23, 2014).
File Excerpt from AZL U.S. Appl. No. 11/233,495: Claims examined in Non-Final Office Action, dated Dec. 1, 2008 (Exhibit No. 1079 filed in interferences 106008, 106007 on Dec. 23, 2014).
File Excerpt from AZL U.S. Appl. No. 11/233,495: Final Office Action dated Aug. 31, 2010 (Exhibit No. 1086 filed in interferences 106008, 106007 on Dec. 23, 2014).
File Excerpt from U.S. Appl. No. 11/233,495: Non-Final Office Action dated Dec. 1, 2008 and Final Office Action dated Jun. 25, 2009 (Exhibit No. 1078 filed in interferences 106008, 106007 on Dec. 23, 2014).
File Excerpt from U.S. Appl. No. 12/198,007: AZL's Preliminary Amendment and Response, as-filed Nov. 7, 2008 (Exhibit No. 1075 filed in interferences 106008, 106007 on Dec. 23, 2014).
File Excerpt from U.S. Appl. No. 12/976,381: AZL's First Preliminary Amendment, as-filed Dec. 22, 2010 (Exhibit No. 1076 filed in interferences 106008, 106007 on Dec. 23, 2014).
File Excerpts from Prosecution History of U.S. Appl. No. 13/270,992 (UWA's U.S. Pat. No. 8,486,907), pp. 122, Exhibit No. 1006 filed in Interference 106,013 on Feb. 17, 2015.
File Excerpts from U.S. Appl. No. 11/233,495: Response to Non-Final Office Action, as filed Jul. 26, 2011 (14 pages), Exhibit No. 1222 filed in Interferences 106,007 and 106,008 on Feb. 17, 2015.
File Excerpts from U.S. Appl. No. 13/270,992 (UWA's U.S. Pat. No. 8,486,907): NFOA, dated Jul. 30, 2012; Applicant-Initiated Interview Summary, dated Nov. 8, 2012; Amendment, as filed Jan. 30, 2013; NOA, dated Apr. 4, 2013, Exhibit No. 1118 (122 pages) filed in interferences 106,007 and 106,008 on Feb. 17, 2015.
Flanagan, W. Michael, et al., "A cytosine analog that confers enhanced potency to antisense oligonucleotides," Proc. Nat'l Acad. Sci. USA, vol. 96, pp. 3513-3518 (Mar. 1999), Exhibit No. 1211 filed in Interferences 106,007 and 106,008 on Feb. 17, 2015.
Flanigan, Kevin M. et al., "Pharmacokinetics and safety of single doses of drisapersen in non-ambulant subjects with Duchenne muscular dystrophy: Results of a double-blind randomized clinical trial," Neuromuscular Disorders, vol. 24:16-24 (2014) (Exhibit No. 2038 filed in interferences 106008, 106013, 106007 on Nov. 18, 2014).
Flanigan, Kevin M., et al. (2003) "Rapid Direct Sequence Analysis of the Dystrophin Gene," Am. J. Hum. Genet. 72:931-939, dated Feb. 17, 2015 (Exhibit No. 2120 filed in interferences 106,007 and 106,008 on Feb. 17, 2015.
Fletcher S., et al, Morpholino oligomer-mediated exon skipping averts the onset of dystrophic pathology in the mdx mouse. Mol Ther 2007;15:1587-1592.
Fletcher, Sue et al., "Dystrophin Isoform Induction In Vivo by Antisense-mediated Alternative Splicing," Molecular Therapy, vol. 18(6):1218-1223 (2010).
Fletcher, Sue et al., "Targeted Exon Skipping to Address 'Leaky' Mutations in the Dystrophin Gene," Molecular Therapy-Nucleic Acids, vol. 1, e48, doi:10.1038/mtna.2012.40, 11 pages (2012).
Fletcher, Susan et al., "Dystrophin expression in the mdx mouse after localised and systemic administration of a morpholino antisense oligonucleotide," J. Gene Med., vol. 8:207-216 (2006).

(56) References Cited

OTHER PUBLICATIONS

Fletcher, Susan et al., "Gene therapy and molecular approaches to the treatment of hereditary muscular disorders," Curr. Opin. Neurol., vol. 13:553-560 (2000).
Foster, Helen et al., "Genetic Therapeutic Approaches for Duchenne Muscular Dystrophy," Human Gene Therapy, vol. 23:676-687 (2012).
Fourth Declaration of Erik Sontheimer, Ph.D. (Pursuant to Bd.R. 41.155(b)(2) and SO ¶¶ in 155.1.3 and 155.1.4), dated Mar. 9, 2015, (University of Western Australia Exhibit 2138, filed Apr. 3, 2015 in Interferences 106007, 106008, and 106013, pp. 1-4).
Fragall, Clayton T. et al., "Mismatched single stranded antisense oligonucleotides can induce efficient dystrophin splice switching," BMC Medical Genetics, vol. 12:141, 8 pages (2011) (Exhibit No. 2019 filed in interferences 106008, 106013, 106007 on Nov. 18, 2014).
Fraley, Robert et al., "New generation liposomes: the engineering of an efficient vehicle for intracellular delivery of nucleic acids," Trends Biochem., vol. 6:77-80 (1981).
Frazier, Kendall S. et al., "Species-specific Inflammatory Responses as a Primary Component for the Development of Glomerular Lesions in Mice and Monkeys Following Chronic Administration of a Second-generation Antisense Oligonucleotide," Toxicologica Pathology, 13 pages (2013).
Friedmann, Theodore, "Progress Toward Human Gene Therapy," Science, vol. 244(4910):1275-1281 (1989).
Gebski, Bianca L. et al., "Morpholino antisense oligonucleotide induced dystrophin exon 23 skipping in mdx mouse muscle," Human Molecular Genetics, vol. 12(15):1801-1811 (2003).
Generic Method for Average Mass Determination Using LC-UV-MS in the Negative Mode, pp. 15, Exhibit No. 1145 filed in Interferences 106,007 and 106,008 on Feb. 16, 2015.
Generic UPLC Purity Method for Oligonucleotides (19- to 25-mers), pp. 18, Exhibit No. 1156 filed in Interferences 106,007 and 106,008 on Feb. 16, 2015.
Gennaro, Alfonso R., (ed.), Remington's Pharmaceutical Sciences, 18th Edition, Mack Publishing, Co., Easton PA, 2020 pages (1990).
Giles, Richard V. et al., "Antisense Morpholino Oligonucleotide Analog Induces Missplicing of C-myc mRNA," Antisense & Nucleic Acid Drug Development, vol. 9:213-220 (1999).
GlaxoSmithKline Press Release, Issued in London, UK, dated Jun. 27, 2013 (5 pages), Exhibit No. 1202 filed in Interferences 106,007 and 106,008 on Feb. 17, 2015.
GlaxoSmithKline, "GSK and Prosensa announce start of Phase III study of investigational Duchenne Muscular Dystrophy medication," press release, 6 pages, dated Jan. 19, 2011 (Exhibit No. 2060 filed in interferences 106008, 106013, 106007 on Nov. 18, 2014).
GlaxoSmithKline, Prosensa regains rights from GSK and retains rights to all other programmes for the treatment of Duchenne muscular dystrophy (DMD), press release, 4 pages, dated Jan. 13, 2014 (Exhibit 2040 in Interferences 106007, 106008, and 106013 on Nov. 18, 2014).
Goemans, Nathalie M. et al., "Systemic Administration of PRO051 in Duchenne's Muscular Dystrophy," The New England Journal of Medicine, vol. 364:1513-1522 (2011) (Exhibit No. 2036 filed in interferences 106008, 106013, 106007 on Nov. 18, 2014).
Gordon, Peter M. et al., "Metal ion catalysis during the exon-ligation step of nuclear pre-mRNA splicing: Extending the parallels between the spliceosome and group II introns," RNA, vol. 6:199-205 (2000) (Exhibit No. 1055 filed in interferences 106008, 106007 on Nov. 18, 2014).
Gordon, Peter M., et al., "Kinetic Characterization of the Second Step of Group II Intron Splicing: Role of Metal Ions and the Cleavage Site 2'-OH in Catalysis," Biochemistry, vol. 39, pp. 12939-12952 (2000), Exhibit No. 1188 filed in Interferences 106,007 and 106,008 on Feb. 17, 2015.
Goyenvalle, Aurelie et al., "Prevention of Dystrophic Pathology in Severely Affected Dystrophin/Utrophin-deficient Mice by Morpholino-oligomer-mediated Exon-skipping," Molecular Therapy, vol. 18(1):198-205 (2010).

Hammond, Suzan M. et al., "Correlating In Vitro Splice Switching Activity With Systemic In Vivo Delivery Using Novel ZEN-modified Oligonucleotides," Molecular Therapy—Nucleic Acids, vol. 3:1, 11 pages (2014) (Exhibit No. 2011 filed in interferences 106008, 106013, 106007 on Nov. 18, 2014).
Hammond, Suzan M., et al., "Genetic therapies for RNA mis-splicing diseases," Cell, vol. 27, No. 5, pp. 196-205 (May 2011), Exhibit No. 1113 filed in interferences 106,007 and 106,008 on Feb. 17, 2015.
Hammond, Suzan M., et al., "PRO-051, an antisense oligonucleotide for the potential treatment of Duchenne muscular dystrophy," Curr. Opinion Mol. Therap., vol. 12, No. 4, pp. 478-486 (2010), Exhibit No. 1121 filed in interferences 106,007 and 106,008 on Feb. 13, 2015.
Harding, PL et al., "The Influence of Antisense Oligonucleotide Length on Dystrophin Exon Skipping," Molecular Therapy, vol. 15(1):157-166 (2007) (Exhibit No. 1030 filed in interferences 106008, 106007 on Nov. 18, 2014).
Harel-Bellan, Annick et al., "Specific Inhibition of c-myc Protein Biosynthesis Using an Antisense Synthetic Deoxy-Oligonucleotide in Human T Lymphocytes," The Journal of Immunology, vol. 140(7):2431-2435 (1988).
Havenga, M.J.E., et al., "Exploiting the Natural Diversity in Adenovirus Tropism for Therapy and Prevention of Disease," J. Virol., vol. 76, No. 9, pp. 4612-4620 (May 2002), Exhibit No. 1123 filed in interferences 106,007 and 106,008 on Feb. 13, 2015.
Heasman, Janet, "Morpholino Oligos: Making Sense of Antisense?" Developmental Biology, vol. 243:209-214 (2002).
Heemskerk, Hans A. et al., "In vivo comparison of 2'-O-methyl phosphorothioate and morpholino antisense oligonucleotides for Duchenne muscular dystrophy exon skipping," The Journal of Gene Medicine, vol. 11:257-266 (2009) (Exhibit No. 2020 filed in interferences 106008, 106013, 106007 on Nov. 18, 2014).
Heid, Christian A. et al., "Real Time Quantitative PCR," Genome Research, vol. 6:986-994 (1996) (Exhibit No. 1061 filed in interferences 106008, 106007 on Nov. 18, 2014).
Confirmation of Dystrophin Exon 52 Deletion in Cell Line R1809 Laboratory; Notebook Entry, pp. 3, Exhibit No. 1168 filed in Interferences 106,007 and 106,008 on Feb. 16, 2015.
Confirmatory Study of Eteplirsen in DMD Patients, an Open-Label, Multi-Center, 48-Week Study With a Concurrent Untreated Control Arm to Evaluate the Efficacy and Safety of Eteplirsen in Duchenne Muscular Dystrophy ,Clinical Trials.gov, Clinical Trial Identifier NCT02255552, Oct. 1, 2014, 3 pages.
Confirmatory Study of Eteplirsen in DMD Patients, an Open-Label, Multi-Center, 48-Week Study With a Concurrent Untreated Control Arm to Evaluate the Efficacy and Safety of Eteplirsen in Duchenne Muscular Dystrophy, Clinical Trials.gov, Clinical Trial Identifier NCT02255552, May 26, 2015, 3 pages.
*Coolidge* v. *Efendic*, 2008 WL 2080735, Int. No. 105,457 (BPAI May 16, 2008), 42 pages, (Academisch Ziekenhuis Leiden Exhibit 1235, filed May 5, 2015 in Interference 106007 and 106008).
Corey, David R. et al., Morpholino antisense oligonucleotides: tools for investigating vertebrate development, Genome Biology, vol. 2(5):1015.1-1015.3 (2001) (Exhibit No. 1026 filed in interferences 106008, 106007 on Nov. 18, 2014).
Corrected Priority Statement filed by UWA in Int. No. 106,008 (as PN 219),pp. 5, Exhibit No. 1002 filed in Interference 106,013 on Feb. 17, 2015.
Cortes, Jesus J., et al., "Mutations in the conserved loop of human U5 snRNA generate use of novel cryptic 5' splice sites in vivo," Embo J., vol. 12, No. 13, pp. 5181-5189 (1993), Exhibit No. 1187 filed in Interferences 106,007 and 106,008 on Feb. 17, 2015.
Crooke, Stanley T., Antisense Drug Technology, Principles, Strategies, and Applications, Marcel Dekker, Inc., New York, Chapters 15 and 16, pp. 375-389, 391-469 (2001) (Exhibit No. 2075 filed in interferences 106008, 106013, 106007 on Nov. 18, 2014).
Curriculum Vitae of Judith van Deutekom, pp. 6, Exhibit No. 1126 filed in interferences 106,007 and 106,008 on Feb. 17, 2015.
Curriculum Vitae, Erik Joseph Sontheimer, 18 pages, dated Sep. 29, 2014 (Exhibit No. 1013 filed in interferences 106008, 106007 on Nov. 18, 2014).
CV, Professor Matthew J.A. Wood, 3 pages (Exhibit No. 2003 filed in interferences 106008, 106007 on Nov. 18, 2014).

(56) References Cited

OTHER PUBLICATIONS

Davis, Richard J. et al., "Fusion of PAX7 to FKHR by the Variant t(1;13)(p36;q14) Translocation in Alveolar Rhabdomyosarcoma," Cancer Research, vol. 54:2869-2872 (1994) (Exhibit No. 1027 filed in interferences 106008, 106007 on Nov. 18, 2014).
De Angelis, Fernanda Gabriella et al., "Chimeric snRNA molecules carrying antisense sequences against the splice junctions of exon 51 of the dystrophic pre-mRNA induce exon skipping and restoration of a dystrophin synthesis in 48-50 DMD cells," PNAS, vol. 99(14):9456-9461 (2002).
Decision on Appeal, *Ex Parte Martin Gleave and Hideaki Miyake*, Appeal No. 2005-2447, U.S. Appl. No. 09/619,908 (Jan. 31, 2006) (2009 WL 6927761 (Bd.Pat.App.& Interf.), pp. 12, Exhibit No. 1207 filed in Interferences 106,007 and 106,008 on Feb. 17, 2015.
Decision on Request for ReHearing, *Ex Parte Roderick John Scott*, Appeal No. 2008-004077, U.S. Appl. No. 10/058,825 (Jan. 6, 2010) (2010 WL 191079 (Bd.Pat.App. & Interf.),pp. 21, Exhibit No. 1208 filed in Interferences 106,007 and 106,008 on Feb. 17, 2015.
Declaration of Judith C.T. van Deutekom Under 37 C.F.R. §1.132, filed on Jan. 27, 2012, in U.S. Patent Reexamination Control No. 90/011,320, regarding U.S. Pat. No. 7,534,879, (University of Western Australia Exhibit 2133, filed Apr. 3, 2015 in Interferences 106,007, 106,008, and 106,013, pp. 1-10).
Declaration of Judith van Deutekom, pp. 45, Exhibit No. 1125 filed in interferences 106,007 and 106,008 on Feb. 17, 2015.
Dellorusso, Christiana et al., "Functional correction of adult mdx mouse muscle using gutted adenoviral vectors expressing full-length dystrophin," PNAS, vol. 99(20):12979-12984 (2002).
Deposition Transcript of Erik J. Sontheimer, Ph.D. of Jan. 21, 2015 (99 pages), Exhibit No. 1215 filed in Interferences 106,007 and 106,008 on Feb. 17, 2015.
Deposition Transcript of Matthew J. A. Wood, M.D. , D. Phil., Jan. 22, 2015, including Errata Sheet, pp. 198, Exhibit No. 1007 filed in Interference 106,013 on Feb. 17, 2015.
Deposition Transcript of Matthew J. A. Wood, M.D., D. Phil., pp. 196, Exhibit No. 1122 filed in interferences 106,007 and 106,008 on Feb. 17, 2015.
Desalting of Oligonucleotides, pp. 2, Exhibit No. 1132 filed in Interferences 106,007 and 106,008 on Feb. 17, 2015.
Dirksen, Wessel P. et al., "Mapping the SF2/ASF Binding Sites in the Bovine Growth Hormone Exonic Splicing Enhancer," The Journal of Biological Chemistry, vol. 275(37)29170-29177 (2000).
Dominski, Zbigniew et al., "Identification and Characterization by Antisense Oligonucleotides of Exon and Intron Sequences Required for Splicing," Molecular and Cellular Biology, vol. 14(11):7445-7454 (1994).
Dominski, Zbigniew et al., "Restoration of correct splicing in thalassemic pre-mRNA by antisense oligonucleotides," Proc. Natl. Acad. Sci. USA, vol. 90:8673-8677 (1993).
Doran, Philip et al., "Proteomic profiling of antisense-induced exon skipping reveals reversal of pathobiochemical abnormalities in dystrophic mdx diaphragm," Proteomics, vol. 9:671-685, DOI 10.1002/pmic.200800441 (2009).
Douglas, Andrew G.L. et al., "Splicing therapy for neuromuscular disease," Molecular and Cellular Neuroscience, vol. 56:169-185 (2013) (Exhibit No. 2005 filed in interferences 106008, 106013, 106007 on Nov. 18, 2014).
Doyle, Donald F., et al. (2001) "Inhibition of Gene Expression Inside Cells by PeptideNucleic Acids: Effect of mRNA Target Sequence, Mismatched Bases, and PNA Length," Biochemistry 40:53-64, (Exhibit No. 2123 filed in interferences 106,007 and 106,008 on Feb. 17, 2015.
Dr. Wood Errata Sheet—Jan. 22, 2015, pp. 2, Exhibit No. 1227 filed in Interferences 106,007 and 106,008 on Feb. 17, 2015.
Dunckley, Matthew G. et al., "Modification of splicing in the dystrophin gene in cultured Mdx muscle cells by antisense oligoribonucleotides," Human Molecular Genetics, vol. 5(1):1083-1090 (1995).

Dunckley, Matthew G. et al., "Modulation of Splicing in the DMD Gene by Antisense Oligoribonucleotides," Nucleosides & Nucleotides, vol. 16(7-9):1665-1668 (1997).
Eckstein, F., "Nucleoside Phosphorothioates," Ann. Rev. Biochem., vol. 54:367-402 (1985) (Exhibit No. 1028 filed in interferences 106008, 106007 on Nov. 18, 2014).
Elayadi, Anissa N. et al., "Application of PNA and LNA oligomers to chemotherapy," Current Opinion in Investigational Drugs, vol. 2(4):558-561 (2001).
Email from Danny Huntington to Interference Trial Section, dated Sep. 21, 2014, pp. 2, Exhibit No. 3001 filed in Interference 106,007, 106,008, and 106,013 on Sep. 26, 2014.
Email From Sharon Crane to Interference Trial Section, dated Nov. 13, 2014, pp. 2, Exhibit No. 3002 filed in Interference 106,007, 106,008, and 106,013 on dated Nov. 14, 2014.
Emery, A.E. H., "Population frequencies of inherited neuromuscular diseases—a world survey," Neuromuscul Disord 1991;1:19-29.
Errata sheet for the Jan. 22, 2015 deposition of Matthew J. A. Wood, M.D., D. Phil., 2 pages, (Exhibit No. 2128 filed in interferences 106,007 and 106,008 on Feb. 17, 2015.
Errata sheet for the Mar. 12, 2015 deposition of Erik J. Sontheimer, Ph.D., (University of Western Australia Exhibit 2149, filed Apr. 3, 2015 in Interferences 106007, 106008, and 106013, p. 1).
Errington, Stephen J. et al., "Target selection for antisense oligonucleotide induced exon skipping in the dystrophin gene," The Journal of Gene Medicine, vol. 5:518-527 (2003).
European Office Action for Application No. 09752572.9, 5 pages, dated Feb. 29, 2012.
European Response, Application No. 10004274.6, 7 pages, dated Nov. 5, 2013 (Exhibit No. 1060 filed in interferences 106008, 106007 on Nov. 18, 2014).
European Response, Application No. 12198517.0, 7 pages, dated Oct. 21, 2014 (Exhibit No. 2084 filed in interferences 106008, 106013, 106007 on Nov. 18, 2014).
European Response, Application No. 13160338.3, 4 pages, dated Jun. 26, 2014 (Exhibit No. 2085 filed in interferences 106008, 106013, 106007 on Nov. 18, 2014).
European Search Report for Application No. 10004274.6, 12 pages, dated Jan. 2, 2013.
European Search Report for Application No. 12162995.0, 11 pages, dated Jan. 15, 2013.
European Search Report, EP15168694.6, dated Jul. 23, 2015, pp. 1-8.
Excerpts from Prosecution History of U.S. Appl. No. 13/741,150: Notice of Allowance dated Mar. 16, 2015; List of References cited by Applicant and Considered by Examiner; Notice of Allowance and Fees due dated Sep. 18, 2014; Amendment in Response to Non-Final Office Action dated Jul. 11, 2014, (Academisch Ziekenhuis Leiden Exhibit 1229, filed Apr. 3, 2015 in Interference 106007 and 106008, pp. 1-133).
Excerpts from Prosecution History of U.S. Appl. No. 13/826,880: Notice of Allowance dated Jan. 26, 2015 and Amendment in Response to Non-Final Office Action dates Oct. 15, 2014, (Academisch Ziekenhuis Leiden Exhibit 1228, filed Apr. 3, 2015 in Interference 106007 and 106008, pp. 1-16).
Excerpts from Yeo (Ed.), "Systems Biology of RNA Binding Proteins," Adv. Exp. Med. Biol., Chapter 9, 56 pages (2014), (Academisch Ziekenhuis Leiden Exhibit 1232, filed Apr. 3, 2015 in Interference 106007 and 106008, pp. 1-56).
Excerpts of SEC Form 8-K, dated Nov. 23 2014, for BioMarin Pharmaceutical Inc., (University of Western Australia Exhibit 2129, filed Apr. 3, 2015 in Interferences 106007, 106008, and 106,013, pp. 1-9).
"Efficacy Study of AVI-4658 to Induce Dystrophin Expression in Selected Duchenne Muscular Dystrophy Patients" ClinicalTrials.gov dated Jan. 22, 2013.
*University of Western Australia* v. *Academisch Ziekenhuis Leiden*, University of Western Australia Opposition 3 (Regarding Patentability Under 35 U.S.C. § 101), 22 pages, Patent Interference No. 106,008, (Doc 404), dated Feb. 17, 2015.
"Efficacy Study of AVI-4658 to Induce Dystrophin Expression in Selected Duchenne Muscular Dystrophy Patients," Clinical Trial Identifier No. NCT01396239, ClinicalTrials.gov, dated Jul. 15, 2011, p. 1-4.

(56) References Cited

OTHER PUBLICATIONS

"Eteplirsen—Inhibitor of Dystrophin Expression—Treatment of Duchenne Muscular Dystrophy", Drugs of the Future, vol. 38(1):13-17 (2013).
2nd Expert Declaration of Dr. Erik Sontheimer ("2nd S Decl.") (Exhibit No. 1067 filed in interferences 106008, 106007 on Dec. 23, 2014).
3rd Declaration of Erik J. Sontheimer, Ph.D. ("3rd S. Decl."), Pages 123, Exhibit No. 1186 filed in Interferences 106,007 and 106,008 on Feb. 17, 2015.
A Comparative Study on AONs between 20 and 50 Nucleotides Designed to Induce the Skipping of Exon 53 from the Dystrophin Pre-mRNA, pp. 6, Exhibit No. 1128 filed in Interferences 106,007 and 106,008 on Feb. 17, 2015.
A Comparative Study on AONs Between 20 and 50 Nucleotides Designed to Induce the Skipping of Exon 51 from the Dystrophin Pre-mRNA, pp. 6, Exhibit No. 1127 filed in Interferences 106,007 and 106,008 on Feb. 17, 2015.
Aartsma-Rus A, et al. "Theoretic applicability of antisense-mediated exon skipping for Duchenne muscular dystrophy mutations," Hum Mutat 2009;30:293-99.
Aartsma-Rus et al., "Antisense-induced exon skipping for duplications in Duchenne muscular dystrophy," BMC Medical Genetics 8:43 (2007), (University of Western Australia Exhibit 2135, filed Apr. 3, 2015 in Interferences 106007, 106008, and 106013, pp. 1-9.).
Aartsma-Rus, Annemieke et al., "194th ENMC international workshop. 3rd ENMC workshop on exon skipping: Towards clinical application of antisense-mediated exon skipping for Duchenne muscular dystrophy Dec. 8-10, 2012, Naarden, The Netherlands," Neuromuscular Disorders, vol. 23:934-944 (2013).
Aartsma-Rus, Annemieke et al., "Antisense-Induced Multiexon Skipping for Duchenne Muscular Dystrophy Makes More Sense," Am. J. Hum. Genet., vol. 74:83-92 (2004).
Aartsma-Rus, Annemieke et al., "Functional Analysis of 114 Exon-Internal AONs for Targeted DMD Exon Skipping: Indication for Steric Hindrance of SR Protein Binding Sites," Oligonucleotides, vol. 15:284-297 (2005) (Exhibit No. 2016 filed in interferences 106008, 106013, 106007 on Nov. 18, 2014).
Aartsma-Rus, Annemieke et al., "Guidelines for Antisense Oligonucleotide Design and Insight Into Splice-modulating Mechanisms," Molecular Therapy, vol. 17(3):548-553 (2009) (Exhibit No. 2014 filed in interferences 106008, 106013, 106007 on Nov. 18, 2014).
Aartsma-Rus, Annemieke et al., "Targeted exon skipping as a potential gene correction therapy for Duchenne muscular dystrophy," Neuromuscular Disorders, vol. 12:S71-S77 (2002).
Aartsma-Rus, Annemieke et al., "Therapeutic antisense-induced exon skipping in cultured muscle cells from six different DMD patients," Human Molecular Genetics, vol. 12(8):907-914 (2003).
Abbs, Stephen et al., "A convenient multiplex PCR system for the detection of dystrophin gene deletions: a comparative analysis with cDNA hybridisation shows mistypings by both methods," J. Med. Genet., vol. 28:304-311 (1991).
Abes, S. et al., "Efficient Splicing Correction by PNA Conjugation to an R6-Penetratin Delivery Peptide", Nucleic Acids Research vol. 35(13):4495-4502 (2007).
Agrawal, Sudhir et al., "GEM 91—An Antisense Oligonucleotide Phosphorothioate as a Therapeutic Agent for AIDS," Antisense Research and Development, vol. 2:261-266 (1992).
Agrawal, Sudhir et al., "Oligodeoxynucleoside phosphoramidates and phosphorothioates as inhibitors of human immunodeficiency virus," Proc. Natl. Acad. Sci. USA, vol. 85:7079-7083 (1988).
Ahmad A, et al., "Mdx mice inducibly expressing dystrophin provide insights into the potential of gene therapy for Duchenne muscular dystrophy," Hum Mol Genet 2000;9:2507-2515.
Akhtar, Saghir et al., "Cellular uptake and intracellular fate of antisense oligonucleotides," Trends in Cell Biology, vol. 2:139-144 (1992).
Akhtar, Saghir, "Delivery Strategies for Antisense Oligonucleotide Therapeutics," CRC Press, Inc., Boca Raton, FL, 160 pages (1995).
Alignments of Dystrophin mRNA and Oligonucleotides, 6 pages, submitted to the Patent Trial and Appeal Board in interference No. 106008, dated Nov. 18, 2014 (Exhibit No. 1054 filed in interferences 106008, 106007 on Nov. 18, 2014).
Alter, Julia et al., "Systemic delivery of morpholino oligonucleotide restores dystrophin expression bodywide and improves dystrophic pathology," Nature Medicine, vol. 12(2):175-177 (2006).
Amendment under 37 CFR 1.312 for U.S. Appl. No. 14/248,279, 5 pages, dated Sep. 19, 2014 (Exhibit No. 2053 filed in interferences 106008, 106013, 106007 on Nov. 18, 2014).
Analysis of Second PCR Product by Gel Electrophoresis, pp. 1, Exhibit No. 1182 filed in Interferences 106,007 and 106,008 on Feb. 16, 2015.
Anderson, W. French, "Human Gene Therapy," Science, vol. 256:808-813 (1992).
Annotated scenario introduced and referred to during Mar. 12, 2015 deposition of Erik J. Sontheimer, Ph.D., (University of Western Australia Exhibit 2139, filed Apr. 3, 2015 in Interferences 106007, 106008, and 106013, p. 1.).
Anthony, Karen et al., "Dystrophin quantification: Biological and Translational Research Implications," Neurology, vol. 83:1-8 (2014) (Exhibit No. 2028 filed in interferences 106008, 106013, 106007 on Nov. 18, 2014).
AON PS1958 Mass Spectrometry Data, pp. 7, Exhibit No. 1146 filed in Interferences 106,007 and 106,008 on Feb. 16, 2015.
AON PS1958 UPLC Data, pp. 2, Exhibit No. 1157 filed in Interferences 106,007 and 106,008 on Feb. 16, 2015.
AON PS1959 Mass Spectrometry Data, pp. 5, Exhibit No. 1147 filed in Interferences 106,007 and 106,008 on Feb. 16, 2015.
AON PS1959 UPLC Data, pp. 2, Exhibit No. 1158 filed in Interferences 106,007 and 106,008 on Feb. 16, 2015.
AON PS1960 Mass Spectrometry Data, pp. 8, Exhibit No. 1148 filed in Interferences 106,007 and 106,008 on Feb. 16, 2015.
AON PS1960 UPLC Data, pp. 2, Exhibit No. 1159 filed in Interferences 106,007 and 106,008 on Feb. 16, 2015.
AON PS1961 Mass Spectrometry Data, pp. 5, Exhibit No. 1149 filed in Interferences 106,007 and 106,008 on Feb. 16, 2015.
AON PS1961 UPLC Data, pp. 2, Exhibit No. 1160 filed in Interferences 106,007 and 106,008 on Feb. 16, 2015.
AON PS1962 Mass Spectrometry Data, pp. 7, Exhibit No. 1150 filed in Interferences 106,007 and 106,008 on Feb. 16, 2015.
AON PS1962 UPLC Data, pp. 2, Exhibit No. 1161 filed in Interferences 106,007 and 106,008 on Feb. 16, 2015.
AON PS1963 Mass Spectrometry Data, pp. 10, Exhibit No. 1151 filed in Interferences 106,007 and 106,008 on Feb. 16, 2015.
AON PS1963 UPLC Data, pp. 2, Exhibit No. 1162 filed in Interferences 106,007 and 106,008 on Feb. 16, 2015.
AON PS1964 Mass Spectrometry Data, pp. 13, Exhibit No. 1152 filed in Interferences 106,007 and 106,008 on Feb. 16, 2015.
AON PS1964 UPLC Data, pp. 2, Exhibit No. 1163 filed in Interferences 106,007 and 106,008 on Feb. 16, 2015.
AON PS1965 Mass Spectrometry Data, pp. 9, Exhibit No. 1153 filed in Interferences 106,007 and 106,008 on Feb. 16, 2015.
AON PS1965 UPLC Data, pp. 2, Exhibit No. 1164 filed in Interferences 106,007 and 106,008 on Feb. 16, 2015.
AON PS1966 Mass Spectrometry Data, pp. 8, Exhibit No. 1154 filed in Interferences 106,007 and 106,008 on Feb. 16, 2015.
AON PS1966 UPLC Data, pp. 2, Exhibit No. 1165 filed in Interferences 106,007 and 106,008 on Feb. 16, 2015.
AON PS1967 Mass Spectrometry Data, pp. 7, Exhibit No. 1155 filed in Interferences 106,007 and 106,008 on Feb. 16, 2015.
AON PS1967 UPLC Data, pp. 2, Exhibit No. 1166 filed in Interferences 106,007 and 106,008 on Feb. 16, 2015.
Patentee's Response to European Patent Application No. 05076770.6, dated Jul. 28, 2006, 4 pages.
*Patrick O. Brown and Tidear D. Shalon v. Stephen P.A. Fodor, Dennis W. Solas and William J. Dower*: Interference Merits Panel, Interference No. 104,358, 24 pages, dated Aug. 9, 1999 (Exhibit No. 2113 filed in interferences 106008, 106013, 106007 on Nov. 18, 2014).
PCT Application as-filed for application No. PCT/NL03/00214, 71 pages, dated Sep. 21, 2005 (Exhibit No. 2042 filed in interferences 106008, 106013, 106007 on Nov. 18, 2014).

(56) References Cited

OTHER PUBLICATIONS

PD-10 Desalting Columns, pp. 12, Exhibit No. 1141 filed in Interferences 106,007 and 106,008 on Feb. 16, 2015.
Popplewell, Linda et al., "Design of phosphorodiamidate morpholino oligmers (PMOs) for the induction of exon skipping of the human DMD gene," Human Gene Therapy 19(10): ESGCT 2008 Poster Presentations, p. 1174, Poster No. P203.
Popplewell, Linda J. et al., "Comparative analysis of antisense oligonucleotide sequences targeting exon 53 of the human DMD gene: Implications for future clinical trials," Neuromuscular Disorders, vol. 20(2):102-110 (2010) 9 pages (Exhibit No. 2031 filed in interferences 106008, 106013, 106007 on Nov. 18, 2014).
Popplewell, Linda J. et al., "Design of Antisense Oligonucleotides for Exon Skipping of the Human Dystrophin Gene," Human Gene Therapy 19(4): BSGT 2008 Poster Presentation, p. 407, Poster No. P-35.
Popplewell, Linda J. et al., "Design of Phosphorodiamidate Morpholino Oligomers (PMOs) for the Induction of Exon Skipping of the Human DMD Gene," Molecular Therapy, vol. 17(3):554-561 (2009).
Popplewell, Linda J. et al., "Targeted Skipping of Exon 53 of the Human DMD Gene Recommendation of the Highly Efficient Antisense Oligonucleotide for Clinical Trial," Human Gene Therapy 20(4): BSGT 2009 Poster Presentations, p. 399, Poster No. P10.
Poster Abstract Listing for the Tenth Annual Meeting of the RNA Society, held at the Banff Centre for Conferences, in Banff, Alberta, Canada, from May 24-29, 2005, (University of Western Australia Exhibit 2137, filed Apr. 3, 2015 in Interferences 106007, 106008, and 106013, pp. 1-11).
Pramono, "Induction of Exon Skipping of the Dystrophin Transcript in Lymphoblastoid Cells by Transfecting an Antisense Oligodeoxynucleotide Complementary to Exon Recognition Sequence," Biochem. Res. Comm., vol. 226, pp. 445-449 (1996), Exhibit No. 1192 filed in Interferences 106,007, and 106,008 on Feb. 17, 2015.
Preliminary Amendment for U.S. Appl. No. 12/976,381, 4 pages, dated Dec. 22, 2010 (Exhibit No. 2066 filed in interferences 106008, 106013, 106007 on Nov. 18, 2014).
Preliminary Amendment for U.S. Appl. No. 12/198,007, 3 pages, dated Nov. 7, 2008 (Exhibit No. 2067 filed in interferences 106008, 106013, 106007 on Nov. 18, 2014).
Program Schedule for the Tenth Annual Meeting of the RNA Society, held at the Banff Centre for Conferences, in Banff, Alberta, Canada, from May 24-29, 2005, (University of Western Australia Exhibit 2136, filed Apr. 3, 2015 in Interferences 106007, 106008, and 106013, pp. 1-4).
Proliferation and Differentiation of Myoblast Cultures, pp. 2, Exhibit No. 1169 filed in Interferences 106,007 and 106,008 on Feb. 16, 2015.
Prosensa Press Release, dated Oct. 10, 2014 (2 pages), Exhibit No. 1203 filed in Interferences 106,007 and 106,008 on Feb. 17, 2015.
Prosensa, "GSK and Prosensa Announce Primary Endpoint Not Met in Phase III Study of Drisapersen in Patients With Duchenne Muscular Dystrophy," press release, 4 pages, dated Sep. 20, 2013 (Exhibit No. 2039 filed in interferences 106008, 106013, 106007 on Nov. 18, 2014).
*Raz et al. v. Davis et al.*, Board of Patent Appeals and Inteferences, Patent and Trademark Office, Int. No. 105,712, Tech. Ctr. 1600, Sep. 29, 2011 (24 pages) (2011 WL 4568986 (Bd.Pat.App. & Interf.), Exhibit No. 1209 filed in Interferences 106,007 and 106,008 on Feb. 17, 2015.
Reese, Colin B. et al., "Reaction Between 1-Arenesulphonyl-3-Nitro-1,2,4-Triazoles and Nucleoside Base Residues Elucidation of the Nature of Side-Reactions During Oligonucleotide Synthesis," Tetrahedron Letters, vol. 21:2265-2268 (1980).
Reese, Colin B. et al., "The Protection of Thymine and Guanine Residues in Oligodeoxyribonucleotide Synthesis," J. Chem. Soc. Perkin Trans. 1, pp. 1263-1271 (1984).

Reexamination Certificate—U.S. Appl. No. 90/011,320, issued Mar. 27, 2012, 2 pages, (Exhibit No. 1072 filed in interferences 106008, 106007 on Dec. 23, 2014).
Reply to EPO Communication dated Jun. 26, 2014 in European Application Serial No. 13160338, (University of Western Australia Exhibit 2145, filed Apr. 3, 2015 in Interferences 106007, 106008, and 106013, pp. 1-4).
Reply to EPO Communication dated Oct. 21, 2014 in European Serial No. 12198517, (University of Western Australia Exhibit 2148, filed Apr. 3, 2015 in Interferences 106007, 106008, and 106013, pp. 1-7).
Reply to EPO Communication dated Oct. 23, 2014 in European Application No. 12198485, (University of Western Australia Exhibit 2147, filed Apr. 3, 2015 in Interferences 106007, 106008, and 106013, pp. 1-8).
Response to Office Action and Amendments to the Claims for U.S. Appl. No. 13/550,210, 10 pages, dated May 12, 2014 (Exhibit No. 2064 filed in interferences 106008, 106013, 106007 on Nov. 18, 2014).
Rhodes et al., "BioMarin Bulks Up," BioCentury, pp. 6-8 (Dec. 2014), Exhibit No. 1193 filed in Interferences 106,007 and 106,008 on Feb. 17, 2015.
RNA Isolation Using RNA-BEE, pp. 1, Exhibit No. 1175 filed in Interferences 106,007 and 106,008 on Feb. 16, 2015.
Roberts, Roland G. et al., "Exon Structure of the Human Dystrophin Gene," Genomics, vol. 16:536-538 (1993).
Roest et al., "Application of In Vitro Myo-Differentiation of Non-Muscle Cells to Enhance Gene Expression and Facilitate Analysis of Muscle Proteins," Neuromuscul. Disord., vol. 6, No. 3, pp. 195-202 (May 1996), Exhibit No. 1124 filed in interferences 106,007 and 106,008 on Feb. 17, 2015.
Rosso, Mario G. et al., "An Arabidopsis thaliana T-DNA mutagenized population (GABI-Kat) for flanking sequence tag-based reverse genetics," Plant Molecular Biology, vol. 53:247-259 (2003).
Saito, T. et al., "First-in-Human Study of NS-065/NCNP-01; the Morpholino Based Antisense Oligonucleotide for Exon 53 Skipping in Duchenne Muscular Dystrophy," ASGCT meeting, May 13, 2015, Abstract [136] 1 page.
Saito, T. et al., "First-in-Human Study of NS-065/NCNP-01; the Morpholino Based Antisense Oligonucleotide for Exon 53 Skipping in Duchenne Muscular Dystrophy," ASGCT meeting, May 13, 2015, pp. 1-11.
Sarepta Therapeutics Press Release, dated Jan. 12, 2015, Exhibit No. 1119 filed in interferences 106,007 and 106,008 on Feb. 17, 2015.
Sarepta, "AVI BioPharma Initiates Dosing in Phase 2 Study of Eteplirsen in Duchenne Muscular Dystrophy Patients," press release, 4 pages, dated Aug. 15, 2011 (Exhibit No. 2082 filed in interferences 106008, 106013, 106007 on Nov. 18, 2014).
Sarepta, "Sarepta Therapeutics Announces Eteplirsen Demonstrates Continued Stability on Walking Test through 120 Weeks in Phase Iib Study in Duchenne Muscular Dystrophy," press release, 3 pages, dated Jan. 15, 2014 (Exhibit No. 2034 filed in interferences 106008, 106013, 106007 on Nov. 18, 2014).
Sarepta, "Sarepta Therapeutics Reports Long-Term Outcomes through 144 Weeks from Phase IIb Study of Eteplirsen in Duchenne Muscular Dystrophy," press release, http://investorrelations.sarepta.com/phoenix.zhtml?c=64231&p=irol-newsArticle&id=1946426, 4 pages, dated Jul. 10, 2014.
Scully, Michele et al., "Review of Phase II and Phase III Clinical Trials for Duchenne Muscular Dystrophy", Expert Opinion on Orphan Drugs, vol. 1(1):33-46 (2013).
Second Preliminary Amendment filed in U.S. Appl. No. 13/550,210, 5 pages, dated Jan. 3, 2013 (Exhibit No. 2062 filed in interferences 106008, 106013, 106007 on Nov. 18, 2014).
Second Written Opinion for Application No. PCT/AU2010/001520, 7 pages, dated Oct. 13, 2011.
Semi Quantitative Lab-on-Chip Analysis of Second PCR Product, pp. 1, Exhibit No. 1183 filed in Interferences 106,007 and 106,008 on Feb. 16, 2015.
Sequence Listing—U.S. Appl. No. 13/550,210, filed Jul. 16, 2012 (9 pages), Exhibit No. 1205 filed in Interferences 106,007 and 106,008 on Feb. 17, 2015.

(56) References Cited

OTHER PUBLICATIONS

Sequence of Exon 46 of Dystrophin Gene, 1 page.
Sequence of Exon 51 of Dystrophin Gene, 1 page.
Shabanpoor et al., "Bi-specific splice-switching PMO oligonucleotides conjugated via a single peptide active in a mouse model of Duchenne muscular dystrophy," Nucleic Acids Res., pp. 1-11 (Dec. 2014), Exhibit No. 1114 filed interferences 106,007, and 106,008 on Feb. 17, 2015.
Shapiro, Marvin B. et al., "RNA splice junctions of different classes of eukaryotes: sequence statistics and functional implications in gene expression," Nucleic Acids Research, vol. 15(17):7155-7174 (1987).
Sherratt, Tim G. et al., "Exon Skipping and Translation in Patients with Frameshift Deletions in the Dystrophin Gene," Am. J. Hum. Genet., vol. 53:1007-1015 (1993).
Shiga, Nobuyuki et al., "Disruption of the Splicing Enhancer Sequence within Exon 27 of the Dystrophin Gene by a Nonsense Mutation Induced Partial Skipping of the Exon and Is Responsible for Becker Muscular Dystrophy," J. Clin. Invest., vol. 100(9):2204-2210 (1997).
Shimizu, Miho et al., "Oligo(2'-O-methyl)ribonucleotides Effective probes for duplex DNA," FEBS Letters, vol. 302 (2):155-158 (1992) (Exhibit No. 1035 filed in interferences 106008, 106007 on Nov. 18, 2014).
*Siemens Healthcare Diagnostics, Inc.* v. *Enzo Life Sciences, Inc.*, 2013 WL 4411227, *11 [Parallel cite: U.S.D.C., D. Mass., Civil No. 10-40124-FDS], Decided Aug. 14, 2013 (12 pages); [Cited as: 2013 WL 4411227], Exhibit No. 1210 filed in Interferences 106,007 and 106,008 on Feb. 17, 2015.
Sierakowska, Halina et al., "Repair of thalassemic human beta-globin mRNA in mammalian cells by antisense oligonucleotides," Proc. Natl. Acad. Sci. USA, vol. 93:12840-12844 (1996).
U.S. Pat. No. 8,637,483 (Wilton et al.), pp. 157, Exhibit No. 1097 filed in interferences 106,007 and 106,008 on Feb. 13, 2015.
U.S. Pat. No. 8,697,858 (Iversen), pp. 95, Exhibit No. 1098 filed in interferences 106,007 and 106,008 on Feb. 13, 2015.
U.S. Pat. No. 8,703,735 (Iversen et al.) pp. 73, Exhibit No. 1099 filed in interferences 106,007 and 106,008 on Feb. 13, 2015.
U.S. Pat. No. 8,741,863 (Moulton et al.), pp. 68, Exhibit No. 1100 filed in interferences 106,007 and 106,008 on Feb. 13, 2015.
U.S. Pat. No. 8,759,307 (Stein et al.), pp. 35, Exhibit No. 1101 filed in interferences 106,007 and 106,008 on Feb. 13, 2015.
U.S. Pat. No. 8,779,128 (Hanson et al.), pp. 104, Exhibit No. 1102 filed in interferences 106,007 and 106,008 on Feb. 13, 2015.
U.S. Pat. No. 8,785,407 (Stein et al.), pp. 35, Exhibit No. 1103 filed in interferences 106,007 and 106,008 on Feb. 13, 2015.
U.S. Pat. No. 8,785,410 (Iversen et al.), pp. 20, Exhibit No. 1104 filed in interferences 106,007 and 106,008 on Feb. 13, 2015.
U.S. Pat. No. 8,835,402 (Kole et al.), pp. 27, Exhibit No. 1105 filed in interferences 106,007 and 106,008 on Feb. 13, 2015.
U.S. Pat. No. 8,865,883 (Sazani et al.), pp. 199, Exhibit No. 1106 filed in interferences 106,007 and 106,008 on Feb. 13, 2015.
U.S. Pat. No. 8,871,918 (Sazani et al.), pp. 195, Exhibit No. 1107 filed in interferences 106,007 and 106,008 on Feb. 13, 2015.
U.S. Pat. No. 8,877,725 (Iversen et al.), pp. 34, Exhibit No. 1108 filed in interferences 106,007 and 106,008 on Feb. 13, 2015.
U.S. Pat. No. 8,895,722 (Iversen et al.), pp. 29, Exhibit No. 1109 filed in interferences 106,007 and 106,008 on Feb. 13, 2015.
U.S. Pat. No. 8,906,872 (Iversen et al.), pp. 69, Exhibit No. 1110 filed in interferences 106,007 and 106,008 on Feb. 13, 2015.
US Abandonment for U.S. Appl. No. 13/902,376, 1 page, dated Jun. 12, 2014 (Exhibit No. 1047 filed in interferences 106008, 106007 on Nov. 18, 2014).
US Amendment After Non-Final Action for U.S. Appl. No. 11/233,495, 31 pages, dated Jun. 24, 2010 (Exhibit No. 2073 filed in interferences 106008, 106013, 106007 on Nov. 18, 2014).
US Amendment for U.S. Appl. No. 11/233,495, 15 pages, dated Apr. 1, 2009 (Exhibit No. 2071 filed in interferences 106008, 106013, 106007 on Nov. 18, 2014).
US Amendment for U.S. Appl. No. 11/233,495, 19 pages, dated Sep. 16, 2009 (Exhibit No. 2072 filed in interferences 106008, 106013, 106007 on Nov. 18, 2014).
US Amendment for U.S. Appl. No. 11/233,495, 9 pages, dated Oct. 31, 2007 (Exhibit No. 2070 filed in interferences 106008, 106013, 106007 on Nov. 18, 2014).
US Amendment for U.S. Appl. No. 11/570,691, 9 pages, dated Jun. 15, 2010 (Exhibit No. 1043 filed in interferences 106008, 106007 on Nov. 18, 2014).
US Amendment for U.S. Appl. No. 13/271,080, 30 pages, dated Jan. 30, 2013 (Exhibit No. 1049 filed in interferences 106008, 106007 on Nov. 18, 2014).
US Amendment for U.S. Appl. No. 13/902,376, 36 pages, dated Mar. 21, 2014 (Exhibit No. 1046 filed in interferences 106008, 106007 on Nov. 18, 2014).
US Amendment in Response to Advisory Action for U.S. Appl. No. 11/233,495, 23 pages, dated Mar. 14, 2011 (Exhibit No. 2074 filed in interferences 106008, 106013, 106007 on Nov. 18, 2014).
US Amendments to the Claims for U.S. Appl. No. 11/233,495, 4 pages, dated May 8, 2014 (Exhibit No. 2077 filed in interferences 106008, 106013, 106007 on Nov. 18, 2014).
US Amendments to the Claims for U.S. Appl. No. 14/198,992, 3 pages, dated Jul. 16, 2014 (Exhibit No. 2079 filed in interferences 106008, 106013, 106007 on Nov. 18, 2014).
US Applicant-Initiated Interview Summary and Notice of Allowance for U.S. Appl. No. 13/550,210, 9 pages dated May 19, 2014 (Exhibit No. 2076 filed in interferences 106008, 106013, 106007 on Nov. 18, 2014).
US application as-filed and Preliminary Amendment for U.S. Appl. No. 13/550,210, 59 pages dated Jul. 16, 2012 (Exhibit No. 2087 filed in interferences 106008, 106013, 106007 on Nov. 18, 2014).
US Application as-filed for U.S. Appl. No. 14/198,992, 52 pages, dated Mar. 6, 2014 (Exhibit No. 2086 filed in interferences 106008, 106013, 106007 on Nov. 18, 2014).
US Application as-filed, Application Data Sheet, and Preliminary Amendment for U.S. Appl. No. 12/837,359, 101 pages, dated Jul. 15, 2010 (Exhibit No. 2100 filed in interferences 106008, 106013, 106007 on Nov. 18, 2014).
US Application for Letters Patent for U.S. Appl. No. 11/233,495 as-filed and preliminary amendment, 77 pages, dated Sep. 21, 2005 (Exhibit No. 2095 filed in interferences 106008, 106013, 106007 on Nov. 18, 2014).
U.S. Appl. No. 11/233,495, 74 pages; excerpts of prosecution history including: US Supplemental Amendment and Response dated May 8, 2014; Second Supplemental Response dated Jul. 25, 2013; Supplemental Amendment dated Jun. 26, 2013; Amendment after Non-final Action dated Nov. 1, 2010; Amendment under 35 USC 1.114 dated Sep. 16, 2009 (Exhibit No. 2054 filed in interferences 106008, 106013, 106007 on Nov. 18, 2014).
U.S. Appl. No. 14/198,992, 17 pages; excerpts of prosecution history including: Supplemental Amendment dated Jul. 16, 2014; Response to Non-Final Office Action dated Jul. 14, 2014 (Exhibit No. 2056 filed in interferences 106008, 106013, 106007 on Nov. 18, 2014).
U.S. Appl. No. 14/248,279, 29 pages; excerpts of prosecution history including: Amendment under 37 CFR 1.312 dated Sep. 19, 2014; Amendment in Response to Final Office Action dated Aug. 7, 2014; Declaration under 37 CFR 1.132 dated May 26, 2014; Declaration under 37 CFR 1.132 dated May 27, 2014; Response dated Jun. 3, 2014 (Exhibit No. 2057 filed in interferences 106008, 106013, 106007 on Nov. 18, 2014).
U.S. Appl. No. 13/550,210, 27 pages; excerpts of prosecution history including: Response and Amendment dated May 12, 2014; Response to Non-Final Office Action dated Jan. 21, 2014; Second Preliminary Amendment dated Jan. 3, 2013 (Exhibit No. 2055 filed in interferences 106008, 106013, 106007 on Nov. 18, 2014).
US claim amendments for U.S. Appl. No. 13/550,210, 3 pages, dated May 12, 2014 (Exhibit No. 2078 filed in interferences 106008, 106013, 106007 on Nov. 18, 2014).
US Claims for U.S. Appl. No. 12/976,381, 1 page, dated Dec. 22, 2010 (Exhibit No. 2065 filed in interferences 106008, 106013, 106007 on Nov. 18, 2014).

(56) References Cited

OTHER PUBLICATIONS

US Declaration of Richard K. Bestwick, for U.S. Appl. No. 11/570,691, 5 pages, dated Jun. 15, 2010 (Exhibit No. 1044 filed in interferences 106008, 106007 on Nov. 18, 2014).
US E-mail from Patent Trial and Appeal Board to Danny Huntington, 2 pages, dated Oct. 9, 2014 (Exhibit No. 2002 filed in interferences 106008 on Oct. 17, 2014).
US Non-Final Office Action for U.S. Appl. No. 11/570,691, 16 pages, dated Mar. 15, 2010 (Exhibit No. 1042 filed in interferences 106008, 106007 on Nov. 18, 2014).
US Office Action for U.S. Appl. No. 13/271,080, 25 pages, dated Jul. 30, 2012 (Exhibit No. 1048 filed in interferences 106008, 106007 on Nov. 18, 2014).
US Office Action for U.S. Appl. No. 13/550,210, 12 pages, dated Sep. 27, 2013 (Exhibit No. 2080 filed in interferences 106008, 106013, 106007 on Nov. 18, 2014).
US Office Action for U.S. Appl. No. 13/902,376, 7 pages, dated Jan. 7, 2014 (Exhibit No. 1045 filed in interferences 106008, 106007 on Nov. 18, 2014).
U.S. Appl. No. 12/198,007, as-filed, 64 pages, dated Aug. 25, 2008 (Exhibit No. 2092 filed in interferences 106008, 106013, and 106007 on Nov. 18, 2014).
US Preliminary Amendment and application as-filed for U.S. Appl. No. 12/976,381,64 pages, dated Dec. 22, 2010 (Exhibit No. 2089 filed in Interferences 106007, 106008, and 106013 on Nov. 18, 2014).
US Preliminary Amendment for U.S. Appl. No. 11/233,495, 10 pages, dated Sep. 21, 2005 (Exhibit No. 2069 filed in interferences 106008, 106013, 106007 on Nov. 18, 2014).
US Preliminary Remarks for U.S. Appl. No. 14/198,992, 1 page, dated Mar. 6, 2014 (Exhibit No. 2097 filed in interferences 106008, 106013, 106007 on Nov. 18, 2014).
US Proposed Terminal Disclaimer for U.S. Appl. No. 12/860,078, 2 pages, dated Oct. 17, 2014 (Exhibit No. 2001 filed in interference 106008 on Oct. 17, 2014).
US Remarks for U.S. Appl. No. 14/248,279, 2 pages, dated Aug. 27, 2014 (Exhibit No. 2110 filed in interferences 106008, 106013, 106007 on Nov. 18, 2014).
US Response and amendments for U.S. Appl. No. 13/550,210, 12 pages, dated Jan. 21, 2014 (Exhibit No. 2063 filed in interferences 106008, 106013, 106007 on Nov. 18, 2014).
US Revised Figure 4H, U.S. Appl. No. 13/271,080, 1 page (Exhibit No. 1050 filed in interferences 106008, 106007 on Nov. 18, 2014).
*University of Western Australia v. Academisch Ziekenhuis Leiden*, University of Western Australia Reply 4 (To Exclude Evidence), filed in Patent Interference No. 106,007, May 12, 2015, pp. 1-13 (Doc 467).
*University of Western Australia v. Academisch Ziekenhuis Leiden*, University of Western Australia Reply 4 (To Exclude Evidence), filed in Patent Interference No. 106,008, May 12, 2015, pp. 1-13 (Doc 475).
*University of Western Australia v. Academisch Ziekenhuis Leiden*, University of Western Australia Request for Oral Argument, filed in Patent Interference No. 106,007, Apr. 10, 2015, pp. 1-4 (Doc 457).
*University of Western Australia v. Academisch Ziekenhuis Leiden*, University of Western Australia Request for Oral Argument, filed in Patent Interference No. 106,008, Apr. 10, 2015, pp. 1-4 (Doc 465).
*University of Western Australia v. Academisch Ziekenhuis Leiden*, University of Western Australia Request for Oral Argument, filed in Patent Interference No. 106,013, Apr. 10, 2015, pp. 1-3 (Doc 190).
*University of Western Australia Academisch Ziekenhuis Leiden*, University of Western Australia Revised Designation of Lead and Backup Counsel, 4 pages, Patent Interference No. 106,007, (Doc 415), dated Mar. 10, 2015.
*University of Western Australia v. Academisch Ziekenhuis Leiden*, University of Western Australia Revised Designation of Lead and Backup Counsel, 4 pages, Patent Interference No. 106,013, (Doc 150 ), dated Mar. 10, 2015.
*University of Western Australia v. Academisch Ziekenhuis Leiden*, University of Western Australia Revised Designation of Lead and Backup Counsel, 5 pages, Patent Interference No. 106,008, (Doc 423 ), dated Mar. 10, 2015.
*University of Western Australia v. Academisch Ziekenhuis Leiden*, University of Western Australia, Exhibit List as of Feb. 17, 2015, 8 pages, Patent Interference No. 106,007, (Doc No. 398) dated Feb. 17, 2015.
*University of Western Australia v. Academisch Ziekenhuis Leiden*, University of Western Australia, Exhibit List as of Feb. 17, 2015, 8 pages, Patent Interference No. 106,008, (Doc No. 406) dated Feb. 17, 2015.
*University of Western Australia v. Academisch Ziekenhuis Leiden*, UWA Clean Involved Claims and Sequence, Patent Interference No. 106,007, 8 pages, dated Aug. 1, 2014 (Doc 12).
*University of Western Australia v. Academisch Ziekenhuis Leiden*, UWA Clean Involved Claims and Sequence, Patent Interference No. 106,013, 7 pages, dated Oct. 14, 2014 (Doc 7).
*University of Western Australia v. Academisch Ziekenhuis Leiden*, UWA Clean Involved Claims and Sequences, Patent Interference No. 106,008, 8 pages, dated Aug. 7, 2014 (Doc 12).
*University of Western Australia v. Academisch Ziekenhuis Leiden*, UWA Exhibit List as of Nov. 18, 2014, 7 pages, Patent Interference No. 106,008, dated Nov. 18, 2014 (Doc 216).
*University of Western Australia v. Academisch Ziekenhuis Leiden*, UWA Exhibit list, 7 pages, Patent Interference No. 106,007, dated Nov. 18, 2014 (Doc 213).
*University of Western Australia v. Academisch Ziekenhuis Leiden*, UWA Exhibit list, 7 pages, Patent Interference No. 106,013, dated Nov. 18, 2014 (Doc 134).
*University of Western Australia v. Academisch Ziekenhuis Leiden*, UWA Exhibit List, 7 pages, Patent Interference Nos. 106,008, dated Dec. 12, 2014 (Doc 221).
*University of Western Australia v. Academisch Ziekenhuis Leiden*, UWA Exhibit List, 8 pages, Patent Interference No. 106,007, dated Dec. 12, 2014 (Doc 217).
*University of Western Australia v. Academisch Ziekenhuis Leiden*, UWA List of Proposed Motions, Patent Interference No. 106,007, 7 pages, dated Sep. 10, 2014 (Doc 17).
*University of Western Australia v. Academisch Ziekenhuis Leiden*, UWA List of Proposed Motions, Patent Interference No. 106,008, 6 pages, dated Sep. 10, 2014 (Doc 16).
*University of Western Australia v. Academisch Ziekenhuis Leiden*, UWA Miscellaneous Motion 1 (for authorization to file terminal disclaimer), 5 pages, Patent Interference No. 106,008, dated Oct. 17, 2014 (Doc 22).
*University of Western Australia v. Academisch Ziekenhuis Leiden*, UWA Motion 1 (for Judgment Under 35 U.S.C., section 112(a)), 40 pages, Patent Interference No. 106,007, dated Nov. 18, 2014 (Doc 210).
*University of Western Australia v. Academisch Ziekenhuis Leiden*, UWA Motion 1 (For Judgment Under 35 § 112(a)) Patent Interference No. 106,008 (Doc 213), 38 Pages, on Nov. 18, 2014.
*University of Western Australia v. Academisch Ziekenhuis Leiden*, UWA Motion 1 (To Maintain Interference between UWA U.S. Pat. No. 8,486,907 and AZL U.S. Appl. No. 14/198,992), 45 pages, Patent Interference No. 106,013, dated Nov. 18, 2014 (Doc 133).
*University of Western Australia v. Academisch Ziekenhuis Leiden*, UWA Motion 2 (For Judgment Under 35 U.S.C. section 112(b)), 32 pages, Patent Interference No. 106,008, dated Nov. 18, 2014 (Doc 214).
*University of Western Australia v. Academisch Ziekenhuis Leiden*, UWA Motion 2 (For Judgment Under 35 U.S.C. section 112(b)), 34 pages, Patent Interference No. 106,007, dated Nov. 18, 2014 (Doc 211).
*University of Western Australia v. Academisch Ziekenhuis Leiden*, UWA Motion 3 (For judgment that Claims 11-12, 14-15, and 17-29 of U.S. Appl. No. 13/550,210 are barred under 35 U.S.C. section 135(b)), 25 Pages, Patent Interference No. 106,008, dated Nov. 18, 2014 (Doc 215).
*University of Western Australia v. Academisch Ziekenhuis Leiden*, UWA Motion 3 Requesting an additional Interference between UWA

(56) References Cited

OTHER PUBLICATIONS

U.S. Pat. No. 8,455,636 and AZL U.S. Appl. No. 14/248,279, 36 pages, Patent Interference No. 106,007, dated Nov. 18, 2014 (Doc 212).
*University of Western Australia v. Academisch Ziekenhuis Leiden*, UWA Notice of Filing Priority Statement, 2 pages, Patent Interference No. 106,007, dated Nov. 18, 2014 (Doc 215).
*University of Western Australia v. Academisch Ziekenhuis Leiden*, UWA Notice of Filing Priority Statement, 2 pages, Patent Interference No. 106,008, dated Nov. 18, 2014 (Doc 218).
*University of Western Australia v. Academisch Ziekenhuis Leiden*, UWA Notice of Recent Authority, filed in Patent Interference No. 106,007, Jul. 2, 2015, pp. 1-16 (Doc 469).
*University of Western Australia v. Academisch Ziekenhuis Leiden*, UWA Notice of Recent Authority, filed in Patent Interference No. 106,007, Sep. 2, 2015, pp. 1-18 (Doc 470).
*University of Western Australia v. Academisch Ziekenhuis Leiden*, UWA Notice of Recent Authority, filed in Patent Interference No. 106,008, Jul. 2, 2015, pp. 1-16 (Doc 477).
*University of Western Australia v. Academisch Ziekenhuis Leiden*, UWA Notice of Recent Authority, filed in Patent Interference No. 106,008, Sep. 2, 2015, pp. 1-18 (Doc 478).
*University of Western Australia v. Academisch Ziekenhuis Leiden*, UWA Notice of Related Proceedings, Patent Interference No. 106,007, 3 pages, dated Aug. 1, 2014 (Doc 11).
*University of Western Australia v. Academisch Ziekenhuis Leiden*, UWA Notice of Related Proceedings, Patent Interference No. 106,008, 5 pages, dated Aug. 7, 2014 (Doc 11).
*University of Western Australia v. Academisch Ziekenhuis Leiden*, UWA Notice of Related Proceedings, Patent Interference No. 106,013, 3 pages, dated Oct. 14, 2014 (Doc 6).
U.S. Pat. No. 7,960,541 (Wilton et al.), pp. 84, Exhibit No. 1002 filed in interferences 106,007 and 106,008 on Nov. 18, 2014.
U.S. Pat. No. 8,450,474 (Wilton et al.), pp. 95, Exhibit No. 1087 filed in interferences 106,007 and 106,008 on Feb. 13, 2015.
U.S. Pat. No. 8,455,634 (Wilton et al.) pp. 96, Exhibit No. 1088 filed in interferences 106,007 and 106,008 on Feb. 13, 2015.
U.S. Pat. No. 8,455,635 (Wilton et al.), pp. 96, Exhibit No. 1089 filed in interferences 106,007 and 106,008 on Feb. 13, 2015.
U.S. Pat. No. 8,455,636 (Wilton et al.), pp. 92, Exhibit No. 1003 filed in interferences 106,007 and 106,008 on Nov. 18, 2014.
U.S. Pat. No. 8,476,423 (Wilton et al.), pp. 95, Exhibit No. 1111 filed in interferences 106,007 and 106,008 on Feb. 13, 2015.
U.S. Pat. No. 8,501,703 (Bennett et al.), pp. 16, Exhibit No. 1090 filed in interferences 106,007 and 106,008 on Feb. 13, 2015.
U.S. Pat. No. 8,501,704 (Mourich et al.), pp. 39, Exhibit No. 1091 filed in interferences 106,007 and 106,008 on Feb. 13, 2015.
U.S. Pat. No. 8,524,676 (Stein et al.), pp. 28, Exhibit No. 1092 filed in interferences 106,007 and 106,008 on Feb. 13, 2015.
U.S. Pat. No. 8,524,880 (Wilton et al.), pp. 89, Exhibit No. 1093 filed in interferences 106,007 and 106,008 on Feb. 13, 2015.
U.S. Pat. No. 8,536,147 (Weller et al.), pp. 95, Exhibit No. 1094 filed in interferences 106,007 and 106,008 on Feb. 17, 2015.
U.S. Pat. No. 8,592,386 (Mourich et al.), pp. 46, Exhibit No. 1095 filed in interferences 106,007 and 106,008 on Feb. 13, 2015.
U.S. Pat. No. 8,618,270 (Iversen et al.), pp. 28, Exhibit No. 1096 filed in interferences 106,007 and 106,008 on Feb. 13, 2015.
*University of Western Australia v. Academisch Ziekenhuis Leiden*, Clean Claims and Sequences, 5 pages, dated Aug. 5, 2014, Interference No. 106,008, (Exhibit No. 2047 filed in interferences 106,008, 106,013, 106,007 on Nov. 18, 2014).
*University of Western Australia v. Academisch Ziekenhuis Leiden*, Clean Claims and Sequences, 5 pages, dated Jul. 31, 2014, Interference No. 106,007, (Exhibit No. 2045 filed in interferences 106,008, 106,013, 106,007 on Nov. 18, 2014).
*University of Western Australia v. Academisch Ziekenhuis Leiden*, Clean Claims and Sequences, 5 pages, dated Oct. 15, 2014., Interference No. 106,013, (Exhibit No. 2050 filed in interferences 106,008, 106,013, 106,007 on Nov. 18, 2014).

*University of Western Australia v. Academisch Ziekenhuis Leiden*, Decision—Motions—37 CFR§ 41.125(a), filed in Patent Interference No. 106,013, Jun. 22, 2015, pp. 1-12 (Doc 192).
*University of Western Australia v. Academisch Ziekenhuis Leiden*, Declaration of Erik Sontheimer dated Nov. 17, 2014, Exhibit 1012 filed in Patent Interference Nos. 106,007 and 106,008, 112 pages, filed Nov. 18, 2014.
*University of Western Australia v. Academisch Ziekenhuis Leiden*, Declaration of Interference, Patent Interference No. 106,007, 7 pages, dated Jul. 18, 2014 (Doc 1).
*University of Western Australia v. Academisch Ziekenhuis Leiden*, Declaration of Interference, Patent Interference No. 106,008, 7 pages, dated Jul. 24, 2014 (Doc 1).
*University of Western Australia v. Academisch Ziekenhuis Leiden*, Declaration of Interference, Patent Interference No. 106,013, 8 pages, dated Sep. 29, 2014 (Doc 1).
*University of Western Australia v. Academisch Ziekenhuis Leiden*, Declaration of Matthew J.A. Wood, Patent Interference Nos. 106,007, 106,008 and 106,013, 184 pages, dated Nov. 18, 2014 (Exhibit No. 2081 filed in interferences 106008, 106013, 106007 on Nov. 18, 2014).
*University of Western Australia v. Academisch Ziekenhuis Leiden*, Joint Stipulation regarding Time Periods 2, 3 and 4, 3 pages, Patent Interference No. 106,013, (Doc 135), dated Nov. 25, 2015.
*University of Western Australia v. Academisch Ziekenhuis Leiden*, Joint Stipulation regarding Time Periods 3-4, 4 pages, Patent Interference No. 106,007, (Doc 243), dated Jan. 29, 2015.
*University of Western Australiav. Academisch Ziekenhuis Leiden*, Joint Stipulation regarding Time Periods 3-4, 4 pages, Patent Interference No. 106,008, (Doc 247), dated Jan. 29, 2015.
*University of Western Australia v. Academisch Ziekenhuis Leiden*, Joint Stipulation regarding Time Periods 3-4, 4 pages, Patent Interference No. 106,013, (Doc 137), dated Jan. 29, 2015.
*University of Western Australia v. Academisch Ziekenhuis Leiden*, Joint Stipulation Regarding Time Periods 4-6, 4 pages, Patent Interference No. 106,007, dated Mar. 19, 2015 (Doc 416).
*University of Western Australia v. Academisch Ziekenhuis Leiden*, Joint Stipulation Regarding Time Periods 4-6, 4 pages, Patent Interference No. 106013, (Doc 151), dated Mar. 19, 2015.
*University of Western Australia v. Academisch Ziekenhuis Leiden*, Joint Stipulation Regarding Time Periods 4-6, 4 pages, Patent Interference No. 106,008, (Doc 424 ), dated Mar. 19, 2015.
*University of Western Australia v. Academisch Ziekenhuis Leiden*, Miscellaneous Order under 37 CFR 41.104(a), 4 pages, Patent Interference Nos. 106,007 and 106,008, dated Dec. 15, 2014.
*University of Western Australia v. Academisch Ziekenhuis Leiden*, Order—Authorizing Motions, Patent Interference No. 106,007, 3 pages, dated Sep. 26, 2014 (Doc 20).
*University of Western Australia v. Academisch Ziekenhuis Leiden*, Order—Authorizing Motions, Patent Interference No. 106,007, 6 pages, dated Sep. 23, 2014 (Doc 19).
*University of Western Australia v. Academisch Ziekenhuis Leiden*, Order—Authorizing Motions, Patent Interference No. 106,008, 6 pages, dated Sep. 23, 2014 (Doc 18).
*University of Western Australia v. Academisch Ziekenhuis Leiden*, Order—Miscellaneous 37 C.F.R. 41.104(a), 2 pages, Patent Interference Nos. 106,007, 106,008, 106,013, dated Nov. 14, 2014.
*University of Western Australia v. Academisch Ziekenhuis Leiden*, Order to Show Cause—37 C.F.R.§ 41.104(a), filed in Patent Interference No. 106,013, Jun. 22, 2015, pp. 1-3 (Doc 193).
*University of Western Australia v. Academisch Ziekenhuis Leiden*, Redeclaration, Patent Interference No. 106,008, 2 pages, dated Sep. 23, 2014 (Doc 19).
*University of Western Australia v. Academisch Ziekenhuis Leiden*, Second Declaration of Matthew J. A. Wood, M.D., D. Phil., Patent Interference Nos. 106,007 and 106,008, 78 pages, dated Feb. 17, 2015 (Exhibit No. 2116 filed in interferences 106,007 and 106,008,on Feb. 17, 2015.
*University of Western Australia v. Academisch Ziekenhuis Leiden*, Statement Concerning Initial Settlement Discussions, 3 pages, Patent Interference No. 106,013, (Doc 136), dated Dec. 30, 2014.

(56) References Cited

OTHER PUBLICATIONS

*University of Western Australia* v. *Academisch Ziekenhuis Leiden,* Statement Concerning Subsequent Settlement Discussions, 3 pages, Patent Interference No. 106,007, (Doc 242), dated Dec. 30, 2014.
*University of Western Australia* v. *Academisch Ziekenhuis Leiden,* Statement Concerning Subsequent Settlement Discussions, 3 pages, Patent Interference No. 106,008, (Doc 246), dated Dec. 30, 2014.
*University of Western Australia* v. *Academisch Ziekenhuis Leiden,* Statement Concerning Subsequent Settlement Discussions, iscussions, filed in Patent Interference No. 106,013, Aug. 24, 2015, pp. 1-3 (Doc 195).
*University of Western Australia* v. *Academisch Ziekenhuis Leiden,* University of Western Austalia Response to Order to Show Cause, filed in Patent Interference No. 106,013, Jul. 20, 2015, pp. 1-28 (Doc 194).
*University of Western Australia* v. *Academisch Ziekenhuis Leiden,* University of Western Australia Exhibit List as of Apr. 10, 2015, filed in Patent Interference No. 106,007, Apr. 10, 2015, pp. 1-10 (Doc 456).
*University of Western Australia* v. *Academisch Ziekenhuis Leiden,* University of Western Australia Exhibit List as of Apr. 10, 2015, filed in Patent Interference No. 106,008, Apr. 10, 2015, pp. 1-10 (Doc 464).
*University of Western Australia* v. *Academisch Ziekenhuis Leiden,* University of Western Australia Exhibit List as of Apr. 3, 2015, filed in Interference 106007, Apr. 3, 2015, pp. 1-10 (Doc 431).
*University of Western Australia* v. *Academisch Ziekenhuis Leiden,* University of Western Australia Exhibit List as of Apr. 3, 2015, filed in Interference 106008, Apr. 3, 2015, pp. 1-10 (Doc 439).
*University of Western Australia* v. *Academisch Ziekenhuis Leiden,* University of Western Australia Exhibit List as of Apr. 3, 2015, filed in Interference 106013, Apr. 3, 2015, pp. 1-10 (Doc 153).
*University of Western Australia* v. *Academisch Ziekenhuis Leiden,* University of Western Australia Miscellaneous Motion 4 (to exclude evidence), filed in Patent Interference No. 106,007, Apr. 10, 2015, pp. 1-21 (Doc 455).
*University of Western Australia* v. *Academisch Ziekenhuis Leiden,* University of Western Australia Miscellaneous Motion 4 (to exclude evidence), filed in Patent Interference No. 106,008, Apr. 10, 2015, pp. 1-21 (Doc 463).
*University of Western Australia* v. *Academisch Ziekenhuis Leiden,* University of Western Australia Opposition 1 (Regarding Patentability Under 35 U.S.C. § 102/103), 38 pages, Patent Interference No. 106,007, (Doc 393), dated Feb. 17, 2015.
*University of Western Australia* v. *Academisch Ziekenhuis Leiden,* University of Western Australia Opposition 1 (Regarding Patentability Under 35 U.S.C. § 102/103), 39 pages, Patent Interference No. 106,008, (Doc 402), dated Feb. 17, 2015.
*University of Western Australia* v. *Academisch Ziekenhuis Leiden,* University of Western Australia Opposition 2 (To Retain UWA's Benefit of AU 2004903474), 31 pages, Patent Interference No. 106,008, (Doc 403), dated Feb. 17, 2015.
*University of Western Australia* v. *Academisch Ziekenhuis Leiden,* University of Western Australia Opposition 2 (To Retain UWA's Benefit of AU 2004903474), 37 pages, Patent Interference No. 106,007, (Doc 394), dated Feb. 17, 2015.
*University of Western Australia* v. *Academisch Ziekenhuis Leiden,* University of Western Australia Opposition 3 (Regarding Patentability Under 35 U.S.C. § 101), 22 pages, Patent Interference No. 106,007, (Doc 395), dated Feb. 17, 2015.
*University of Western Australia* v. *Academisch Ziekenhuis Leiden,* University of Western Australia Opposition 4 (To deny entry of AZL's Proposed New Claims 104 and 105), 36 pages, Patent Interference No. 106,007, (Doc 397), dated Feb. 17, 2015.
*University of Western Australia* v. *Academisch Ziekenhuis Leiden,* University of Western Australia Opposition 4 (To deny entry of AZL's Proposed New Claims 30 and 31), 36 pages, Patent Interference No. 106,008, (Doc 405), dated Feb. 17, 2015.
*University of Western Australia* v. *Academisch Ziekenhuis Leiden,* University of Western Australia Reply 1 (to AZL Opposition 1), filed Apr. 3, 2015 in interference 106007, pp. 1-28 (Doc 428).
*University of Western Australia* v. *Academisch Ziekenhuis Leiden,* University of Western Australia Reply 1 (to AZL Opposition 1), filed Apr. 3, 2015 in Interference 106008, pp. 1-28 (Doc 436).
*University of Western Australia* v. *Academisch Ziekenhuis Leiden,* University of Western Australia Reply 1 (to Maintain the Interference) filed Apr. 3, 2015 in Interference 106013, pp. 1-17 (Doc 152).
*University of Western Australia* v. *Academisch Ziekenhuis Leiden,* University of Western Australia Reply 2 (to AZL1 Opposition 2) filed Apr. 3, 2015 in Interference 106007, pp. 1-22 (Doc 429).
*University of Western Australia* v. *Academisch Ziekenhuis Leiden,* University of Western Australia Reply 2 (to AZL Opposition 2) filed Apr. 3, 2015 in Interference 106008, pp. 1-22 (Doc 437).
*University of Western Australia* v. *Academisch Ziekenhuis Leiden,* University of Western Australia Reply 3 (for Judgment under 35 U.S.C. §135(b)) filed Apr. 3, 2015 in Interference 106008, pp. 1-19 (Doc 438).
*University of Western Australia* v. *Academisch Ziekenhuis Leiden,* University of Western Australia Reply 3 (to Institute an Interference) filed Apr. 3, 2015 in Interference 106007, pp. 1-17 (Doc 430).
Sontheimer et al., "Metal ion catalysis during group II intron self-splicing: parallels with the spliceosome," Genes & Development, vol. 13, pp. 1729-1741 (1999), Exhibit No. 1195 filed in Interferences 106,007 and 106,008 on Feb. 17, 2015.
Sontheimer et al., "Three Novel Functional Variants of Human U5 Small Nuclear RNA," vol. 12, No. 2, pp. 734-746 (Feb. 1992), Exhibit No. 1194 filed in Interferences 106,007 and 106,008 on Feb. 17, 2015.
Sontheimer, Erik J. et al., "Metal ion catalysis during splicing of premessenger RNA" Nature, vol. 388:801-805 (1997) (Exhibit No. 1036 filed in interferences 106008, 106007 on Nov. 18, 2014).
Sontheimer, Erik J. et al., "The U5 and U6 Small Nuclear RNAs as Active Site Components of the Spliceosome," Science, vol. 262:1989-1997 (1993) (Exhibit No. 1058 filed in interferences 106008, 106007 on Nov. 18, 2014).
Standard Operating Procedure FPLC Desalting, pp. 6, Exhibit No. 1144 filed in Interferences 106,007 and 106,008 on Feb. 16, 2015.
Stanton, Robert et al., "Chemical Modification Study of Antisense Gapmers", Nucleic Acid Therapeutics, vol. 22(5): 344-359 (2012).
Statement on a Nonproprietary Name Adopted by the USAN Council, ETEPLIRSEN, Chemical Structure, 2010, pp. 1-5.
Stein, CA, "Delivery of antisense oligonucleotides to cells: a consideration of some of the barriers," Monographic supplement series: Oligos & Peptides—Chimica Oggi—Chemistry Today, vol. 32(2):4-7 (2014) (Exhibit No. 2022 filed in interferences 106008, 106013, 106007 on Nov. 18, 2014).
Stein, Cy A. et al., "Therapeutic Oligonucleotides: The Road Not Taken," Clin. Cancer Res., vol. 17(20):6369-6372 (2011) (Exhibit No. 2026 filed in interferences 106008, 106013, 106007 on Nov. 18, 2014).
Stein, David et al., "A Specificity Comparison of Four Antisense Types: Morpholino, 2'-O-Methyl RNA, DNA, and PHosphorothioate DNA," Antisense & Nucleic Acid Drug Development, vol. 7:151-157 (1997).
Strober JB, "Therapeutics in Duchenne muscular dystrophy," NeuroRX 2006; 3:225-34.
Summary of Professional Experience (Dr. Erik J. Sontheimer), pp. 4, Exhibit No. 1223 filed in Interferences 106,007 and 106,008 on Feb. 17, 2015.
Summerton, James et al., "Morpholino and Phosphorothioate Antisense Oligomers Compared in Cell-Free and In-Cell Systems," Antisense & Nucleic Acid Drug Development, vol. 7:63-70 (1997).
Summerton, James et al., "Morpholino Antisense Oligomers: Design, Preparation, and Properties," Antisense & Nucleic Acid Drug Development, vol. 7:187-195 (1997).
Summerton, James, "Morpholino antisense oligomers: the case for an Rnase H-independent structural type," Biochimica et Biophysica Acta, vol. 1489:141-158 (1999) (Exhibit No. 1038 filed in interferences 106008, 106013, 106007 on Nov. 18, 2014).
Supplementary European Search Report for Application No. 10829367.1, 8 pages, dated May 22, 2013.

(56) References Cited

OTHER PUBLICATIONS

Suter et al., "Double-target antisense U7 snRNAs promote efficient skipping of an aberrant exon in three human Beta-thalassemic mutations," 8:13 Human Molecular Genetics 2415-2423 (1999) (Exhibit No. 1083 filed in interferences 106008, 106007 on Dec. 23, 2014).
T Hoen, Peter A.C. et al., "Generation and Characterization of Transgenic Mice with the Full-length Human DMD Gene," The Journal of Biological Chemistry, vol. 283(9):5899-5907 (2008) Exhibit No. 2030 filed in interferences 106008, 106013, 106007 on Nov. 18, 2014).
Table 1: Primer and Product Details for Exon 51 and 53 Reports on AONs of 20 to 50 Nucleotides dd Jan. 7, 2015, pp. 1, Exhibit No. 1177 filed in Interferences 106,007 and 106,008 on Feb. 16, 2015.
Takeshima et al., "Oligonucleotides against a splicing enhancer sequence led to dystrophin production in muscle cells from a Duchenne muscular dystrophy patient," Brain & Dev., vol. 23, pp. 788-790 (2001), Exhibit No. 1196 filed in Interferences 106,007 and 106,008 on Feb. 17, 2015.
Takeshima, Yasuhiro et al., "Modulation of In Vitro Splicing of the Upstream Intron by Modifying an Intra-Exon Sequence Which Is Deleted from the Dystrophin Gene in Dystrophin Kobe," J. Clin. Invest., vol. 95:515-520 (1995).
Tanaka, Kenji et al., "Polypurine Sequences within a Downstream Exon Function as a Splicing Enhancer," Molecular and Cellular Biology, vol. 14(2):1347-1354 (1994).
Thanh, Le Thiet et al., "Characterization of Revertant Muscle Fibers in Duchenne Muscular Dystrophy, Using Exon-Specific Monoclonal Antibodies against Dystrophin," Am. J. Hum. Genet., vol. 56:725-731 (1995).
*The Regents of the University of California v. Dako North America, Inc.*, U.S.D.C., N.D. California, No. C05-03955 MHP, Apr. 22, 2009 (2009 WL 1083446 (N.D.Cal.), Exhibit No. 1206 filed in Interferences 106,007 and 106,008 on Feb. 17, 2015.
Tian, Xiaobing et al., "Imaging Oncogene Expression," Ann. N.Y. Acad. Sci., vol. 1002:165-188 (2003) (Exhibit No. 2029 filed in interferences 106008, 106013, 106007 on Nov. 18, 2014).
Transcript of 2nd Deposition of Erik J. Sontheimer, Ph.D., dated Mar. 12, 2015, (Academisch Ziekenhuis Leiden Exhibit 1231, filed Apr. 3, 2015 in Interference 106007 and 106008, pp. 1-185).
Transcript of 2nd Deposition of Matthew J.A. Wood, M.D., D. Phil, dated Mar. 5, 2015, (Academisch Ziekenhuis Leiden Exhibit 1230, filed Apr. 3, 2015 in Interference 106007 and 106008, pp. 1-117).
Transcript of Dec. 12, 2014 Teleconference with Administrative Patent Judge Schafer (rough draft) (previously filed in Int. No. 106,008 as Ex. 2114), pp. 28 Exhibit No. 1001 filed in Interference 106,013 on Feb. 17, 2015.
Transcript of the Jan. 21, 2015 deposition of Erik Sontheimer, Ph.D., Patent Interference Nos. 106,007 and 106,008, 98 pages, dated Jan. 21, 2015 (Exhibit No. 2122 filed in interferences 106,007 and 106,008 on Feb. 17, 2015.
Transcript of the Mar. 11, 2015 deposition of Judith van Deutekom, Ph.D., (University of Western Australia Exhibit 2141, filed Apr. 3, 2015 in Interferences 106007, 106008, and 106013, pp. 1-168).
Transcript of the Mar. 12, 2015 deposition of Erik J. Sontheimer, Ph.D., (University of Western Australia Exhibit 2142, filed Apr. 3, 2015 in Interferences 106007, 106008, and 106013, pp. 1-183).
Transcript of the Mar. 5, 2015 deposition of Matthew J. A. Wood, M.D., D. Phil., (University of Western Australia Exhibit 2146, filed Apr. 3, 2015 in Interferences 106007, 106008, and 106013, pp. 1-115).
Transfection of AON, pp. 1, Exhibit No. 1170 filed in Interferences 106,007 and 106,008 on Feb. 16, 2015.
U.S. Food and Drug Administration Statement, dated Dec. 30, 2014 (2 pages), Exhibit No. 1204 filed in Interferences 106,007 and 106,008 on Feb. 17, 2015.
U.S. Appl. No. 12/198,007, filed Aug. 25, 2008 ("the '007 Application") (Exhibit No. 1073 filed in interferences 106008, 106007 on Dec. 23, 2014).
U.S. Appl. No. 12/976,381, filed Dec. 22, 2010 ("the '381 Application") (Exhibit No. 1074 filed in interferences 106008, 106007 on Dec. 23, 2014).
U.S. Patent Application Publication No. 2001/0056077 ("Matsuo") 10 pages, (Exhibit No. 1080 filed in interferences 106008, 106007 on Dec. 23, 2014).
U.S. Patent Application Publication No. 2002/0049173 ("Bennett et al.") 50 pages, (Exhibit No. 1081 filed in interferences 106008, 106007 on Dec. 23, 2014).
U.S. Pat. No. 5,190,931 ("the '931 Patent") 22 pages,(Exhibit No. 1069 filed in interferences 106008, 106007 on Dec. 23, 2014).
U.S. Pat. No. 7,001,761 (the "Xiao" Patent) 64 pages, (Exhibit No. 1070 filed in interferences 106008, 106007 on Dec. 23, 2014).
University of Western Australia Objections to Opposition Evidence, served on Feb. 24, 2015 filed in Interference No. 106,007, Exhibit 2150, filed Apr. 10, 2015 in Interference Nos. 106007 and 106008, pp. 1-15.
University of Western Australia Objections to Opposition Evidence, served on Feb. 24, 2015, filed in Interference No. 106,008, Exhibit 2151, filed Apr. 10, 2015, in Interference Nos. 106007and 106008, pp. 1-15.
*University of Western Australia v. Academisch Ziekenhuis Leiden*, Academisch Ziekenhuis Leiden List of Exhibits (as of Apr. 3, 2015), filed in Patent Interference No. 106,007, Apr. 3, 2015, pp. 1-18, (Doc 423).
*University of Western Australia v. Academisch Ziekenhuis Leiden*, Academisch Ziekenhuis Leiden List of Exhibits (as of Apr. 3, 2015), filed in Patent Interference No. 106,008, Apr. 3, 2015, pp. 1-18 (Doc 435).
*University of Western Australia v. Academisch Ziekenhuis Leiden*, Academisch Ziekenhuis Leiden List of Exhibits, 18 pages, Patent Interference No. 106,007, (Doc 391), dated Feb. 17, 2015.
*University of Western Australia v. Academisch Ziekenhuis Leiden*, Academisch Ziekenhuis Leiden List of Exhibits, 18 pages, Patent Interference No. 106,008, (Doc 398), dated Feb. 17, 2015.
*University of Western Australia v. Academisch Ziekenhuis Leiden*, Academisch Ziekenhuis Leiden List of Exhibits, 3 pages, Patent Interference No. 106,013, (Doc 147), dated Feb. 17, 2015.
*University of Western Australia v. Academisch Ziekenhuis Leiden*, Academisch Ziekenhuis Leiden Notice of Service of Supplemental Evidence, 3 pages, Patent Interference No. 106,007 (Doc 414), dated Mar. 9, 2015.
*University of Western Australia v. Academisch Ziekenhuis Leiden*, Academisch Ziekenhuis Leiden Notice of Service of Supplemental Evidence, 3 pages, Patent Interference No. 106,008 (Doc 422), dated Mar. 9, 2015.
*University of Western Australia v. Academisch Ziekenhuis Leiden*, Academisch Ziekenhuis Leiden Opposition 1 (35 U. S.C. § 112(a)), 83 pages, Patent Interference No. 106,008, (Doc 400), dated Feb. 17, 2015.
Aartsma-Rus, Annemieke et al., "Guidelines for Antisense Oligonucleotide Design and Insight Into Splice-modulating Mechanisms," Molecular Therapy, vol. 17(3):548-553 (2009). Supplementary Table 1.
International Preliminary Report on Patentability, PCT/US2014/029689, dated Sep. 15, 2015, pp. 1-10.
International Preliminary Report on Patentability, PCT/US2014/029766, dated Sep. 15, 2015, pp. 1-10.
Popplewell, et al., Design of Phosphorodiamidate Morpholino Oligomers (PMOs) For the Induction of Exon Skipping of the Human DMD Gene, DSGT Poster, 2008, 1 page.
*University of Western Australia v. Academisch Ziekenhuis Leiden*, Decision—Priority 37 CFR § 41.125 (a), 2 pages, Patent Interference No. 106,013, (Doc 196), dated Sep. 29, 2015.
*University of Western Australia v. Academisch Ziekenhuis Leiden*, Judgment—37 CFR § 41.127, 2 pages, Patent Interference No. 106,013, (Doc 197), dated Sep. 29, 2015.
*Telios Pharms., Inc. v. Merck KgaA*, No. 96/1307, 1998 WL 35272018 (S.D. Cal. Nov. 18, 1998), 11 pages (Exhibit No. 2153 filed in interference 106013 on Oct. 29, 2015).

(56) References Cited

OTHER PUBLICATIONS

*University of Western Australia v. Academisch Ziekenhuis Leiden,* University of Western Australia Exhibit List As of Oct. 29, 2015, filed in Patent Interference No. 106,013, Oct. 29, 2015, pp. 1-10 (Doc 199).

*University of Western Australia v. Academisch Ziekenhuis Leiden,* University of Western Australia Request for Rehearing, filed in Patent Interference No. 106,013, Oct. 29, 2015, pp. 1-20 (Doc 198).

*Vikase Corp. v. Am. Nat'l. Can Co.,* No. 93/7651, 1996 WL 377054 (N.D. Ill. Jul. 1, 1996), 3 pages (Exhibit No. 2152 filed in interference 106013 on Oct. 29, 2015).

Exon 51S.3 (RD)
High-Purity Synthesis, 3.0uM, RD Cells

| Oligo | Name; SEQ ID NO | Lot |
|---|---|---|
| NG-07-1160 | AVI-5658; 588 | 09MY11-R(E4) |
| NG-09-0053 | 053; 324 | 09JNJ12-R(A4) |
| NG-09-0054 | 054; 326 | 09JNJ12-R(B4) |
| NG-09-0055 | 055; 327 | 09JNJ12-R(E4) |

| NG-09-0053 (SEQ ID NO:324) | NG-09-0054 (SEQ ID NO:326) | NG-09-0055 (SEQ ID NO:327) | NG-07-1160 (SEQ ID NO:588) |
|---|---|---|---|
| 4.65% ±1.89 | 7.40% ±0.75 | 9.89% ±1.37 | 5.26% ±0.66 |

*FIG. 2B*

Selected Dystrophin Exon 50 Oligos
DMD Gene 1756

| Compound | EC$_{50}$ (micromolar)* |
|---|---|
| AVI-5656 (SEQ ID NO:584) | 0.921 |
| AVI-5915 (SEQ ID NO:585) | 3.693 |
| NG-08-0731 (SEQ ID NO:277) | 1.741 |
| AVI-5038 (SEQ ID NO:287) | 0.966 |
| NG-08-0741 (SEQ ID NO:290) | 1.836 |
| NG-08-0742 (SEQ ID NO:291) | 2.402 |

*Determined from dose-ranging studies in RD cells
AVI #00453 - 02FEB2009

FIG. 3B

Exon53 RD Cell Dose-Range Summary

Percent Exon Skipped

| Treatment (uM) | 746 (SEQ ID NO:422) | 749 (SEQ ID NO:428) | 750 (SEQ ID NO:429) | 751 (SEQ ID NO:431) |
|---|---|---|---|---|
| 1.0 | 0.00 | 1.05 | 4.83 | 0.79 |
| 2.0 | 0.00 | 1.72 | 10.44 | 1.98 |
| 3.0 | 0.00 | 2.40 | 17.28 | 2.74 |
| 5.0 | 0.54 | 2.62 | 23.29 | 4.18 |
| 10 | 3.53 | 4.63 | 57.67 | 13.89 |
| $EC_{50}$ (uM) | NA | 72.2 | 9.3 | 25.3 |

FIG. 4G

Exon44 RD Cell Dose-Range Summary

Percent Exon Skipped

| Treatment (uM) | 792 (SEQ ID NO:4) | 796 (SEQ ID NO:8) | 799 (SEQ ID NO:11) | 800 (SEQ ID NO:12) | 801 (SEQ ID NO:13) |
|---|---|---|---|---|---|
| 0.1 | 3.14 | 4.14 | 3.00 | 7.49 | 2.10 |
| 0.3 | 4.66 | 6.69 | 8.41 | 16.01 | 4.06 |
| 1 | 7.56 | 17.41 | 21.48 | 18.81 | 9.01 |
| 3 | 21.64 | 39.74 | 32.92 | 46.71 | 22.50 |
| 10 | 64.94 | 97.39 | 88.47 | 96.52 | 69.38 |
| $EC_{50}$ (uM) | 7.166 | 3.024 | 3.594 | 2.795 | 6.277 |

*FIG. 5H*

Exon45 RD Cell Dose-Range Summary

Percent Exon Skipped

| Treatment (uM) | 770 (SEQ ID NO:27) | 771 (SEQ ID NO:29) | 774 (SEQ ID NO:34) | 777 (SEQ ID NO:39) | 782 (SEQ ID NO:49) |
|---|---|---|---|---|---|
| 1.0 | 0.00 | 0.53 | 3.05 | 0.00 | 0.00 |
| 2.0 | 0.43 | 1.99 | 13.33 | 0.00 | 0.00 |
| 3.0 | 0.60 | 4.91 | 31.12 | 0.55 | 0.00 |
| 5.0 | 1.15 | 14.25 | 79.20 | 1.63 | 0.78 |
| 10 | 4.17 | 84.37 | 97.68 | 7.86 | 2.11 |
| $EC_{50}$ (uM) | 54.37 | 7.25 | 3.69 | NA | NA |

*FIG. 6H*

SEQUENCE LISTING

<160> NUMBER OF SEQ ID NOS: 651

<210> SEQ ID NO 1
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 1
ctgcaggtaa aagcatatgg atcaa                                           25

<210> SEQ ID NO 2
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 2
atcgcctgca ggtaaaagca tatgg                                           25

<210> SEQ ID NO 3
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 3
gtcaaatcgc ctgcaggtaa aagca                                           25

<210> SEQ ID NO 4
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 4
gatctgtcaa atcgcctgca ggtaa                                           25

<210> SEQ ID NO 5
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 5
caacagatct gtcaaatcgc ctgca                                              25

<210> SEQ ID NO 6
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 6
tttctcaaca gatctgtcaa atcgc                                              25

<210> SEQ ID NO 7
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 7
ccatttctca acagatctgt caaat                                              25

<210> SEQ ID NO 8
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 8
ataatgaaaa cgccgccatt tctca                                              25

<210> SEQ ID NO 9
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 9
aaatatcttt atatcataat gaaaa                                              25

<210> SEQ ID NO 10
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 10
tgttagccac tgattaaata tcttt                                              25

<210> SEQ ID NO 11
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 11
aaactgttca gcttctgtta gccac                                              25

```
<210> SEQ ID NO 12
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 12
ttgtgtcttt ctgagaaact gttca                                           25

<210> SEQ ID NO 13
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 13
ccaattctca ggaatttgtg tcttt                                           25

<210> SEQ ID NO 14
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 14
gtatttagca tgttcccaat tctca                                           25

<210> SEQ ID NO 15
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 15
cttaagatac catttgtatt tagca                                           25

<210> SEQ ID NO 16
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 16
cttaccttaa gataccattt gtatt                                           25

<210> SEQ ID NO 17
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 17
aaagacttac cttaagatac cattt                                           25
```

<210> SEQ ID NO 18
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 18
aaatcaaaga cttaccttaa gatac                                              25

<210> SEQ ID NO 19
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 19
aaaacaaatc aaagacttac cttaa                                              25

<210> SEQ ID NO 20
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 20
tcgaaaaaac aaatcaaaga cttac                                              25

<210> SEQ ID NO 21
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 21
ctgtaagata ccaaaaaggc aaaac                                              25

<210> SEQ ID NO 22
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 22
cctgtaagat accaaaaagg caaaa                                              25

<210> SEQ ID NO 23
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 23
agttcctgta agataccaaa aaggc                                              25

```
<210> SEQ ID NO 24
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 24
gagttcctgt aagataccaa aaagg                                           25

<210> SEQ ID NO 25
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 25
cctggagttc ctgtaagata ccaaa                                           25

<210> SEQ ID NO 26
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 26
tcctggagtt cctgtaagat accaa                                           25

<210> SEQ ID NO 27
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 27
gccatcctgg agttcctgta agata                                           25

<210> SEQ ID NO 28
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 28
tgccatcctg gagttcctgt aagat                                           25

<210> SEQ ID NO 29
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 29
ccaatgccat cctggagttc ctgta                                           25

<210> SEQ ID NO 30
```

```
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 30
cccaatgcca tcctggagtt cctgt                                          25

<210> SEQ ID NO 31
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 31
gctgcccaat gccatcctgg agttc                                          25

<210> SEQ ID NO 32
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 32
cgctgcccaa tgccatcctg gagtt                                          25

<210> SEQ ID NO 33
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 33
aacagtttgc cgctgcccaa tgcca                                          25

<210> SEQ ID NO 34
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 34
ctgacaacag tttgccgctg cccaa                                          25

<210> SEQ ID NO 35
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 35
gttgcattca atgttctgac aacag                                          25

<210> SEQ ID NO 36
<211> LENGTH: 25
```

```
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 36
gctgaattat ttcttcccca gttgc                                         25

<210> SEQ ID NO 37
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 37
attatttctt ccccagttgc attca                                         25

<210> SEQ ID NO 38
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 38
ggcatctgtt tttgaggatt gctga                                         25

<210> SEQ ID NO 39
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 39
tttgaggatt gctgaattat ttctt                                         25

<210> SEQ ID NO 40
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 40
aatttttcct gtagaatact ggcat                                         25

<210> SEQ ID NO 41
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 41
atactggcat ctgttttga ggatt                                          25

<210> SEQ ID NO 42
<211> LENGTH: 25
<212> TYPE: DNA
```

```
<213> ORGANISM: Artificial Sequence
<220> FEATURE:
<223> OTHER INFORMATION: Antisense sequence to target splice site of
      proprocessed human dystrophin

<400> SEQUENCE: 42
accgcagatt caggcttccc aattt                                               25

<210> SEQ ID NO 43
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 43
aatttttcct gtagaatact ggcat                                               25

<210> SEQ ID NO 44
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 44
ctgtttgcag acctcctgcc accgc                                               25

<210> SEQ ID NO 45
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 45
agattcaggc ttcccaattt ttcct                                               25

<210> SEQ ID NO 46
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 46
ctcttttttc tgtctgacag ctgtt                                               25

<210> SEQ ID NO 47
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 47
acctcctgcc accgcagatt caggc                                               25

<210> SEQ ID NO 48
<211> LENGTH: 25
<212> TYPE: DNA
<213> ORGANISM: Artificial Sequence
```

```
<220> FEATURE:
<223> OTHER INFORMATION: Antisense sequence to target splice site of
      proprocessed human dystrophin

<400> SEQUENCE: 48
cctacctctt ttttctgtct gacag                                          25

<210> SEQ ID NO 49
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 49
gacagctgtt tgcagacctc ctgcc                                          25

<210> SEQ ID NO 50
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 50
gtcgccctac ctcttttttc tgtct                                          25

<210> SEQ ID NO 51
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 51
gatctgtcgc cctacctctt ttttc                                          25

<210> SEQ ID NO 52
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 52
tattagatct gtcgccctac ctctt                                          25

<210> SEQ ID NO 53
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 53
attcctatta gatctgtcgc cctac                                          25

<210> SEQ ID NO 54
<211> LENGTH: 20
<212> TYPE: DNA
<213> ORGANISM: Artificial Sequence
<220> FEATURE:
```

```
<223> OTHER INFORMATION: Antisense sequence to target splice site of
      proprocessed human dystrophin

<400> SEQUENCE: 54
agataccaaa aaggcaaaac                                                   20

<210> SEQ ID NO 55
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 55
aagataccaa aaaggcaaaa                                                   20

<210> SEQ ID NO 56
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 56
cctgtaagat accaaaaagg                                                   20

<210> SEQ ID NO 57
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 57
gagttcctgt aagataccaa                                                   20

<210> SEQ ID NO 58
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 58
tcctggagtt cctgtaagat                                                   20

<210> SEQ ID NO 59
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 59
tgccatcctg gagttcctgt                                                   20

<210> SEQ ID NO 60
<211> LENGTH: 20
<212> TYPE: DNA
<213> ORGANISM: Artificial Sequence
<220> FEATURE:
<223> OTHER INFORMATION: Antisense sequence to target splice site of
```

-continued proprocessed human dystrophin

<400> SEQUENCE: 60
cccaatgcca tcctggagtt                                                20

<210> SEQ ID NO 61
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 61
cgctgcccaa tgccatcctg                                                20

<210> SEQ ID NO 62
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 62
ctgacaacag tttgccgctg                                                20

<210> SEQ ID NO 63
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 63
gttgcattca atgttctgac                                                20

<210> SEQ ID NO 64
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 64
attatttctt ccccagttgc                                                20

<210> SEQ ID NO 65
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 65
tttgaggatt gctgaattat                                                20

<210> SEQ ID NO 66
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 66
atactggcat ctgtttttga                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 67
aatttttcct gtagaatact                                               20

<210> SEQ ID NO 68
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 68
agattcaggc ttcccaattt                                               20

<210> SEQ ID NO 69
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 69
acctcctgcc accgcagatt                                               20

<210> SEQ ID NO 70
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 70
gacagctgtt tgcagacctc                                               20

<210> SEQ ID NO 71
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 71 ctctttttc tgtctgacag                                                20

<210> SEQ ID NO 72
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 72
cctacctctt ttttctgtct                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 73
gtcgccctac ctcttttttc                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 74
gatctgtcgc cctacctctt                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 75
tattagatct gtcgccctac                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 76
attcctatta gatctgtcgc                                              20

<210> SEQ ID NO 77
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 77
gggggatttg agaaaataaa attac                                        25

<210> SEQ ID NO 78
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 78
atttgagaaa ataaaattac cttga                                          25

<210> SEQ ID NO 79
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 79
ctagcctgga gaaagaagaa taaaa                                          25

<210> SEQ ID NO 80
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 80
agaaaataaa attaccttga cttgc                                          25

<210> SEQ ID NO 81
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 81
ttcttctagc ctggagaaag aagaa                                          25

<210> SEQ ID NO 82
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 82
ataaaattac cttgacttgc tcaag                                          25

<210> SEQ ID NO 83
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 83
ttttgttctt ctagcctgga gaaag                                          25

<210> SEQ ID NO 84
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 84
attaccttga cttgctcaag ctttt                                             25

<210> SEQ ID NO 85
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 85
tattcttttg ttcttctagc ctgga                                             25

<210> SEQ ID NO 86
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 86
cttgacttgc tcaagctttt ctttt                                             25

<210> SEQ ID NO 87
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 87
caagatattc ttttgttctt ctagc                                             25

<210> SEQ ID NO 88
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 88
cttttagttg ctgctctttt ccagg                                             25

<210> SEQ ID NO 89
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 89
ccaggttcaa gtgggatact agcaa                                             25

<210> SEQ ID NO 90
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 90
atctctttga aattctgaca agata                                             25

<210> SEQ ID NO 91
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 91
agcaatgtta tctgcttcct ccaac                                              25

<210> SEQ ID NO 92
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 92
aacaaattca tttaaatctc tttga                                              25

<210> SEQ ID NO 93
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 93
ccaaccataa aacaaattca tttaa                                              25

<210> SEQ ID NO 94
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 94
ttcctccaac cataaaacaa attca                                              25

<210> SEQ ID NO 95
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 95
tttaaatctc tttgaaattc tgaca                                              25

<210> SEQ ID NO 96
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 96
tgacaagata ttcttttgtt cttct                                              25

<210> SEQ ID NO 97
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 97
ttcaagtggg atactagcaa tgtta                                          25

<210> SEQ ID NO 98
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 98
agatattctt ttgttcttct agcct                                          25

<210> SEQ ID NO 99
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 99
ctgctctttt ccaggttcaa gtggg                                          25

<210> SEQ ID NO 100
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 100
ttcttttgtt cttctagcct ggaga                                          25

<210> SEQ ID NO 101
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 101
cttttctttt agttgctgct ctttt                                          25

<210> SEQ ID NO 102
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 102
ttgttcttct agcctggaga aagaa                                          25

```
<210> SEQ ID NO 103
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 103
cttctagcct ggagaaagaa gaata                                              25

<210> SEQ ID NO 104
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 104
agcctggaga aagaagaata aaatt                                              25

<210> SEQ ID NO 105
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 105
ctggagaaag aagaataaaa ttgtt                                              25

<210> SEQ ID NO 106
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 106
gaaagaagaa taaaattgtt                                                    20

<210> SEQ ID NO 107
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 107
ggagaaagaa gaataaaatt                                                    20

<210> SEQ ID NO 108
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 108
agcctggaga aagaagaata                                                    20

<210> SEQ ID NO 109
```

<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 109
cttctagcct ggagaaagaa                                              20

<210> SEQ ID NO 110
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 110
ttgttcttct agcctggaga                                              20

<210> SEQ ID NO 111
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 111
ttcttttgtt cttctagcct                                              20

<210> SEQ ID NO 112
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 112
tgacaagata ttcttttgtt                                              20

<210> SEQ ID NO 113
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 113
atctctttga aattctgaca                                              20

<210> SEQ ID NO 114
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 114
aacaaattca tttaaatctc                                              20

<210> SEQ ID NO 115
<211> LENGTH: 20

```
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 115
ttcctccaac cataaaacaa                                                 20

<210> SEQ ID NO 116
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 116
agcaatgtta tctgcttcct                                                 20

<210> SEQ ID NO 117
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 117
ttcaagtggg atactagcaa                                                 20

<210> SEQ ID NO 118
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 118
ctgctctttt ccaggttcaa                                                 20

<210> SEQ ID NO 119
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 119
cttttctttt agttgctgct                                                 20

<210> SEQ ID NO 120
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 120
cttgacttgc tcaagctttt                                                 20

<210> SEQ ID NO 121
<211> LENGTH: 20
<212> TYPE: DNA
```

```
<213> ORGANISM: Artificial Sequence
<220> FEATURE:
<223> OTHER INFORMATION: Antisense sequence to target splice site of
      proprocessed human dystrophin

<400> SEQUENCE: 121
attaccttga cttgctcaag                                                    20

<210> SEQ ID NO 122
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 122
ataaaattac cttgacttgc                                                    20

<210> SEQ ID NO 123
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 123
agaaaataaa attaccttga                                                    20

<210> SEQ ID NO 124
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 124
atttgagaaa ataaaattac                                                    20

<210> SEQ ID NO 125
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 125
gggggatttg agaaaataaa                                                    20

<210> SEQ ID NO 126
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 126
ctgaaacaga caaatgcaac aacgt                                              25

<210> SEQ ID NO 127
<211> LENGTH: 25
<212> TYPE: DNA
<213> ORGANISM: Artificial Sequence
```

```
<220> FEATURE:
<223> OTHER INFORMATION: Antisense sequence to target splice site of
      proprocessed human dystrophin

<400> SEQUENCE: 127
agtaactgaa acagacaaat gcaac                                              25

<210> SEQ ID NO 128
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 128
ccaccagtaa ctgaaacaga caaat                                              25

<210> SEQ ID NO 129
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 129
ctcttccacc agtaactgaa acaga                                              25

<210> SEQ ID NO 130
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 130
ggcaactctt ccaccagtaa ctgaa                                              25

<210> SEQ ID NO 131
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 131 gcagggggcaa ctcttccacc agtaa                                             25

<210> SEQ ID NO 132
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 132
ctggcgcagg ggcaactctt ccacc                                              25

<210> SEQ ID NO 133
<211> LENGTH: 25
<212> TYPE: DNA
<213> ORGANISM: Artificial Sequence
<220> FEATURE:
```

```
<223> OTHER INFORMATION: Antisense sequence to target splice site of
      proprocessed human dystrophin

<400> SEQUENCE: 133
tttaattgtt tgagaattcc ctggc                                              25

<210> SEQ ID NO 134
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 134
ttgtttgaga attccctggc gcagg                                              25

<210> SEQ ID NO 135
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 135
gcacgggtcc tccagtttca tttaa                                              25

<210> SEQ ID NO 136
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 136
tccagtttca tttaattgtt tgaga                                              25

<210> SEQ ID NO 137
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 137
gcttatggga gcacttacaa gcacg                                              25

<210> SEQ ID NO 138
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 138
tacaagcacg ggtcctccag tttca                                              25

<210> SEQ ID NO 139
<211> LENGTH: 25
<212> TYPE: DNA
<213> ORGANISM: Artificial Sequence
<220> FEATURE:
<223> OTHER INFORMATION: Antisense sequence to target splice site of
```

-continued proprocessed human dystrophin

<400> SEQUENCE: 139
agtttatctt gctcttctgg gctta                                              25

<210> SEQ ID NO 140
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 140
tctgcttgag cttattttca agttt                                              25

<210> SEQ ID NO 141
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 141
atcttgctct tctgggctta tggga                                              25

<210> SEQ ID NO 142
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 142
ctttatccac tggagatttg tctgc                                              25

<210> SEQ ID NO 143
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 143
cttattttca agtttatctt gctct                                              25

<210> SEQ ID NO 144
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 144 ctaacctta tccactggag atttg                                               25

<210> SEQ ID NO 145
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 145
atttgtctgc ttgagcttat tttca                                          25

<210> SEQ ID NO 146
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 146
aatgtctaac ctttatccac tggag                                          25

<210> SEQ ID NO 147
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 147
tggttaatgt ctaaccttta tccac                                          25

<210> SEQ ID NO 148
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 148
agagatggtt aatgtctaac cttta                                          25

<210> SEQ ID NO 149
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 149
acggaagaga tggttaatgt ctaac                                          25

<210> SEQ ID NO 150
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 150
acagacaaat gcaacaacgt                                                20

<210> SEQ ID NO 151
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 151
ctgaaacaga caaatgcaac                                                20

<210> SEQ ID NO 152
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 152
agtaactgaa acagacaaat                                                20

<210> SEQ ID NO 153
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 153
ccaccagtaa ctgaaacaga                                                20

<210> SEQ ID NO 154
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 154
ctcttccacc agtaactgaa                                                20

<210> SEQ ID NO 155
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 155
ggcaactctt ccaccagtaa                                                20

<210> SEQ ID NO 156
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 156
ctggcgcagg ggcaactctt                                                20

<210> SEQ ID NO 157
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 157

```
ttgtttgaga attccctggc                                          20

<210> SEQ ID NO 158
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 158
tccagtttca tttaattgtt                                          20

<210> SEQ ID NO 159
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 159
tacaagcacg ggtcctccag                                          20

<210> SEQ ID NO 160
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 160
gcttatggga gcacttacaa                                          20

<210> SEQ ID NO 161
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 161
atcttgctct tctgggctta                                          20

<210> SEQ ID NO 162
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 162
cttattttca agtttatctt                                          20

<210> SEQ ID NO 163
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 163
```
atttgtctgc ttgagcttat                                           20

<210> SEQ ID NO 164
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 164
ctttatccac tggagatttg                                           20

<210> SEQ ID NO 165
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 165
ctaaccttta tccactggag                                           20

<210> SEQ ID NO 166
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 166
aatgtctaac ctttatccac                                           20

<210> SEQ ID NO 167
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 167
tggttaatgt ctaaccttta                                           20

<210> SEQ ID NO 168
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 168
agagatggtt aatgtctaac                                           20

<210> SEQ ID NO 169
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 169
acggaagaga tggttaatgt                                           20

<210> SEQ ID NO 170
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 170
ctgaaaggaa aatacatttt aaaaa                                          25

<210> SEQ ID NO 171
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 171
cctgaaagga aatacatttt taaaa                                          25

<210> SEQ ID NO 172
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 172
gaaacctgaa aggaaaatac atttt                                          25

<210> SEQ ID NO 173
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 173
ggaaacctga aggaaaata cattt                                           25

<210> SEQ ID NO 174
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 174
ctctggaaac ctgaaaggaa aatac                                          25

<210> SEQ ID NO 175
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 175
gctctggaaa cctgaaagga aaata                                          25

```
<210> SEQ ID NO 176
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 176
gtaaagctct ggaaacctga aagga                                               25

<210> SEQ ID NO 177
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 177
tcaggtaaag ctctggaaac ctgaa                                               25

<210> SEQ ID NO 178
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 178
ctcaggtaaa gctctggaaa cctga                                               25

<210> SEQ ID NO 179
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 179
gtttctcagg taaagctctg gaaac                                               25

<210> SEQ ID NO 180
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 180
tgtttctcag gtaaagctct ggaaa                                               25

<210> SEQ ID NO 181
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 181
aatttctcct tgtttctcag gtaaa                                               25
```

-continued

<210> SEQ ID NO 182
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 182
tttgagcttc aatttctcct tgttt                                           25

<210> SEQ ID NO 183
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 183
ttttatttga gcttcaattt ctcct                                           25

<210> SEQ ID NO 184
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 184
aagctgccca aggtctttta tttga                                           25

<210> SEQ ID NO 185
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 185
aggtcttcaa gcttttttc aagct                                            25

<210> SEQ ID NO 186
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 186
ttcaagcttt ttttcaagct gccca                                           25

<210> SEQ ID NO 187
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 187
gatgatttaa ctgctcttca aggtc                                           25

<210> SEQ ID NO 188

```
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 188
ctgctcttca aggtcttcaa gcttt                                        25

<210> SEQ ID NO 189
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 189
aggagataac cacagcagca gatga                                        25

<210> SEQ ID NO 190
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 190
cagcagatga tttaactgct cttca                                        25

<210> SEQ ID NO 191
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 191
atttccaact gattcctaat aggag                                        25

<210> SEQ ID NO 192
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 192
cttggtttgg ttggttataa atttc                                        25

<210> SEQ ID NO 193
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 193
caactgattc ctaataggag ataac                                        25

<210> SEQ ID NO 194
<211> LENGTH: 25
```

```
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 194
cttaacgtca aatggtcctt cttgg                                              25

<210> SEQ ID NO 195
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 195
ttggttataa atttccaact gattc                                              25

<210> SEQ ID NO 196
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 196
cctaccttaa cgtcaaatgg tcctt                                              25

<210> SEQ ID NO 197
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 197
tccttcttgg tttggttggt tataa                                              25

<210> SEQ ID NO 198
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 198
agttccctac cttaacgtca aatgg                                              25

<210> SEQ ID NO 199
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 199
caaaaagttc cctaccttaa cgtca                                              25

<210> SEQ ID NO 200
<211> LENGTH: 25
<212> TYPE: DNA
```

```
<213> ORGANISM: Artificial Sequence
<220> FEATURE:
<223> OTHER INFORMATION: Antisense sequence to target splice site of
      proprocessed human dystrophin

<400> SEQUENCE: 200
taaagcaaaa agttccctac cttaa                                              25

<210> SEQ ID NO 201
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 201
atatttaaag caaaaagttc cctac                                              25

<210> SEQ ID NO 202
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 202
aggaaaatac attttaaaaa                                                    20

<210> SEQ ID NO 203
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 203
aaggaaaata cattttaaaa                                                    20

<210> SEQ ID NO 204
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 204
cctgaaagga aaatacattt                                                    20

<210> SEQ ID NO 205
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 205
ggaaacctga aaggaaaata                                                    20

<210> SEQ ID NO 206
<211> LENGTH: 20
<212> TYPE: DNA
<213> ORGANISM: Artificial Sequence
```

```
<220> FEATURE:
<223> OTHER INFORMATION: Antisense sequence to target splice site of
      proprocessed human dystrophin

<400> SEQUENCE: 206
gctctggaaa cctgaaagga                                              20

<210> SEQ ID NO 207
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 207
gtaaagctct ggaaacctga                                              20

<210> SEQ ID NO 208
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 208
ctcaggtaaa gctctggaaa                                              20

<210> SEQ ID NO 209
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 209
aatttctcct tgtttctcag                                              20

<210> SEQ ID NO 210
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 210
ttttatttga gcttcaattt                                              20

<210> SEQ ID NO 211
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 211
aagctgccca aggtctttta                                              20

<210> SEQ ID NO 212
<211> LENGTH: 20
<212> TYPE: DNA
<213> ORGANISM: Artificial Sequence
<220> FEATURE:
```

<223> OTHER INFORMATION: Antisense sequence to target splice site of
      proprocessed human dystrophin

<400> SEQUENCE: 212
ttcaagcttt ttttcaagct                                                     20

<210> SEQ ID NO 213
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 213
ctgctcttca aggtcttcaa                                                     20

<210> SEQ ID NO 214
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 214
cagcagatga tttaactgct                                                     20

<210> SEQ ID NO 215
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 215
aggagataac cacagcagca                                                     20

<210> SEQ ID NO 216
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 216
caactgattc ctaataggag                                                     20

<210> SEQ ID NO 217
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 217
ttggttataa atttccaact                                                     20

<210> SEQ ID NO 218
<211> LENGTH: 20
<212> TYPE: DNA
<213> ORGANISM: Artificial Sequence
<220> FEATURE:
<223> OTHER INFORMATION: Antisense sequence to target splice site of proprocessed human dystrophin

<400> SEQUENCE: 218
tccttcttgg tttggttggt                                               20

<210> SEQ ID NO 219
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 219
cttaacgtca aatggtcctt                                               20

<210> SEQ ID NO 220
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 220
cctaccttaa cgtcaaatgg                                               20

<210> SEQ ID NO 221
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 221
agttccctac cttaacgtca                                               20

<210> SEQ ID NO 222
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 222
caaaaagttc cctaccttaa                                               20

<210> SEQ ID NO 223
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 223
taaagcaaaa agttccctac                                               20

<210> SEQ ID NO 224
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 224
atatttaaag caaaaagttc                                                   20

<210> SEQ ID NO 225
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 225
ctggggaaaa gaacccatat agtgc                                             25

<210> SEQ ID NO 226
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 226
tcctggggaa aagaacccat atagt                                             25

<210> SEQ ID NO 227
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 227
gtttcctggg gaaagaacc catat                                              25

<210> SEQ ID NO 228
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 228
cagtttcctg gggaaaagaa cccat                                             25

<210> SEQ ID NO 229
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 229
tttcagtttc ctggggaaaa gaacc                                             25

<210> SEQ ID NO 230
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin -continued

```
<400> SEQUENCE: 230
tatttcagtt tcctggggaa aagaa                                            25

<210> SEQ ID NO 231
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 231
tgctatttca gtttcctggg gaaaa                                            25

<210> SEQ ID NO 232
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 232
actgctattt cagtttcctg gggaa                                            25

<210> SEQ ID NO 233
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 233
tgaactgcta tttcagtttc ctggg                                            25

<210> SEQ ID NO 234
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 234
cttgaactgc tatttcagtt tcctg                                            25

<210> SEQ ID NO 235
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 235
tagcttgaac tgctatttca gtttc                                            25

<210> SEQ ID NO 236
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 236
```
tttagcttga actgctattt cagtt					25

<210> SEQ ID NO 237
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 237
ttccacatcc ggttgtttag cttga					25

<210> SEQ ID NO 238
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 238
tgccctttag acaaaatctc ttcca					25

<210> SEQ ID NO 239
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 239
tttagacaaa atctcttcca catcc					25

<210> SEQ ID NO 240
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 240 gttttttcctt gtacaaatgc tgccc					25

<210> SEQ ID NO 241
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 241
gtacaaatgc tgccctttag acaaa					25

<210> SEQ ID NO 242
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 242

```
cttcactggc tgagtggctg gtttt                                          25

<210> SEQ ID NO 243
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 243
ggctggtttt tccttgtaca aatgc                                          25

<210> SEQ ID NO 244
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 244
attaccttca ctggctgagt ggctg                                          25

<210> SEQ ID NO 245
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 245
gcttcattac cttcactggc tgagt                                          25

<210> SEQ ID NO 246
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 246
aggttgcttc attaccttca ctggc                                          25

<210> SEQ ID NO 247
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 247
gctagaggtt gcttcattac cttca                                          25

<210> SEQ ID NO 248
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 248
atattgctag aggttgcttc attac                                          25
```

<210> SEQ ID NO 249
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 249
gaaaagaacc catatagtgc                                                    20

<210> SEQ ID NO 250
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 250
gggaaaagaa cccatatagt                                                    20

<210> SEQ ID NO 251
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 251
tcctggggaa aagaacccat                                                    20

<210> SEQ ID NO 252
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 252
cagtttcctg gggaaaagaa                                                    20

<210> SEQ ID NO 253
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 253
tatttcagtt tcctggggaa                                                    20

<210> SEQ ID NO 254
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 254
actgctattt cagtttcctg                                                    20

```
<210> SEQ ID NO 255
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 255
cttgaactgc tatttcagtt                                             20

<210> SEQ ID NO 256
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 256
tttagcttga actgctattt                                             20

<210> SEQ ID NO 257
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 257
ttccacatcc ggttgtttag                                             20

<210> SEQ ID NO 258
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 258
tttagacaaa atctcttcca                                             20

<210> SEQ ID NO 259
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 259
gtacaaatgc tgccctttag                                             20

<210> SEQ ID NO 260
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 260
ggctggtttt tccttgtaca                                             20
```

-continued

```
<210> SEQ ID NO 261
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 261
cttcactggc tgagtggctg                                              20

<210> SEQ ID NO 262
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 262
attaccttca ctggctgagt                                              20

<210> SEQ ID NO 263
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 263
gcttcattac cttcactggc                                              20

<210> SEQ ID NO 264
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 264
aggttgcttc attaccttca                                              20

<210> SEQ ID NO 265
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 265
gctagaggtt gcttcattac                                              20

<210> SEQ ID NO 266
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 266
atattgctag aggttgcttc                                              20

<210> SEQ ID NO 267
```

<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 267
ctttaacaga aaagcataca catta                                       25

<210> SEQ ID NO 268
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 268
tcctctttaa cagaaaagca tacac                                       25

<210> SEQ ID NO 269
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 269
ttcctcttta acagaaaagc ataca                                       25

<210> SEQ ID NO 270
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 270
taacttcctc tttaacagaa aagca                                       25

<210> SEQ ID NO 271
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 271
ctaacttcct ctttaacaga aaagc                                       25

<210> SEQ ID NO 272
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 272
tcttctaact tcctctttaa cagaa                                       25

<210> SEQ ID NO 273
<211> LENGTH: 25

```
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 273
atcttctaac ttcctcttta acaga                                          25

<210> SEQ ID NO 274
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 274
tcagatcttc taacttcctc tttaa                                          25

<210> SEQ ID NO 275
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 275
ctcagatctt ctaacttcct cttta                                          25

<210> SEQ ID NO 276
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 276
agagctcaga tcttctaact tcctc                                          25

<210> SEQ ID NO 277
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 277
cagagctcag atcttctaac ttcct                                          25

<210> SEQ ID NO 278
<211> LENGTH: 24
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 278
cactcagagc tcagatcttc tact                                           24

<210> SEQ ID NO 279
<211> LENGTH: 25
<212> TYPE: DNA
```

-continued

```
<213> ORGANISM: Artificial Sequence
<220> FEATURE:
<223> OTHER INFORMATION: Antisense sequence to target splice site of
      proprocessed human dystrophin

<400> SEQUENCE: 279
ccttccactc agagctcaga tcttc                                              25

<210> SEQ ID NO 280
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 280
gtaaacggtt taccgccttc cactc                                              25

<210> SEQ ID NO 281
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 281
ctttgccctc agctcttgaa gtaaa                                              25

<210> SEQ ID NO 282
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 282
ccctcagctc ttgaagtaaa cggtt                                              25

<210> SEQ ID NO 283
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 283
ccaggagcta ggtcaggctg ctttg                                              25

<210> SEQ ID NO 284
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 284
ggtcaggctg ctttgccctc agctc                                              25

<210> SEQ ID NO 285
<211> LENGTH: 25
<212> TYPE: DNA
<213> ORGANISM: Artificial Sequence
```

```
<220> FEATURE:
<223> OTHER INFORMATION: Antisense sequence to target splice site of
      proprocessed human dystrophin

<400> SEQUENCE: 285
aggctccaat agtggtcagt ccagg                                              25

<210> SEQ ID NO 286
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 286
tcagtccagg agctaggtca ggctg                                              25

<210> SEQ ID NO 287
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 287
cttacaggct ccaatagtgg tcagt                                              25

<210> SEQ ID NO 288
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 288
gtatacttac aggctccaat agtgg                                              25

<210> SEQ ID NO 289
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 289
atccagtata cttacaggct ccaat                                              25

<210> SEQ ID NO 290
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 290
atgggatcca gtatacttac aggct                                              25

<210> SEQ ID NO 291
<211> LENGTH: 25
<212> TYPE: DNA
<213> ORGANISM: Artificial Sequence
<220> FEATURE:
```

<223> OTHER INFORMATION: Antisense sequence to target splice site of
      proprocessed human dystrophin

<400> SEQUENCE: 291
agagaatggg atccagtata cttac                                      25

<210> SEQ ID NO 292
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 292
acagaaaagc atacacatta                                            20

<210> SEQ ID NO 293
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 293
tttaacagaa aagcatacac                                            20

<210> SEQ ID NO 294
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 294
tcctctttaa cagaaaagca                                            20

<210> SEQ ID NO 295
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 295
taacttcctc tttaacagaa                                            20

<210> SEQ ID NO 296
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 296
tcttctaact tcctctttaa                                            20

<210> SEQ ID NO 297
<211> LENGTH: 20
<212> TYPE: DNA
<213> ORGANISM: Artificial Sequence
<220> FEATURE:
<223> OTHER INFORMATION: Antisense sequence to target splice site of -continued proprocessed human dystrophin

<400> SEQUENCE: 297
tcagatcttc taacttcctc                                            20

<210> SEQ ID NO 298
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 298
ccttccactc agagctcaga                                            20

<210> SEQ ID NO 299
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 299
gtaaacggtt taccgccttc                                            20

<210> SEQ ID NO 300
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 300
ccctcagctc ttgaagtaaa                                            20

<210> SEQ ID NO 301
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 301
ggtcaggctg ctttgccctc                                            20

<210> SEQ ID NO 302
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 302
tcagtccagg agctaggtca                                            20

<210> SEQ ID NO 303
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 303
aggctccaat agtggtcagt                                               20

<210> SEQ ID NO 304
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 304
cttacaggct ccaatagtgg                                               20

<210> SEQ ID NO 305
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 305
gtatacttac aggctccaat                                               20

<210> SEQ ID NO 306
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 306
atccagtata cttacaggct                                               20

<210> SEQ ID NO 307
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 307
atgggatcca gtatacttac                                               20

<210> SEQ ID NO 308
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 308
agagaatggg atccagtata                                               20

<210> SEQ ID NO 309
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

```
<400> SEQUENCE: 309
ctaaaatatt tgggttttt gcaaaa                                         26

<210> SEQ ID NO 310
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 310
gctaaaatat tgggttttt tgcaaa                                         26

<210> SEQ ID NO 311
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 311
taggagctaa aatatttggg gttttt                                        26

<210> SEQ ID NO 312
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 312
agtaggagct aaaatatttt gggtt                                         25

<210> SEQ ID NO 313
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 313
tgagtaggag ctaaaatatt ttggg                                         25

<210> SEQ ID NO 314
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 314
ctgagtagga gctaaaatat ttggg                                         26

<210> SEQ ID NO 315
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 315
```
cagtctgagt aggagctaaa atatt                                   25

<210> SEQ ID NO 316
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 316
acagtctgag taggagctaa aatatt                                  26

<210> SEQ ID NO 317
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 317
gagtaacagt ctgagtagga gctaaa                                  26

<210> SEQ ID NO 318
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 318
cagagtaaca gtctgagtag gagct                                   25

<210> SEQ ID NO 319
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 319
caccagagta acagtctgag taggag                                  26

<210> SEQ ID NO 320
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 320
gtcaccagag taacagtctg agtag                                   25

<210> SEQ ID NO 321
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 321

```
aaccacaggt tgtgtcacca gagtaa                                            26

<210> SEQ ID NO 322
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 322
gttgtgtcac cagagtaaca gtctg                                             25

<210> SEQ ID NO 323
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 323
tggcagtttc cttagtaacc acaggt                                            26

<210> SEQ ID NO 324
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 324
atttctagtt tggagatggc agtttc                                            26

<210> SEQ ID NO 325
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 325
ggaagatggc atttctagtt tggag                                             25

<210> SEQ ID NO 326
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 326
catcaaggaa gatggcattt ctagtt                                            26

<210> SEQ ID NO 327
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 327
gagcaggtac ctccaacatc aaggaa                                            26
```

<210> SEQ ID NO 328
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 328
atctgccaga gcaggtacct ccaac                                          25

<210> SEQ ID NO 329
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 329
aagttctgtc caagcccggt tgaaat                                         26

<210> SEQ ID NO 330
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 330
cggttgaaat ctgccagagc aggtac                                         26

<210> SEQ ID NO 331
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 331
gagaaagcca gtcggtaagt tctgtc                                         26

<210> SEQ ID NO 332
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 332
gtcggtaagt tctgtccaag cccgg                                          25

<210> SEQ ID NO 333
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 333
ataacttgat caagcagaga aagcca                                         26

<210> SEQ ID NO 334
<211> LENGTH: 25
<212> TYPE: DNA
<213> ORGANISM: Artificial Sequence
<220> FEATURE:
<223> OTHER INFORMATION: Antisense sequence to target splice site of proprocessed human dystrophin

<400> SEQUENCE: 334
aagcagagaa agccagtcgg taagt                                        25

<210> SEQ ID NO 335
<211> LENGTH: 26
<212> TYPE: DNA
<213> ORGANISM: Artificial Sequence
<220> FEATURE:
<223> OTHER INFORMATION: Antisense sequence to target splice site of proprocessed human dystrophin

<400> SEQUENCE: 335
caccctctgt gattttataa cttgat                                       26

<210> SEQ ID NO 336
<211> LENGTH: 26
<212> TYPE: DNA
<213> ORGANISM: Artificial Sequence
<220> FEATURE:
<223> OTHER INFORMATION: Antisense sequence to target splice site of proprocessed human dystrophin

<400> SEQUENCE: 336
caaggtcacc caccatcacc ctctgt                                       26

<210> SEQ ID NO 337
<211> LENGTH: 25
<212> TYPE: DNA
<213> ORGANISM: Artificial Sequence
<220> FEATURE:
<223> OTHER INFORMATION: Antisense sequence to target splice site of proprocessed human dystrophin

<400> SEQUENCE: 337
catcaccctc tgtgatttta taact                                        25

<210> SEQ ID NO 338
<211> LENGTH: 26
<212> TYPE: DNA
<213> ORGANISM: Artificial Sequence
<220> FEATURE:
<223> OTHER INFORMATION: Antisense sequence to target splice site of proprocessed human dystrophin

<400> SEQUENCE: 338
cttctgcttg atgatcatct cgttga                                       26

<210> SEQ ID NO 339
<211> LENGTH: 26
<212> TYPE: DNA
<213> ORGANISM: Artificial Sequence
<220> FEATURE:
<223> OTHER INFORMATION: Antisense sequence to target splice site of proprocessed human dystrophin

<400> SEQUENCE: 339
ccttctgctt gatgatcatc tcgttg                                       26

```
<210> SEQ ID NO 340
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 340
atctcgttga tatcctcaag gtcacc                                           26

<210> SEQ ID NO 341
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 341
tcataccttc tgcttgatga tcatct                                           26

<210> SEQ ID NO 342
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 342 tcatttttc tcataccttc tgcttg                                            26

<210> SEQ ID NO 343
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 343
ttttctcata ccttctgctt gatgat                                           26

<210> SEQ ID NO 344
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 344
ttttatcatt ttttctcata ccttct                                           26

<210> SEQ ID NO 345
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 345
ccaactttta tcatttttc tcatac                                            26

<210> SEQ ID NO 346
```

```
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 346
atattttggg tttttgcaaa                                              20

<210> SEQ ID NO 347
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 347
aaaatatttt gggttttgc                                               20

<210> SEQ ID NO 348
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 348
gagctaaaat attttgggtt                                              20

<210> SEQ ID NO 349
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 349
agtaggagct aaaatatttt                                              20

<210> SEQ ID NO 350
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 350
gtctgagtag gagctaaaat                                              20

<210> SEQ ID NO 351
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 351
taacagtctg agtaggagct                                              20

<210> SEQ ID NO 352
<211> LENGTH: 20
```

```
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 352
cagagtaaca gtctgagtag                                                   20

<210> SEQ ID NO 353
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 353
cacaggttgt gtcaccagag                                                   20

<210> SEQ ID NO 354
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 354
agtttcctta gtaaccacag                                                   20

<210> SEQ ID NO 355
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 355
tagtttggag atggcagttt                                                   20

<210> SEQ ID NO 356
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 356
ggaagatggc atttctagtt                                                   20

<210> SEQ ID NO 357
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 357
tacctccaac atcaaggaag                                                   20

<210> SEQ ID NO 358
<211> LENGTH: 20
<212> TYPE: DNA
```

```
<213> ORGANISM: Artificial Sequence
<220> FEATURE:
<223> OTHER INFORMATION: Antisense sequence to target splice site of
      proprocessed human dystrophin

<400> SEQUENCE: 358
atctgccaga gcaggtacct                                              20

<210> SEQ ID NO 359
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 359
ccaagcccgg ttgaaatctg                                              20

<210> SEQ ID NO 360
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 360
gtcggtaagt tctgtccaag                                              20

<210> SEQ ID NO 361
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 361
aagcagagaa agccagtcgg                                              20

<210> SEQ ID NO 362
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 362
ttttataact tgatcaagca                                              20

<210> SEQ ID NO 363
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 363
catcaccctc tgtgatttta                                              20

<210> SEQ ID NO 364
<211> LENGTH: 20
<212> TYPE: DNA
<213> ORGANISM: Artificial Sequence
```

```
<220> FEATURE:
<223> OTHER INFORMATION: Antisense sequence to target splice site of
      proprocessed human dystrophin

<400> SEQUENCE: 364
ctcaaggtca cccaccatca                                              20

<210> SEQ ID NO 365
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 365
catctcgttg atatcctcaa                                              20

<210> SEQ ID NO 366
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 366
cttctgcttg atgatcatct                                              20

<210> SEQ ID NO 367
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 367
cataccttct gcttgatgat                                              20

<210> SEQ ID NO 368
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 368
tttctcatac cttctgcttg                                              20

<210> SEQ ID NO 369
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 369
cattttttct cataccttct                                              20

<210> SEQ ID NO 370
<211> LENGTH: 20
<212> TYPE: DNA
<213> ORGANISM: Artificial Sequence
<220> FEATURE:
```

```
<223> OTHER INFORMATION: Antisense sequence to target splice site of
      proprocessed human dystrophin

<400> SEQUENCE: 370
tttatcattt tttctcatac                                                    20

<210> SEQ ID NO 371
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 371
caacttttat cattttttct                                                    20

<210> SEQ ID NO 372
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 372
ctgtaagaac aaatatccct tagta                                              25

<210> SEQ ID NO 373
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 373
tgcctgtaag aacaaatatc cctta                                              25

<210> SEQ ID NO 374
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 374
gttgcctgta agaacaaata tccct                                              25

<210> SEQ ID NO 375
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 375
attgttgcct gtaagaacaa atatc                                              25

<210> SEQ ID NO 376
<211> LENGTH: 25
<212> TYPE: DNA
<213> ORGANISM: Artificial Sequence
<220> FEATURE:
<223> OTHER INFORMATION: Antisense sequence to target splice site of
```

-continued proprocessed human dystrophin

<400> SEQUENCE: 376
gcattgttgc ctgtaagaac aaata                                          25

<210> SEQ ID NO 377
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 377
cctgcattgt tgcctgtaag aacaa                                          25

<210> SEQ ID NO 378
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 378
atcctgcatt gttgcctgta agaac                                          25

<210> SEQ ID NO 379
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 379
caaatcctgc attgttgcct gtaag                                          25

<210> SEQ ID NO 380
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 380
tccaaatcct gcattgttgc ctgta                                          25

<210> SEQ ID NO 381
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 381
tgttccaaat cctgcattgt tgcct                                          25

<210> SEQ ID NO 382
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

```
<400> SEQUENCE: 382
tctgttccaa atcctgcatt gttgc                                              25

<210> SEQ ID NO 383
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 383
aactggggac gcctctgttc caaat                                              25

<210> SEQ ID NO 384
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 384
gcctctgttc caaatcctgc attgt                                              25

<210> SEQ ID NO 385
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 385
cagcggtaat gagttcttcc aactg                                              25

<210> SEQ ID NO 386
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 386
cttccaactg gggacgcctc tgttc                                              25

<210> SEQ ID NO 387
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 387 cttgttttc aaattttggg cagcg                                               25

<210> SEQ ID NO 388
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin
```

<400> SEQUENCE: 388
ctagcctctt gattgctggt cttgt                                      25

<210> SEQ ID NO 389
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 389
ttttcaaatt ttgggcagcg gtaat                                      25

<210> SEQ ID NO 390
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 390
ttcgatccgt aatgattgtt ctagc                                      25

<210> SEQ ID NO 391
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 391
gattgctggt cttgttttc aaatt                                       25

<210> SEQ ID NO 392
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 392
cttacttcga tccgtaatga ttgtt                                      25

<210> SEQ ID NO 393
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 393
ttgttctagc ctcttgattg ctggt                                      25

<210> SEQ ID NO 394
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 394

```
aaaaacttac ttcgatccgt aatga                                          25
```

<210> SEQ ID NO 395
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 395

```
tgttaaaaaa cttacttcga tccgt                                          25
```

<210> SEQ ID NO 396
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 396

```
atgcttgtta aaaacttac ttcga                                           25
```

<210> SEQ ID NO 397
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 397

```
gtcccatgct tgttaaaaaa cttac                                          25
```

<210> SEQ ID NO 398
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 398

```
agaacaaata tcccttagta                                                20
```

<210> SEQ ID NO 399
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 399

```
gtaagaacaa atatcccttα                                                20
```

<210> SEQ ID NO 400
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 400
tgcctgtaag aacaaatatc                                          20

<210> SEQ ID NO 401
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 401
attgttgcct gtaagaacaa                                          20

<210> SEQ ID NO 402
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 402
cctgcattgt tgcctgtaag                                          20

<210> SEQ ID NO 403
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 403
caaatcctgc attgttgcct                                          20

<210> SEQ ID NO 404
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 404
gcctctgttc caaatcctgc                                          20

<210> SEQ ID NO 405
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 405
cttccaactg gggacgcctc                                          20

<210> SEQ ID NO 406
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 406
cagcggtaat gagttcttcc                                          20

<210> SEQ ID NO 407
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 407
ttttcaaatt ttgggcagcg                                            20

<210> SEQ ID NO 408
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 408
gattgctggt cttgttttc                                             20

<210> SEQ ID NO 409
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 409
ttgttctagc ctcttgattg                                            20

<210> SEQ ID NO 410
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 410
ttcgatccgt aatgattgtt                                            20

<210> SEQ ID NO 411
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 411
cttacttcga tccgtaatga                                            20

<210> SEQ ID NO 412
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 412
aaaaacttac ttcgatccgt                                            20

<210> SEQ ID NO 413
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 413
tgttaaaaaa cttacttcga                                          20

<210> SEQ ID NO 414
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 414
atgcttgtta aaaacttac                                           20

<210> SEQ ID NO 415
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 415
gtcccatgct tgttaaaaaa                                          20

<210> SEQ ID NO 416
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 416
ctagaataaa aggaaaata aatat                                     25

<210> SEQ ID NO 417
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 417
aactagaata aaggaaaaa taaat                                     25

<210> SEQ ID NO 418
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 418
ttcaactaga ataaaggaa aaata                                     25

```
<210> SEQ ID NO 419
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 419
ctttcaacta gaataaaagg aaaaa                                            25

<210> SEQ ID NO 420
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 420
attctttcaa ctagaataaa aggaa                                            25

<210> SEQ ID NO 421
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 421
gaattctttc aactagaata aaagg                                            25

<210> SEQ ID NO 422
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 422
tctgaattct ttcaactaga ataaa                                            25

<210> SEQ ID NO 423
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 423
attctgaatt ctttcaacta gaata                                            25

<210> SEQ ID NO 424
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 424
ctgattctga attctttcaa ctaga                                            25

<210> SEQ ID NO 425
```

```
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 425
cactgattct gaattctttc aacta                                            25

<210> SEQ ID NO 426
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 426
tcccactgat tctgaattct ttcaa                                            25

<210> SEQ ID NO 427
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 427
catcccactg attctgaatt ctttc                                            25

<210> SEQ ID NO 428
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 428
tacttcatcc cactgattct gaatt                                            25

<210> SEQ ID NO 429
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 429
ctgaaggtgt tcttgtactt catcc                                            25

<210> SEQ ID NO 430
<211> LENGTH: 24
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 430
cggttctgaa ggtgttcttg tact                                             24

<210> SEQ ID NO 431
<211> LENGTH: 25
```

```
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 431
ctgttgcctc cggttctgaa ggtgt                                         25

<210> SEQ ID NO 432
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 432
tttcattcaa ctgttgcctc cggtt                                         25

<210> SEQ ID NO 433
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 433
taacatttca ttcaactgtt gcctc                                         25

<210> SEQ ID NO 434
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 434
ttgtgttgaa tcctttaaca tttca                                         25

<210> SEQ ID NO 435
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 435
tcttccttag cttccagcca ttgtg                                         25

<210> SEQ ID NO 436
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 436
cttagcttcc agccattgtg ttgaa                                         25

<210> SEQ ID NO 437
<211> LENGTH: 25
<212> TYPE: DNA
```

<213> ORGANISM: Artificial Sequence
<220> FEATURE:
<223> OTHER INFORMATION: Antisense sequence to target splice site of
      proprocessed human dystrophin

<400> SEQUENCE: 437
gtcctaagac ctgctcagct tcttc                                              25

<210> SEQ ID NO 438
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 438
ctgctcagct tcttccttag cttcc                                              25

<210> SEQ ID NO 439
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 439
ctcaagcttg gctctggcct gtcct                                              25

<210> SEQ ID NO 440
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 440
ggcctgtcct aagacctgct cagct                                              25

<210> SEQ ID NO 441
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 441
tagggaccct ccttccatga ctcaa                                              25

<210> SEQ ID NO 442
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 442
tttggattgc atctactgta taggg                                              25

<210> SEQ ID NO 443
<211> LENGTH: 25
<212> TYPE: DNA
<213> ORGANISM: Artificial Sequence

```
<220> FEATURE:
<223> OTHER INFORMATION: Antisense sequence to target splice site of
      proprocessed human dystrophin

<400> SEQUENCE: 443
accctccttc catgactcaa gcttg                                         25

<210> SEQ ID NO 444
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 444
cttggtttct gtgattttct tttgg                                         25

<210> SEQ ID NO 445
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 445
atctactgta tagggaccct ccttc                                         25

<210> SEQ ID NO 446
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 446
ctaaccttgg tttctgtgat tttct                                         25

<210> SEQ ID NO 447
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 447
tttcttttgg attgcatcta ctgta                                         25

<210> SEQ ID NO 448
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 448
tgatactaac cttggtttct gtgat                                         25

<210> SEQ ID NO 449
<211> LENGTH: 25
<212> TYPE: DNA
<213> ORGANISM: Artificial Sequence
<220> FEATURE:
```

```
<223> OTHER INFORMATION: Antisense sequence to target splice site of
      proprocessed human dystrophin

<400> SEQUENCE: 449
atctttgata ctaaccttgg tttct                                              25

<210> SEQ ID NO 450
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 450
aaggtatctt tgatactaac cttgg                                              25

<210> SEQ ID NO 451
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 451
ttaaaaaggt atctttgata ctaac                                              25

<210> SEQ ID NO 452
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 452
ataaaaggaa aaataaatat                                                    20

<210> SEQ ID NO 453
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 453
gaataaaagg aaaaataaat                                                    20

<210> SEQ ID NO 454
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 454
aactagaata aaaggaaaaa                                                    20

<210> SEQ ID NO 455
<211> LENGTH: 20
<212> TYPE: DNA
<213> ORGANISM: Artificial Sequence
<220> FEATURE:
<223> OTHER INFORMATION: Antisense sequence to target splice site of
``` proprocessed human dystrophin

<400> SEQUENCE: 455
ctttcaacta gaataaaagg                                               20

<210> SEQ ID NO 456
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 456
gaattctttc aactagaata                                               20

<210> SEQ ID NO 457
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 457
attctgaatt ctttcaacta                                               20

<210> SEQ ID NO 458
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 458
tacttcatcc cactgattct                                               20

<210> SEQ ID NO 459
<211> LENGTH: 19
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 459
ctgaaggtgt tcttgtact                                                19

<210> SEQ ID NO 460
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 460
ctgttgcctc cggttctgaa                                               20

<210> SEQ ID NO 461
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 461
taacatttca ttcaactgtt					20

<210> SEQ ID NO 462
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 462
ttgtgttgaa tcctttaaca					20

<210> SEQ ID NO 463
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 463
cttagcttcc agccattgtg					20

<210> SEQ ID NO 464
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 464
ctgctcagct tcttccttag					20

<210> SEQ ID NO 465
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 465
ggcctgtcct aagacctgct					20

<210> SEQ ID NO 466
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 466
ctcaagcttg gctctggcct					20

<210> SEQ ID NO 467
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 467 acctccttc catgactcaa                                               20

<210> SEQ ID NO 468
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 468
atctactgta tagggaccct                                              20

<210> SEQ ID NO 469
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 469 tttctttgg attgcatcta                                               20

<210> SEQ ID NO 470
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 470
cttggtttct gtgattttct                                              20

<210> SEQ ID NO 471
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 471
ctaaccttgg tttctgtgat                                              20

<210> SEQ ID NO 472
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 472
tgatactaac cttggtttct                                              20

<210> SEQ ID NO 473
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 473

```
atctttgata ctaaccttgg                                            20

<210> SEQ ID NO 474
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 474
aaggtatctt tgatactaac                                            20

<210> SEQ ID NO 475
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 475
ttaaaaaggt atctttgata                                            20

<210> SEQ ID NO 476
<211> LENGTH: 24
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 476
ctatagattt ttatgagaaa gaga                                       24

<210> SEQ ID NO 477
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 477
aactgctata gatttttatg agaaa                                      25

<210> SEQ ID NO 478
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 478
tggccaactg ctatagattt ttatg                                      25

<210> SEQ ID NO 479
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 479
```

```
gtctttggcc aactgctata gattt                                          25

<210> SEQ ID NO 480
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 480
cggaggtctt tggccaactg ctata                                          25

<210> SEQ ID NO 481
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 481
actggcggag gtctttggcc aactg                                          25

<210> SEQ ID NO 482
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 482
tttgtctgcc actggcggag gtctt                                          25

<210> SEQ ID NO 483
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 483
agtcatttgc cacatctaca tttgt                                          25

<210> SEQ ID NO 484
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 484
tttgccacat ctacatttgt ctgcc                                          25

<210> SEQ ID NO 485
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 485
ccggagaagt ttcagggcca agtca                                          25
```

<210> SEQ ID NO 486
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 486
gtatcatctg cagaataatc ccgga                                              25

<210> SEQ ID NO 487
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 487
taatcccgga gaagtttcag ggcca                                              25

<210> SEQ ID NO 488
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 488
ttatcatgtg gacttttctg gtatc                                              25

<210> SEQ ID NO 489
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 489
agaggcattg atattctctg ttatc                                              25

<210> SEQ ID NO 490
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 490
atgtggactt ttctggtatc atctg                                              25

<210> SEQ ID NO 491
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 491
cttttatgaa tgcttctcca agagg                                              25

<210> SEQ ID NO 492
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 492
atattctctg ttatcatgtg gactt                                              25

<210> SEQ ID NO 493
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 493 cataccttt atgaatgctt ctcca                                               25

<210> SEQ ID NO 494
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 494
ctccaagagg cattgatatt ctctg                                              25

<210> SEQ ID NO 495
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 495
taattcatac cttttatgaa tgctt                                              25

<210> SEQ ID NO 496
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 496
cttttatgaa tgcttctcca agagg                                              25

<210> SEQ ID NO 497
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 497
taatgtaatt cataccttt atgaa                                               25

```
<210> SEQ ID NO 498
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 498
agaaataatg taattcatac ctttt                                          25

<210> SEQ ID NO 499
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 499
gttttagaaa taatgtaatt catac                                          25

<210> SEQ ID NO 500
<211> LENGTH: 19
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 500
gatttttatg agaaagaga                                                 19

<210> SEQ ID NO 501
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 501
ctatagattt ttatgagaaa                                                20

<210> SEQ ID NO 502
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 502
aactgctata gatttttatg                                                20

<210> SEQ ID NO 503
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 503
tggccaactg ctatagattt                                                20

<210> SEQ ID NO 504
```

```
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 504
gtctttggcc aactgctata                                               20

<210> SEQ ID NO 505
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 505
cggaggtctt tggccaactg                                               20

<210> SEQ ID NO 506
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 506
tttgtctgcc actggcggag                                               20

<210> SEQ ID NO 507
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 507
tttgccacat ctacatttgt                                               20

<210> SEQ ID NO 508
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 508
ttcagggcca agtcatttgc                                               20

<210> SEQ ID NO 509
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 509
taatcccgga gaagtttcag                                               20

<210> SEQ ID NO 510
<211> LENGTH: 20
```

```
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 510
gtatcatctg cagaataatc                                                   20

<210> SEQ ID NO 511
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 511
atgtggactt ttctggtatc                                                   20

<210> SEQ ID NO 512
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 512
atattctctg ttatcatgtg                                                   20

<210> SEQ ID NO 513
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 513
ctccaagagg cattgatatt                                                   20

<210> SEQ ID NO 514
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 514
cttttatgaa tgcttctcca                                                   20

<210> SEQ ID NO 515
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 515 cataccttttt atgaatgctt                                                  20

<210> SEQ ID NO 516
<211> LENGTH: 20
<212> TYPE: DNA
```

```
<213> ORGANISM: Artificial Sequence
<220> FEATURE:
<223> OTHER INFORMATION: Antisense sequence to target splice site of
      proprocessed human dystrophin

<400> SEQUENCE: 516
taattcatac cttttatgaa                                              20

<210> SEQ ID NO 517
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 517
taatgtaatt cataccttt                                               20

<210> SEQ ID NO 518
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 518
agaaataatg taattcatac                                              20

<210> SEQ ID NO 519
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 519
gttttagaaa taatgtaatt                                              20

<210> SEQ ID NO 520
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 520
ctgcaaagga ccaaatgttc agatg                                        25

<210> SEQ ID NO 521
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 521
tcaccctgca aaggaccaaa tgttc                                        25

<210> SEQ ID NO 522
<211> LENGTH: 25
<212> TYPE: DNA
<213> ORGANISM: Artificial Sequence
```

```
<220> FEATURE:
<223> OTHER INFORMATION: Antisense sequence to target splice site of
      proprocessed human dystrophin

<400> SEQUENCE: 522
ctcactcacc ctgcaaagga ccaaa                                         25

<210> SEQ ID NO 523
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 523
tctcgctcac tcaccctgca aagga                                         25

<210> SEQ ID NO 524
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 524
cagcctctcg ctcactcacc ctgca                                         25

<210> SEQ ID NO 525
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 525
caaagcagcc tctcgctcac tcacc                                         25

<210> SEQ ID NO 526
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 526
tcttccaaag cagcctctcg ctcac                                         25

<210> SEQ ID NO 527
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 527
tctatgagtt tcttccaaag cagcc                                         25

<210> SEQ ID NO 528
<211> LENGTH: 25
<212> TYPE: DNA
<213> ORGANISM: Artificial Sequence
<220> FEATURE:
```

```
<223> OTHER INFORMATION: Antisense sequence to target splice site of
      proprocessed human dystrophin

<400> SEQUENCE: 528
gttgcagtaa tctatgagtt tcttc                                              25

<210> SEQ ID NO 529
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 529
gaactgttgc agtaatctat gagtt                                              25

<210> SEQ ID NO 530
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 530
ttccaggtcc aggggggaact gttgc                                             25

<210> SEQ ID NO 531
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 531
gtaagccagg caagaaactt ttcca                                              25

<210> SEQ ID NO 532
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 532
ccaggcaaga aacttttcca ggtcc                                              25

<210> SEQ ID NO 533
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 533
tggcagttgt ttcagcttct gtaag                                              25

<210> SEQ ID NO 534
<211> LENGTH: 25
<212> TYPE: DNA
<213> ORGANISM: Artificial Sequence
<220> FEATURE:
<223> OTHER INFORMATION: Antisense sequence to target splice site of
``` proprocessed human dystrophin

<400> SEQUENCE: 534
ggtagcatcc tgtaggacat tggca                                              25

<210> SEQ ID NO 535
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 535
gacattggca gttgtttcag cttct                                              25

<210> SEQ ID NO 536
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 536
tctaggagcc tttccttacg ggtag                                              25

<210> SEQ ID NO 537
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 537
cttttactcc cttggagtct tctag                                              25

<210> SEQ ID NO 538
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 538
gagcctttcc ttacgggtag catcc                                              25

<210> SEQ ID NO 539
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 539
ttgccattgt ttcatcagct ctttt                                              25

<210> SEQ ID NO 540
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

```
<400> SEQUENCE: 540
cttggagtct tctaggagcc tttcc                                          25

<210> SEQ ID NO 541
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 541
cttacttgcc attgtttcat cagct                                          25

<210> SEQ ID NO 542
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 542
cagctctttt actcccttgg agtct                                          25

<210> SEQ ID NO 543
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 543
cctgacttac ttgccattgt ttcat                                          25

<210> SEQ ID NO 544
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 544
aaatgcctga cttacttgcc attgt                                          25

<210> SEQ ID NO 545
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 545
agcggaaatg cctgacttac ttgcc                                          25

<210> SEQ ID NO 546
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin
```

```
<400> SEQUENCE: 546
gctaaagcgg aaatgcctga cttac                                          25

<210> SEQ ID NO 547
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 547
aaggaccaaa tgttcagatg                                                20

<210> SEQ ID NO 548
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 548
ctgcaaagga ccaaatgttc                                                20

<210> SEQ ID NO 549
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 549
tcaccctgca aaggaccaaa                                                20

<210> SEQ ID NO 550
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 550
ctcactcacc ctgcaaagga                                                20

<210> SEQ ID NO 551
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 551
tctcgctcac tcaccctgca                                                20

<210> SEQ ID NO 552
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 552
```

```
cagcctctcg ctcactcacc                                           20
```

<210> SEQ ID NO 553
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 553

```
caaagcagcc tctcgctcac                                           20
```

<210> SEQ ID NO 554
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 554

```
tctatgagtt tcttccaaag                                           20
```

<210> SEQ ID NO 555
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 555

```
gaactgttgc agtaatctat                                           20
```

<210> SEQ ID NO 556
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 556

```
ttccaggtcc aggggaact                                            20
```

<210> SEQ ID NO 557
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 557

```
ccaggcaaga aacttttcca                                           20
```

<210> SEQ ID NO 558
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 558
ttcagcttct gtaagccagg                                              20

<210> SEQ ID NO 559
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 559
gacattggca gttgtttcag                                              20

<210> SEQ ID NO 560
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 560
ggtagcatcc tgtaggacat                                              20

<210> SEQ ID NO 561
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 561
gagcctttcc ttacgggtag                                              20

<210> SEQ ID NO 562
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 562
cttggagtct tctaggagcc                                              20

<210> SEQ ID NO 563
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 563
cagctctttt actcccttgg                                              20

<210> SEQ ID NO 564
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 564
ttgccattgt ttcatcagct                                              20

<210> SEQ ID NO 565
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 565
cttacttgcc attgtttcat                                           20

<210> SEQ ID NO 566
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 566
cctgacttac ttgccattgt                                           20

<210> SEQ ID NO 567
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 567
aaatgcctga cttacttgcc                                           20

<210> SEQ ID NO 568
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 568
agcggaaatg cctgacttac                                           20

<210> SEQ ID NO 569
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 569
gctaaagcgg aaatgcctga                                           20

<210> SEQ ID NO 570
<211> LENGTH: 10
<212> TYPE: PRT
<213> ORGANISM: Artificial Sequence
<220> FEATURE:
<223> OTHER INFORMATION: Peptide Transporter for Intracellular Delivery
      of PMO

<400> SEQUENCE: 570

Arg Arg Arg Gln Arg Arg Lys Lys Arg Cys
 1               5                  10

```
<210> SEQ ID NO 571
<211> LENGTH: 12
<212> TYPE: PRT
<213> ORGANISM: Artificial Sequence
<220> FEATURE:
<223> OTHER INFORMATION: Peptide Transporter for Intracellular Delivery
      of PMO

<400> SEQUENCE: 571

Arg Arg Arg Arg Arg Arg Arg Arg Arg Phe Phe Cys
1               5                   10

<210> SEQ ID NO 572
<211> LENGTH: 13
<212> TYPE: PRT
<213> ORGANISM: Artificial Sequence
<220> FEATURE:
<223> OTHER INFORMATION: Peptide Transporter for Intracellular Delivery
      of PMO
<220> FEATURE:
<221> NAME/KEY: MOD_RES
<222> LOCATION: 3, 6, 9, 12
<223> OTHER INFORMATION: X = 6-aminohexanoic acid
<220> FEATURE:
<221> NAME/KEY: MOD_RES
<222> LOCATION: 13
<223> OTHER INFORMATION: X = beta alanine

<400> SEQUENCE: 572

Arg Arg Xaa Arg Arg Xaa Arg Arg Xaa Arg Arg Xaa Xaa
1               5                   10

<210> SEQ ID NO 573
<211> LENGTH: 14
<212> TYPE: PRT
<213> ORGANISM: Artificial Sequence
<220> FEATURE:
<223> OTHER INFORMATION: Peptide Transporter for Intracellular Delivery
      of PMO
<220> FEATURE:
<221> NAME/KEY: MOD_RES
<222> LOCATION: 2, 5, 8, 11, 13
<223> OTHER INFORMATION: X = 6-aminohexanoic acid
<220> FEATURE:
<221> NAME/KEY: MOD_RES
<222> LOCATION: 14
<223> OTHER INFORMATION: X = beta alanine

<400> SEQUENCE: 573

Arg Xaa Arg Arg Xaa Arg Arg Xaa Arg Arg Xaa Arg Xaa Xaa
1               5                   10

<210> SEQ ID NO 574
<211> LENGTH: 14
<212> TYPE: PRT
<213> ORGANISM: Artificial Sequence
<220> FEATURE:
<223> OTHER INFORMATION: Peptide Transporter for Intracellular Delivery
      of PMO
<220> FEATURE:
<221> NAME/KEY: MOD_RES
<222> LOCATION: 1, 4, 7, 10, 13
<223> OTHER INFORMATION: X = 6-aminohexanoic acid
<220> FEATURE:
<221> NAME/KEY: MOD_RES
<222> LOCATION: 14
<223> OTHER INFORMATION: X = beta alanine

<400> SEQUENCE: 574

Xaa Arg Arg Xaa Arg Arg Xaa Arg Arg Xaa Arg Arg Xaa Xaa
```

```
1               5               10
```

<210> SEQ ID NO 575
<211> LENGTH: 13
<212> TYPE: PRT
<213> ORGANISM: Artificial Sequence
<220> FEATURE:
<223> OTHER INFORMATION: Peptide Transporter for Intracellular Delivery
      of PMO
<220> FEATURE:
<221> NAME/KEY: MOD_RES
<222> LOCATION: 2, 4, 6, 8, 10, 12
<223> OTHER INFORMATION: X = 6-aminohexanoic acid
<220> FEATURE:
<221> NAME/KEY: MOD_RES
<222> LOCATION: 13
<223> OTHER INFORMATION: X = beta alanine

<400> SEQUENCE: 575

```
Arg Xaa Arg Xaa Arg Xaa Arg Xaa Arg Xaa Arg Xaa Xaa
1               5                   10
```

<210> SEQ ID NO 576
<211> LENGTH: 17
<212> TYPE: PRT
<213> ORGANISM: Artificial Sequence
<220> FEATURE:
<223> OTHER INFORMATION: Peptide Transporter for Intracellular Delivery
      of PMO
<220> FEATURE:
<221> NAME/KEY: MOD_RES
<222> LOCATION: 2, 4, 6, 8, 10, 12, 14, 16
<223> OTHER INFORMATION: X = 6-aminohexanoic acid
<220> FEATURE:
<221> NAME/KEY: MOD_RES
<222> LOCATION: 17
<223> OTHER INFORMATION: X = beta alanine

<400> SEQUENCE: 576

```
Arg Xaa Arg Xaa Arg Xaa Arg Xaa Arg Xaa Arg Xaa Arg Xaa Arg Xaa
1               5                   10                  15

Xaa
```

<210> SEQ ID NO 577
<211> LENGTH: 17
<212> TYPE: PRT
<213> ORGANISM: Artificial Sequence
<220> FEATURE:
<223> OTHER INFORMATION: Peptide Transporter for Intracellular Delivery
      of PMO
<220> FEATURE:
<221> NAME/KEY: MOD_RES
<222> LOCATION: 2, 5, 8, 11, 14, 16
<223> OTHER INFORMATION: X = 6-aminohexanoic acid
<220> FEATURE:
<221> NAME/KEY: MOD_RES
<222> LOCATION: 17
<223> OTHER INFORMATION: X = beta alanine

<400> SEQUENCE: 577

```
Arg Xaa Arg Arg Xaa Arg Arg Xaa Arg Arg Xaa Arg Arg Xaa Arg Xaa
1               5                   10                  15

Xaa
```

<210> SEQ ID NO 578
<211> LENGTH: 14
<212> TYPE: PRT
<213> ORGANISM: Artificial Sequence
<220> FEATURE:
<223> OTHER INFORMATION: Peptide Transporter for Intracellular Delivery

```
        of PMO
<220> FEATURE:
<221> NAME/KEY: MOD_RES
<222> LOCATION: 2, 8, 13
<223> OTHER INFORMATION: X = 6-aminohexanoic acid
<220> FEATURE:
<221> NAME/KEY: MOD_RES
<222> LOCATION: 5, 11, 14
<223> OTHER INFORMATION: X = beta alanine

<400> SEQUENCE: 578

Arg Xaa Arg Arg Xaa Arg Arg Xaa Arg Arg Xaa Arg Xaa Xaa
 1               5                  10

<210> SEQ ID NO 579
<211> LENGTH: 7
<212> TYPE: PRT
<213> ORGANISM: Artificial Sequence
<220> FEATURE:
<223> OTHER INFORMATION: Peptide Transporter for Intracellular Delivery
      of PMO

<400> SEQUENCE: 579

Ala Ser Ser Leu Asn Ile Ala
 1               5

<210> SEQ ID NO 580
<211> LENGTH: 9
<212> TYPE: PRT
<213> ORGANISM: Artificial Sequence
<220> FEATURE:
<223> OTHER INFORMATION: Cell Penetrating Peptide / Homing Peptide / PMO
      Conjugates
<220> FEATURE:
<221> NAME/KEY: MOD_RES
<222> LOCATION: 8
<223> OTHER INFORMATION: X = a neutral amino acid C(=O) (CHR)n NH-,
      where n is 2 to 7 and each R is independently H or methyl
<220> FEATURE:
<221> NAME/KEY: MOD_RES
<222> LOCATION: 9
<223> OTHER INFORMATION: X = Beta alanine

<400> SEQUENCE: 580

Ala Ser Ser Leu Asn Ile Ala Xaa Xaa
 1               5

<210> SEQ ID NO 581
<211> LENGTH: 22
<212> TYPE: PRT
<213> ORGANISM: Artificial Sequence
<220> FEATURE:
<223> OTHER INFORMATION: Cell Penetrating Peptide / Homing Peptide / PMO
      Conjugates
<220> FEATURE:
<221> NAME/KEY: MOD_RES
<222> LOCATION: 2, 8, 13, 22
<223> OTHER INFORMATION: X = a neutral amino acid C(=O) (CHR)n NH-,
      where n is 2 to 7 and each R is independently H or methyl
<220> FEATURE:
<221> NAME/KEY: MOD_RES
<222> LOCATION: 5, 11, 14
<223> OTHER INFORMATION: X = beta alanine

<400> SEQUENCE: 581

Arg Xaa Arg Arg Xaa Arg Arg Xaa Arg Arg Xaa Arg Xaa Xaa Ala Ser
 1               5                  10                  15

Ser Leu Asn Ile Ala Xaa
            20
```

```
<210> SEQ ID NO 582
<211> LENGTH: 21
<212> TYPE: PRT
<213> ORGANISM: Artificial Sequence
<220> FEATURE:
<223> OTHER INFORMATION: Cell Penetrating Peptide / Homing Peptide / PMO
      Conjugates
<220> FEATURE:
<221> NAME/KEY: MOD_RES
<222> LOCATION: 8, 10, 16
<223> OTHER INFORMATION: X = a neutral amino acid C(=O) (CHR)n NH-,
      where n is 2 to 7 and each R is independently H or methyl
<220> FEATURE:
<221> NAME/KEY: MOD_RES
<222> LOCATION: 13, 19, 21
<223> OTHER INFORMATION: Xaa = beta alanine

<400> SEQUENCE: 582

Ala Ser Ser Leu Asn Ile Ala Xaa Arg Xaa Arg Arg Xaa Arg Xaa
 1               5                  10                  15

Arg Arg Xaa Arg Xaa
            20

<210> SEQ ID NO 583
<211> LENGTH: 14
<212> TYPE: PRT
<213> ORGANISM: Artificial Sequence
<220> FEATURE:
<223> OTHER INFORMATION: Cell Penetrating Peptide / Homing Peptide / PMO
      Conjugates
<220> FEATURE:
<221> NAME/KEY: MOD_RES
<222> LOCATION: 2, 8, 13
<223> OTHER INFORMATION: X = a neutral amino acid C(=O) (CHR)n NH-,
      where n is 2 to 7 and each R is independently H or methyl
<220> FEATURE:
<221> NAME/KEY: MOD_RES
<222> LOCATION: 5, 11, 14
<223> OTHER INFORMATION: X = beta alanine

<400> SEQUENCE: 583

Arg Xaa Arg Arg Xaa Arg Arg Xaa Arg Arg Xaa Arg Xaa Xaa
 1               5                  10

<210> SEQ ID NO 584
<211> LENGTH: 29
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 584
ccactcagag ctcagatctt ctaacttcc                                    29

<210> SEQ ID NO 585
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 585
gggatccagt atacttacag gctcc                                        25

<210> SEQ ID NO 586
<211> LENGTH: 27
<212> TYPE: DNA
<213> ORGANISM: Artificial Sequence
```

```
<220> FEATURE:
<223> OTHER INFORMATION: Antisense sequence to target splice site of
      proprocessed human dystrophin

<400> SEQUENCE: 586
cttccactca gagctcagat cttctaa                                            27

<210> SEQ ID NO 587
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 587
acatcaagga agatggcatt tctagtttgg                                         30

<210> SEQ ID NO 588
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 588
ctccaacatc aaggaagatg gcatttctag                                         30

<210> SEQ ID NO 589
<211> LENGTH: 24
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 589
ttctgtccaa gcccggttga aatc                                               24

<210> SEQ ID NO 590
<211> LENGTH: 21
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 590
cacccaccat caccctcygt g                                                  21

<210> SEQ ID NO 591
<211> LENGTH: 22
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 591
atcatctcgt tgatatcctc aa                                                 22

<210> SEQ ID NO 592
<211> LENGTH: 25
<212> TYPE: DNA
<213> ORGANISM: Artificial Sequence
<220> FEATURE:
```

```
<223> OTHER INFORMATION: Antisense sequence to target splice site of
      proprocessed human dystrophin

<400> SEQUENCE: 592
acatcaagga agatggcatt tctag                                           25

<210> SEQ ID NO 593
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 593
accagagtaa cagtctgagt aggagc                                          26

<210> SEQ ID NO 594
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 594
tcaaggaaga tggcatttct                                                 20

<210> SEQ ID NO 595
<211> LENGTH: 23
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 595
cctctgtgat tttataactt gat                                             23

<210> SEQ ID NO 596
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 596
atcatttttt ctcataccttt ctgct                                          25

<210> SEQ ID NO 597
<211> LENGTH: 23
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 597 ctcataccttt ctgcttgatg atc                                            23

<210> SEQ ID NO 598
<211> LENGTH: 17
<212> TYPE: DNA
<213> ORGANISM: Artificial Sequence
<220> FEATURE:
<223> OTHER INFORMATION: Antisense sequence to target splice site of
```

-continued proprocessed human dystrophin

<400> SEQUENCE: 598
tggcatttct agtttgg                                                  17

<210> SEQ ID NO 599
<211> LENGTH: 23
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 599
ccagagcagg tacctccaac atc                                           23

<210> SEQ ID NO 600
<211> LENGTH: 24
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 600
tgttcagctt ctgttagcca ctga                                          24

<210> SEQ ID NO 601
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 601
tttgtgtctt tctgagaaac                                               20

<210> SEQ ID NO 602
<211> LENGTH: 19
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 602
cgccgccatt tctcaacag                                                19

<210> SEQ ID NO 603
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 603
atctgtcaaa tcgcctgcag                                               20

<210> SEQ ID NO 604
<211> LENGTH: 20
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 604
tgtttttgag gattgctgaa                                              20

<210> SEQ ID NO 605
<211> LENGTH: 19
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 605
gctgaattat ttcttcccc                                               19

<210> SEQ ID NO 606
<211> LENGTH: 17
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 606
gcccaatgcc atcctgg                                                 17

<210> SEQ ID NO 607
<211> LENGTH: 26
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 607
ccaatgccat cctggagttc ctgtaa                                       26

<210> SEQ ID NO 608
<211> LENGTH: 31
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 608
cattcaactg ttgcctccgg ttctgaaggt g                                 31

<210> SEQ ID NO 609
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 609
ctgaaggtgt tcttgtactt catcc                                        25

<210> SEQ ID NO 610
<211> LENGTH: 18
<212> TYPE: DNA
<213> ORGANISM: Artificial Sequence
<220> FEATURE:
<223> OTHER INFORMATION: Antisense sequence to target splice site of
      proprocessed human dystrophin

```
<400> SEQUENCE: 610
ctgttgcctc cggttctg                                                    18

<210> SEQ ID NO 611
<211> LENGTH: 22
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 611
attctttcaa ctagaataaa ag                                               22

<210> SEQ ID NO 612
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 612
gccatcctgg agttcctgta agataccaaa                                       30

<210> SEQ ID NO 613
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 613
ccaatgccat cctggagttc ctgtaagata                                       30

<210> SEQ ID NO 614
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 614
gccgctgccc aatgccatcc tggagttcct                                       30

<210> SEQ ID NO 615
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 615
gtttgccgct gcccaatgcc atcctggagt                                       30

<210> SEQ ID NO 616
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 616
```
caacagtttg ccgctgccca atgccatcct                                    30

<210> SEQ ID NO 617
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 617
ctgacaacag tttgccgctg cccaatgcca                                    30

<210> SEQ ID NO 618
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 618
tgttctgaca acagtttgcc gctgcccaat                                    30

<210> SEQ ID NO 619
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 619
caatgttctg acaacagttt gccgctgccc                                    30

<210> SEQ ID NO 620
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 620
cattcaatgt tctgacaaca gtttgccgct                                    30

<210> SEQ ID NO 621
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 621
tatttcttcc ccagttgcat tcaatgttct                                    30

<210> SEQ ID NO 622
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 622

```
gctgaattat tcttcccca gttgcattca                                              30

<210> SEQ ID NO 623
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 623
ggattgctga attatttctt ccccagttgc                                             30

<210> SEQ ID NO 624
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 624
tttgaggatt gctgaattat tcttcccca                                              30

<210> SEQ ID NO 625
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 625
gtacttcatc ccactgattc tgaattcttt                                             30

<210> SEQ ID NO 626
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 626
tcttgtactt catcccactg attctgaatt                                             30

<210> SEQ ID NO 627
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 627
tgttcttgta cttcatccca ctgattctga                                             30

<210> SEQ ID NO 628
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 628
cggttctgaa ggtgttcttg tacttcatcc                                             30
```

<210> SEQ ID NO 629
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 629
ctccggttct gaaggtgttc ttgtacttca                                         30

<210> SEQ ID NO 630
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 630
tgcctccggt tctgaaggtg ttcttgtact                                         30

<210> SEQ ID NO 631
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 631
tgttgcctcc ggttctgaag gtgttcttgt                                         30

<210> SEQ ID NO 632
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 632
aactgttgcc tccggttctg aaggtgttct                                         30

<210> SEQ ID NO 633
<211> LENGTH: 30
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 633
ttcaactgtt gcctccggtt ctgaaggtgt                                         30

<210> SEQ ID NO 634
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 634
taaagctctg gaaacctgaa aggaa                                              25

```
<210> SEQ ID NO 635
<211> LENGTH: 25
<212> TYPE: DNA
<213> ORGANISM: Artificial Sequence
<220> FEATURE:
<223> OTHER INFORMATION: Antisense sequence to target splice site of
      proprocessed human dystrophin

<400> SEQUENCE: 635
ttcagcttct gtaagccagg caaga                                          25

<210> SEQ ID NO 636
<211> LENGTH: 25
<212> TYPE: DNA
<213> ORGANISM: Artificial Sequence
<220> FEATURE:
<223> OTHER INFORMATION: Antisense oligomer

<400> SEQUENCE: 636
ggccaaacct cggcttacct gaaat                                          25

<210> SEQ ID NO 637
<211> LENGTH: 12
<212> TYPE: PRT
<213> ORGANISM: Artificial Sequence
<220> FEATURE:
<223> OTHER INFORMATION: arginine-rich peptide transport
<220> FEATURE:
<221> NAME/KEY: VARIANT
<222> LOCATION: 1, 3, 4, 7, 9, 10
<223> OTHER INFORMATION: Xaa = K, R or arginine analog
<220> FEATURE:
<221> NAME/KEY: MOD_RES
<222> LOCATION: 2, 8
<223> OTHER INFORMATION: Xaa = a neutral amino acid C(=O) (CHR)n NH-,
      where n is 2 to 7 and each R is independently H or methyl
<220> FEATURE:
<221> NAME/KEY: VARIANT
<222> LOCATION: 5, 6, 11, 12
<223> OTHER INFORMATION: Xaa = an alpha-amino acid having a neutral
      aralkyl side chain

<400> SEQUENCE: 637

Xaa Xaa Xaa Xaa Xaa Xaa Xaa Xaa Xaa Xaa Xaa Xaa
 1               5                  10

<210> SEQ ID NO 638
<211> LENGTH: 12
<212> TYPE: PRT
<213> ORGANISM: Artificial Sequence
<220> FEATURE:
<223> OTHER INFORMATION: arginine-rich peptide transport
<220> FEATURE:
<221> NAME/KEY: MOD_RES
<222> LOCATION: 2, 6, 8, 12
<223> OTHER INFORMATION: Xaa = a neutral amino acid C(=O) (CHR)n NH-,
      where n is 2 to 7 and each R is independently H or methyl

<400> SEQUENCE: 638

Arg Xaa Arg Arg Arg Xaa Arg Xaa Arg Arg Arg Xaa
 1               5                  10

<210> SEQ ID NO 639
<211> LENGTH: 9
<212> TYPE: PRT
<213> ORGANISM: Artificial Sequence
<220> FEATURE:
<223> OTHER INFORMATION: arginine-rich peptide transport
<220> FEATURE:
<221> NAME/KEY: MOD_RES
```

```
<222> LOCATION: 3, 5, 9
<223> OTHER INFORMATION: Xaa = a neutral amino acid C(=O) (CHR)n NH-,
      where n is 2 to 7 and each R is independently H or methyl

<400> SEQUENCE: 639

Arg Arg Xaa Arg Xaa Arg Arg Arg Xaa
 1               5

<210> SEQ ID NO 640
<211> LENGTH: 24
<212> TYPE: DNA
<213> ORGANISM: Artificial Sequence
<220> FEATURE:
<223> OTHER INFORMATION: PCR Primer

<400> SEQUENCE: 640
ccagagcttt acctgagaaa caag                                           24

<210> SEQ ID NO 641
<211> LENGTH: 21
<212> TYPE: DNA
<213> ORGANISM: Artificial Sequence
<220> FEATURE:
<223> OTHER INFORMATION: PCR Primer

<400> SEQUENCE: 641
ccagccactc agccagtgaa g                                              21

<210> SEQ ID NO 642
<211> LENGTH: 24
<212> TYPE: DNA
<213> ORGANISM: Artificial Sequence
<220> FEATURE:
<223> OTHER INFORMATION: PCR Primer

<400> SEQUENCE: 642
cgatccgtaa tgattgttct agcc                                           24

<210> SEQ ID NO 643
<211> LENGTH: 24
<212> TYPE: DNA
<213> ORGANISM: Artificial Sequence
<220> FEATURE:
<223> OTHER INFORMATION: PCR Primer

<400> SEQUENCE: 643
catttcattc aactgttgcc tccg                                           24

<210> SEQ ID NO 644
<211> LENGTH: 21
<212> TYPE: DNA
<213> ORGANISM: Artificial Sequence
<220> FEATURE:
<223> OTHER INFORMATION: PCR Primer

<400> SEQUENCE: 644
caatgctcct gacctctgtg c                                              21

<210> SEQ ID NO 645
<211> LENGTH: 22
<212> TYPE: DNA
<213> ORGANISM: Artificial Sequence
<220> FEATURE:
<223> OTHER INFORMATION: PCR Primer

<400> SEQUENCE: 645
```

```
gtctacaaca aagctcaggt cg                                              22

<210> SEQ ID NO 646
<211> LENGTH: 25
<212> TYPE: DNA
<213> ORGANISM: Artificial Sequence
<220> FEATURE:
<223> OTHER INFORMATION: PCR Primer

<400> SEQUENCE: 646
gcaatgttat ctgcttcctc caacc                                           25

<210> SEQ ID NO 647
<211> LENGTH: 22
<212> TYPE: DNA
<213> ORGANISM: Artificial Sequence
<220> FEATURE:
<223> OTHER INFORMATION: PCR Primer

<400> SEQUENCE: 647
gctcttttcc aggttcaagt gg                                              22

<210> SEQ ID NO 648
<211> LENGTH: 23
<212> TYPE: DNA
<213> ORGANISM: Artificial Sequence
<220> FEATURE:
<223> OTHER INFORMATION: PCR Primer

<400> SEQUENCE: 648
cttggacaga acttaccgac tgg                                             23

<210> SEQ ID NO 649
<211> LENGTH: 21
<212> TYPE: DNA
<213> ORGANISM: Artificial Sequence
<220> FEATURE:
<223> OTHER INFORMATION: PCR Primer

<400> SEQUENCE: 649
gcaggatttg gaacagaggc g                                               21

<210> SEQ ID NO 650
<211> LENGTH: 23
<212> TYPE: DNA
<213> ORGANISM: Artificial Sequence
<220> FEATURE:
<223> OTHER INFORMATION: PCR Primer

<400> SEQUENCE: 650
catctacatt tgtctgccac tgg                                             23

<210> SEQ ID NO 651
<211> LENGTH: 23
<212> TYPE: DNA
<213> ORGANISM: Artificial Sequence
<220> FEATURE:
<223> OTHER INFORMATION: PCR Primer

<400> SEQUENCE: 651
gtttcttcca aagcagcctc tcg                                             23
```

MULTIPLE EXON SKIPPING COMPOSITIONS FOR DMD

CROSS-REFERENCE TO RELATED APPLICATION

This application is a continuation of U.S. patent application Ser. No. 14/523,610, filed Oct. 24, 2014, which is a divisional of U.S. patent application Ser. No. 12/605,276, filed Oct. 23, 2009, now issued as U.S. Pat. No. 8,871,918, which claims the benefit of U.S. Provisional Patent Application No. 61/108,416, filed Oct. 24, 2008. The contents of the aforementioned applications are hereby incorporated by reference.

STATEMENT REGARDING SEQUENCE LISTING

The Sequence Listing associated with this application is provided in text format in lieu of a paper copy, and is hereby incorporated by reference into the specification. The name of the text file containing the sequence Listing is AVN009DVCN1_Sequence_Listing.txt. The text file is 157 KB, was created on Sep. 3, 2015 and is being submitted electronically via EFS-Web.

FIELD OF THE INVENTION

The present invention relates to novel antisense compounds and compositions suitable for facilitating exon skipping in the human dystrophin gene. It also provides methods for inducing exon skipping using the antisense compositions adapted for use in the methods of the invention.

BACKGROUND OF THE INVENTION

Antisense technologies are being developed using a range of chemistries to affect gene expression at a variety of different levels (transcription, splicing, stability, translation). Much of that research has focused on the use of antisense compounds to correct or compensate for abnormal or disease-associated genes in a wide range of indications. Antisense molecules are able to inhibit gene expression with specificity, and because of this, many research efforts concerning oligonucleotides as modulators of gene expression have focused on inhibiting the expression of targeted genes or the function of cis-acting elements. The antisense oligonucleotides are typically directed against RNA, either the sense strand (e.g., mRNA) or minus-strand in the case of some viral RNA targets. To achieve a desired effect of specific gene down-regulation, the oligonucleotides generally either promote the decay of the targeted mRNA, block translation of the mRNA or block the function of cis-acting RNA elements thereby effectively preventing either de novo synthesis of the target protein or replication of the viral RNA.

However, such techniques are not useful where the object is to up-regulate production of the native protein or compensate for mutations that induce premature termination of translation such as nonsense or frame-shifting mutations. In these cases, the defective gene transcript should not be subjected to targeted degradation or steric inhibition, so the antisense oligonucleotide chemistry should not promote target mRNA decay or block translation.

In a variety of genetic diseases, the effects of mutations on the eventual expression of a gene can be modulated through a process of targeted exon skipping during the splicing process. The splicing process is directed by complex multi-component machinery that brings adjacent exon-intron junctions in pre-mRNA into close proximity and performs cleavage of phosphodiester bonds at the ends of the introns with their subsequent reformation between exons that are to be spliced together. This complex and highly precise process is mediated by sequence motifs in the pre-mRNA that are relatively short semi-conserved RNA segments to which bind the various nuclear splicing factors that are then involved in the splicing reactions. By changing the way the splicing machinery reads or recognizes the motifs involved in pre-mRNA processing, it is possible to create differentially spliced mRNA molecules. It has now been recognized that the majority of human genes are alternatively spliced during normal gene expression, although the mechanisms involved have not been identified.

In cases where a normally functional protein is prematurely terminated because of mutations therein, a means for restoring some functional protein production through antisense technology has been shown to be possible through intervention during the splicing processes, and that if exons associated with disease-causing mutations can be specifically deleted from some genes, a shortened protein product can sometimes be produced that has similar biological properties of the native protein or has sufficient biological activity to ameliorate the disease caused by mutations associated with the exon (Sierakowska, Sambade et al. 1996; Wilton, Lloyd et al. 1999; van Deutekom, Bremmer-Bout et al. 2001; Lu, Mann et al. 2003; Aartsma-Rus, Janson et al. 2004). Kole et al. (U.S. Pat. Nos. 5,627,274; 5,916,808; 5,976,879; and 5,665,593) disclose methods of combating aberrant splicing using modified antisense oligonucleotide analogs that do not promote decay of the targeted pre-mRNA. Bennett et al (U.S. Pat. No. 6,210,892) describe antisense modulation of wild-type cellular mRNA processing also using antisense oligonucleotide analogs that do not induce RNAse H-mediated cleavage of the target RNA.

The process of targeted exon skipping is likely to be particularly useful in long genes where there are many exons and introns, where there is redundancy in the genetic constitution of the exons or where a protein is able to function without one or more particular exons. Efforts to redirect gene processing for the treatment of genetic diseases associated with truncations caused by mutations in various genes have focused on the use of antisense oligonucleotides that either: (1) fully or partially overlap with the elements involved in the splicing process; or (2) bind to the pre-mRNA at a position sufficiently close to the element to disrupt the binding and function of the splicing factors that would normally mediate a particular splicing reaction which occurs at that element.

Duchenne muscular dystrophy (DMD) is caused by a defect in the expression of the protein dystrophin. The gene encoding the protein contains 79 exons spread out over more than 2 million nucleotides of DNA. Any exonic mutation that changes the reading frame of the exon, or introduces a stop codon, or is characterized by removal of an entire out of frame exon or exons or duplications of one or more exons has the potential to disrupt production of functional dystrophin, resulting in DMD.

A less severe form of muscular dystrophy, Becker muscular dystrophy (BMD) has been found to arise where a mutation, typically a deletion of one or more exons, results in a correct reading frame along the entire dystrophin transcript, such that translation of mRNA into protein is not prematurely terminated. If the joining of the upstream and downstream exons in the processing of a mutated dystrophin pre-mRNA maintains the correct reading frame of the gene, the result is an mRNA coding for a protein with a short internal deletion that retains some activity resulting in a Becker phenotype.

Deletions of an exon or exons which do not alter the reading frame of a dystrophin protein give rise to a BMD phenotype, whereas an exon deletion that causes a frame-shift will give rise to DMD (Monaco, Bertelson et al. 1988). In general, dystrophin mutations including point mutations and exon deletions that change the reading frame and thus interrupt proper protein translation result in DMD. It should also be noted that some BMD and DMD patients have exon deletions covering multiple exons.

Although antisense molecules may provide a tool in the treatment of Duchenne Muscular Dystrophy (DMD), attempts to induce exon skipping using antisense molecules have had mixed success. Successful skipping of dystrophin exon 19 from the dystrophin pre-mRNA was achieved using a variety of antisense molecules directed at the flanking splice sites or motifs within the exon involved in exon definition as described by Errington et al., (Errington, Mann et al. 2003).

The first example of specific and reproducible exon skipping in the mdx mouse model was reported by Wilton et al (Wilton, Lloyd et al. 1999). By directing an antisense molecule to the donor splice site, exon 23 skipping was induced in the dystrophin mRNA within 6 hours of treatment of the cultured cells. Wilton et al also describe targeting the acceptor region of the mouse dystrophin pre-mRNA with longer antisense oligonucleotides. While the first antisense oligonucleotide directed at the intron 23 donor splice site induced exon skipping in primary cultured myoblasts, this compound was found to be much less efficient in immortalized cell cultures expressing higher levels of dystrophin.

Despite these efforts, there remains a need for improved antisense oligomers targeted to multiple dystrophin exons and improved muscle delivery compositions and methods for DMD therapeutic applications.

BRIEF SUMMARY OF THE INVENTION

Embodiments of the present invention relate generally to antisense compounds capable of binding to a selected target to induce exon skipping, and methods of use thereof to induce exon skipping. In certain embodiments, it is possible to combine two or more antisense oligonucleotides of the present invention together to induce single or multiple exon skipping.

In certain embodiments, it is possible to improve exon skipping of a single or multiple exons by covalently linking together two or more antisense oligonucleotide molecules (see, e.g., Aartsma-Rus, Janson et al. 2004).

In certain embodiments, the antisense compounds of the present invention induce exon skipping in the human dystrophin gene, and thereby allow muscle cells to produce a functional dystrophin protein.

The antisense oligonucleotide compounds (also referred to herein as oligomers) of the present invention typically: (i) comprise morpholino subunits and phosphorus-containing intersubunit linkages joining a morpholino nitrogen of one subunit to a 5' exocyclic carbon of an adjacent subunit, (ii) contain between 10-40 nucleotide bases, preferably 20-35 bases (iii) comprise a base sequence effective to hybridize to at least 12 contiguous bases of a target sequence in dystrophin pre-mRNA and induce exon skipping.

In certain embodiments, the antisense compounds of the present invention may comprise phosphorus-containing intersubunit linkages joining a morpholino nitrogen of one subunit to a 5' exocyclic carbon of an adjacent subunit, in accordance with the following structure (I):

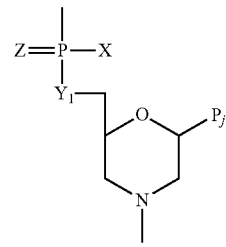

wherein:

$Y_1$ is —O—, —S—, —NH—, or —CH$_2$—;

Z is O or S;

Pj is a purine or pyrimidine base-pairing moiety effective to bind, by base-specific hydrogen bonding, to a base in a polynucleotide; and X is fluoro, optionally substituted alkyl, optionally substituted alkoxy, optionally substituted thioalkoxy, amino, optionally substituted alkylamino, or optionally substituted heterocyclyl.

In certain embodiments, the above intersubunit linkages, which are uncharged, may be interspersed with linkages that are positively charged at physiological pH, where the total number of positively charged linkages is between 2 and no more than half of the total number of linkages. For example, the positively charged linkages may have the above structure in which X is optionally substituted 1-piperazinyl. In other embodiments, the positively charged linkages may have the above structure in which X is substituted 1-piperazinyl, wherein the 1-piperazinyl is substituted at the 4-position with an optionally substituted alkyl guanidynyl moiety.

Where the antisense compound administered is effective to target a splice site of preprocessed human dystrophin, it may have a base sequence complementary to a target region containing at least 12 contiguous bases in a preprocessed messenger RNA (mRNA) human dystrophin transcript. Exemplary antisense sequences include those identified by SEQ ID NOS: 1 to 569 and 612 to 633.

In certain embodiments, an antisense sequence of the present invention is contained within:
  (a) any of the sequences identified by SEQ ID NOS: 1-20, preferably SEQ ID NOS: 4, 8, 11 and 12, and more preferably SEQ ID NO:12 for use in producing skipping of exon 44 in the processing of human dystrophin pre-processed mRNA;
  (b) any of the sequences identified by SEQ ID NOS: 21-76 and 612 to 624, preferably SEQ ID NOS: 27, 29, 34 and 39, and more preferably SEQ ID NO: 34 for use in producing skipping of exon 45 in the processing of human dystrophin pre-processed mRNA;
  (c) any of the sequences identified by SEQ ID NOS: 77-125, preferably SEQ ID NOS: 21 to 53, and more preferably SEQ ID NOS: 82, 84-87, 90, 96, 98, 99 and 101, for use in producing skipping of exon 46 in the processing of human dystrophin pre-processed mRNA;
  (d) any of the sequences identified by SEQ ID NOS: 126-169, preferably SEQ ID NOS: 126-149, and more preferably SEQ ID NOS: 126, 128-130, 132, 144 and 146-149, for use in producing skipping of exon 47 in the processing of human dystrophin pre-processed mRNA;
  (e) any of the sequences identified by SEQ ID NOS: 170-224 and 634, preferably SEQ ID NOS: 170-201 and 634, and more preferably SEQ ID NOS: 176, 178, 181-183, 194 and 198-201, for use in producing skipping of exon 48 in the processing of human dystrophin pre-processed mRNA;

(f) any of the sequences identified by SEQ ID NOS: 225-266, preferably SEQ ID NOS: 225-248, and more preferably SEQ ID NOS: 227, 229, 234, 236, 237 and 244-248, for use in producing skipping of exon 49 in the processing of human dystrophin pre-processed mRNA;

(g) any of the sequences identified by SEQ ID NOS: 267-308, preferably SEQ ID NOS: 277, 287 and 290, and more preferably SEQ ID NO: 287, for use in producing skipping of exon 50 in the processing of human dystrophin pre-processed mRNA;

(h) any of the sequences identified by SEQ ID NOS: 309-371, preferably SEQ ID NOS: 324, 326 and 327, and more preferably SEQ ID NO: 327 for use in producing skipping of exon 51 in the processing of human dystrophin pre-processed mRNA;

(i) any of the sequences identified by SEQ ID NOS: 372-415, preferably SEQ ID NOS: 372-397, and more preferably SEQ ID NOS: 379-382, 384, 390 and 392-395 for use in producing skipping of exon 52 in the processing of human dystrophin pre-processed mRNA;

(j) any of the sequences identified by SEQ ID NOS: 416-475 and 625-633, preferably SEQ ID NOS: 428, 429 and 431, and more preferably SEQ ID NO: 429, for use in producing skipping of exon 53 in the processing of human dystrophin pre-processed mRNA;

(k) any of the sequences identified by SEQ ID NOS: 476-519, preferably SEQ ID NOS: 476-499, and more preferably SEQ ID NOS: 479-482, 484, 489 and 491-493, for use in producing skipping of exon 54 in the processing of human dystrophin pre-processed mRNA; and (l) any of the sequences identified by SEQ ID NOS: 520-569 and 635, preferably SEQ ID NOS: 520-546 and 635, and more preferably SEQ ID NOS: 524-528, 537, 539, 540, 542 and 544, for use in producing skipping of exon 55 in the processing of human dystrophin pre-processed mRNA;

In certain embodiments, the compound may be conjugated to an arginine-rich polypeptide effective to promote uptake of the compound into cells. Exemplary peptides include those identified by SEQ ID NOS: 570 to 578, among others described herein.

In one exemplary embodiment, the arginine-rich polypeptide is covalently coupled at its N-terminal or C-terminal residue to the 3' or 5' end of the antisense compound. Also in an exemplary embodiment, the antisense compound is composed of morpholino subunits and phosphorus-containing intersubunit linkages joining a morpholino nitrogen of one subunit to a 5' exocyclic carbon of an adjacent subunit.

In general, the peptide-oligomer conjugate may further comprise a homing peptide which is selective for a selected mammalian tissue, i.e., the same tissue being targeted by the cell-penetrating peptide. The conjugate may be of the form: cell penetrating peptide-homing peptide-antisense oligomer, or, more preferably, of the form: homing peptide-cell penetrating peptide-antisense oligomer. For example, a peptide conjugate compound for use in treating Duchenne muscular dystrophy, as described above, can further comprise a homing peptide which is selective for muscle tissue, such as the peptide having the sequence identified as SEQ ID NO: 579, conjugated to the cell-penetrating peptide. Exemplary conjugates of this type include those represented herein as CP06062-MSP-PMO (cell penetrating peptide-homing peptide-antisense oligomer) and as MSP-CP06062-PMO (homing peptide-cell penetrating peptide-antisense oligomer) (see SEQ ID NOs: 580-583).

In some embodiments, the peptide is conjugated to the oligomer via a linker moiety. In certain embodiments the linker moiety may comprise an optionally substituted piperazynyl moiety. In other embodiments, the linker moiety may further comprise a beta alanine and/or a 6-aminohexanoic acid subunit. In yet other embodiments, the peptide is conjugated directly to the oligomer without a linker moiety.

Conjugation of the peptide to the oligomer may be at any position suitable for forming a covalent bond between the peptide and the oligomer or between the linker moiety and the oligomer. For example, in some embodiments conjugation of the peptide may be at the 3' end of the oligomer. In other embodiments, conjugation of the peptide to the oligomer may be at the 5' end of the oligomer. In yet other embodiments, the peptide may be conjugated to the oligomer through any of the intersubunit linkages.

In some embodiments, the peptide is conjugated to the oligomer at the 5' end of the oligomer. In embodiments comprising phosphorus-containing intersubunit linkages, the peptide may be conjugated to the oligomer via a covalent bond to the phosphorous of the terminal linkage group. Conjugation in this manner may be with or without the linker moiety described above.

In yet other embodiments, the peptide may be conjugated to the oligomer at the 3' end of the oligomer. In some further embodiments, the peptide may be conjugated to the nitrogen atom of the 3' terminal morpholino group of the oligomer. In this respect, the peptide may be conjugated to the oligomer directly or via the linker moiety described above.

In some embodiments, the oligomer may be conjugated to a moiety that enhances the solubility of the oligomer in aqueous medium. In some embodiments, the moiety that enhances solubility of the oligomer in aqueous medium is a polyethyleneglycol. In yet further embodiments, the moiety that enhances solubility of the oligomer in aqueous medium is triethylene glycol. For example, in some embodiments the moiety that enhances solubility in aqueous medium may be conjugated to the oligomer at the 5' end of the oligomer. Conjugation of the moiety that enhances solubility of the oligomer in aqueous medium to the oligomer may be either directly or through the linker moiety described above.

Certain embodiments of the present invention provide antisense molecules selected and or adapted to aid in the prophylactic or therapeutic treatment of a genetic disorder comprising at least an antisense molecule in a form suitable for delivery to a patient.

Certain embodiments of the invention provide methods for treating a patient suffering from a genetic disease wherein there is a mutation in a gene encoding a particular protein and the affect of the mutation can be abrogated by exon skipping, comprising the steps of: (a) selecting an antisense molecule in accordance with the methods described herein; and (b) administering the molecule to a patient in need of such treatment. The present invention also includes the use of purified and isolated antisense oligonucleotides of the invention, for the manufacture of a medicament for treatment of a genetic disease.

Certain embodiments provide a method of treating muscular dystrophy, such as a condition characterized by Duchenne muscular dystrophy, which method comprises administering to a patient in need of treatment an effective amount of an appropriately designed antisense oligonucleotide, as described herein, relevant to the particular genetic lesion in that patient. Further, certain embodiments provide a method for prophylactically treating a patient to prevent or at least minimize muscular dystrophy, including Duchene muscular dystrophy, comprising the step of: administering to the patient an effective amount of an antisense oligonucleotide or a pharmaceutical composition comprising one or more of these biological molecules.

Certain embodiments relate to methods of treating muscular dystrophy in a subject, comprising administering to the subject an effective amount of a substantially uncharged antisense compound containing 20-35 morpholino subunits linked by phosphorus-containing intersubunit linkages joining a morpholino nitrogen of one subunit to a 5' exocyclic carbon of an adjacent subunit, comprising a sequence selected from the group consisting SEQ ID NOS:1 to 569 and 612 to 635, and capable of forming with the complementary mRNA sequence in a dystrophin-gene exon a heteroduplex structure between said compound and mRNA having a Tm of at least 45° C., wherein the exon is selected from the group consisting of exons 44-55.

In certain embodiments, the muscular dystrophy is Duchenne's muscular dystrophy (DMD). In certain embodiments, the muscular dystrophy is Becker muscular dystrophy (BMD).

In certain embodiments, the sequence is selected from the group consisting SEQ ID NOS: 1-20, and the exon is exon 44. In certain embodiments, the sequence is selected from the group consisting SEQ ID NOS: 21-76 and 612 to 624, and the exon is exon 45. In certain embodiments, the sequence is selected from the group consisting SEQ ID NOS: 77-125, and the exon is exon 46. In certain embodiments, the sequence selected from the group consisting SEQ ID NOS: 126-169, and the exon is exon 47.

In certain embodiments, the sequence is selected from the group consisting SEQ ID NOS: 170-224 and 634, and the exon is exon 48. In certain embodiments, the sequence selected from the group consisting SEQ ID NOS: 225-266, and the exon is exon 49.

In certain embodiments, the sequence is selected from the group consisting SEQ ID NOS: 267-308, and the exon is exon 50. In certain embodiments, the sequence is selected from the group consisting SEQ ID NOS: 309-371, and the exon is exon 51.

In certain embodiments, the sequence is selected from the group consisting SEQ ID NOS: 372-415, and the exon is exon 52. In certain embodiments, the sequence is selected from the group consisting SEQ ID NOS: 416-475 and 625-633, and the exon is exon 53. In certain embodiments, the sequence is selected from the group consisting SEQ ID NOS: 476-519, and the exon is exon 54. In certain embodiments, the sequence is selected from the group consisting SEQ ID NOS: 520-569 and 635, and the exon is exon 55. In certain embodiments, the sequence comprises or consists essentially of SEQ ID NO:287.

Certain embodiments provide kits for treating a genetic disease, which kits comprise at least an antisense oligonucleotide of the present invention, packaged in a suitable container and instructions for its use.

These and other objects and features will be more fully understood when the following detailed description of the invention is read in conjunction with the figures.

BRIEF DESCRIPTION OF THE FIGURES

FIG. 2B-C shows the relative activity in cultured human rhabdomyosarcoma (RD) cells and human primary skeletal muscle cells of the three best oligomers selected from the exon 51 scan (SEQ ID NOs: 324, 326 and 327) relative to sequences (AVI-5658; SEQ ID NO: 588 and h51AON1; SEQ ID NO:594) that are effective at inducing exon 51 skipping.

FIG. 3B shows the relative location and activity of antisense sequences selected from the exon 50 scan (SEQ ID NOS: 277, 287, 290 and 291) compared to other sequences (SEQ ID NOS: 584 and 585).

DETAILED DESCRIPTION OF THE INVENTION

Figure 1A:
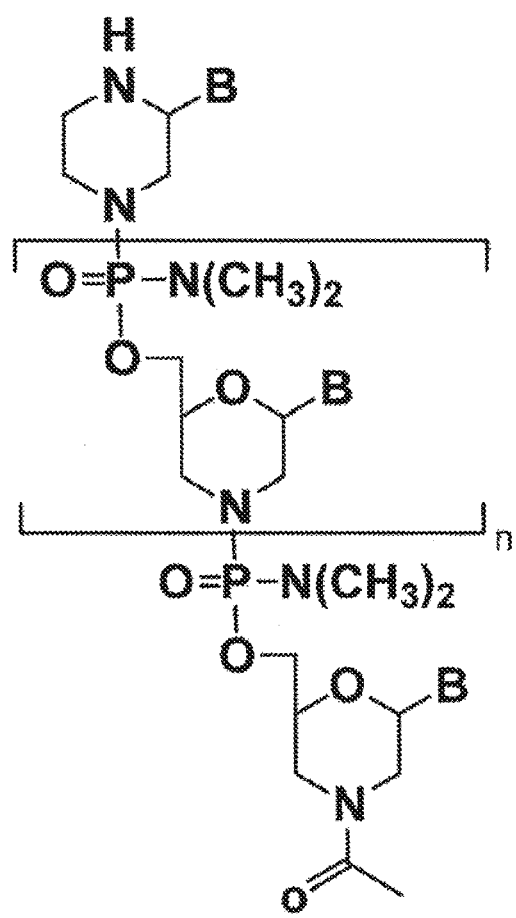
FIG. 1A shows an exemplary morpholino oligomer structure with a phosphorodiamidate linkage.

Embodiments of the present invention relate generally to improved antisense compounds, and methods of use thereof, which are specifically designed to induce exon skipping in the dystrophin gene. Dystrophin plays a vital role in muscle function, and various muscle-related diseases are characterized by mutated forms of this gene. Hence, in certain embodiments, the improved antisense compounds described herein induce exon skipping in mutated forms of the human dystrophin gene, such as the mutated dystrophin genes found in Duchenne's muscular dystrophy (DMD) and Becker's muscular dystrophy (BMD).

Due to aberrant mRNA splicing events caused by mutations, these mutated human dystrophin genes either express defective dystrophin protein or express no measurable dystrophin at all, a condition that leads to various forms of muscular dystrophy. To remedy this condition, the antisense compounds of the present invention typically hybridize to selected regions of a pre-processed RNA of a mutated human dystrophin gene, induce exon skipping and differential splicing in that otherwise aberrantly spliced dystrophin mRNA, and thereby allow muscle cells to produce an mRNA transcript that encodes a functional dystrophin protein. In certain embodiments, the resulting dystrophin protein is not necessarily the "wild-type" form of dystrophin, but is rather a truncated, yet functional or semi-functional, form of dystrophin.

By increasing the levels of functional dystrophin protein in muscle cells, these and related embodiments may be useful in the prophylaxis and treatment of muscular dystrophy, especially those forms of muscular dystrophy, such as DMD and BMD, that are characterized by the expression of defective dystrophin proteins due to aberrant mRNA splicing. The specific oligomers described herein further provide improved, dystrophin-exon-specific targeting over other oligomers in use, and thereby offer significant and practical advantages over alternate methods of treating relevant forms of muscular dystrophy.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

DEFINITIONS

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5' and/or 3' terminus.

The terms "cell penetrating peptide" or "CPP" are used interchangeably and refer to cationic cell penetrating peptides, also called transport peptides, carrier peptides, or peptide transduction domains. The peptides, as shown herein, have the capability of inducing cell penetration within 30%, 40%, 50%, 60%, 70%, 80%, 90%, or 100% of cells of a given cell culture population, including all integers in between, and allow macromolecular translocation within multiple tissues in vivo upon systemic administration.

The terms "antisense oligomer" or "antisense compound" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid: oligomer heteroduplex within the target sequence. The cyclic subunits are based on ribose or another pentose sugar or, in a preferred embodiment, a morpholino group (see description of morpholino oligomers below).

Such an antisense oligomer can be designed to block or inhibit translation of mRNA or to inhibit natural pre-mRNA splice processing, and may be said to be "directed to" or "targeted against" a target sequence with which it hybridizes.

In certain embodiments, the target sequence includes a region including an AUG start codon of an mRNA, a 3' or 5' splice site of a pre-processed mRNA, or a branch point. The target sequence may be within an exon or within an intron. The target sequence for a splice site may include an mRNA sequence having its 5' end 1 to about 25 base pairs downstream of a normal splice acceptor junction in a preprocessed mRNA. A preferred target sequence for a splice is any region of a preprocessed mRNA that includes a splice site or is contained entirely within an exon coding sequence or spans a splice acceptor or donor site. An oligomer is more generally said to be "targeted against" a biologically relevant target, such as a protein, virus, or bacteria, when it is targeted against the nucleic acid of the target in the manner described above. Included are antisense oligomers that comprise, consist essentially of, or consist of one or more of SEQ ID NOS:1 to 569 and 612 to 635. Also included are variants of these antisense oligomers, including variant oligomers having 80%, 85%, 90%, 95%, 97%, 98%, or 99% (including all integers in between) sequence identity or sequence homology to any one of SEQ ID NOS:1 to 569 and 612 to 635, and/or variants that differ from these sequences by about 1, 2, 3, 4, 5, 6, 7, 8, 9, or 10 nucleotides, preferably those variants that induce exon skipping of one or more selected human dystrophin exons. Also included are oligomers of any on or more of SEQ ID NOS:584-611 and 634-635, which comprise a suitable number of charged linkages, as described herein, e.g. up to about 1 per every 2-5 uncharged linkages, such as about 4-5 per every 10 uncharged linkages, and/or which comprise an Arg-rich peptide attached thereto, as also described herein.

The terms "morpholino oligomer" or "PMO" (phosphoramidate- or phosphorodiamidate morpholino oligomer) refer to an oligonucleotide analog composed of morpholino subunit structures, where (i) the structures are linked together by phosphorus-containing linkages, one to three atoms long, preferably two atoms long, and preferably uncharged or cat-ionic, joining the morpholino nitrogen of one subunit to a 5' exocyclic carbon of an adjacent subunit, and (ii) each morpholino ring bears a purine or pyrimidine base-pairing moiety effective to bind, by base specific hydrogen bonding, to a base in a polynucleotide. See, e.g., the structure in FIG. 1A, which shows a preferred phosphorodiamidate linkage type. Variations can be made to this linkage as long as they do not interfere with binding or activity. For example, the oxygen attached to phosphorus may be substituted with sulfur (thio-phosphorodiamidate). The 5' oxygen may be substituted with amino or lower alkyl substituted amino. The pendant nitrogen attached to phosphorus may be unsubstituted, monosubstituted, or disubstituted with (optionally substituted) lower alkyl. See also the discussion of cationic linkages below. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, and PCT Appn. No. PCT/US07/11435 (cationic linkages), all of which are incorporated herein by reference.

The purine or pyrimidine base pairing moiety is typically adenine, cytosine, guanine, uracil, thymine or inosine. Also included are bases such as pyridin-4-one, pyridin-2-one, phenyl, pseudouracil, 2,4,6-trime115thoxy benzene, 3-methyl uracil, dihydrouridine, naphthyl, aminophenyl, 5-alkylcy-tidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluri-dine), propyne, quesosine, 2-thiouridine, 4-thiouridine, wybutosine, wybutoxosine, 4-acetyltidine, 5-(carboxyhy-droxymethyl)uridine, 5"-carboxymethylaminomethyl-2-thiouridine, 5-carboxymethylaminomethyluridine, β-D-ga-lactosylqueosine, 1-methyladenosine, 1-methylinosine, 2,2-dimethylguanosine, 3-methylcytidine, 2-methyladenosine, 2-methylguanosine, N6-methyladenosine, 7-methylgua-nosine, 5-methoxyaminomethyl-2-thiouridine, 5-methy-laminomethyluridine, 5-methylcarbonyhnethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine (A), guanine (G), cytosine (C), thymine (T), and uracil (U), as illustrated above; such bases can be used at any position in the antisense molecule. Persons skilled in the art will appreciate that depending on the uses of the oligomers, Ts and Us are interchangeable. For instance, with other antisense chemistries such as 2'-O-methyl antisense oligonucleotides that are more RNA-like, the T bases may be shown as U (see, e.g., Sequencce ID Listing).

An "amino acid subunit" or "amino acid residue" can refer to an α-amino acid residue (e.g., —CO—CHR—NH—) or a 13- or other amino acid residue (e.g., —CO—$(CH_2)_n$CHR—NH—), where R is a side chain (which may include hydrogen) and n is 1 to 6, preferably 1 to 4.

The term "naturally occurring amino acid" refers to an amino acid present in proteins found in nature, such as the 20 (L)-amino acids utilized during protein biosynthesis as well as others such as 4-hydroxyproline, hydroxylysine, desmo-sine, isodesmosine, homocysteine, citrulline and ornithine. The term "non-natural amino acids" refers to those amino acids not present in proteins found in nature, examples include beta-alanine (β-Ala; or B), 6-aminohexanoic acid (Ahx) and 6-aminopentanoic acid. Additional examples of "non-natural amino acids" include, without limitation, (D)-amino acids, norleucine, norvaline, p-fluorophenylalanine, ethionine and the like, which are known to a person skilled in the art.

An "effective amount" or "therapeutically effective amount" refers to an amount of therapeutic compound, such as an antisense oligomer, administered to a mammalian subject, either as a single dose or as part of a series of doses, which is effective to produce a desired physiological response or therapeutic effect in the subject. One example of a desired physiological response includes increased expression of a relatively functional or biologically active form of the dystrophin protein, mainly in muscle tissues or cells that contain a defective dystrophin protein or no dystrophin, as compared no antisense oligomer or a control oligomer. Examples of desired therapeutic effects include, without limitation, improvements in the symptoms or pathology of muscular dystrophy, reducing the progression of symptoms or pathology of muscular dystrophy, and slowing the onset of symptoms or pathology of muscular dystrophy, among others. Examples of such symptoms include fatigue, mental retardation, muscle weakness, difficulty with motor skills (e.g., running, hopping, jumping), frequent falls, and difficulty walking. The pathology of muscular dystrophy can be characterized, for example, by muscle fibre damage and membrane leakage. For an antisense oligomer, this effect is typically brought about by altering the splice-processing of a selected target sequence (e.g., dystrophin), such as to induce exon skipping.

An "exon" refers to a defined section of nucleic acid that encodes for a protein, or a nucleic acid sequence that is represented in the mature form of an RNA molecule after either portions of a pre-processed (or precursor) RNA have been removed by splicing. The mature RNA molecule can be a messenger RNA (mRNA) or a functional form of a non-coding RNA, such as rRNA or tRNA. The human dystrophin gene has about 75 exons.

An "intron" refers to a nucleic acid region (within a gene) that is not translated into a protein. An intron is a non-coding section that is transcribed into a precursor mRNA (pre-mRNA), and subsequently removed by splicing during formation of the mature RNA.

"Exon skipping" refers generally to the process by which an entire exon, or a portion thereof, is removed from a given pre-processed RNA, and is thereby excluded from being present in the mature RNA, such as the mature mRNA that is translated into a protein. Hence, the portion of the protein that is otherwise encoded by the skipped exon is not present in the expressed form of the protein, typically creating an altered, though still functional, form of the protein. In certain embodiments, the exon being skipped is an aberrant exon from the human dystrophin gene, which may contain a mutation or other alteration in its sequence that otherwise causes aberrant splicing. In certain embodiments, the exon being skipped is any one or more of exons 1-75 of the dystrophin gene, though any one or more of exons 44, 45, 46, 47, 48, 49, 50, 51, 52, 53, 54, and/or 55 of the human dystrophin gene are preferred.

"Dystrophin" is a rod-shaped cytoplasmic protein, and a vital part of the protein complex that connects the cytoskeleton of a muscle fiber to the surrounding extracellular matrix through the cell membrane. Dystrophin contains multiple functional domains. For instance, dystrophin contains an actin binding domain at about amino acids 14-240 and a central rod domain at about amino acids 253-3040. This large central domain is formed by 24 spectrin-like triple-helical elements of about 109 amino acids, which have homology to alpha-actinin and spectrin. The repeats are typically interrupted by four proline-rich non-repeat segments, also referred to as hinge regions. Repeats 15 and 16 are separated by an 18 amino acid stretch that appears to provide a major site for proteolytic cleavage of dystrophin. The sequence identity between most repeats ranges from 10-25%. One repeat contains three alpha-helices: 1, 2 and 3. Alpha-helices 1 and 3 are each formed by 7 helix turns, probably interacting as a coiled-coil through a hydrophobic interface. Alpha-helix 2 has a more complex structure and is formed by segments of four and three helix turns, separated by a Glycine or Proline residue. Each repeat is encoded by two exons, typically interrupted by an intron between amino acids 47 and 48 in the first part of alpha-helix 2. The other intron is found at different positions in the repeat, usually scattered over helix-3. Dystrophin also contains a cysteine-rich domain at about amino acids 3080-3360), including a cysteine-rich segment (i.e., 15 Cysteines in 280 amino acids) showing homology to the C-terminal domain of the slime mold (*Dictyostelium discoideum*) alpha-actinin. The carboxy-terminal domain is at about amino acids 3361-3685.

The amino-terminus of dystrophin binds to F-actin and the carboxy-terminus binds to the dystrophin-associated protein complex (DAPC) at the sarcolemma. The DAPC includes the dystroglycans, sarcoglycans, integrins and caveolin, and mutations in any of these components cause autosomally inherited muscular dystrophies. The DAPC is destabilized when dystrophin is absent, which results in diminished levels of the member proteins, and in turn leads to progressive fibre damage and membrane leakage. In various forms of muscular dystrophy, such as Duchenne's muscular dystrophy (DMD) and Becker's muscular dystrophy (BMD), muscle cells produce an altered and functionally defective form of dystrophin, or no dystrophin at all, mainly due to mutations in the gene sequence that lead to incorrect splicing. The predominant expression of the defective dystrophin protein, or the complete lack of dystrophin or a dystrophin-like protein, leads to rapid progression of muscle degeneration, as noted above. In this regard, a "defective" dystrophin protein may be characterized by the forms of dystrophin that are produced in certain subjects with DMD or BMD, as known in the art, or by the absence of detectable dystrophin.

Table A provides an illustration of the various dystrophin domains, the amino acid residues that encompass these domains, and the exons that encode them.

TABLE A

| Domain | Sub Domain | Residue Nos | Exons |
|---|---|---|---|
| actin binding domain | | 14-240 | 2-8 |
| central rod domain | | 253-3040 | 8-61 |
| | hinge 1 | 253-327 | (8)-9 |
| | repeat 1 | 337-447 | 10-11 |
| | repeat 2 | 448-556 | 12-14 |
| | repeat 3 | 557-667 | 14-16 |
| | hinge 2 | 668-717 | 17 |
| | repeat 4 | 718-828 | (17)-20 |
| | repeat 5 | 829-934 | 20-21 |
| | repeat 6 | 935-1045 | 22-23 |
| | repeat 7 | 1046-1154 | (23)-(26) |
| | repeat 8 | 1155-1263 | 26-27 |
| | repeat 9 | 1264-1367 | 28-(30) |
| | repeat 10 | 1368-1463 | 30-32 |
| | repeat 11 | 1464-1568 | 32-(34) |
| | repeat 12 | 1569-1676 | 34-35 |
| | repeat 13 | 1677-1778 | 36-37 |
| | repeat 14 | 1779-1874 | 38-(40) |
| | repeat 15 | 1875-1973 | 40-41 |
| | interruption | 1974-1991 | 42 |
| | repeat 16 | 1992-2101 | 42-43 |
| | repeat 17 | 2102-2208 | 44-45 |
| | repeat 18 | 2209-2318 | 46-48 |
| | repeat 19 | 2319-2423 | 48-50 |
| | hinge 3 | 2424-2470 | 50-51 |
| | repeat 20 | 2471-2577 | 51-53 |
| | repeat 21 | 2578-2686 | 53-(55) |
| | repeat 22 | 2687-2802 | 55-(57) |
| | repeat 23 | 2803-2931 | 57-59 |
| | repeat 24 | 2932-3040 | 59-(61) |
| | hinge 4 | 3041-3112 | 61-64 |
| Cysteine-rich domain | | 3080-3360 | 63-69 |
| | dystroglycan binding site | 3080-3408 | 63-70 |
| | WW domain | 3056-3092 | 62-63 |
| | EF-hand 1 | 3130-3157 | 65 |
| | EF-hand 2 | 3178-3206 | 65-66 |
| | ZZ domain | 3307-3354 | 68-69 |
| Carboxy-terminal domain | | 3361-3685 | 70-79 |
| | alpha1-syntrophin binding site | 3444-3494 | 73-74 |
| | β1-syntrophin binding site | 3495-3535 | 74-75 |
| | (Leu)6-heptad repeat | 3558-3593 | 75 |

As used herein, the terms "function" and "functional" and the like refer to a biological, enzymatic, or therapeutic function.

A "functional" dystrophin protein refers generally to a dystrophin protein having sufficient biological activity to reduce the progressive degradation of muscle tissue that is otherwise characteristic of muscular dystrophy, typically as compared to the altered or "defective" form of dystrophin protein that is present in certain subjects with DMD or BMD. In certain embodiments, a functional dystrophin protein may have about 10%, 20%, 30%, 40%, 50%, 60%, 70%, 80%, 90%, or 100% (including all integers in between) of the in vitro or in vivo biological activity of wild-type dystrophin, as measured according to routine techniques in the art. As one example, dystrophin-related activity in muscle cultures in vitro can be measured according to myotube size, myofibril organization (or disorganization), contractile activity, and spontaneous clustering of acetylcholine receptors (see, e.g., Brown et al., *Journal of Cell Science.* 112:209-216, 1999). Animal models are also valuable resources for studying the pathogenesis of disease, and provide a means to test dystrophin-related activity. Two of the most widely used animal models for DMD research are the mdx mouse and the golden retriever muscular dystrophy (GRMD) dog, both of which are dystrophin negative (see, e.g., Collins & Morgan, *Int J Exp Pathol* 84: 165-172, 2003). These and other animal models can be used to measure the functional activity of various dystrophin proteins. Included are truncated forms of dystrophin, such as those forms that are produced by certain of the exon-skipping antisense compounds of the present invention.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

By "isolated" is meant material that is substantially or essentially free from components that normally accompany it in its native state. For example, an "isolated polynucleotide," as used herein, may refer to a polynucleotide that has been purified or removed from the sequences that flank it in a naturally-occurring state, e.g., a DNA fragment that has been removed from the sequences that are normally adjacent to the fragment.

By "enhance" or "enhancing," or "increase" or "increasing," or "stimulate" or "stimulating," refers generally to the ability of one or antisense compounds or compositions to produce or cause a greater physiological response (i.e., downstream effects) in a cell or a subject, as compared to the response caused by either no antisense compound or a control compound. A measurable physiological response may include increased expression of a functional form of a dystrophin protein, or increased dystrophin-related biological activity in muscle tissue, among other responses apparent from the understanding in the art and the description herein. Increased muscle function can also be measured, including increases or improvements in muscle function by about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100%. The percentage of muscle fibres that express a functional dystrophin can also be measured, including increased dystrophin expression in about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of muscle fibres. For instance, it has been shown that around 40% of muscle function improvement can occur if 25-30% of fibers express dystrophin (see, e.g., DelloRusso et al, *Proc Natl Acad Sci USA* 99: 12979-12984, 2002). An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7, 1.8, etc.) the amount produced by no antisense compound (the absence of an agent) or a control compound.

The term "reduce" or "inhibit" may relate generally to the ability of one or more antisense compounds of the invention to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of muscular dystrophy, or reductions in the expression of defective forms of dystrophin, such as the altered forms of dystrophin that are expressed in individuals with DMD or BMD. A "decrease" in a response may be statistically significant as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

"Homology" refers to the percentage number of amino acids that are identical or constitute conservative substitutions. Homology may be determined using sequence comparison programs such as GAP (Deveraux et al., 1984, *Nucleic Acids Research* 12, 387-395). In this way sequences of a similar or substantially different length to those cited herein could be compared by insertion of gaps into the alignment, such gaps being determined, for example, by the comparison algorithm used by GAP.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence," "comparison window," "sequence identity," "percentage of sequence identity," and "substantial identity". A "reference sequence" is at least 8 or 10 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

"Treatment" or "treating" of an individual (e.g., a mammal, such as a human) or a cell may include any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition associated with the dystrophin protein, as in certain forms of muscular dystrophy, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

Hence, included are methods of treating muscular dystrophy, such as DMD and BMD, by administering one or more antisense oligomers of the present invention (e.g., SEQ ID NOS: 1 to 569 and 612 to 635, and variants thereof), optionally as part of a pharmaceutical formulation or dosage form, to a subject in need thereof. Also included are methods of inducing exon-skipping in a subject by administering one or more antisense oligomers, in which the exon is one of exons 44, 45, 46, 47, 48, 49, 50, 51, 52, 53, 54, and/or 55 from the dystrophin gene, preferably the human dystrophin gene. A "subject," as used herein, includes any animal that exhibits a symptom, or is at risk for exhibiting a symptom, which can be treated with an antisense compound of the invention, such as a subject that has or is at risk for having DMD or BMD, or any of the symptoms associated with these conditions (e.g., muscle fibre loss). Suitable subjects (patients) include laboratory animals (such as mouse, rat, rabbit, or guinea pig), farm animals, and domestic animals or pets (such as a cat or dog). Non-human primates and, preferably, human patients, are included.

Also included are vector delivery systems that are capable of expressing the oligomeric, dystrophin-targeting sequences of the present invention, such as vectors that express a polynucleotide sequence comprising any one or more of SEQ ID NOS: 1 to 569 and 612 to 635, or variants thereof, as described herein. By "vector" or "nucleic acid construct" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated.

A vector or nucleic acid construct system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector or nucleic acid construct is preferably one which is operably functional in a mammalian cell, such as a muscle cell. The vector can also include a selection marker such as an antibiotic or drug resistance gene, or a reporter gene (i.e., green fluorescent protein, luciferase), that can be used for selection or identification of suitable transformants or transfectants. Exemplary delivery systems may include viral vector systems (i.e., viral-mediated transduction) including, but not limited to, retroviral (e.g., lentiviral) vectors, adenoviral vectors, adeno-associated viral vectors, and herpes viral vectors, among others known in the art.

The term "operably linked" as used herein means placing an oligomer-encoding sequence under the regulatory control of a promoter, which then controls the transcription of the oligomer.

A wild-type gene or gene product is that which is most frequently observed in a population and is thus arbitrarily designed the "normal" or "wild-type" form of the gene.

"Alkyl" or "alkylene" both refer to a saturated straight or branched chain hydrocarbon radical containing from 1 to 18 carbons. Examples include without limitation methyl, ethyl, propyl, iso-propyl, butyl, iso-butyl, tert-butyl, n-pentyl and n-hexyl. The term "lower alkyl" refers to an alkyl group, as defined herein, containing between 1 and 8 carbons.

"Alkenyl" refers to an unsaturated straight or branched chain hydrocarbon radical containing from 2 to 18 carbons and comprising at least one carbon to carbon double bond. Examples include without limitation ethenyl, propenyl, iso-propenyl, butenyl, iso-butenyl, tert-butenyl, n-pentenyl and n-hexenyl. The term "lower alkenyl" refers to an alkenyl group, as defined herein, containing between 2 and 8 carbons.

"Alkynyl" refers to an unsaturated straight or branched chain hydrocarbon radical containing from 2 to 18 carbons comprising at least one carbon to carbon triple bond. Examples include without limitation ethynyl, propynyl, iso-propynyl, butynyl, iso-butynyl, tert-butynyl, pentynyl and hexynyl.

The term "lower alkynyl" refers to an alkynyl group, as defined herein, containing between 2 and 8 carbons.

"Cycloalkyl" refers to a mono- or poly-cyclic alkyl radical. Examples include without limitation cyclobutyl, cycopentyl, cyclohexyl, cycloheptyl and cyclooctyl.

"Aryl" refers to a cyclic aromatic hydrocarbon moiety containing from 5 to 18 carbons having one or more closed ring(s). Examples include without limitation phenyl, benzyl, naphthyl, anthracenyl, phenanthracenyl and biphenyl.

"Aralkyl" refers to a radical of the formula RaRb where Ra is an alkylene chain as defined above and Rb is one or more aryl radicals as defined above, for example, benzyl, diphenylmethyl and the like.

"Thioalkoxy" refers to a radical of the formula —SRc where Rc is an alkyl radical as defined herein. The term "lower thioalkoxy" refers to an alkoxy group, as defined herein, containing between 1 and 8 carbons.

"Alkoxy" refers to a radical of the formula —ORda where Rd is an alkyl radical as defined herein. The term "lower alkoxy" refers to an alkoxy group, as defined herein, containing between 1 and 8 carbons. Examples of alkoxy groups include, without limitation, methoxy and ethoxy.

"Alkoxyalkyl" refers to an alkyl group substituted with an alkoxy group.

"Carbonyl" refers to the —C(=O)— radical.

"Guanidynyl" refers to the $H_2N(C=NH_2)$—NH— radical.

"Amidinyl" refers to the $H_2N(C=NH_2)CH$— radical.

"Amino" refers to the —$NH_2$ radical.

"Alkylamino" refers to a radical of the formula —NHRd or —NRdRd where each Rd is, independently, an alkyl radical as defined herein. The term "lower alkylamino" refers to an alkylamino group, as defined herein, containing between 1 and 8 carbons.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Thus, in addition to the heteroaryls listed below, heterocycles also include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydrothiophenyl, tetrahydrothiopyranyl, tetrahydropyrimidinyl, tetrahydrothiopyranyl, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

The terms "optionally substituted alkyl", "optionally substituted alkenyl", "optionally substituted alkoxy", "optionally substituted thioalkoxy", "optionally substituted alkyl amino", "optionally substituted lower alkyl", "optionally substituted lower alkenyl", "optionally substituted lower alkoxy", "optionally substituted lower thioalkoxy", "optionally substituted lower alkyl amino" and "optionally substituted heterocyclyl" mean that, when substituted, at least one hydrogen atom is replaced with a substituent. In the case of an oxo substituent (=O) two hydrogen atoms are replaced. In this regard, substituents include: deuterium, optionally substituted alkyl, optionally substituted alkenyl, optionally substituted alkynyl, optionally substituted aryl, optionally substituted heterocycle, optionally substituted cycloalkyl, oxo, halogen, —CN, —ORx, NRxRy, NRxC(=O)Ry, NRxSO2Ry, —NRxC(=O)NRxRy, C(=O)Rx, C(=O) ORx, C(=O)NRxRy, —SOmRx and —SOmNRxRy, wherein m is 0, 1 or 2, Rx and Ry are the same or different and independently hydrogen, optionally substituted alkyl, optionally substituted alkenyl, optionally substituted alkynyl, optionally substituted aryl, optionally substituted heterocycle or optionally substituted cycloalkyl and each of said optionally substituted alkyl, optionally substituted alkenyl, optionally substituted alkynyl, optionally substituted aryl, optionally substituted heterocycle and optionally substituted cycloalkyl substituents may be further substituted with one or more of oxo, halogen, —CN, —ORx, NRxRy, NRxC(=O) Ry, NRxSO2Ry, —NRxC(=O)NRxRy, C(=O)Rx, C(=O) ORx, C(=O)NRxRy, —SOmRx and —SOmNRxRy.

Constructing Antisense Oligonucleotides

Figure 1B:
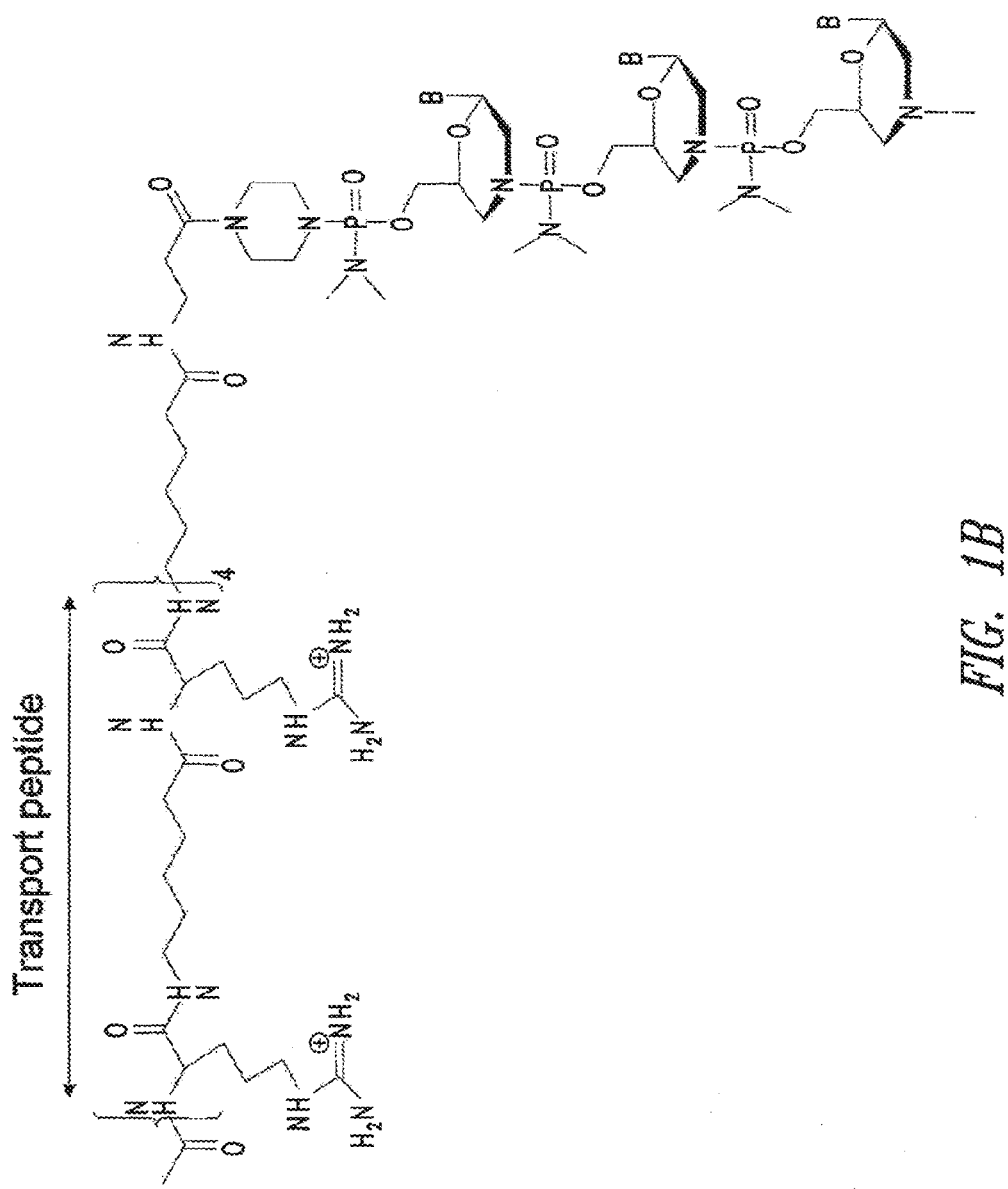
FIG. 1B shows a conjugate of an arginine-rich peptide and an antisense oligomer, in accordance with an embodiment of the invention.
Figure 1C:
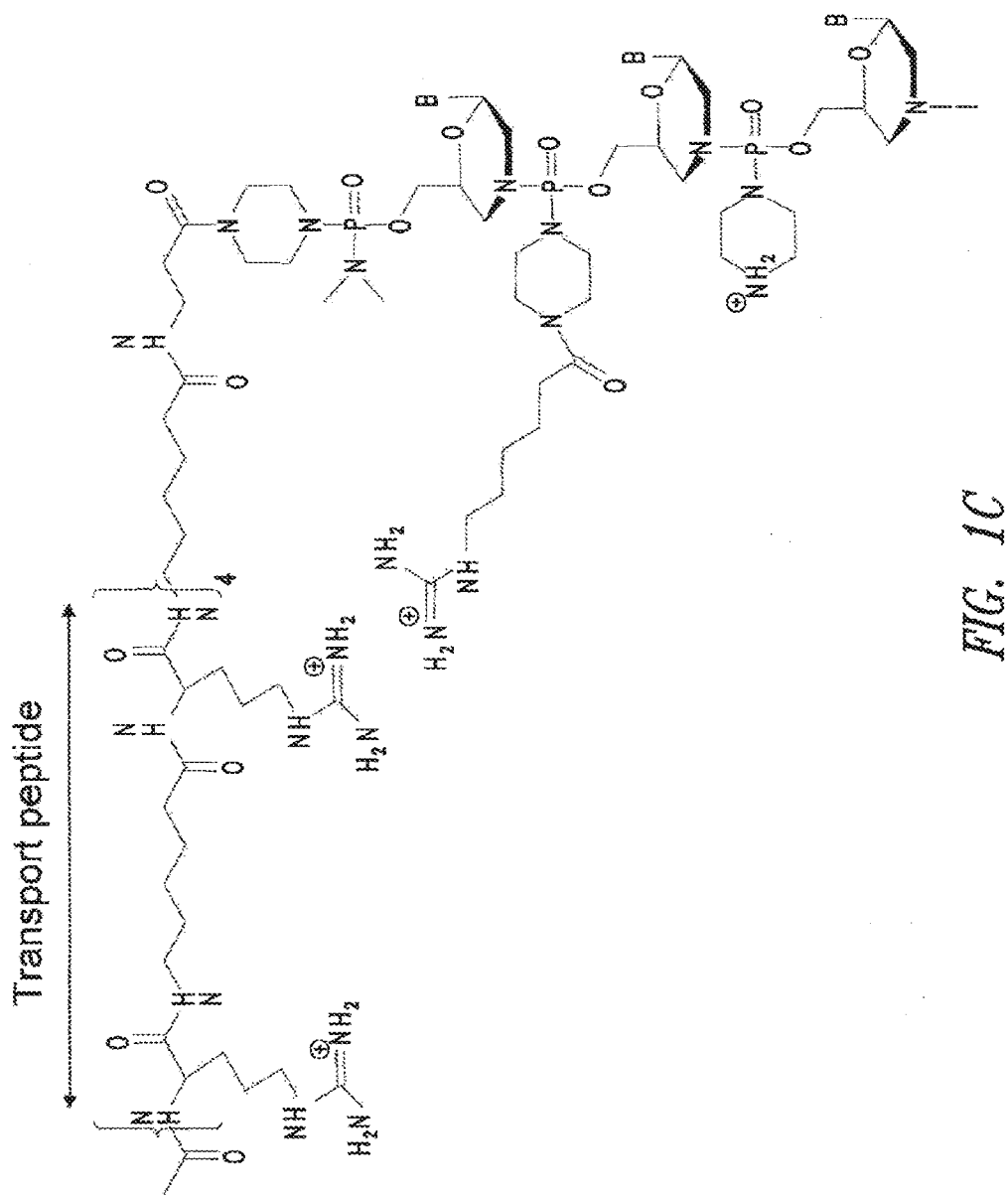
FIG. 1C shows a conjugate as in FIG. 1B, wherein the backbone linkages contain one or more positively charged groups.

Examples of morpholino oligonucleotides having phosphorus-containing backbone linkages are illustrated in FIGS. 1A-1C. Especially preferred is a phosphorodiamidate-linked morpholino oligonucleotide such as shown in FIG. 1C, which is modified, in accordance with one aspect of the present invention, to contain positively charged groups at preferably 10%-50% of its backbone linkages. Morpholino oligonucleotides with uncharged backbone linkages and their preparation, including antisense oligonucleotides, are detailed, for example, in (Summerton and Weller 1997) and in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: 1) the ability to be linked in a oligomeric form by stable, uncharged or positively charged backbone linkages; 2) the ability to support a nucleotide base (e.g. adenine, cytosine, guanine, thymidine, uracil and inosine) such that the polymer formed can hybridize with a complementary-base target nucleic acid, including target RNA, Tm values above about 45° C. in relatively short oligonucleotides (e.g., 10-15 bases); 3) the ability of the oligonucleotide to be actively or passively transported into mammalian cells; and 4) the ability of the antisense oligonucleotide:RNA heteroduplex to resist RNAse and RNaseH degradation, respectively.

Figure 1D:
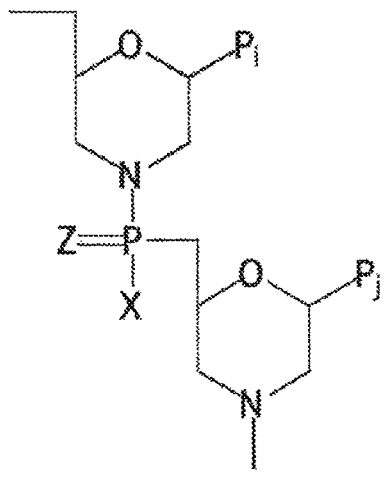
FIGS. 1D-G show the repeating subunit segment of exemplary morpholino oligonucleotides, designated D through G.
Figure 1E:
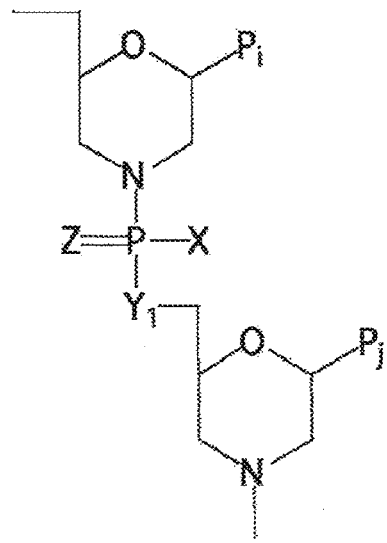

Exemplary backbone structures for antisense oligonucleotides of the claimed subject matter include the morpholino subunit types shown in FIGS. 1D-G, each linked by an uncharged or positively charged, phosphorus-containing subunit linkage. FIG. 1D shows a phosphorus-containing linkage which forms the five atom repeating-unit backbone, wherein the morpholino rings are linked by a 1-atom phosphoamide linkage. FIG. 1E shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1F:
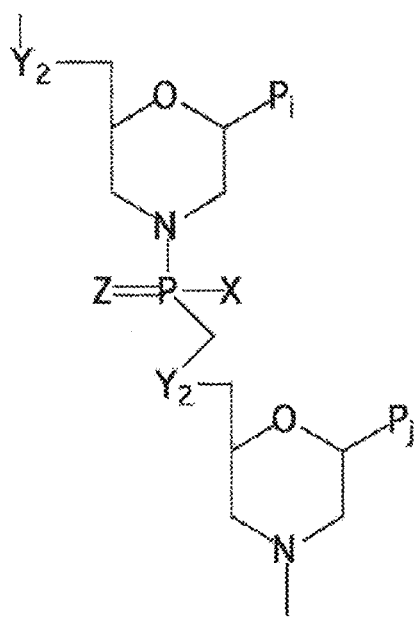
Figure 1G:
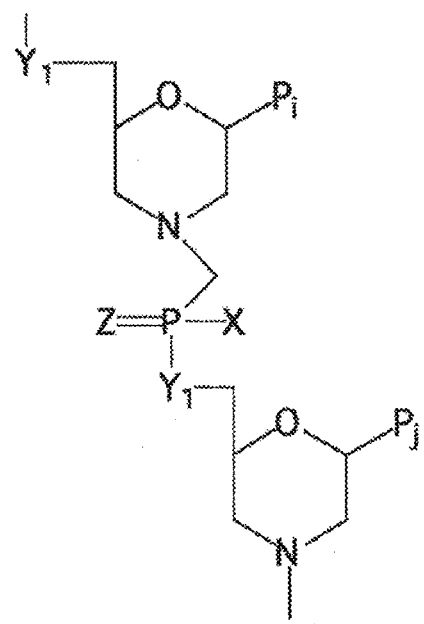

The linkages shown in FIGS. 1F and 1G are designed for 7-atom unit-length backbones. In structure 1F, the X moiety is as in Structure 1E, and the Y moiety may be methylene, sulfur, or, preferably, oxygen. In Structure 1G, the X and Y moieties are as in Structure 1E. Particularly preferred morpholino oligonucleotides include those composed of morpholino subunit structures of the form shown in FIG. 1E, where X=$NH_2$, N(CH$_3$)$_2$, optionally substituted 1-piperazinyl, or other charged group, Y=O, and Z=O.

As noted above, the uncharged or substantially uncharged oligonucleotide may be modified, in accordance with an aspect of the invention, to include charged linkages, e.g. up to about 1 per every 2-5 uncharged linkages, such as about 4-5 per every 10 uncharged linkages. Optimal improvement in antisense activity may be seen when about 25% of the backbone linkages are cationic, including about 20% to about 30%. Also included are oligomers in which about 35%, 40%, 45%, 50%, 55%, 60% (including all integers in between), or more of the backbone linkages are cationic. Enhancement is also seen with a small number, e.g., 5% or 10-20%, of cationic linkages.

A substantially uncharged, phosphorus containing backbone in an oligonucleotide analog is typically one in which a majority of the subunit linkages, e.g., between 50%-100%, typically at least 60% to 100% or 75% or 80% of its linkages, are uncharged at physiological pH and contain a single phosphorous atom.

Additional experiments conducted in support of the present invention indicate that the enhancement seen with added cationic backbone charges may, in some cases, be further enhanced by distributing the bulk of the charges close to the "center-region" backbone linkages of the antisense oligonucleotide, e.g., in a 20mer oligonucleotide with 8 cationic backbone linkages, having at least 70% of these charged linkages localized in the 10 centermost linkages.

The antisense compounds can be prepared by stepwise solid-phase synthesis, employing methods detailed in the references cited above, and below with respect to the synthesis of oligonucleotides having a mixture of uncharged and cationic backbone linkages. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

As noted above, the antisense compound can be constructed to contain a selected number of cationic linkages interspersed with uncharged linkages of the type described above. The intersubunit linkages, both uncharged and cationic, preferably are phosphorus-containing linkages, having the structure (II):

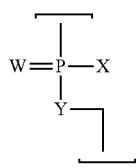

(II)

wherein:
W is —S— or —O—, and is preferably —O—,
X=-NR$^1$R$^2$ or —OR$^6$,
Y=-O— or —NR', and
each said linkage in the oligomer is selected from:
(a) an uncharged linkage (a), wherein each of R$^1$, R$^2$, R$^6$ and R$^7$ is independently selected from hydrogen and lower alkyl;

(b1) a cationic linkage (b1), wherein X=-NR$^1$R$^2$ and Y=-O—, and —NR$^1$R$^2$ represents an optionally substituted piperazinyl moiety, such that R$^1$R$^2$=-CHRCHRN(R$^3$)(R$^4$)CHRCHR—, wherein:
each R is independently H or —CH$_3$,
R$^4$ is H, —CH$_3$, or an electron pair, and
R$^3$ is selected from H, optionally substituted lower alkyl, —C(═NH)NH$_2$, —Z-L-NHC(═NH)NH$_2$, and [—C(═O)CHR'NH]$_m$H, where: Z is —C(═O)— or a direct bond, L is an optional linker up to 18 atoms in length, preferably up to 12 atoms, and more preferably up to 8 atoms in length, having bonds selected from optionally substituted alkyl, optionally substituted alkoxy, and optionally substituted alkylamino, R' is a side chain of a naturally occurring amino acid or a one- or two-carbon homolog thereof, and m is 1 to 6, preferably 1 to 4;

(b2) a cationic linkage (b2), wherein X=-NR$^1$R$^2$ and Y=-O—, R$^1$=H or —CH$_3$, and R$^2$=LNR$^3$R$^4$R$^5$, wherein L, R$^3$, and R$^4$ are as defined above, and R$^5$ is H, optionally substituted lower alkyl, or optionally substituted lower (alkoxy)alkyl; and (b3) a cationic linkage (b3), wherein Y=-NR' and X=-OR$^6$, and R$^7$=-LNR$^3$R$^4$R$^5$, wherein L, R$^3$, R$^4$ and R$^5$ are as defined above, and R$^6$ is H or optionally substituted lower alkyl; and at least one said linkage is selected from cationic linkages (b1), (b2), and (b3).

Preferably, the oligomer includes at least two consecutive linkages of type (a) (i.e. uncharged linkages). In further embodiments, at least 5% of the linkages in the oligomer are cationic linkages (i.e. type (b1), (b2), or (b3)); for example, 10% to 60%, and preferably 20-50% linkages may be cationic linkages.

In one embodiment, at least one linkage is of type (b1), where, preferably, each R is H, R$^4$ is H, —CH$_3$, or an electron pair, and R$^3$ is selected from H, optionally substituted lower alkyl, —C(═NH)NH$_2$, and —C(═O)-L-NHC(═NH)NH$_2$. The latter two embodiments of R$^3$ provide a guanidino moiety, either attached directly to the piperazine ring, or pendant to a linker group L, respectively. For ease of synthesis, the variable Z in R$^3$ is preferably —C(═O)—, as shown.

The linker group L, as noted above, contains bonds in its backbone selected from optionally substituted alkyl, optionally substituted alkoxy, and optionally substituted alkylamino, wherein the terminal atoms in L (e.g., those adjacent to carbonyl or nitrogen) are carbon atoms. Although branched linkages are possible, the linker is preferably unbranched. In one embodiment, the linker is a linear alkyl linker. Such a linker may have the structure —(CH$_2$)$_n$—, where n is 1-12, preferably 2-8, and more preferably 2-6.

The morpholino subunits have the following structure (III):

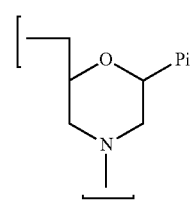

(III)

wherein Pi is a base-pairing moiety, and the linkages depicted above connect the nitrogen atom of (III) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits (III) may be illustrated graphically as follows:

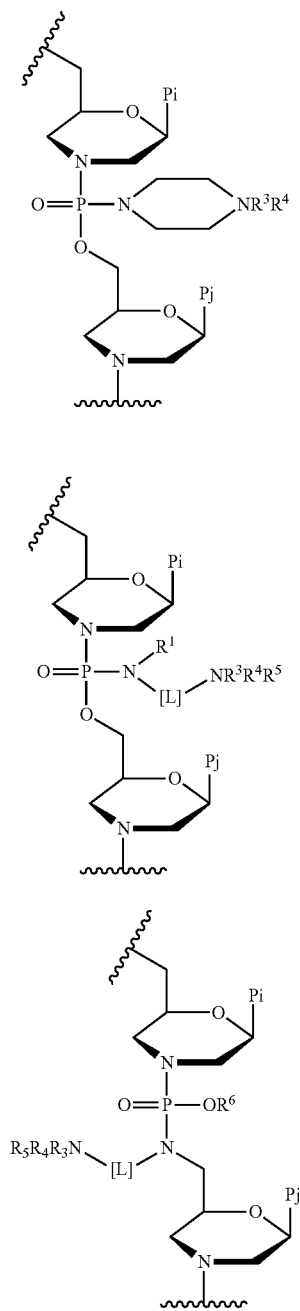

Preferably, all cationic linkages in the oligomer are of the same type; i.e. all of type (b1), all of type (b2), or all of type (b3).

In further embodiments, the cationic linkages are selected from linkages (b1') and (b1") as shown below, where (b1') is referred to herein as a "Pip" linkage and (b1") is referred to herein as a "GuX" linkage:

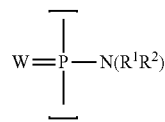

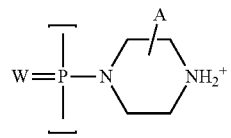

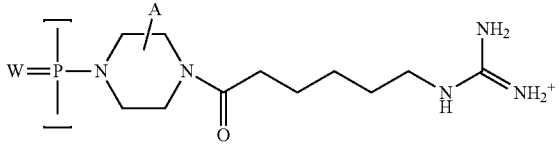

In the structures above, W is S or O, and is preferably O; each of $R^1$ and $R^2$ is independently selected from hydrogen and optionally substituted lower alkyl, and is preferably methyl; and A represents hydrogen or a non-interfering substituent (i.e. a substituent that does not adversely affect the ability of an oligomer to bind to its intended target) on one or more carbon atoms in (b1') and (b1"). Preferably, the ring carbons in the piperazine ring are unsubstituted; however, the ring carbons of the piperazine ring may include non-interfering substituents, such as methyl or fluorine. Preferably, at most one or two carbon atoms is so substituted.

In further embodiments, at least 10% of the linkages are of type (b1') or (b1"); for example, 10%-60% and preferably 20% to 50%, of the linkages may be of type (b1') or (b1").

In other embodiments, the oligomer contains no linkages of the type (b1') above. Alternatively, the oligomer contains no linkages of type (b1) where each R is H, $R^3$ is H or —$CH_3$, and $R^4$ is H, —$CH_3$, or an electron pair.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5'nitrogen atom on a morpholino ring could be employed in a sulfamide linkage or a urea linkage (where phosphorus is replaced with carbon or sulfur, respectively) and modified in a manner analogous to the 5'-nitrogen atom in structure (b3) above.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 10 to 30 subunits, and typically 15-25 bases, including those having 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases. In certain embodiments, an oligomer of the invention having 19-20 subunits, a useful length for an antisense compound, may ideally have two to ten, e.g., four to eight, cationic linkages, and the remainder uncharged linkages. An oligomer having 14-15 subunits may ideally have two to seven, e.g., 3 to 5, cationic linkages, and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (e.g., A, G, C, T or U) or an analog, such as hypoxanthine (the base component of the nucleoside inosine) or 5-methyl cytosine.

Peptide Transporters

The antisense compounds of the invention may include an oligonucleotide moiety conjugated to an arginine-rich peptide transport moiety effective to enhance transport of the compound into cells. The transport moiety is preferably attached to a terminus of the oligomer, as shown, for example, in FIGS. 1B and 1C. The peptide transport moiety preferably comprises 6 to 16 subunits selected from X' subunits, Y' subunits, and Z' subunits, wherein:

(a) each X' subunit independently represents lysine, arginine or an arginine analog, said analog being a cationic α-amino acid comprising a side chain of the structure $R^1N=C(NH_2)R^2$, where $R^1$ is H or R; $R^2$ is R, —$NH_2$, —NHR, or —$NR_2$, where R is optionally substituted lower alkyl or optionally substituted lower alkenyl; $R^1$ and $R^2$ may join together to form a ring; and the side chain is linked to said amino acid via $R^1$ or $R^2$;

(b) each Y' subunit independently represents a neutral amino acid —C(=O)—(CHR)$_n$—NH—, where n is 2 to 7 and each R is independently H or methyl; and (c) each Z' subunit independently represents an α-amino acid having a neutral aralkyl side chain;

wherein the peptide comprises a sequence represented by at least one of (X'Y'X')$_p$, (X'Y')$_m$, and/or (X'Z'Z')$_p$, where p is 2 to 5 and m is 2 to 8. Certain embodiments include various combinations selected independently from (X'Y'X')$_p$, (X'Y')$_m$, and/or (X'Z'Z')$_p$, including, for example, peptides having the sequence (X'Y'X')(X'Z'Z')(X'Y'X')(X'Z'Z') (SEQ ID NO:637).

In selected embodiments, for each X', the side chain moiety is guanidyl, as in the amino acid subunit arginine (Arg). In certain embodiments, each Y' is independently —C(=O)—(CH$_2$)$_n$—CHR—NH—, where n is 2 to 7 and R is H. For example, when n is 5 and R is H, Y' is a 6-aminohexanoic acid subunit, abbreviated herein as Ahx; when n is 2 and R is H, Y' is a β-alanine subunit, abbreviated herein as B. Certain embodiments relate to carrier peptides having a combination of different neutral amino acids, including, for example, peptides comprising the sequence —RahxRRBRRAhxRRBRAhxB- (SEQ ID NO:578), which contains both β-alanine and 6-aminohexanoic acid.

Preferred peptides of this type include those comprising arginine dimers alternating with single Y' subunits, where Y' is preferably Ahx or B or both. Examples include peptides having the formula (RY'R)$_p$ and/or the formula (RRY')$_p$, where p is 1 to 2 to 5 and where Y' is preferably Ahx. In one embodiment, Y' is a 6-aminohexanoic acid subunit, R is arginine and p is 4. Certain embodiments include various linear combinations of at least two of (RY'R)$_p$ and (RRY')$_p$, including, for example, illustrative peptides having the sequence (RY'R)(RRY')(RY'R)(RRY') (SEQ ID NO:638), or (RRY')(RY'R)(RRY') (SEQ ID NO:639). Other combinations are contemplated. In a further illustrative embodiment, each Z' is phenylalanine, and m is 3 or 4.

The conjugated peptide is preferably linked to a terminus of the oligomer via a linker Ahx-B, where Ahx is a 6-aminohexanoic acid subunit and B is a β-alanine subunit, as shown, for example, in FIGS. 1B and 1C.

In selected embodiments, for each X', the side chain moiety is independently selected from the group consisting of guanidyl (HN=C(NH$_2$)NH—), amidinyl (HN=C(NH$_2$)CH—), 2-aminodihydropyrimidyl, 2-aminotetrahydropyrimidyl, 2-aminopyridinyl, and 2-aminopyrimidonyl, and it is preferably selected from guanidyl and amidinyl. In one embodiment, the side chain moiety is guanidyl, as in the amino acid subunit arginine (Arg).

In certain embodiments, the Y' subunits may be contiguous, in that no X' subunits intervene between Y' subunits, or interspersed singly between X' subunits. In certain embodiments, the linking subunit may be between Y' subunits. In one embodiment, the Y' subunits are at a terminus of the transporter; in other embodiments, they are flanked by X' subunits. In further preferred embodiments, each Y' is —C(=O)—(CH$_2$)$_n$—CHR—NH—, where n is 2 to 7 and R is H. For example, when n is 5 and R is H, Y' is a 6-aminohexanoic acid subunit, abbreviated herein as Ahx. In selected embodiments of this group, each X' comprises a guanidyl side chain moiety, as in an arginine subunit. Preferred peptides of this type include those comprising arginine dimers alternating with single Y' subunits, where Y' is preferably Ahx. Examples include peptides having the formula (RY'R)$_4$ or the formula (RRY')$_4$, where Y' is preferably Ahx. In the latter case, the nucleic acid analog is preferably linked to a terminal Y' subunit, preferably at the C-terminus, as shown, for example, in FIGS. 1B and 1C. The preferred linker is of the structure AhxB, where Ahx is a 6-aminohexanoic acid subunit and B is a β-alanine subunit.

The transport moieties as described above have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake is preferably evidenced by at least a two-fold increase, and preferably a four-fold increase, in the uptake of the compound into mammalian cells relative to uptake of the agent by an attached transport moiety lacking the hydrophobic subunits Y'. Uptake is preferably enhanced at least twenty fold, and more preferably forty fold, relative to the unconjugated compound.

A further benefit of the transport moiety is its expected ability to stabilize a duplex between an antisense compound and its target nucleic acid sequence, presumably by virtue of electrostatic interaction between the positively charged transport moiety and the negatively charged nucleic acid. The number of charged subunits in the transporter is less than 14, as noted above, and preferably between 8 and 11, since too high a number of charged subunits may lead to a reduction in sequence specificity.

The use of arginine-rich peptide transporters (i.e., cell-penetrating peptides) is particularly useful in practicing the present invention. Certain peptide transporters have been shown to be highly effective at delivery of antisense compounds into primary cells including muscle cells (Marshall, Oda et al. 2007; Jearawiriyapaisarn, Moulton et al. 2008; Wu, Moulton et al. 2008). Furthermore, compared to other peptide transporters such as Penetratin and the Tat peptide, the peptide transporters described herein, when conjugated to an antisense PMO, demonstrate an enhanced ability to alter splicing of several gene transcripts (Marshall, Oda et al. 2007). Especially preferred are the P007, CP06062 and CP04057 transport peptides listed below in Table 3 (SEQ ID NOS: 573, 578 and 577, respectively).

Exemplary peptide transporters, including linkers (B or AhxB) are given below in Table B below. Preferred sequences are those designated CP06062 (SEQ ID NO: 578), P007 (SEQ ID NO: 573) and CPO4057 (SEQ ID NO: 577).

TABLE B

Exemplary Peptide Transporters for Intracellular Delivery of PMO

| Peptide | Sequence (N-terminal to C-terminal) | SEQ ID NO: |
|---|---|---|
| rTAT | RRRQRRKKRC | 570 |
| R$_9$F$_2$ | RRRRRRRRRFFC | 571 |
| (RRAhx)$_4$B | RRAhxRRAhxRRAhxRRAhxB | 572 |
| (RAhxR)$_4$AhxB; (P007) | RAhxRRAhxRRAhxRRAhxRAhxB | 573 |
| (AhxRR)$_4$AhxB | AhxRRAhxRRAhxRRAhxRRAhxB | 574 |
| (RAhx)$_6$B | RAhxRAhxRAhxRAhxRAhxRAhxB | 575 |
| (RAhx)$_8$B | RAhxRAhxRAhxRAhxRAhxRAhxRAhxRAhxB | 576 |
| (RAhxR)$_5$AhxB (CP05057) | RAhxRRAhxRRAhxRRAhxRRAhxRAhxB | 577 |
| (RAhxRRBR)$_2$AhxB; (CP06062) | RAhxRRBRRAhxRRBRAhxB | 578 |
| MSP | ASSLNIA | 579 |

Formulations

In certain embodiments, the present invention provides formulations or compositions suitable for the therapeutic delivery of antisense oligomers, as described herein. Hence, in certain embodiments, the present invention provides pharmaceutically acceptable compositions that comprise a therapeutically-effective amount of one or more of the oligomers described herein, formulated together with one or more pharmaceutically acceptable carriers (additives) and/or diluents. While it is possible for an oligomer of the present invention to be administered alone, it is preferable to administer the compound as a pharmaceutical formulation (composition).

Methods for the delivery of nucleic acid molecules are described, for example, in Akhtar et al., 1992, *Trends Cell Bio.*, 2:139; and *Delivery Strategies for Antisense Oligonucleotide Therapeutics*, ed. Akhtar; Sullivan et al., PCT WO 94/02595. These and other protocols can be utilized for the delivery of virtually any nucleic acid molecule, including the isolated oligomers of the present invention.

As detailed below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Some examples of materials that can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Additional non-limiting examples of agents suitable for formulation with the antisense oligomers of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues; biodegradable polymers, such as poly (DL-lactide-coglycolide) microspheres for sustained release delivery after implantation (Emerich, D F et al., 1999, *Cell Transplant*, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (*Prog Neuropsychopharmacol Biol Psychiatry*, 23, 941-949, 1999).

The invention also features the use of the composition comprising surface-modified liposomes containing poly(ethylene glycol) lipids (PEG-modified, branched and unbranched or combinations thereof, or long-circulating liposomes or stealth liposomes). Oligomers of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

In a further embodiment, the present invention includes oligomer compositions prepared for delivery as described in U.S. Pat. Nos. 6,692,911, 7,163,695 and 7,070,807. In this regard, in one embodiment, the present invention provides an oligomer of the present invention in a composition comprising copolymers of lysine and histidine (HK) as described in U.S. Pat. Nos. 7,163,695, 7,070,807, and 6,692,911 either alone or in combination with PEG (e.g., branched or unbranched PEG or a mixture of both), in combination with PEG and a targeting moiety or any of the foregoing in combination with a crosslinking agent. In certain embodiments, the present invention provides antisense oligomers in compositions comprising gluconic-acid-modified polyhistidine or gluconylated-polyhistidine/transferrin-polylysine. One skilled in the art will also recognize that amino acids with properties similar to His and Lys may be substituted within the composition.

Certain embodiments of the oligomers described herein may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject oligomers include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain embodiments, the oligomers of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from cyclodextrins, celluloses, liposomes, micelle forming agents, e.g., bile acids, and polymeric carriers, e.g., polyesters and polyanhydrides; and an oligomer of the present invention. In certain embodiments, an aforementioned formulation renders orally bioavailable an oligomer of the present invention.

Methods of preparing these formulations or compositions include the step of bringing into association an oligomer of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and *acacia* or tragacanth), powders, granules, or as a solution or a suspension in an aqueous or non-aqueous liquid, or as an oil-inwater or water-in-oil liquid emulsion, or as an elixir or syrup, or as pastilles (using an inert base, such as gelatin and glycerin, or sucrose and *acacia*) and/or as mouth washes and the like, each containing a predetermined amount of a compound of the present invention as an active ingredient. An oligomer of the present invention may also be administered as a bolus, electuary or paste.

In solid dosage forms of the invention for oral administration (capsules, tablets, pills, dragees, powders, granules, trouches and the like), the active ingredient may be mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or *acacia*; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (e.g., gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations or dosage forms for the topical or transdermal administration of an oligomer as provided herein include powders, sprays, ointments, pastes, creams, lotions, gels, solutions, patches and inhalants. The active oligomers may be mixed under sterile conditions with a pharmaceutically-acceptable carrier, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an oligomer of the present invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an oligomer of the present invention to the body. Such dosage forms can be made by dissolving or dispersing the oligomer in the proper medium. Absorption enhancers can also be used to increase the flux of the agent across the skin. The rate of such flux can be controlled by either providing a rate controlling membrane or dispersing the agent in a polymer matrix or gel, among other methods known in the art.

Pharmaceutical compositions suitable for parenteral administration may comprise one or more oligomers of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject oligomers may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility, among other methods known in the art. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms may be made by forming microencapsule matrices of the subject oligomers in biodegradable polymers such as polylactide-polyglycolide. Depending on the ratio of oligomer to polymer, and the nature of the particular polymer employed, the rate of oligomer release can be controlled. Examples of other biodegradable polymers include poly(orthoesters) and poly(anhydrides). Depot injectable formulations may also prepared by entrapping the drug in liposomes or microemulsions that are compatible with body tissues.

When the oligomers of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

As noted above, the formulations or preparations of the present invention may be given orally, parenterally, topically, or rectally. They are typically given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the oligomers of the present invention, which may be used in a suitable hydrated form, and/or the pharmaceutical compositions of the present invention, may be formulated into pharmaceutically-acceptable dosage forms by conventional methods known to those of skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being unacceptably toxic to the patient.

The selected dosage level will depend upon a variety of factors including the activity of the particular oligomer of the present invention employed, or the ester, salt or amide thereof, the route of administration, the time of administration, the rate of excretion or metabolism of the particular oligomer being employed, the rate and extent of absorption, the duration of the treatment, other drugs, compounds and/or materials used in combination with the particular oligomer employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. In certain situations, dosing is one administration per day. In certain embodiments, dosing is one or more administration per every 2, 3, 4, 5, 6, 7, 8, 9, 10, 11, 12, 13, 14 days, or every 1, 2, 3, 4, 5, 6, 7, 8, 9, 10, 11, 12 weeks, or every 1, 2, 3, 4, 5, 6, 7, 8, 9, 10, 11, 12 months, as needed, to maintain the desired expression of a functional dystrophin protein.

Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres, as described herein and known in the art. In certain embodiments, microemulsification technology may be utilized to improve bioavailability of lipophilic (water insoluble) pharmaceutical agents. Examples include Trimetrine (Dordunoo, S. K., et al., *Drug Development and Industrial Pharmacy,* 17(12), 1685-1713, 1991 and REV 5901 (Sheen, P. C., et al., *J Pharm Sci* 80(7), 712-714, 1991). Among other benefits, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from an oligomer as provided herein and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Examples of amphiphilic carriers include saturated and monounsaturated polyethyleneglycolyzed fatty acid glycerides, such as those obtained from fully or partially hydrogenated various vegetable oils. Such oils may advantageously consist of tri-, di-, and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers may be particularly useful, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. In certain embodiments, polymers have a molecular weight of from about 100 or 120 daltons up to about 5,000 or 10,000 daltons, or from about 300 daltons to about 5,000 daltons. In other embodiments, the polymer is polyethyleneglycol having a molecular weight of from about 100 to about 5,000 daltons, or having a molecular weight of from about 300 to about 5,000 daltons. In certain embodiments, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and copolymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter α, β, or γ, respectively. The glucose units are linked by α-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17α-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing an oligomer of the present invention, where the liposome membrane is formulated to provide a liposome with increased carrying capacity. Alternatively or in addition, the compound of the present invention may be contained within, or adsorbed onto, the liposome bilayer of the liposome. An oligomer of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPGs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMOs in the micromolar range; higher CMC surfactants may be utilized to prepare micelles entrapped within liposomes of the present invention.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993. For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988). In certain embodiments, reagents such as DharmaFECT® and Lipofectamine® may be utilized to introduce polynucleotides or proteins into cells.

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In most cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range is typically between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

An oligomer may be formulated to be contained within, or, adapted to release by a surgical or medical device or implant. In certain aspects, an implant may be coated or otherwise treated with an oligomer. For example, hydrogels, or other polymers, such as biocompatible and/or biodegradable polymers, may be used to coat an implant with the compositions of the present invention (i.e., the composition may be adapted for use with a medical device by using a hydrogel or other polymer). Polymers and copolymers for coating medical devices with an agent are well-known in the art. Examples of implants include, but are not limited to, stents, drug-eluting stents, sutures, prosthesis, vascular catheters, dialysis catheters, vascular grafts, prosthetic heart valves, cardiac pacemakers, implantable cardioverter defibrillators, IV needles, devices for bone setting and formation, such as pins, screws, plates, and other devices, and artificial tissue matrices for wound healing.

In addition to the methods provided herein, the oligomers for use according to the invention may be formulated for administration in any convenient way for use in human or veterinary medicine, by analogy with other pharmaceuticals. The antisense oligomers and their corresponding formulations may be administered alone or in combination with other therapeutic strategies in the treatment of muscular dystrophy, such as myoblast transplantation, stem cell therapies, administration of aminoglycoside antibiotics, proteasome inhibitors, and up-regulation therapies (e.g., upregulation of utrophin, an autosomal paralogue of dystrophin).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

REFERENCES

Aartsma-Rus, A., A. A. Janson, et al. (2004). "Antisense-induced multiexon skipping for Duchenne muscular dystrophy makes more sense." Am J Hum Genet 74(1): 83-92.
Dunckley, M. G., I. C. Eperon, et al. (1997). "Modulation of splicing in the DMD gene by antisense oligoribonucleotides." Nucleosides & Nucleotides 16(7-9): 1665-1668.
Dunckley, M. G., M. Manoharan, et al. (1998). "Modification of splicing in the dystrophin gene in cultured Mdx muscle cells by antisense oligoribonucleotides." Hum Mol Genet 7(7): 1083-90.
Errington, S. J., C. J. Mann, et al. (2003). "Target selection for antisense oligonucleotide induced exon skipping in the dystrophin gene." J Gene Med 5(6): 518-27.
Jearawiriyapaisarn, N., H. M. Moulton, et al. (2008). "Sustained Dystrophin Expression Induced by Peptide-conjugated Morpholino Oligomers in the Muscles of mdx Mice." Mol Ther.
Lu, Q. L., C. J. Mann, et al. (2003). "Functional amounts of dystrophin produced by skipping the mutated exon in the mdx dystrophic mouse." Nat Med 9(8): 1009-14.
Mann, C. J., K. Honeyman, et al. (2002). "Improved antisense oligonucleotide induced exon skipping in the mdx mouse model of muscular dystrophy." J Gene Med 4(6): 644-54.
Marshall, N. B., S. K. Oda, et al. (2007). "Arginine-rich cell-penetrating peptides facilitate delivery of antisense oligomers into murine leukocytes and alter pre-mRNA splicing." Journal of Immunological Methods 325(1-2): 114-126.
Matsuo, M., T. Masumura, et al. (1991). "Exon skipping during splicing of dystrophin mRNA precursor due to an intraexon deletion in the dystrophin gene of Duchenne muscular dystrophy kobe." J Clin Invest 87(6): 2127-31.
Monaco, A. P., C. J. Bertelson, et al. (1988). "An explanation for the phenotypic differences between patients bearing partial deletions of the DMD locus." Genomics 2(1): 90-5.
Pramono, Z. A., Y. Takeshima, et al. (1996). "Induction of exon skipping of the dystrophin transcript in lymphoblastoid cells by transfecting an antisense oligodeoxynucleotide complementary to an exon recognition sequence." Biochem Biophys Res Commun 226(2): 445-9.
Sazani, P., R. Kole, et al. (2007). Splice switching oligomers for the TNF superfamily receptors and their use in treatment of disease. PCT WO2007058894, University of North Carolina
Sierakowska, H., M. J. Sambade, et al. (1996). "Repair of thalassemic human beta-globin mRNA in mammalian cells by antisense oligonucleotides." Proc Natl Acad Sci USA 93(23): 12840-4.
Summerton, J. and D. Weller (1997). "Morpholino antisense oligomers: design, preparation, and properties." Antisense Nucleic Acid Drug Dev 7(3): 187-95.
Takeshima, Y., H. Nishio, et al. (1995). "Modulation of in vitro splicing of the upstream intron by modifying an intraexon sequence which is deleted from the dystrophin gene in dystrophin Kobe." J Clin Invest 95(2): 515-20.
van Deutekom, J. C., M. Bremmer-Bout, et al. (2001). "Antisense-induced exon skipping restores dystrophin expression in DMD patient derived muscle cells." Hum Mol Genet 10(15): 1547-54.
van Deutekom, J. C., A. A. Janson, et al. (2007). "Local dystrophin restoration with antisense oligonucleotide PRO051." N Enql J Med 357(26): 2677-86.
Wilton, S. D., A. M. Fall, et al. (2007). "Antisense oligonucleotide-induced exon skipping across the human dystrophin gene transcript." Mol Ther 15(7): 1288-96.
Wilton, S. D., F. Lloyd, et al. (1999). "Specific removal of the nonsense mutation from the mdx dystrophin mRNA using antisense oligonucleotides." Neuromuscul Disord 9(5): 330-8.
Wu, B., H. M. Moulton, et al. (2008). "Effective rescue of dystrophin improves cardiac function in dystrophin-deficient mice by a modified morpholino oligomer." Proc Natl Acad Sci USA 105(39): 14814-9.
Yin, H., H. M. Moulton, et al. (2008). "Cell-penetrating peptide-conjugated antisense oligonucleotides restore systemic muscle and cardiac dystrophin expression and function." Hum Mol Genet 17(24): 3909-18.

EXAMPLES

Materials and Methods

Cells and Tissue Culture Treatment Conditions

Human Rhabdomyosarcoma cells (ATCC, CCL-136; RD cells) preserved in a 5% DMSO solution (Sigma) at a low passage number were thawed in a 37° C. water bath until the ice sliver was no longer visible. Cells were seeded into tissue culture-treated T75 flasks (Nunc) at $1.5 \times 10^6$ cells/flask in 24 mL of warmed DMEM with L-Glutamine (HyClone), 10% fetal bovine serum, and 1% Penicillin-Streptomycin antibiotic solution (CelGro); after 24 hours, media was aspirated, cells were washed once in warmed PBS, and fresh media was added. Cells were grown to 80% confluence in a 37° C. incubator at 5.0% CO2.

Media was aspirated from T75 flasks; cells were washed once in warmed PBS and aspirated. 3 mL of Trypsin/EDTA, warmed in a 37° C. water bath, was added to each T75. Cells were incubated at 37° C. 5 2-5 minutes until, with gentle agitation, they released from the flask. Cell suspension was transferred to a 15.0 mL conical tube; flasks were rinsed with 1.0 mL of Trypsin/EDTA solution to gather remaining cells. Cells were counted with a Vi-Cell XR cell counter (Beckman Coulter). Cells were seeded into tissue culture-treated 12-well plates (Falcon) at $2.0 \times 10^5$ viable cells per well in 1.0 mL media. Cells were incubated overnight in a 37° C. incubator at 5.0% $CO_2$.

Twelve-well seeded plates were examined for even cellular distribution and plate adherence. Lyophilized peptide conjugated phosphorodiamidate morpholino oligomers (PPMOs) were re-suspended at 2.0 mM in nuclease-free water (Ambion), and kept on ice during cell treatment; to verify molarity, PPMOs were measured using a NanoDrop 2000 spectrophotometer (Thermo Scientific). Immediately prior to PPMO treatment, media was aspirated, and cells were rinsed in warmed PBS. PPMOs were diluted in warmed media to the desired molarity; cells were treated in a total of 1.0 mL PPMO per well. PPMOs were tested in triplicate. For no-treatment controls, fresh, warmed media was added in 1.0 mL total volume. Cells were incubated for 48 hours in a 37° C. incubator at 5.0% CO2.

RNA Extraction

Media was aspirated, and cells were rinsed in warmed PBS. RNA was extracted with the QuickGene-Mini80 system, QuickGene RNA cultured cell HC kit S, and MagNAlyser with ceramic bead homogenization using the manufacturers' recommended protocols. Briefly, cells were lysed in treatment plates with 350 uL LRP (10 uL β-Mercaptoethanol added per 100 uL LRP) lysis buffer; homogenate was gently triturated to ensure full lysis, and transferred to MagNAlyser tubes. Tubes were spun at 2800 rpm for 30 seconds in the MagNAlyser to ensure full homogenization, and iced briefly. 50 uL SRP solubilization buffer was added and homogenate was vortexed for 15 seconds. 170 uL >99% ethanol was added to each tube, and homogenate was vortexed for 60 seconds. Homogenate was flash-spun and transferred to Mini80 RNA cartridges, samples were pressurized and flow-through was discarded. Cartridges were washed in 750 uL WRP wash buffer and pressurized. 40 uL of DNase solution (1.25 uL Qiagen DNaseI, 35 uL RDD Buffer, 3.75 uL nuclease-free water) was added directly to the cartridge membrane; cartridges were incubated four minutes at room temperature. Cartridges were washed twice with 750 uL WRP, pressurizing after each wash. Cartridges were placed over nuclease-free tubes. 50 uL CRP elution buffer was added to each membrane; membranes were incubated for five minutes at room-temperature. Cartridges were pressurized and eluate was collected. RNA was stored at −80° C. pending quantification. RNA was quantified using the NanoDrop™ 2000 spectrophotometer.

Nested RT-PCR

Primer-specific, exon-specific, optimized nested RT-PCR amplification was performed using the primer pair sets for each dystrophin exon as shown below in Table 1.

TABLE 1

Primer pair sets used to PCR amplify human dystrophin mRNA to detect exon-skipping.

| Name | F/R | I/O | Sequence (5'-3') | Exon | Purpose | SEQ ID NO: |
|---|---|---|---|---|---|---|
| PS170 | F | O | CCAGAGCTTTACCTGAGAAACAAG | 48 | Detection | 640 |
| PS172 | F | I | CCAGCCACTCAGCCAGTGAAG | 49 | of Exon 50 | 641 |
| PS174 | R | I | CGATCCGTAATGATTGTTCTAGCC | 52 | and 51 | 642 |
| PS176 | R | O | CATTTCATTCAACTGTTGCCTCCG | 53 | Skipping in Human Dystrophin | 643 |
| PS186 | F | O | CAATGCTCCTGACCTCTGTGC | 42 | Detection | 644 |
| PS187 | F | I | GTCTACAACAAAGCTCAGGTCG | 43 | of Exon 44 | 645 |
| PS189 | F | I | GCAATGTTATCTGCTTCCTCCAACC | 46 | and 45 | 646 |
| PS190 | R | O | GCTCTTTTCCAGGTTCAAGTGG | 46 | Skipping in Human Dystrophin | 647 |
| PS192 | F | O | CTTGGACAGAACTTACCGACTGG | 51 | Detection | 648 |
| PS193 | F | I | GCAGGATTTGGAACAGAGGCG | 52 | of Exon 53 | 649 |
| PS195 | R | I | CATCTACATTTGTCTGCCACTGG | 54 | Skipping in | 650 |
| PS197 | R | O | GTTTCTTCCAAAGCAGCCTCTCG | 55 | Human Dystrophin | 651 |

The indicated primer pairs are shown as either forward or reverse (F/R) and either outer or inner primer pairs (I/O) corresponding to primary or secondary amplifications, respectively. The location of the primer target is indicated in the Exon column and the Purpose indicates the exon-skipping events can be detected. For example, PS170 and PS176 primers amplify a region from exon 48 to 53 in the primary amplification. Primers PS172 and PS174 then amplify a region from exon 49 to 52 in the secondary amplication. This nested PCR reaction will detect exon skipping of both exons 50 and/or exon 51. The specific nested RT-PCR reaction conditions are provided below.

RNA extracted from treated cells (described above) was diluted to 20 ng/ul for all samples.

TABLE 2

Reaction setup for RT-PCR and primary amplification (50 μl reaction):

| | |
|---|---|
| 2× Reaction mix | 25 μl |
| PS XXX Forward Primer (30 μM) | 0.5 μl |

TABLE 2-continued

Reaction setup for RT-PCR and primary amplification (50 μl reaction):

| | |
|---|---|
| (see Table 1) | |
| PS XXX Reverse Primer (30 μM) | 0.5 μl |
| (see Table 1) | |
| Superscript III Platinum Taq mix | 2 μl |
| Template RNA (20 ng/μl) | 10 μl |
| Nuclease-Free Water (50 μl total volume) | 12 μl |

TABLE 3

RT-PCR and primary amplification program:

| | Temperature | Time | |
|---|---|---|---|
| Reverse Transcription | 55° C. | 30 minutes | |
| RT Inactivation | 94° C. | 2 minutes | |
| Denaturing | 94° C. | 1 minute | 8 Cycles |
| Annealing | 59° C. | 1 minute | |
| Extension | 68° C. | 1 minute | |
| | 4° C. | ∞ | |

TABLE 4

Reaction setup for nested secondary amplification (50 μl reaction):

| | |
|---|---|
| 10× PCR Buffer | 5 μl |
| dNTP solution (10 mM) | 0.5 μl |
| 50 mM MgCl | 1.5 μl |
| PS XXX Forward Primer (30 μM) | 0.33 μl |
| (see Table 1) | |
| PS XXX Reverse Primer (30 μM) | 0.33 μl |
| (see Table 1) | |
| Platinum Taq DNA polymerase | 0.2 μl |
| 0.1 mM Cy5-dCTP | 1 μl |
| RT-PCR product (from Step 1) | 1 μl |
| Nuclease-Free Water (50 μl total volume) | 40.15 μl |

TABLE 5

Nested secondary amplication program program:

| | Temperature | Time | |
|---|---|---|---|
| Primary Denature | 94° C. | 3 minutes | |
| Denaturing | 94° C. | 45 seconds | 28-30 Cycles |
| Annealing | 59° C. | 30 seconds | |
| Extension | 68° C. | 1 minute | |
| | 4° C. | ∞ | |

Gel Electrophoresis Analysis

Ten microliters of 5× Ficoll loading dye was added to each 50 microliter nested RT-PCR reaction. Fifteen microliters of PCR/dye mixture was run on a 10% TBE gel at 300 volts for 30 minutes. After electrophoresis, the gel was washed in diH2O for at least one hour, changing the water every 30 minutes. The gel was then scanned on a Typhoon Trio Variable Mode Imager (GE Healthcare). For exon 44 skipping, the nested RT-PCR product from full-length dystrophin transcript is 571 bp, and 423 bp from Exon 44-skipped mRNA (exon 44 is 148 bp). For exon 45, the nested RT-PCR product from full-length dystrophin transcript is 571 bp, and 395 bp from Exon 45-skipped mRNA (exon 45 is 176 bp). For exon 53, the PCR product from full-length dystrophin transcript is 365 bp, and 153 bp from exon 53-skipped mRNA (exon 53 is 212 bp).

The gel images were subjected to quantitative analysis by measuring the band intensities of the full-length PCR product compared to the exon-skipped product. In some cases, the percent skipping at a fixed PPMO concentration (e.g., 3 micromolar) was used to determine the relative activity of a series of PPMO to induce exon skipping of a given exon. In other situations, a PPMO dose-range was used to treat cells (e.g., 0.1, 0.3, 1.0, 3.0 and 10 micromolar) and an $EC_{50}$ was calculated based on the percent skipping induced at each concentration.

Example 1

Exon 51 Scan

Figure 2A:
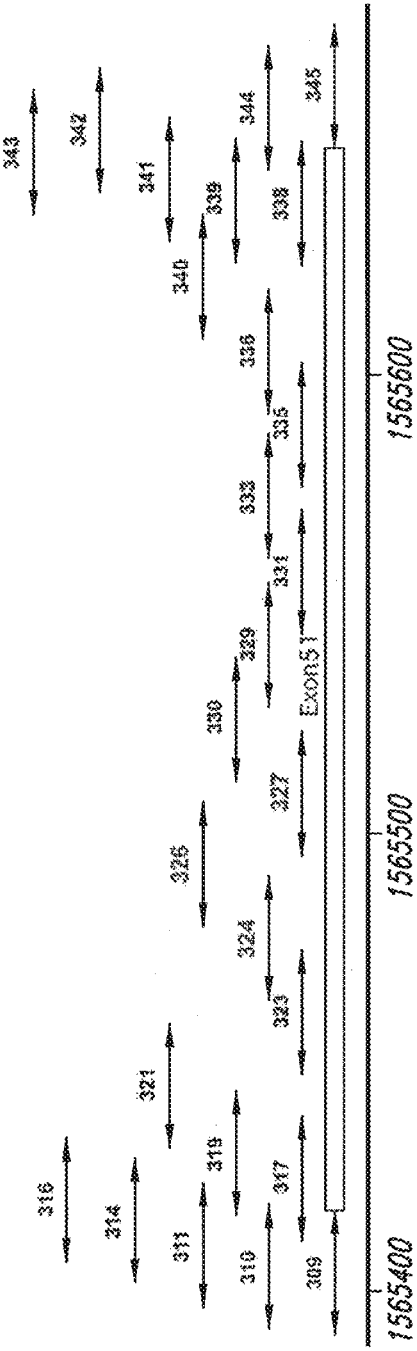
FIG. 2A shows the relative location and results of an antisense oligomer exon 51 scan designed to induce skipping of human dystrophin exon 51.
Figure 2C:

A series of overlapping antisense PPMOs that target human dystrophin exon 51 were designed, synthesized and used to treat either human rhabdomyosarcoma cells (RD cells) or primary human skeletal muscle cells. This strategy is termed an "exon scan" and was used similarly for several other dystrophin exons as described below. All the PPMOs were synthesized as peptide-conjugated PMO (PPMO) using the CP06062 peptide (SEQ ID NO: 578) and a 3' terminal PMO linkage. For exon 51, a series of 26 PPMOs, each 26 bases in length, were made (SEQ ID NOS: 309-311, 314, 316, 317, 319, 321, 323, 324, 326, 327, 329-331, 333, 335, 336, 338-345) as shown in FIG. 2A. The PPMOs were evaluated for exon skipping efficacy by treating RD cells at various concentrations as described above in the Materials and Methods. Three PPMOs (SEQ ID NOS: 324, 326 and 327) were identified as effective in inducing exon-skipping and selected for additional evaluation. Dose-ranging experiments in RD cells and primary human skeletal muscle cells were used to confirm the relative efficacy of these three PPMO sequences. SEQ ID NO: 327 was shown to be most effective at inducing exon 51 skipping as shown in FIGS. 2B and 2C.

Figure 2D:
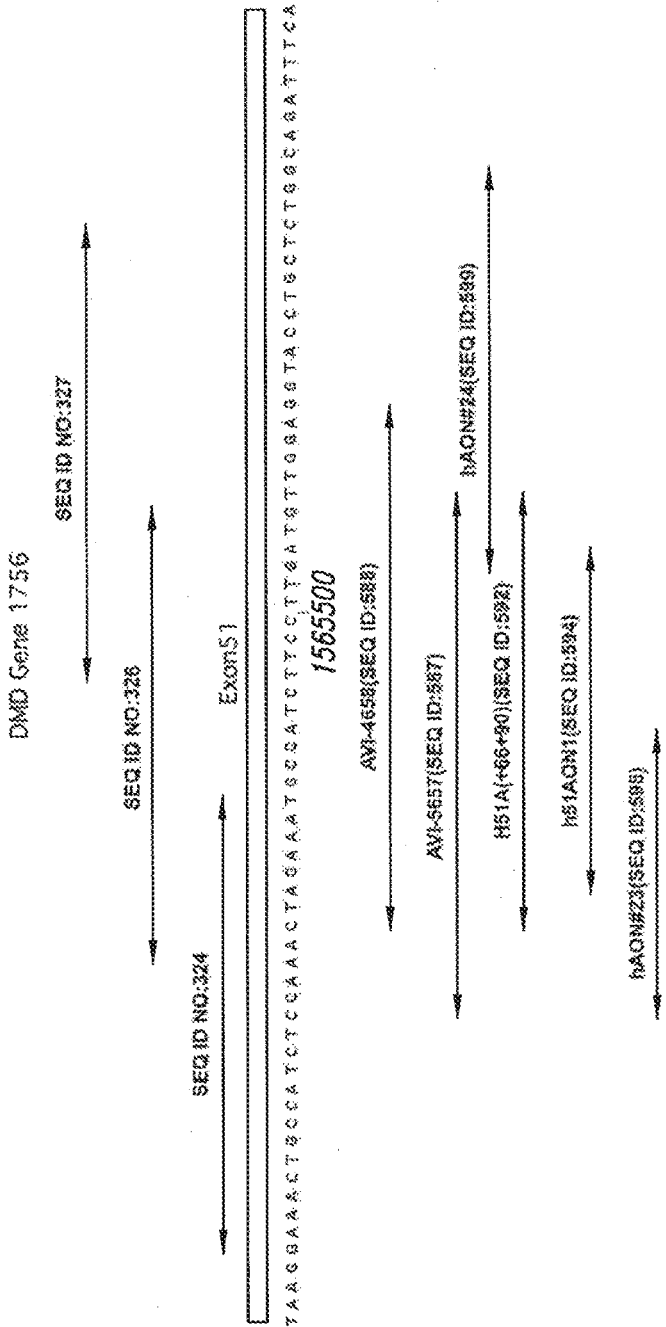
FIG. 2D shows the relative location within exon 51 of three selected oligomers compared to certain sequences.

A comparison of the relative effectiveness of SEQ ID NO: 327 to other exon 51-targeted antisense sequences was performed in RD cells and primary human skeletal muscle cells, as described above. All the evaluated sequences were made as peptide-conjugated PMOs using the CP06062 peptide (SEQ ID NO: 578). This allowed direct comparison of the relative effectiveness of the antisense sequences without regard to antisense chemistry or cell delivery. The relative location of the certain exon 51-targeted oligos compared to SEQ ID NO: 327 is shown in FIG. 2D. As shown in FIG. 2C, there is a ranked hierarchy of exon-skipping effectiveness, with SEQ ID NO: 327 being the most effective by at least a factor of several-fold compared to other sequences.

Example 2

Exon 50 Scan

Figure 3A:
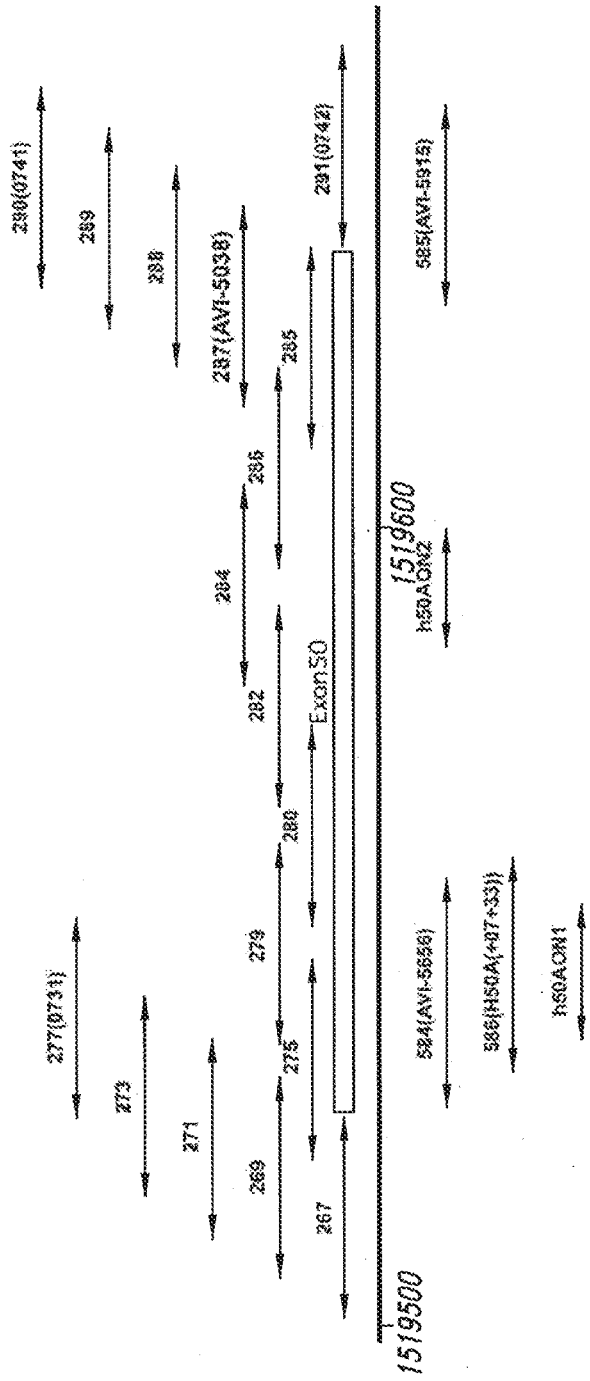
FIG. 3A shows the relative location and results of an antisense oligomer exon 50 scan designed to induce skipping of human dystrophin exon 50 compared to other sequences that induce exon 50 skipping.

A series of overlapping antisense PPMOs that target human dystrophin exon 50 were designed and synthesized. For exon 50, a series of 17 PPMOs, each 25 bases in length, were made (SEQ ID NOS:267, 269, 271, 273, 275, 277, 279, 280, 282 and 284-291) as shown in FIG. 3A. The PPMOs were evaluated for exon skipping efficacy by treating RD cells at various concentrations as described above in the Materials and Methods. Four PPMOs (SEQ ID NOS: 277, 287, 290 and 291) were identified as effective in inducing exon-skipping and selected for additional evaluation. Dose-ranging experiments in RD cells were used to confirm the relative efficacy of these four PMO sequences. SEQ ID NOs: 584 (AVI-5656) and 287 (AVI-5038) were shown to be most effective at inducing exon 50 skipping as shown in FIG. 3B. The EC$_{50}$ values were derived from the dose-ranging experiments and represent the calculated concentration where 50% of the PCR product is from the mRNA lacking exon 50 relative to the PCR product produced from the mRNA containing exon 50. Compared to other sequences (see, e.g., SEQ ID NOs: 584 and 585 correspond to SEQ ID NOs: 173 and 175 in WO2006/000057, respectively) AVI-5038 (SEQ ID NO: 287) is equivalent or better at inducing exon-skipping activity in the RD cell assay as shown in FIG. 3B.

Example 3

Exon 53 Scan

Figure 4A:
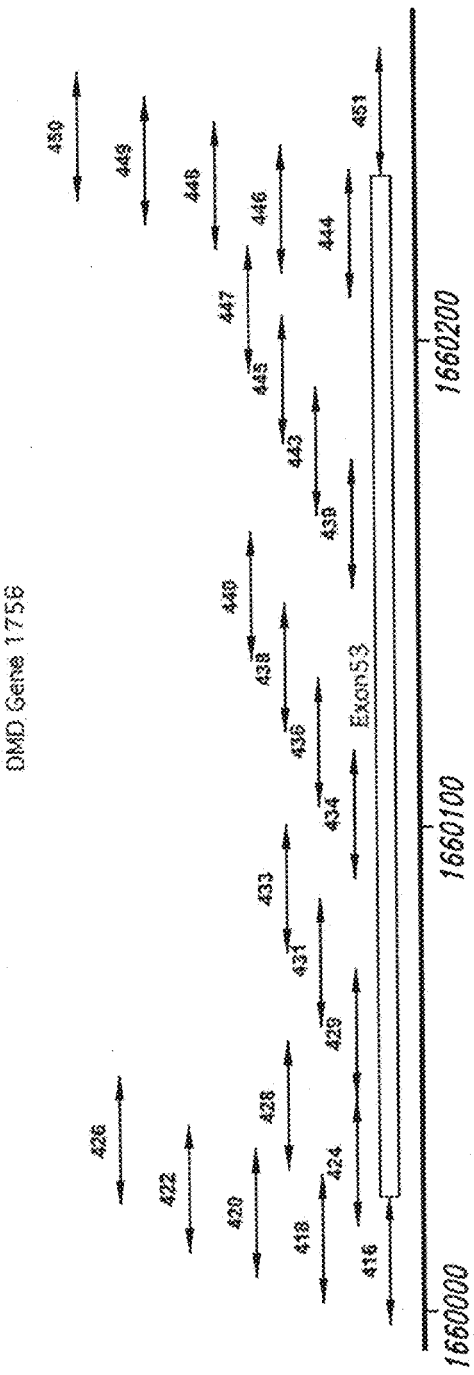
FIG. 4A shows the relative location and results of an antisense oligomer exon 53 scan designed to induce skipping of human dystrophin exon 53.
Figure 4B:
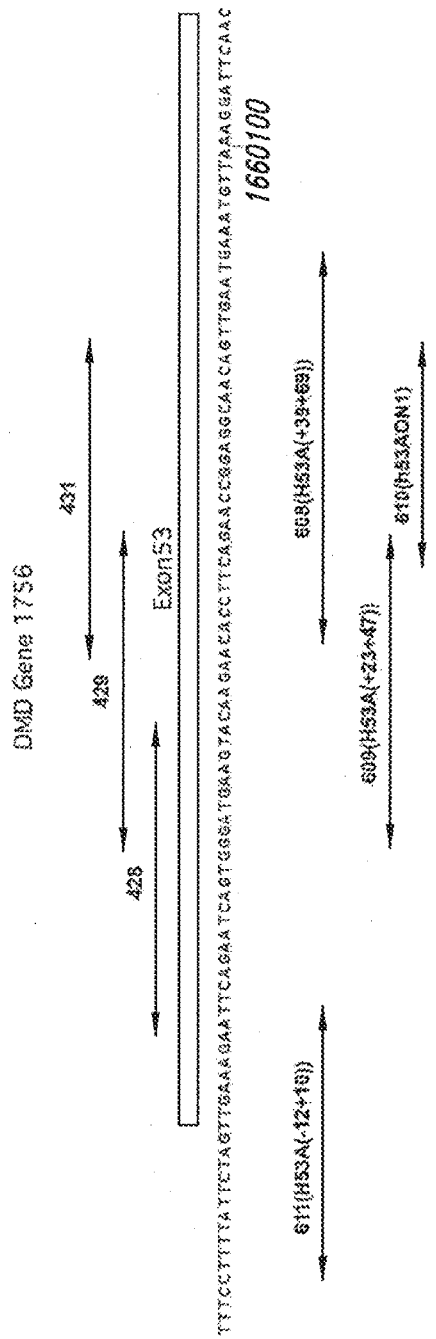
FIG. 4B shows the relative location of certain sequences used to compare the exon-skipping activity of those oligomers selected as being most active in the exon 53 scan.
Figure 4C:
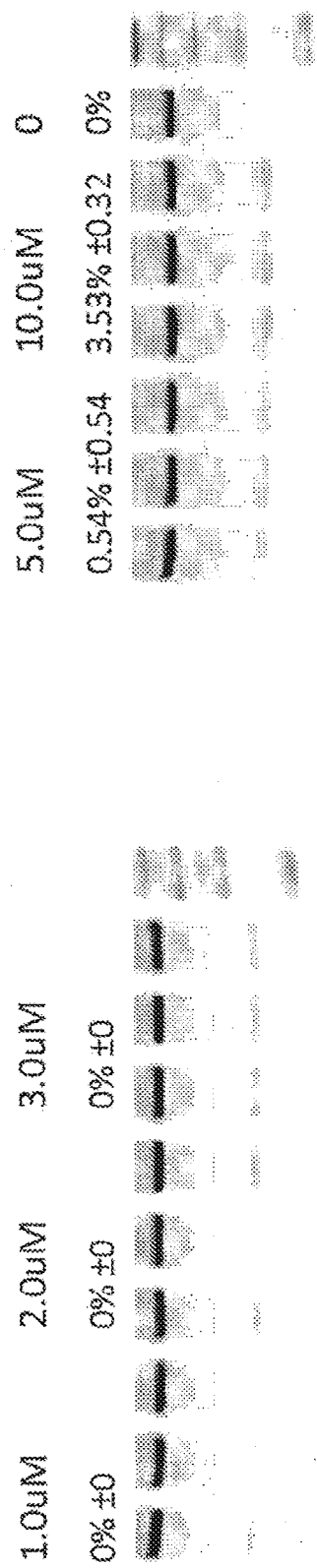
FIGS. 4C-F show the results of dose-ranging studies, summarized in FIG. 4G, using the oligomers selected as being most efficacious in the exon 53 scan (SEQ ID NOS:422, 428, 429 and 431).
Figure 4D:
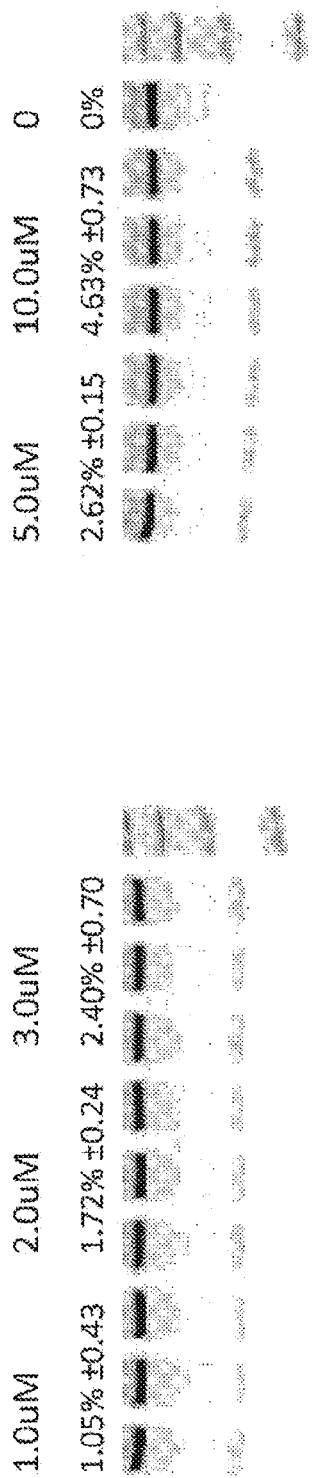
Figure 4E:
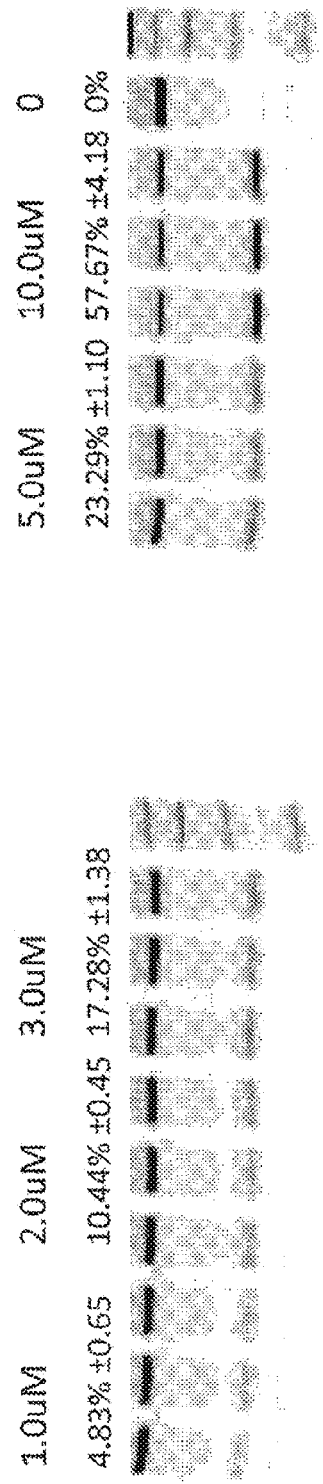
Figure 4F:
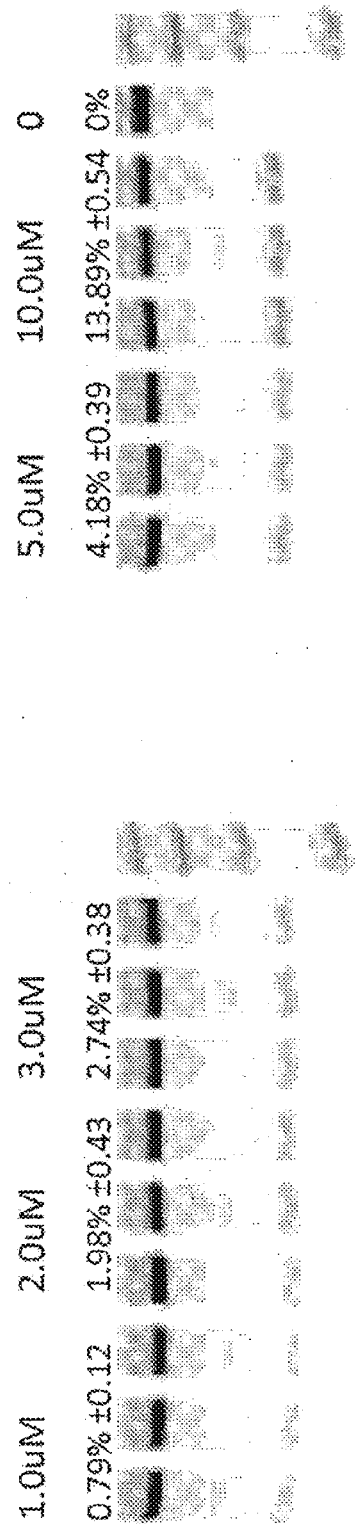
Figure 4H:
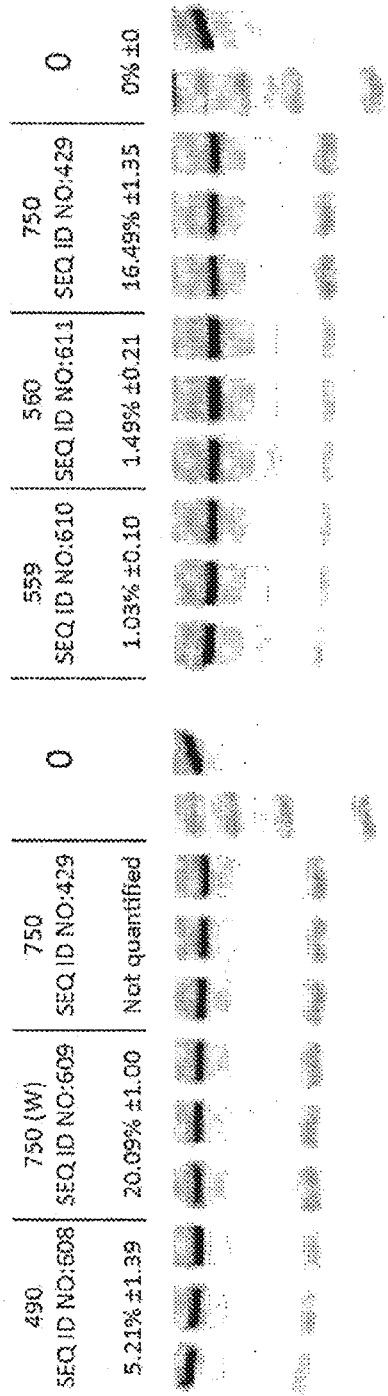
FIGS. 4H and 4I show the relative activity of certain sequences (SEQ ID NOS: 608-611) compared to the activity of the most active exon 53-skipping oligomer (SEQ ID NO:429) in both RD cells and human primary skeletal muscle cells.
Figure 4I:
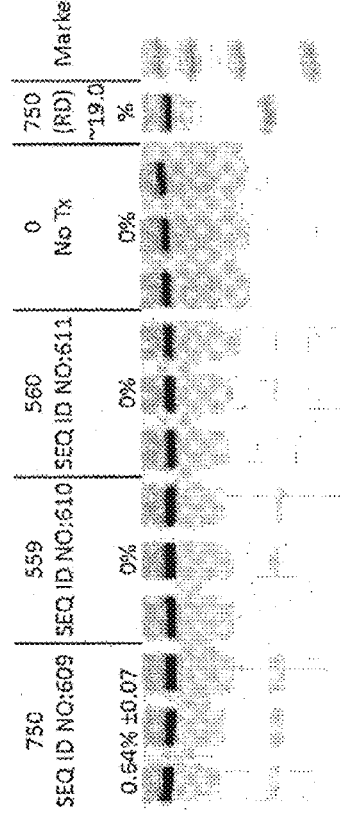

A series of overlapping antisense PPMOs that target human dystrophin exon 53 were designed and synthesized. For exon 53, a series of 24 PPMOs, each 25 bases in length, were made (SEQ ID NOS:416, 418, 420, 422, 424, 426, 428, 429, 431, 433, 434, 436, 438-440 and 443-451) as shown in FIG. 4A. The PPMOs were evaluated for exon skipping efficacy by treating RD cells and primary human skeletal muscle cells at various concentrations as described above in the Materials and Methods. Three PPMOs (SEQ ID NOS: 428, 429 and 431) were identified as effective in inducing exon-skipping and selected for additional evaluation. Dose-ranging experiments in RD cells were used to confirm the relative efficacy of these three PMO sequences. SEQ ID NO: 429 was shown to be most effective at inducing exon 53 skipping as shown in FIGS. 4B-F. However, when compared to other exon 53 antisense sequences, SEQ ID NO: 429 proved identical to H53A(+23+47) which is listed as SEQ ID NO: 195 in WO2006/000057 and SEQ ID NO: 609 in the present application. Other sequences were compared to SEQ ID NO: 429 including H53A(+39+69) and H53A(-12+10) (listed as SEQ ID NOs:193 and 199 in WO2006/000057, respectively) and h53AON1 (listed as SEQ ID NO:39 in U.S. application Ser. No. 11/233,507) and listed as SEQ ID NOs: 608, 611 and 610, respectively, in the present application. All the evaluated sequences were made as peptide-conjugated PMOs using the CP06062 peptide (SEQ ID NO: 578). This allowed direct comparison of the relative effectiveness of the antisense sequences without regard to antisense chemistry or cell delivery. As shown in FIGS. 4I and 4G-H, SEQ ID NO: 429 was shown to be superior to each of these four sequences.

Example 4

Exon 44 Scan

Figure 5A:
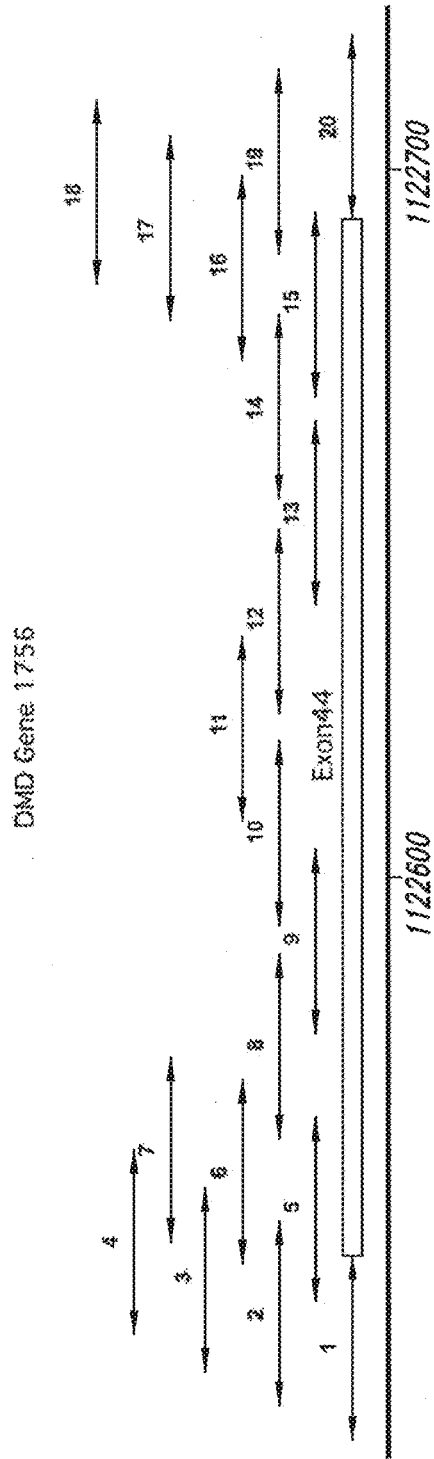
FIG. 5A shows the relative location and results of an antisense oligomer exon 44 scan designed to induce skipping of human dystrophin exon 44.

A series of overlapping antisense PPMOs that target human dystrophin exon 44 were designed and synthesized. For exon 44, a series of PPMOs, each 25 bases in length, were made (SEQ ID NOS:1-20) as shown in FIG. 5A. The PPMOs were evaluated for exon skipping efficacy by treating RD cells at various concentrations as described above in the Materials and Methods. Five PPMOs (SEQ ID NOS:4, 8, 11, 12 and 13) were identified as effective in inducing exon-skipping and selected for additional evaluation. Dose-ranging experiments in RD cells were used to confirm the relative efficacy of these five PPMO sequences as shown in FIGS. 5C to 5H. SEQ ID NOs: 8, 11 and 12 were shown to be most effective at inducing exon 44 skipping as shown in FIG. 5H with SEQ ID NO:12 proving the most efficacious.

Comparison of SEQ ID NO: 12 to other exon 44 antisense sequences was done in both RD cells and human primary skeletal muscle cells. All the evaluated sequences were made as peptide-conjugated PMOs using the CP06062 peptide (SEQ ID NO: 578). This allowed direct comparison of the relative effectiveness of the antisense sequences without regard to antisense chemistry or cell delivery.

Figure 5B:
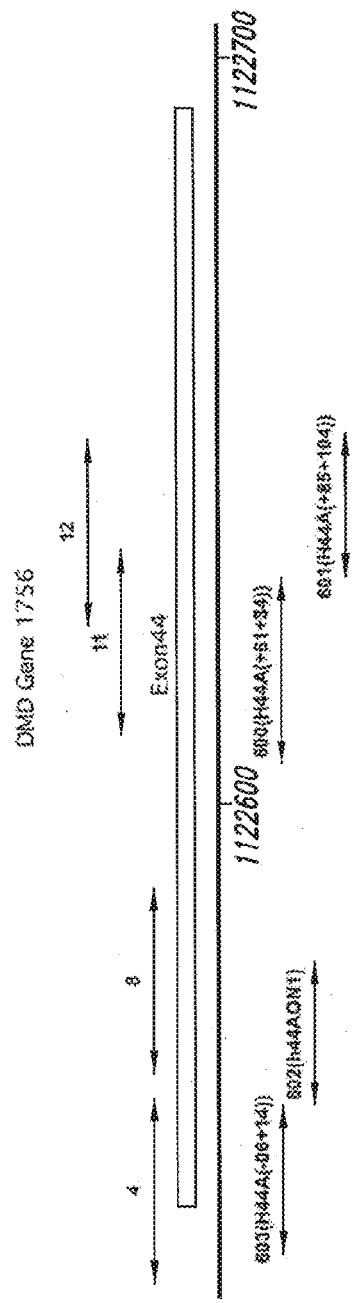
FIG. 5B shows the relative location within exon 44 of certain sequences used to compare the exon-skipping activity to those oligomers selected as being most active in the exon 44 scan.
Figure 5C:
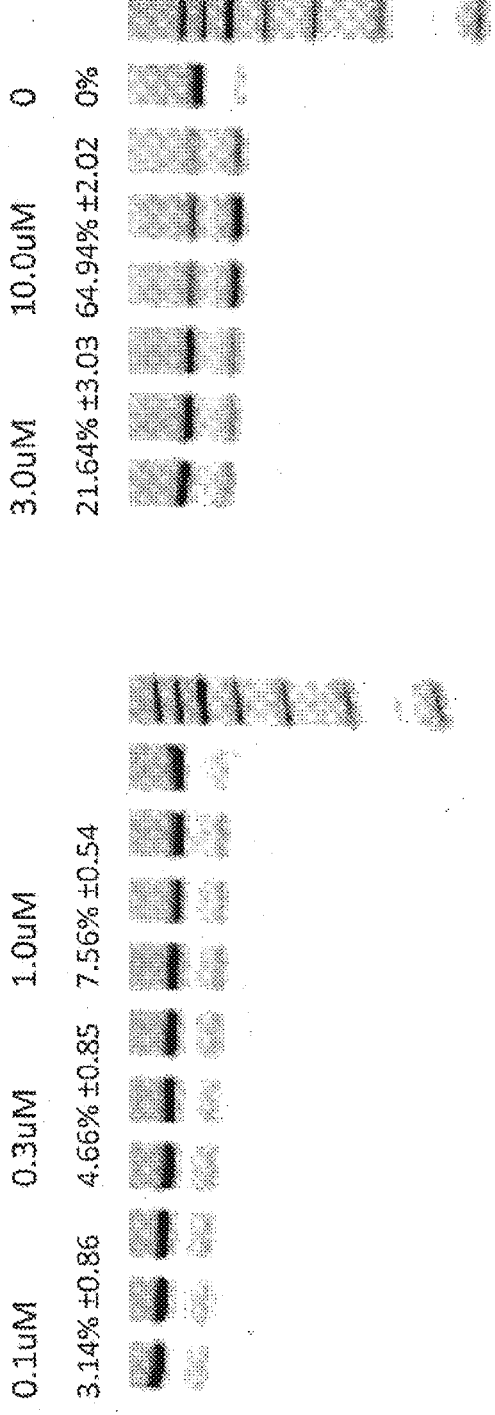
FIGS. 5C-G show the results of dose-ranging studies, summarized in FIG. 5H, using the oligomers selected as being most efficacious in the exon 44 scan (SEQ ID NOS: 4, 8, 11, 12 and 13).
Figure 5D:
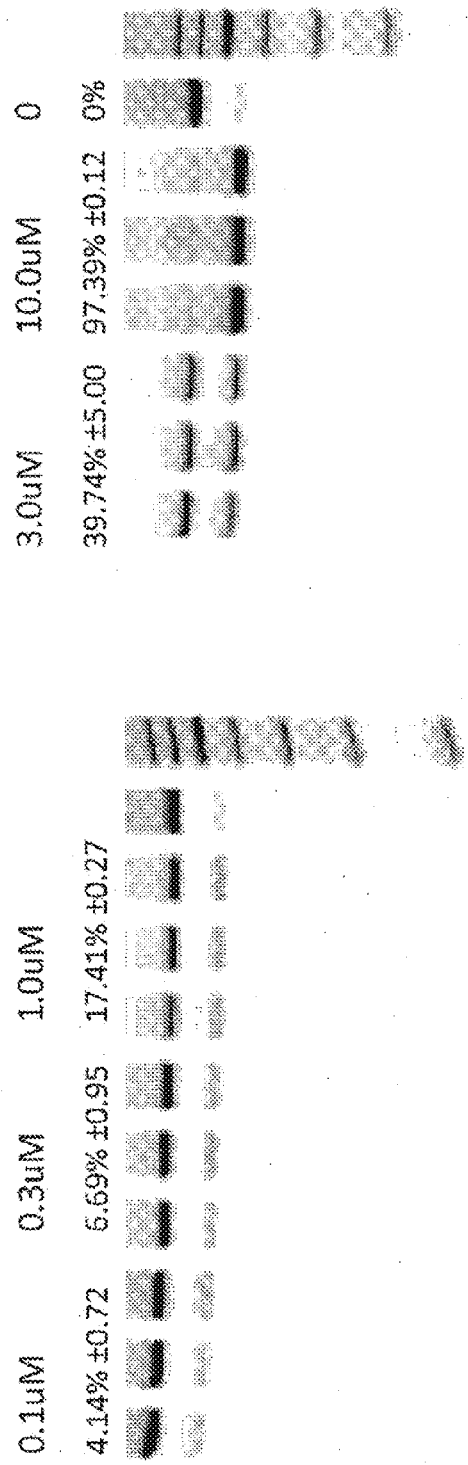
Figure 5E:
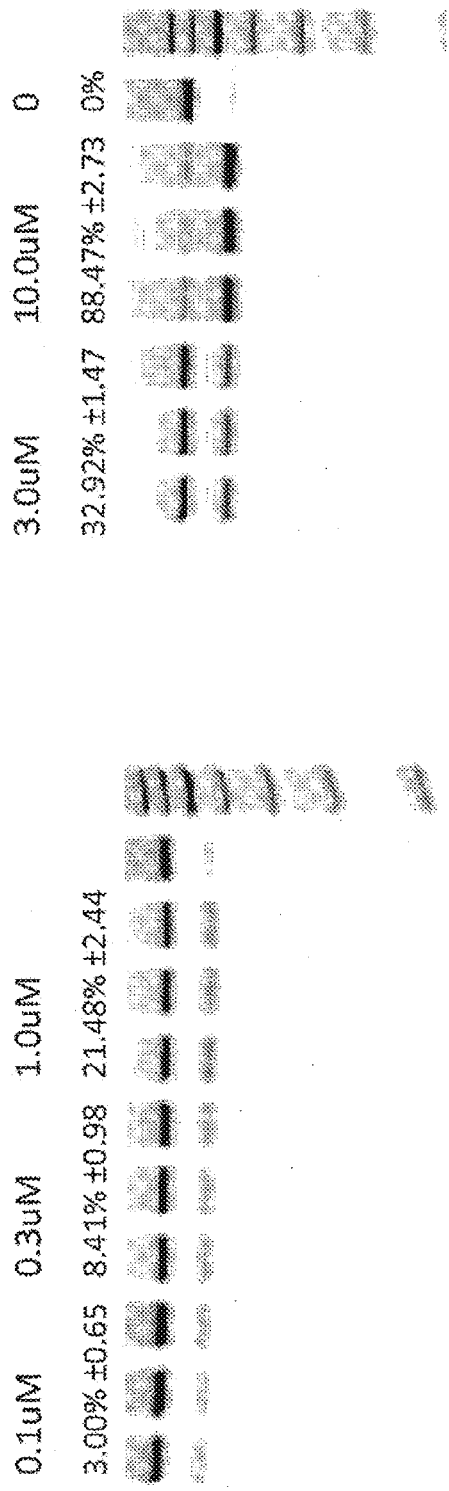
Figure 5F:
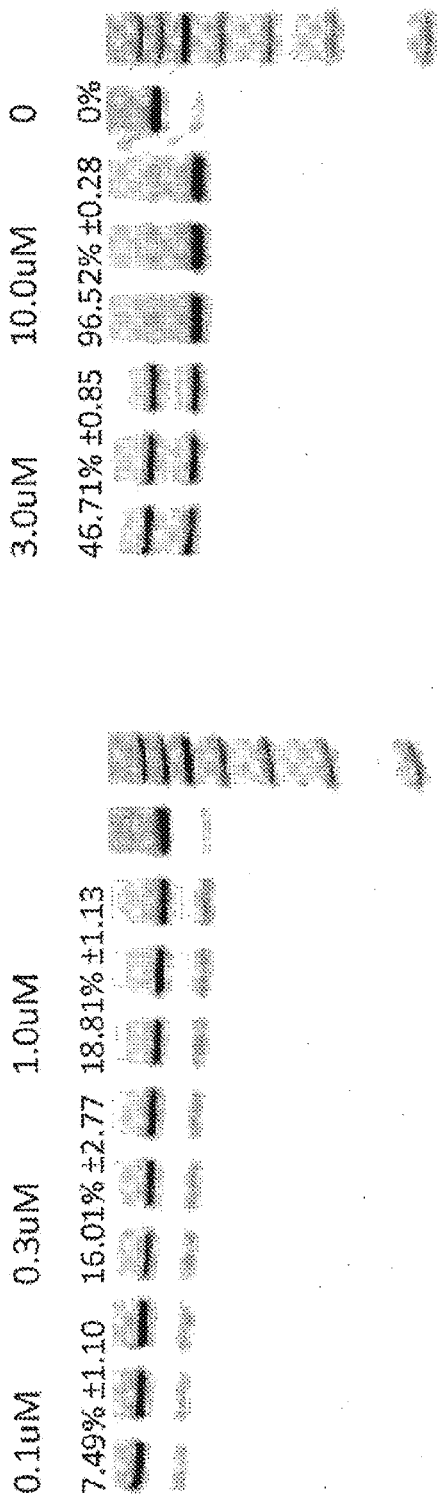
Figure 5G:
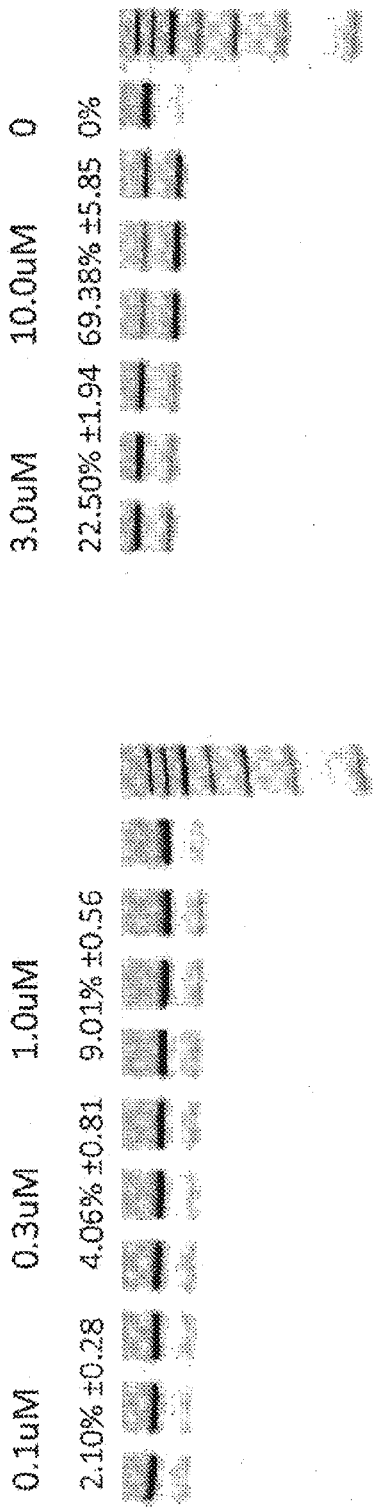
Figure 5I:
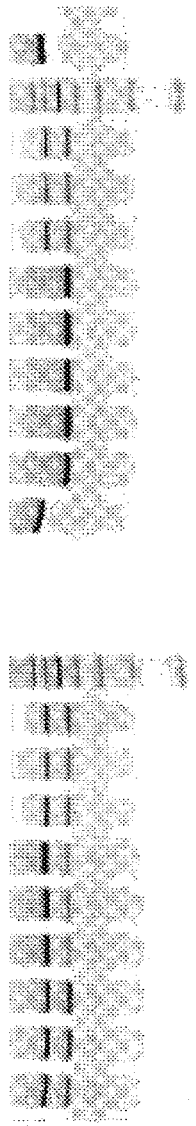
FIGS. 5I and 5J show the relative activity of certain sequences (SEQ ID NOS: 600-603) compared to the activity of the most active exon 53-skipping oligomer (SEQ ID NO:12) in both RD cells and human primary skeletal muscle cells.
Figure 5J:
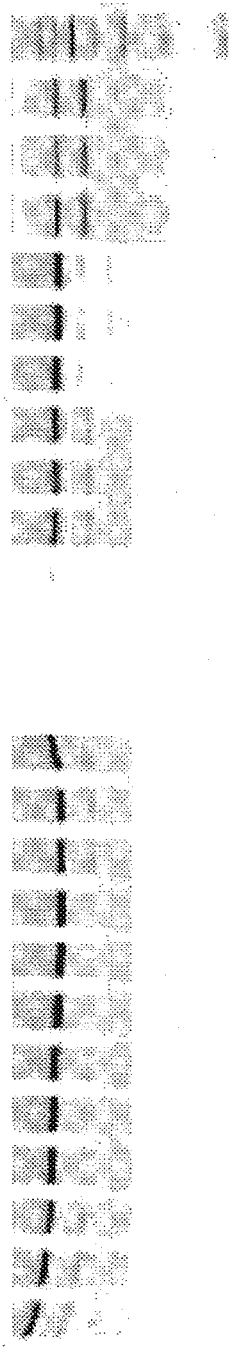

The alignment of the sequences (SEQ ID NOS: 600, 601, 602 and 603) with SEQ ID NOS: 4, 8, 11 and 12 is shown in FIG. 5B. SEQ ID NOS: 601 and 603 are listed as SEQ ID NOS: 165 and 167 in WO2006/000057. SEQ ID NO:602 is listed in WO2004/083446 and as SEQ ID NO: 21 in U.S. application Ser. No. 11/233,507. SEQ ID NO:600 was published in 2007 (Wilton, Fall et al. 2007). The comparison in RD cells showed that both SEQ ID NOS: 602 and 603 were superior to SEQ ID NO:12 (FIG. 5I). However, as shown in FIG. 5J, in human primary skeletal muscle cells SEQ ID NO:12 was superior (8.86% exon skipping) to SEQ ID NO:602 (6.42%). Similar experiments are performed with SEQ ID NO:603.

Example 5

Exon 45 Scan

Figure 6A:
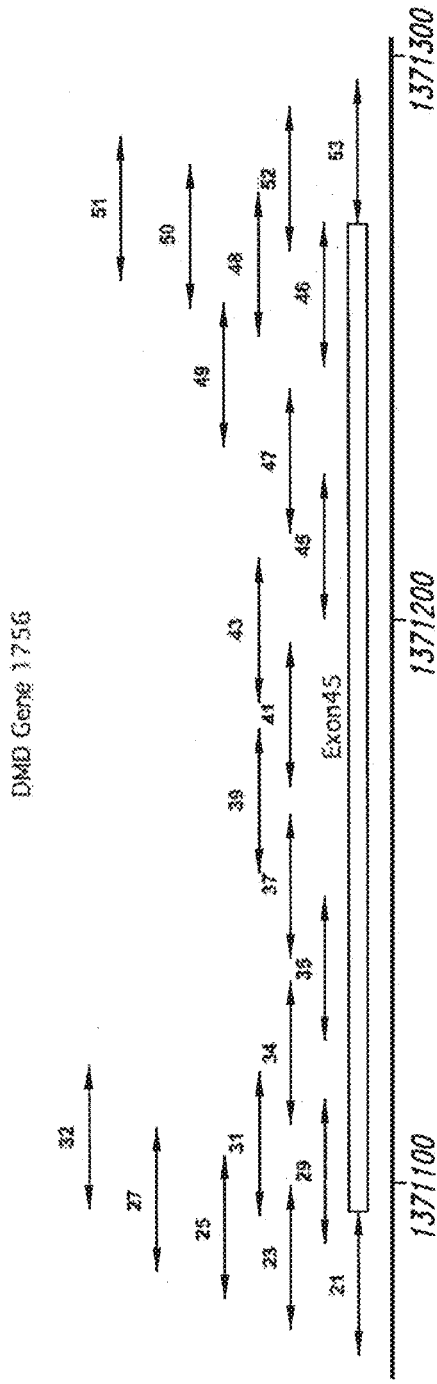
FIG. 6A shows the relative location and results of an antisense oligomer exon 45 scan designed to induce skipping of human dystrophin exon 45.

A series of overlapping antisense PPMOs that target human dystrophin exon 45 were designed and synthesized. For exon 45, a series of 22 PPMOs, each 25 bases in length, were made (SEQ ID NOS: 21, 23, 25, 27, 29, 31, 32, 34, 35, 37, 39, 41, 43 and 45-53) as shown in FIG. 6A. The PPMOs were evaluated for exon skipping efficacy by treating RD cells and human primary skeletal muscle cells at various concentrations as described above in the Materials and Methods. Five PPMOs (SEQ ID NOS:27, 29, 34, and 39) were identified as effective in inducing exon-skipping and selected for additional evaluation. Dose-ranging experiments in RD cells were used to confirm the relative efficacy of these four PMO sequences as shown in FIGS. 6C-G and summarized in FIG. 6H. SEQ ID NO: 49 was used as a negative control in these experiments. SEQ ID NOs: 29 and 34 were shown to be most effective at inducing exon 45 skipping as shown in FIG. 6H.

Figure 6B:
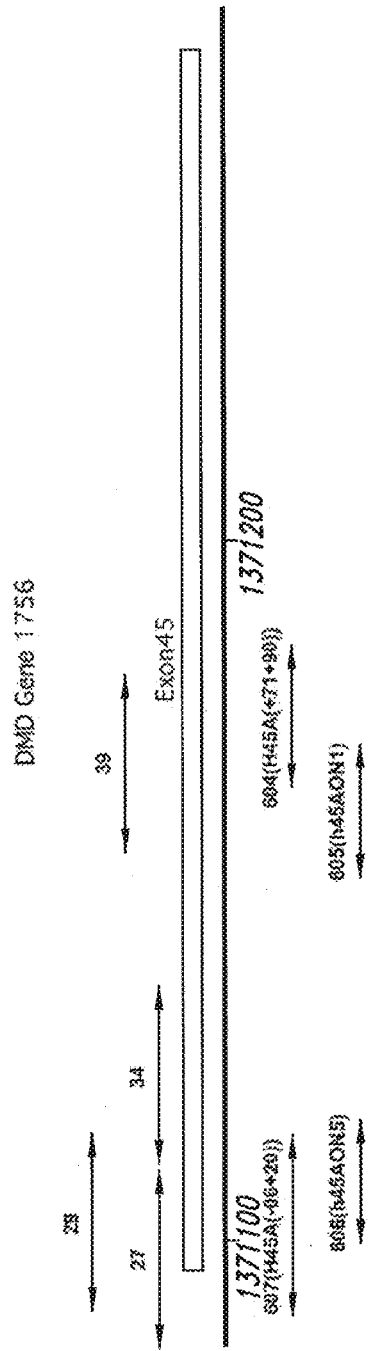
FIG. 6B shows the relative location within exon 45 of certain sequences used to compare the exon-skipping activity to those oligomers selected as being most active in the exon 45 scan.
Figure 6C:
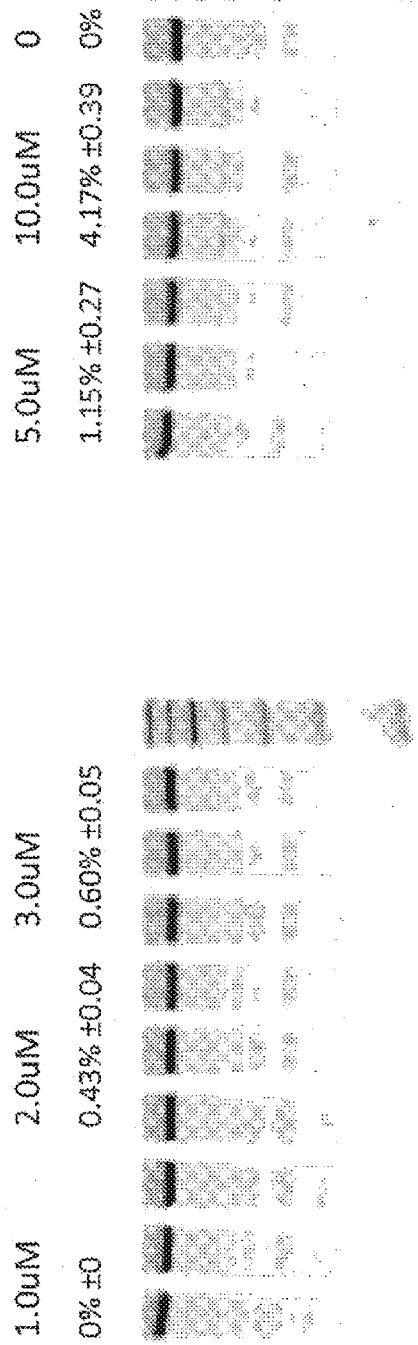
FIGS. 6C-F show the results of dose-ranging studies, summarized in FIG. 6H, using the oligomers selected as being most efficacious in the exon 45 scan (SEQ ID NOS: 27, 29, 34 and 39).
Figure 6D:
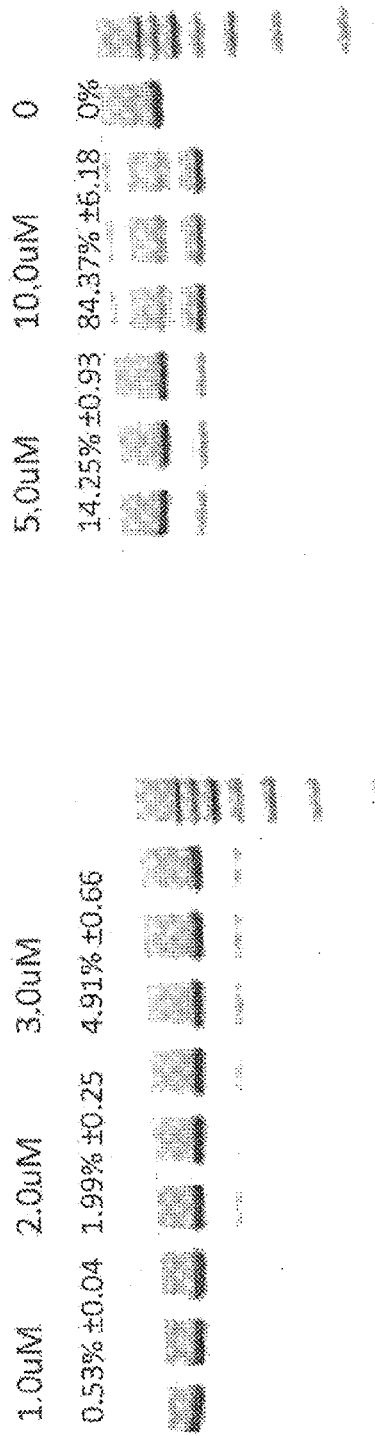
Figure 6E:
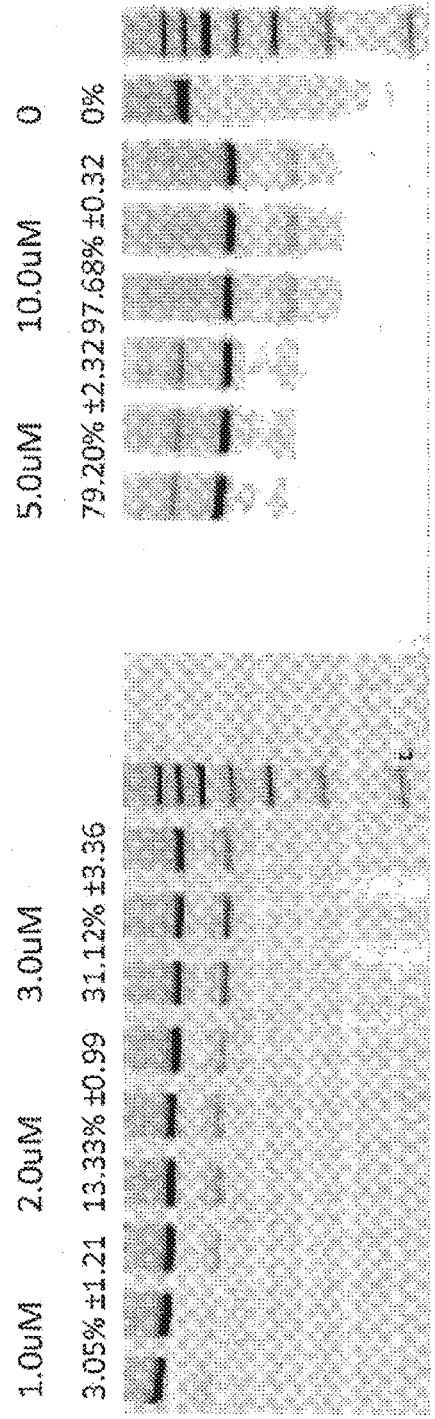
Figure 6F:
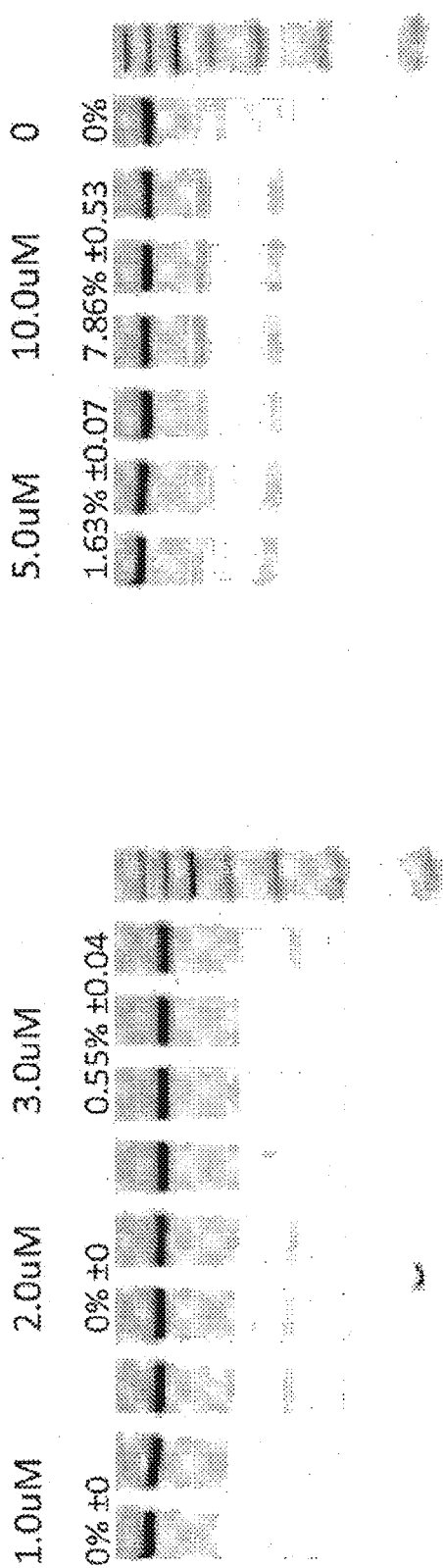
Figure 6G:
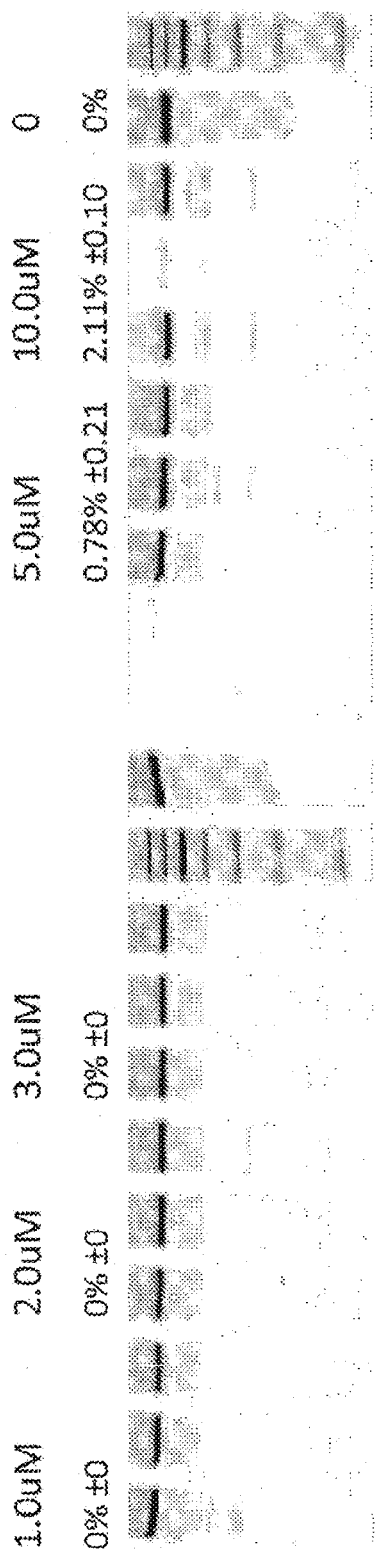
FIG. 6G uses a relatively inactive oligomer (SEQ ID NO: 49) as a negative control.
Figure 6I:
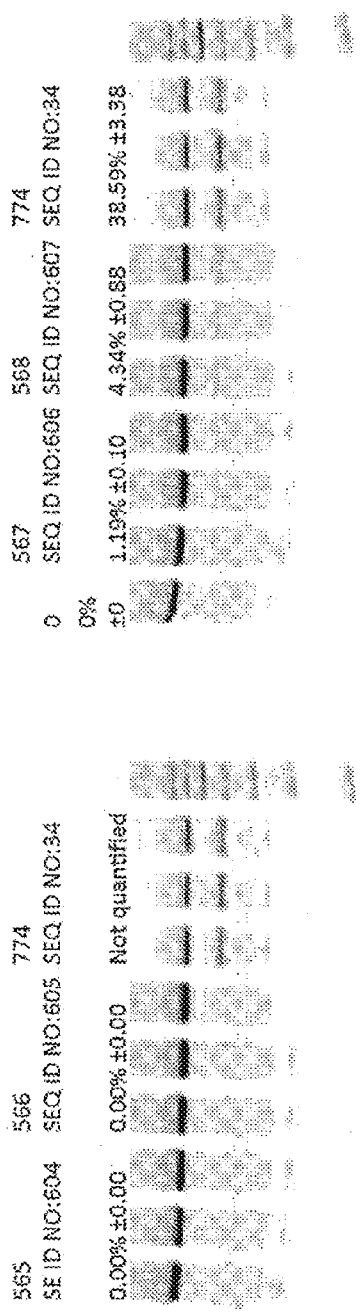
FIGS. 6I and 6J show the relative activity of certain sequences (SEQ ID NOS: 604-607) compared to the activity of the most active exon 53-skipping oligomer (SEQ ID NO: 34) in both RD cells and human primary skeletal muscle cells.
Figure 6J:
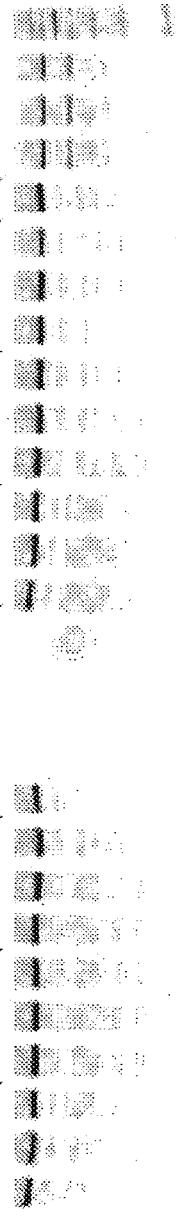

Comparison of SEQ ID NO: 34 to other exon 45 antisense sequences was done in both RD cells and human primary skeletal muscle cells. All the evaluated sequences were made as peptide-conjugated PMOs using the CP06062 peptide (SEQ ID NO: 578). This allowed direct comparison of the relative effectiveness of the antisense sequences without regard to antisense chemistry or cell delivery. The alignment of the sequences (SEQ ID NOS: 604, 605, 606 and 607) with SEQ ID NOS: 27, 29, 34 and 39 is shown in FIG. 6B. SEQ ID NOS: 604 and 607 are listed as SEQ ID NOS: 211 and 207 in WO2006/000057, respectively. SEQ ID NOS:605 and 606 are listed in U.S. application Ser. No. 11/233,507 as SEQ ID NOS: 23 and 1, respectively. The comparison in RD cells showed that SEQ ID NO: 34 was superior to all four sequences evaluated as shown in FIG. 6I. Testing of these compounds in different populations of human primary skeletal muscle cells is performed as described above.

Sequence ID Listing

Sequences are shown using the nucleotide base symbols common for DNA: A, G, C and T. Other antisense chemistries such as 2'-O-methyl use U in place of T. Any of the bases may be substituted with inosine (I) especially in stretches of three or more G residues.

| Name | Sequences | SEQ ID NO. |
|---|---|---|
| Oligomer Targeting Sequences (5' to 3'): | | |
| Hu.DMD.Exon44.25.001 | CTGCAGGTAAAAGCATATGGATCAA | 1 |
| Hu.DMD.Exon44.25.002 | ATCGCCTGCAGGTAAAAGCATATGG | 2 |
| Hu.DMD.Exon44.25.003 | GTCAAATCGCCTGCAGGTAAAAGCA | 3 |
| Hu.DMD.Exon44.25.004 | GATCTGTCAAATCGCCTGCAGGTAA | 4 |
| Hu.DMD.Exon44.25.005 | CAACAGATCTGTCAAATCGCCTGCA | 5 |
| Hu.DMD.Exon44.25.006 | TTTCTCAACAGATCTGTCAAATCGC | 6 |
| Hu.DMD.Exon44.25.007 | CCATTTCTCAACAGATCTGTCAAAT | 7 |
| Hu.DMD.Exon44.25.008 | ATAATGAAAACGCCGCCATTTCTCA | 8 |
| Hu.DMD.Exon44.25.009 | AAATATCTTTATATCATAATGAAAA | 9 |
| Hu.DMD.Exon44.25.010 | TGTTAGCCACTGATTAAATATCTTT | 10 |
| Hu.DMD.Exon44.25.011 | AAACTGTTCAGCTTCTGTTAGCCAC | 11 |
| Hu.DMD.Exon44.25.012 | TTGTGTCTTTCTGAGAAACTGTTCA | 12 |
| Hu.DMD.Exon44.25.013 | CCAATTCTCAGGAATTTGTGTCTTT | 13 |
| Hu.DMD.Exon44.25.014 | GTATTTAGCATGTTCCCAATTCTCA | 14 |
| Hu.DMD.Exon44.25.015 | CTTAAGATACCATTTGTATTTAGCA | 15 |
| Hu.DMD.Exon44.25.016 | CTTACCTTAAGATACCATTTGTATT | 16 |
| Hu.DMD.Exon44.25.017 | AAAGACTTACCTTAAGATACCATTT | 17 |
| Hu.DMD.Exon44.25.018 | AAATCAAAGACTTACCTTAAGATAC | 18 |
| Hu.DMD.Exon44.25.019 | AAAACAAATCAAAGACTTACCTTAA | 19 |
| Hu.DMD.Exon44.25.020 | TCGAAAAACAAATCAAAGACTTAC | 20 |
| Hu.DMD.Exon45.25.001 | CTGTAAGATACCAAAAGGCAAAAC | 21 |
| Hu.DMD.Exon45.25.002 | CCTGTAAGATACCAAAAGGCAAAA | 22 |
| Hu.DMD.Exon45.25.002.2 | AGTTCCTGTAAGATACCAAAAGGC | 23 |
| Hu.DMD.Exon45.25.003 | GAGTTCCTGTAAGATACCAAAAGG | 24 |
| Hu.DMD.Exon45.25.003.2 | CCTGGAGTTCCTGTAAGATACCAA | 25 |
| Hu.DMD.Exon45.25.004 | TCCTGGAGTTCCTGTAAGATACCAA | 26 |
| Hu.DMD.Exon45.25.004.2 | GCCATCCTGGAGTTCCTGTAAGATA | 27 |
| Hu.DMD.Exon45.25.005 | TGCCATCCTGGAGTTCCTGTAAGAT | 28 |
| Hu.DMD.Exon45.25.005.2 | CCAATGCCATCCTGGAGTTCCTGTA | 29 |
| Hu.DMD.Exon45.25.006 | CCCAATGCCATCCTGGAGTTCCTGT | 30 |
| Hu.DMD.Exon45.25.006.2 | GCTGCCCAATGCCATCCTGGAGTTC | 31 |
| Hu.DMD.Exon45.25.007 | CGCTGCCCAATGCCATCCTGGAGTT | 32 |
| Hu.DMD.Exon45.25.008 | AACAGTTTGCCGCTGCCCAATGCCA | 33 |
| Hu.DMD.Exon45.25.008.2 | CTGACAACAGTTTGCCGCTGCCCAA | 34 |
| Hu.DMD.Exon45.25.009 | GTTGCATTCAATGTTCTGACAACAG | 35 |
| Hu.DMD.Exon45.25.010 | GCTGAATTATTTCTTCCCCAGTTGC | 36 |
| Hu.DMD.Exon45.25.010.2 | ATTATTTCTTCCCCAGTTGCATTCA | 37 |
| Hu.DMD.Exon45.25.011 | GGCATCTGTTTTGAGGATTGCTGA | 38 |
| Hu.DMD.Exon45.25.011.2 | TTTGAGGATTGCTGAATTATTTCTT | 39 |

-continued

| Name | Sequences | SEQ ID NO. |
|---|---|---|
| Hu.DMD.Exon45.25.012 | AATTTTTCCTGTAGAATACTGGCAT | 40 |
| Hu.DMD.Exon45.25.012.2 | ATACTGGCATCTGTTTTGAGGATT | 41 |
| Hu.DMD.Exon45.25.013 | ACCGCAGATTCAGGCTTCCCAATTT | 42 |
| Hu.DMD.Exon45.25.013.2 | AATTTTTCCTGTAGAATACTGGCAT | 43 |
| Hu.DMD.Exon45.25.014 | CTGTTTGCAGACCTCCTGCCACCGC | 44 |
| Hu.DMD.Exon45.25.014.2 | AGATTCAGGCTTCCCAATTTTTCCT | 45 |
| Hu.DMD.Exon45.25.015 | CTCTTTTTTCTGTCTGACAGCTGTT | 46 |
| Hu.DMD.Exon45.25.015.2 | ACCTCCTGCCACCGCAGATTCAGGC | 47 |
| Hu.DMD.Exon45.25.016 | CCTACCTCTTTTTTCTGTCTGACAG | 48 |
| Hu.DMD.Exon45.25.016.2 | GACAGCTGTTTGCAGACCTCCTGCC | 49 |
| Hu.DMD.Exon45.25.017 | GTCGCCCTACCTCTTTTTTCTGTCT | 50 |
| Hu.DMD.Exon45.25.018 | GATCTGTCGCCCTACCTCTTTTTTC | 51 |
| Hu.DMD.Exon45.25.019 | TATTAGATCTGTCGCCCTACCTCTT | 52 |
| Hu.DMD.Exon45.25.020 | ATTCCTATTAGATCTGTCGCCCTAC | 53 |
| Hu.DMD.Exon45.20.001 | AGATACCAAAAGGCAAAAC | 54 |
| Hu.DMD.Exon45.20.002 | AAGATACCAAAAGGCAAAA | 55 |
| Hu.DMD.Exon45.20.003 | CCTGTAAGATACCAAAAGG | 56 |
| Hu.DMD.Exon45.20.004 | GAGTTCCTGTAAGATACCAA | 57 |
| Hu.DMD.Exon45.20.005 | TCCTGGAGTTCCTGTAAGAT | 58 |
| Hu.DMD.Exon45.20.006 | TGCCATCCTGGAGTTCCTGT | 59 |
| Hu.DMD.Exon45.20.007 | CCCAATGCCATCCTGGAGTT | 60 |
| Hu.DMD.Exon45.20.008 | CGCTGCCCAATGCCATCCTG | 61 |
| Hu.DMD.Exon45.20.009 | CTGACAACAGTTTGCCGCTG | 62 |
| Hu.DMD.Exon45.20.010 | GTTGCATTCAATGTTCTGAC | 63 |
| Hu.DMD.Exon45.20.011 | ATTATTTCTTCCCCAGTTGC | 64 |
| Hu.DMD.Exon45.20.012 | TTTGAGGATTGCTGAATTAT | 65 |
| Hu.DMD.Exon45.20.013 | ATACTGGCATCTGTTTTTGA | 66 |
| Hu.DMD.Exon45.20.014 | AATTTTTCCTGTAGAATACT | 67 |
| Hu.DMD.Exon45.20.015 | AGATTCAGGCTTCCCAATTT | 68 |
| Hu.DMD.Exon45.20.016 | ACCTCCTGCCACCGCAGATT | 69 |
| Hu.DMD.Exon45.20.017 | GACAGCTGTTTGCAGACCTC | 70 |
| Hu.DMD.Exon45.20.018 | CTCTTTTTTCTGTCTGACAG | 71 |
| Hu.DMD.Exon45.20.019 | CCTACCTCTTTTTTCTGTCT | 72 |
| Hu.DMD.Exon45.20.020 | GTCGCCCTACCTCTTTTTTC | 73 |
| Hu.DMD.Exon45.20.021 | GATCTGTCGCCCTACCTCTT | 74 |
| Hu.DMD.Exon45.20.022 | TATTAGATCTGTCGCCCTAC | 75 |
| Hu.DMD.Exon45.20.023 | ATTCCTATTAGATCTGTCGC | 76 |
| Hu.DMD.Exon46.25.001 | GGGGGATTTGAGAAAATAAAATTAC | 77 |

-continued

| Name | Sequences | SEQ ID NO. |
|---|---|---|
| Hu.DMD.Exon46.25.002 | ATTTGAGAAAATAAAATTACCTTGA | 78 |
| Hu.DMD.Exon46.25.002.2 | CTAGCCTGGAGAAAGAAGAATAAAA | 79 |
| Hu.DMD.Exon46.25.003 | AGAAAATAAAATTACCTTGACTTGC | 80 |
| Hu.DMD.Exon46.25.003.2 | TTCTTCTAGCCTGGAGAAAGAAGAA | 81 |
| Hu.DMD.Exon46.25.004 | ATAAAATTACCTTGACTTGCTCAAG | 82 |
| Hu.DMD.Exon46.25.004.2 | TTTTGTTCTTCTAGCCTGGAGAAAG | 83 |
| Hu.DMD.Exon46.25.005 | ATTACCTTGACTTGCTCAAGCTTTT | 84 |
| Hu.DMD.Exon46.25.005.2 | TATTCTTTTGTTCTTCTAGCCTGGA | 85 |
| Hu.DMD.Exon46.25.006 | CTTGACTTGCTCAAGCTTTTCTTTT | 86 |
| Hu.DMD.Exon46.25.006.2 | CAAGATATTCTTTTGTTCTTCTAGC | 87 |
| Hu.DMD.Exon46.25.007 | CTTTTAGTTGCTGCTCTTTTCCAGG | 88 |
| Hu.DMD.Exon46.25.008 | CCAGGTTCAAGTGGGATACTAGCAA | 89 |
| Hu.DMD.Exon46.25.008.2 | ATCTCTTTGAAATTCTGACAAGATA | 90 |
| Hu.DMD.Exon46.25.009 | AGCAATGTTATCTGCTTCCTCCAAC | 91 |
| Hu.DMD.Exon46.25.009.2 | AACAAATTCATTTAAATCTCTTTGA | 92 |
| Hu.DMD.Exon46.25.010 | CCAACCATAAAACAAATTCATTTAA | 93 |
| Hu.DMD.Exon46.25.010.2 | TTCCTCCAACCATAAAACAAATTCA | 94 |
| Hu.DMD.Exon46.25.011 | TTTAAATCTCTTTGAAATTCTGACA | 95 |
| Hu.DMD.Exon46.25.012 | TGACAAGATATTCTTTTGTTCTTCT | 96 |
| Hu.DMD.Exon46.25.012.2 | TTCAAGTGGGATACTAGCAATGTTA | 97 |
| Hu.DMD.Exon46.25.013 | AGATATTCTTTTGTTCTTCTAGCCT | 98 |
| Hu.DMD.Exon46.25.013.2 | CTGCTCTTTTCCAGGTTCAAGTGGG | 99 |
| Hu.DMD.Exon46.25.014 | TTCTTTTGTTCTTCTAGCCTGGAGA | 100 |
| Hu.DMD.Exon46.25.014.2 | CTTTTCTTTTAGTTGCTGCTCTTTT | 101 |
| Hu.DMD.Exon46.25.015 | TTGTTCTTCTAGCCTGGAGAAAGAA | 102 |
| Hu.DMD.Exon46.25.016 | CTTCTAGCCTGGAGAAAGAAGAATA | 103 |
| Hu.DMD.Exon46.25.017 | AGCCTGGAGAAAGAAGAATAAAATT | 104 |
| Hu.DMD.Exon46.25.018 | CTGGAGAAAGAAGAATAAAATTGTT | 105 |
| Hu.DMD.Exon46.20.001 | GAAAGAAGAATAAAATTGTT | 106 |
| Hu.DMD.Exon46.20.002 | GGAGAAAGAAGAATAAAATT | 107 |
| Hu.DMD.Exon46.20.003 | AGCCTGGAGAAAGAAGAATA | 108 |
| Hu.DMD.Exon46.20.004 | CTTCTAGCCTGGAGAAAGAA | 109 |
| Hu.DMD.Exon46.20.005 | TTGTTCTTCTAGCCTGGAGA | 110 |
| Hu.DMD.Exon46.20.006 | TTCTTTTGTTCTTCTAGCCT | 111 |
| Hu.DMD.Exon46.20.007 | TGACAAGATATTCTTTTGTT | 112 |
| Hu.DMD.Exon46.20.008 | ATCTCTTTGAAATTCTGACA | 113 |
| Hu.DMD.Exon46.20.009 | AACAAATTCATTTAAATCTC | 114 |
| Hu.DMD.Exon46.20.010 | TTCCTCCAACCATAAAACAA | 115 |
| Hu.DMD.Exon46.20.011 | AGCAATGTTATCTGCTTCCT | 116 |

-continued

| Name | Sequences | SEQ ID NO. |
|---|---|---|
| Hu.DMD.Exon46.20.012 | TTCAAGTGGGATACTAGCAA | 117 |
| Hu.DMD.Exon46.20.013 | CTGCTCTTTTCCAGGTTCAA | 118 |
| Hu.DMD.Exon46.20.014 | CTTTTCTTTTAGTTGCTGCT | 119 |
| Hu.DMD.Exon46.20.015 | CTTGACTTGCTCAAGCTTTT | 120 |
| Hu.DMD.Exon46.20.016 | ATTACCTTGACTTGCTCAAG | 121 |
| Hu.DMD.Exon46.20.017 | ATAAAATTACCTTGACTTGC | 122 |
| Hu.DMD.Exon46.20.018 | AGAAAATAAAATTACCTTGA | 123 |
| Hu.DMD.Exon46.20.019 | ATTTGAGAAAATAAAATTAC | 124 |
| Hu.DMD.Exon46.20.020 | GGGGGATTTGAGAAAATAAA | 125 |
| Hu.DMD.Exon47.25.001 | CTGAAACAGACAAATGCAACAACGT | 126 |
| Hu.DMD.Exon47.25.002 | AGTAACTGAAACAGACAAATGCAAC | 127 |
| Hu.DMD.Exon47.25.003 | CCACCAGTAACTGAAACAGACAAAT | 128 |
| Hu.DMD.Exon47.25.004 | CTCTTCCACCAGTAACTGAAACAGA | 129 |
| Hu.DMD.Exon47.25.005 | GGCAACTCTTCCACCAGTAACTGAA | 130 |
| Hu.DMD.Exon47.25.006 | GCAGGGGCAACTCTTCCACCAGTAA | 131 |
| Hu.DMD.Exon47.25.007 | CTGGCGCAGGGGCAACTCTTCCACC | 132 |
| Hu.DMD.Exon47.25.008 | TTTAATTGTTTGAGAATTCCCTGGC | 133 |
| Hu.DMD.Exon47.25.008.2 | TTGTTTGAGAATTCCCTGGCGCAGG | 134 |
| Hu.DMD.Exon47.25.009 | GCACGGGTCCTCCAGTTTCATTTAA | 135 |
| Hu.DMD.Exon47.25.009.2 | TCCAGTTTCATTTAATTGTTTGAGA | 136 |
| Hu.DMD.Exon47.25.010 | GCTTATGGGAGCACTTACAAGCACG | 137 |
| Hu.DMD.Exon47.25.010.2 | TACAAGCACGGGTCCTCCAGTTTCA | 138 |
| Hu.DMD.Exon47.25.011 | AGTTTATCTTGCTCTTCTGGGCTTA | 139 |
| Hu.DMD.Exon47.25.012 | TCTGCTTGAGCTTATTTTCAAGTTT | 140 |
| Hu.DMD.Exon47.25.012.2 | ATCTTGCTCTTCTGGGCTTATGGGA | 141 |
| Hu.DMD.Exon47.25.013 | CTTTATCCACTGGAGATTTGTCTGC | 142 |
| Hu.DMD.Exon47.25.013.2 | CTTATTTTCAAGTTTATCTTGCTCT | 143 |
| Hu.DMD.Exon47.25.014 | CTAACCTTTATCCACTGGAGATTTG | 144 |
| Hu.DMD.Exon47.25.014.2 | ATTTGTCTGCTTGAGCTTATTTTCA | 145 |
| Hu.DMD.Exon47.25.015 | AATGTCTAACCTTTATCCACTGGAG | 146 |
| Hu.DMD.Exon47.25.016 | TGGTTAATGTCTAACCTTTATCCAC | 147 |
| Hu.DMD.Exon47.25.017 | AGAGATGGTTAATGTCTAACCTTTA | 148 |
| Hu.DMD.Exon47.25.018 | ACGGAAGAGATGGTTAATGTCTAAC | 149 |
| Hu.DMD.Exon47.20.001 | ACAGACAAATGCAACAACGT | 150 |
| Hu.DMD.Exon47.20.002 | CTGAAACAGACAAATGCAAC | 151 |
| Hu.DMD.Exon47.20.003 | AGTAACTGAAACAGACAAAT | 152 |
| Hu.DMD.Exon47.20.004 | CCACCAGTAACTGAAACAGA | 153 |
| Hu.DMD.Exon47.20.005 | CTCTTCCACCAGTAACTGAA | 154 |

-continued

| Name | Sequences | SEQ ID NO. |
|---|---|---|
| Hu.DMD.Exon47.20.006 | GGCAACTCTTCCACCAGTAA | 155 |
| Hu.DMD.Exon47.20.007 | CTGGCGCAGGGGCAACTCTT | 156 |
| Hu.DMD.Exon47.20.008 | TTGTTTGAGAATTCCCTGGC | 157 |
| Hu.DMD.Exon47.20.009 | TCCAGTTTCATTTAATTGTT | 158 |
| Hu.DMD.Exon47.20.010 | TACAAGCACGGGTCCTCCAG | 159 |
| Hu.DMD.Exon47.20.011 | GCTTATGGGAGCACTTACAA | 160 |
| Hu.DMD.Exon47.20.012 | ATCTTGCTCTTCTGGGCTTA | 161 |
| Hu.DMD.Exon47.20.013 | CTTATTTTCAAGTTTATCTT | 162 |
| Hu.DMD.Exon47.20.014 | ATTTGTCTGCTTGAGCTTAT | 163 |
| Hu.DMD.Exon47.20.015 | CTTTATCCACTGGAGATTTG | 164 |
| Hu.DMD.Exon47.20.016 | CTAACCTTTATCCACTGGAG | 165 |
| Hu.DMD.Exon47.20.017 | AATGTCTAACCTTTATCCAC | 166 |
| Hu.DMD.Exon47.20.018 | TGGTTAATGTCTAACCTTTA | 167 |
| Hu.DMD.Exon47.20.019 | AGAGATGGTTAATGTCTAAC | 168 |
| Hu.DMD.Exon47.20.020 | ACGGAAGAGATGGTTAATGT | 169 |
| Hu.DMD.Exon48.25.001 | CTGAAAGGAAAATACATTTTAAAAA | 170 |
| Hu.DMD.Exon48.25.002 | CCTGAAAGGAAAATACATTTTAAAA | 171 |
| Hu.DMD.Exon48.25.002.2 | GAAACCTGAAAGGAAAATACATTTT | 172 |
| Hu.DMD.Exon48.25.003 | GGAAACCTGAAAGGAAAATACATTT | 173 |
| Hu.DMD.Exon48.25.003.2 | CTCTGGAAACCTGAAAGGAAAATAC | 174 |
| Hu.DMD.Exon48.25.004 | GCTCTGGAAACCTGAAAGGAAAATA | 175 |
| Hu.DMD.Exon48.25.004.2 | TAAAGCTCTGGAAACCTGAAAGGAA | 634 |
| Hu.DMD.Exon48.25.005 | GTAAAGCTCTGGAAACCTGAAAGGA | 176 |
| Hu.DMD.Exon48.25.005.2 | TCAGGTAAAGCTCTGGAAACCTGAA | 177 |
| Hu.DMD.Exon48.25.006 | CTCAGGTAAAGCTCTGGAAACCTGA | 178 |
| Hu.DMD.Exon48.25.006.2 | GTTTCTCAGGTAAAGCTCTGGAAAC | 179 |
| Hu.DMD.Exon48.25.007 | TGTTTCTCAGGTAAAGCTCTGGAAA | 180 |
| Hu.DMD.Exon48.25.007.2 | AATTTCTCCTTGTTTCTCAGGTAAA | 181 |
| Hu.DMD.Exon48.25.008 | TTTGAGCTTCAATTTCTCCTTGTTT | 182 |
| Hu.DMD.Exon48.25.008 | TTTTATTTGAGCTTCAATTTCTCCT | 183 |
| Hu.DMD.Exon48.25.009 | AAGCTGCCCAAGGTCTTTTATTTGA | 184 |
| Hu.DMD.Exon48.25.010 | AGGTCTTCAAGCTTTTTTTCAAGCT | 185 |
| Hu.DMD.Exon48.25.010.2 | TTCAAGCTTTTTTTCAAGCTGCCCA | 186 |
| Hu.DMD.Exon48.25.011 | GATGATTTAACTGCTCTTCAAGGTC | 187 |
| Hu.DMD.Exon48.25.011.2 | CTGCTCTTCAAGGTCTTCAAGCTTT | 188 |
| Hu.DMD.Exon48.25.012 | AGGAGATAACCACAGCAGCAGATGA | 189 |
| Hu.DMD.Exon48.25.012.2 | CAGCAGATGATTTAACTGCTCTTCA | 190 |
| Hu.DMD.Exon48.25.013 | ATTTCCAACTGATTCCTAATAGGAG | 191 |
| Hu.DMD.Exon48.25.014 | CTTGGTTTGGTTGGTTATAAATTTC | 192 |

-continued

| Name | Sequences | SEQ ID NO. |
|---|---|---|
| Hu.DMD.Exon48.25.014.2 | CAACTGATTCCTAATAGGAGATAAC | 193 |
| Hu.DMD.Exon48.25.015 | CTTAACGTCAAATGGTCCTTCTTGG | 194 |
| Hu.DMD.Exon48.25.015.2 | TTGGTTATAAATTTCCAACTGATTC | 195 |
| Hu.DMD.Exon48.25.016 | CCTACCTTAACGTCAAATGGTCCTT | 196 |
| Hu.DMD.Exon48.25.016.2 | TCCTTCTTGGTTTGGTTGGTTATAA | 197 |
| Hu.DMD.Exon48.25.017 | AGTTCCCTACCTTAACGTCAAATGG | 198 |
| Hu.DMD.Exon48.25.018 | CAAAAGTTCCCTACCTTAACGTCA | 199 |
| Hu.DMD.Exon48.25.019 | TAAAGCAAAAGTTCCCTACCTTAA | 200 |
| Hu.DMD.Exon48.25.020 | ATATTTAAAGCAAAAGTTCCCTAC | 201 |
| Hu.DMD.Exon48.20.001 | AGGAAAATACATTTTAAAAA | 202 |
| Hu.DMD.Exon48.20.002 | AAGGAAAATACATTTTAAAA | 203 |
| Hu.DMD.Exon48.20.003 | CCTGAAAGGAAAATACATTT | 204 |
| Hu.DMD.Exon48.20.004 | GGAAACCTGAAAGGAAAATA | 205 |
| Hu.DMD.Exon48.20.005 | GCTCTGGAAACCTGAAAGGA | 206 |
| Hu.DMD.Exon48.20.006 | GTAAAGCTCTGGAAACCTGA | 207 |
| Hu.DMD.Exon48.20.007 | CTCAGGTAAAGCTCTGGAAA | 208 |
| Hu.DMD.Exon48.20.008 | AATTTCTCCTTGTTTCTCAG | 209 |
| Hu.DMD.Exon48.20.009 | TTTTATTTGAGCTTCAATTT | 210 |
| Hu.DMD.Exon48.20.010 | AAGCTGCCCAAGGTCTTTTA | 211 |
| Hu.DMD.Exon48.20.011 | TTCAAGCTTTTTTTCAAGCT | 212 |
| Hu.DMD.Exon48.20.012 | CTGCTCTTCAAGGTCTTCAA | 213 |
| Hu.DMD.Exon48.20.013 | CAGCAGATGATTTAACTGCT | 214 |
| Hu.DMD.Exon48.20.014 | AGGAGATAACCACAGCAGCA | 215 |
| Hu.DMD.Exon48.20.015 | CAACTGATTCCTAATAGGAG | 216 |
| Hu.DMD.Exon48.20.016 | TTGGTTATAAATTTCCAACT | 217 |
| Hu.DMD.Exon48.20.017 | TCCTTCTTGGTTTGGTTGGT | 218 |
| Hu.DMD.Exon48.20.018 | CTTAACGTCAAATGGTCCTT | 219 |
| Hu.DMD.Exon48.20.019 | CCTACCTTAACGTCAAATGG | 220 |
| Hu.DMD.Exon48.20.020 | AGTTCCCTACCTTAACGTCA | 221 |
| Hu.DMD.Exon48.20.021 | CAAAAGTTCCCTACCTTAA | 222 |
| Hu.DMD.Exon48.20.022 | TAAAGCAAAAGTTCCCTAC | 223 |
| Hu.DMD.Exon48.20.023 | ATATTTAAAGCAAAAGTTC | 224 |
| Hu.DMD.Exon49.25.001 | CTGGGGAAAAGAACCCATATAGTGC | 225 |
| Hu.DMD.Exon49.25.002 | TCCTGGGGAAAAGAACCCATATAGT | 226 |
| Hu.DMD.Exon49.25.002.2 | GTTTCCTGGGGAAAAGAACCCATAT | 227 |
| Hu.DMD.Exon49.25.003 | CAGTTTCCTGGGGAAAAGAACCCAT | 228 |
| Hu.DMD.Exon49.25.003.2 | TTTCAGTTTCCTGGGGAAAAGAACC | 229 |
| Hu.DMD.Exon49.25.004 | TATTTCAGTTTCCTGGGGAAAAGAA | 230 |

-continued

| Name | Sequences | SEQ ID NO. |
|---|---|---|
| Hu.DMD.Exon49.25.004.2 | TGCTATTTCAGTTTCCTGGGGAAAA | 231 |
| Hu.DMD.Exon49.25.005 | ACTGCTATTTCAGTTTCCTGGGAA | 232 |
| Hu.DMD.Exon49.25.005.2 | TGAACTGCTATTTCAGTTTCCTGGG | 233 |
| Hu.DMD.Exon49.25.006 | CTTGAACTGCTATTTCAGTTTCCTG | 234 |
| Hu.DMD.Exon49.25.006.2 | TAGCTTGAACTGCTATTTCAGTTTC | 235 |
| Hu.DMD.Exon49.25.007 | TTTAGCTTGAACTGCTATTTCAGTT | 236 |
| Hu.DMD.Exon49.25.008 | TTCCACATCCGGTTGTTTAGCTTGA | 237 |
| Hu.DMD.Exon49.25.009 | TGCCCTTTAGACAAAATCTCTTCCA | 238 |
| Hu.DMD.Exon49.25.009.2 | TTTAGACAAAATCTCTTCCACATCC | 239 |
| Hu.DMD.Exon49.25.010 | GTTTTTCCTTGTACAAATGCTGCCC | 240 |
| Hu.DMD.Exon49.25.010.2 | GTACAAATGCTGCCCTTTAGACAAA | 241 |
| Hu.DMD.Exon49.25.011 | CTTCACTGGCTGAGTGGCTGGTTTT | 242 |
| Hu.DMD.Exon49.25.011.2 | GGCTGGTTTTCCTTGTACAAATGC | 243 |
| Hu.DMD.Exon49.25.012 | ATTACCTTCACTGGCTGAGTGGCTG | 244 |
| Hu.DMD.Exon49.25.013 | GCTTCATTACCTTCACTGGCTGAGT | 245 |
| Hu.DMD.Exon49.25.014 | AGGTTGCTTCATTACCTTCACTGGC | 246 |
| Hu.DMD.Exon49.25.015 | GCTAGAGGTTGCTTCATTACCTTCA | 247 |
| Hu.DMD.Exon49.25.016 | ATATTGCTAGAGGTTGCTTCATTAC | 248 |
| Hu.DMD.Exon49.20.001 | GAAAAGAACCCATATAGTGC | 249 |
| Hu.DMD.Exon49.20.002 | GGGAAAAGAACCCATATAGT | 250 |
| Hu.DMD.Exon49.20.003 | TCCTGGGAAAAGAACCCAT | 251 |
| Hu.DMD.Exon49.20.004 | CAGTTTCCTGGGAAAAGAA | 252 |
| Hu.DMD.Exon49.20.005 | TATTTCAGTTTCCTGGGAA | 253 |
| Hu.DMD.Exon49.20.006 | ACTGCTATTTCAGTTTCCTG | 254 |
| Hu.DMD.Exon49.20.007 | CTTGAACTGCTATTTCAGTT | 255 |
| Hu.DMD.Exon49.20.008 | TTTAGCTTGAACTGCTATTT | 256 |
| Hu.DMD.Exon49.20.009 | TTCCACATCCGGTTGTTTAG | 257 |
| Hu.DMD.Exon49.20.010 | TTTAGACAAAATCTCTTCCA | 258 |
| Hu.DMD.Exon49.20.011 | GTACAAATGCTGCCCTTTAG | 259 |
| Hu.DMD.Exon49.20.012 | GGCTGGTTTTCCTTGTACA | 260 |
| Hu.DMD.Exon49.20.013 | CTTCACTGGCTGAGTGGCTG | 261 |
| Hu.DMD.Exon49.20.014 | ATTACCTTCACTGGCTGAGT | 262 |
| Hu.DMD.Exon49.20.015 | GCTTCATTACCTTCACTGG | 263 |
| Hu.DMD.Exon49.20.016 | AGGTTGCTTCATTACCTTCA | 264 |
| Hu.DMD.Exon49.20.017 | GCTAGAGGTTGCTTCATTAC | 265 |
| Hu.DMD.Exon49.20.018 | ATATTGCTAGAGGTTGCTTC | 266 |
| Hu.DMD.Exon50.25.001 | CTTTAACAGAAAAGCATACACATTA | 267 |
| Hu.DMD.Exon50.25.002 | TCCTCTTTAACAGAAAAGCATACAC | 268 |
| Hu.DMD.Exon50.25.002.2 | TTCCTCTTTAACAGAAAAGCATACA | 269 |

-continued

| Name | Sequences | SEQ ID NO. |
|---|---|---|
| Hu.DMD.Exon50.25.003 | TAACTTCCTCTTTAACAGAAAAGCA | 270 |
| Hu.DMD.Exon50.25.003.2 | CTAACTTCCTCTTTAACAGAAAAGC | 271 |
| Hu.DMD.Exon50.25.004 | TCTTCTAACTTCCTCTTTAACAGAA | 272 |
| Hu.DMD.Exon50.25.004.2 | ATCTTCTAACTTCCTCTTTAACAGA | 273 |
| Hu.DMD.Exon50.25.005 | TCAGATCTTCTAACTTCCTCTTTAA | 274 |
| Hu.DMD.Exon50.25.005.2 | CTCAGATCTTCTAACTTCCTCTTTA | 275 |
| Hu.DMD.Exon50.25.006 | AGAGCTCAGATCTTCTAACTTCCTC | 276 |
| Hu.DMD.Exon50.25.006.2 NG-08-0731 | CAGAGCTCAGATCTTCTAACTTCCT | 277 |
| Hu.DMD.Exon50.25.007 | CACTCAGAGCTCAGATCTTCTACT | 278 |
| Hu.DMD.Exon50.25.007.2 | CCTTCCACTCAGAGCTCAGATCTTC | 279 |
| Hu.DMD.Exon50.25.008 | GTAAACGGTTTACCGCCTTCCACTC | 280 |
| Hu.DMD.Exon50.25.009 | CTTTGCCCTCAGCTCTTGAAGTAAA | 281 |
| Hu.DMD.Exon50.25.009.2 | CCCTCAGCTCTTGAAGTAAACGGTT | 282 |
| Hu.DMD.Exon50.25.010 | CCAGGAGCTAGGTCAGGCTGCTTTG | 283 |
| Hu.DMD.Exon50.25.010.2 | GGTCAGGCTGCTTTGCCCTCAGCTC | 284 |
| Hu.DMD.Exon50.25.011 | AGGCTCCAATAGTGGTCAGTCCAGG | 285 |
| Hu.DMD.Exon50.25.011.2 | TCAGTCCAGGAGCTAGGTCAGGCTG | 286 |
| Hu.DMD.Exon50.25.012 AVI-5038 | CTTACAGGCTCCAATAGTGGTCAGT | 287 |
| Hu.DMD.Exon50.25.013 | GTATACTTACAGGCTCCAATAGTGG | 288 |
| Hu.DMD.Exon50.25.014 | ATCCAGTATACTTACAGGCTCCAAT | 289 |
| Hu.DMD.Exon50.25.015 NG-08-0741 | ATGGGATCCAGTATACTTACAGGCT | 290 |
| Hu.DMD.Exon50.25.016 NG-08-0742 | AGAGAATGGGATCCAGTATACTTAC | 291 |
| Hu.DMD.Exon50.20.001 | ACAGAAAAGCATACACATTA | 292 |
| Hu.DMD.Exon50.20.002 | TTTAACAGAAAAGCATACAC | 293 |
| Hu.DMD.Exon50.20.003 | TCCTCTTTAACAGAAAAGCA | 294 |
| Hu.DMD.Exon50.20.004 | TAACTTCCTCTTTAACAGAA | 295 |
| Hu.DMD.Exon50.20.005 | TCTTCTAACTTCCTCTTTAA | 296 |
| Hu.DMD.Exon50.20.006 | TCAGATCTTCTAACTTCCTC | 297 |
| Hu.DMD.Exon50.20.007 | CCTTCCACTCAGAGCTCAGA | 298 |
| Hu.DMD.Exon50.20.008 | GTAAACGGTTTACCGCCTTC | 299 |
| Hu.DMD.Exon50.20.009 | CCCTCAGCTCTTGAAGTAAA | 300 |
| Hu.DMD.Exon50.20.010 | GGTCAGGCTGCTTTGCCCTC | 301 |
| Hu.DMD.Exon50.20.011 | TCAGTCCAGGAGCTAGGTCA | 302 |
| Hu.DMD.Exon50.20.012 | AGGCTCCAATAGTGGTCAGT | 303 |
| Hu.DMD.Exon50.20.013 | CTTACAGGCTCCAATAGTGG | 304 |
| Hu.DMD.Exon50.20.014 | GTATACTTACAGGCTCCAAT | 305 |

-continued

| Name | Sequences | SEQ ID NO. |
|---|---|---|
| Hu.DMD.Exon50.20.015 | ATCCAGTATACTTACAGGCT | 306 |
| Hu.DMD.Exon50.20.016 | ATGGGATCCAGTATACTTAC | 307 |
| Hu.DMD.Exon50.20.017 | AGAGAATGGGATCCAGTATA | 308 |
| Hu.DMD.Exon51.25.001-44 | CTAAAATATTTTGGGTTTTGCAAAA | 309 |
| Hu.DMD.Exon51.25.002-45 | GCTAAAATATTTTGGGTTTTGCAAA | 310 |
| Hu.DMD.Exon51.25.002.2-46 | TAGGAGCTAAAATATTTTGGGTTTT | 311 |
| Hu.DMD.Exon51.25.003 | AGTAGGAGCTAAAATATTTTGGGTT | 312 |
| Hu.DMD.Exon51.25.003.2 | TGAGTAGGAGCTAAAATATTTTGGG | 313 |
| Hu.DMD.Exon51.25.004 | CTGAGTAGGAGCTAAAATATTTTGGG | 314 |
| Hu.DMD.Exon51.25.004.2 | CAGTCTGAGTAGGAGCTAAAATATT | 315 |
| Hu.DMD.Exon51.25.005 | ACAGTCTGAGTAGGAGCTAAAATATT | 316 |
| Hu.DMD.Exon51.25.005.2 | GAGTAACAGTCTGAGTAGGAGCTAAA | 317 |
| Hu.DMD.Exon51.25.006 | CAGAGTAACAGTCTGAGTAGGAGCT | 318 |
| Hu.DMD.Exon51.25.006.2 | CACCAGAGTAACAGTCTGAGTAGGAG | 319 |
| Hu.DMD.Exon51.25.007 | GTCACCAGAGTAACAGTCTGAGTAG | 320 |
| Hu.DMD.Exon51.25.007.2 | AACCACAGGTTGTGTCACCAGAGTAA | 321 |
| Hu.DMD.Exon51.25.008 | GTTGTGTCACCAGAGTAACAGTCTG | 322 |
| Hu.DMD.Exon51.25.009 | TGGCAGTTTCCTTAGTAACCACAGGT | 323 |
| Hu.DMD.Exon51.25.010 | ATTTCTAGTTTGGAGATGGCAGTTTC | 324 |
| Hu.DMD.Exon51.25.010.2 | GGAAGATGGCATTTCTAGTTTGGAG | 325 |
| Hu.DMD.Exon51.25.011 | CATCAAGGAAGATGGCATTTCTAGTT | 326 |
| Hu.DMD.Exon51.25.011.2 | GAGCAGGTACCTCCAACATCAAGGAA | 327 |
| Hu.DMD.Exon51.25.012 | ATCTGCCAGAGCAGGTACCTCCAAC | 328 |
| Hu.DMD.Exon51.25.013 | AAGTTCTGTCCAAGCCCGGTTGAAAT | 329 |
| Hu.DMD.Exon51.25.013.2 | CGGTTGAAATCTGCCAGAGCAGGTAC | 330 |
| Hu.DMD.Exon51.25.014 | GAGAAAGCCAGTCGGTAAGTTCTGTC | 331 |
| Hu.DMD.Exon51.25.014.2 | GTCGGTAAGTTCTGTCCAAGCCCGG | 332 |
| Hu.DMD.Exon51.25.015 | ATAACTTGATCAAGCAGAGAAAGCCA | 333 |
| Hu.DMD.Exon51.25.015.2 | AAGCAGAGAAAGCCAGTCGGTAAGT | 334 |
| Hu.DMD.Exon51.25.016 | CACCCTCTGTGATTTTATAACTTGAT | 335 |
| Hu.DMD.Exon51.25.017 | CAAGGTCACCCACCATCACCCTCTGT | 336 |
| Hu.DMD.Exon51.25.017.2 | CATCACCCTCTGTGATTTTATAACT | 337 |
| Hu.DMD.Exon51.25.018 | CTTCTGCTTGATGATCATCTCGTTGA | 338 |
| Hu.DMD.Exon51.25.019 | CCTTCTGCTTGATGATCATCTCGTTG | 339 |
| Hu.DMD.Exon51.25.019.2 | ATCTCGTTGATATCCTCAAGGTCACC | 340 |
| Hu.DMD.Exon51.25.020 | TCATACCTTCTGCTTGATGATCATCT | 341 |
| Hu.DMD.Exon51.25.020.2 | TCATTTTTTCTCATACCTTCTGCTTG | 342 |
| Hu.DMD.Exon51.25.021 | TTTTCTCATACCTTCTGCTTGATGAT | 343 |
| Hu.DMD.Exon51.25.022 | TTTTATCATTTTTTCTCATACCTTCT | 344 |

-continued

| Name | Sequences | SEQ ID NO. |
|---|---|---|
| Hu.DMD.Exon51.25.023 | CCAACTTTTATCATTTTTTCTCATAC | 345 |
| Hu.DMD.Exon51.20.001 | ATATTTTGGGTTTTTGCAAA | 346 |
| Hu.DMD.Exon51.20.002 | AAAATATTTTGGGTTTTTGC | 347 |
| Hu.DMD.Exon51.20.003 | GAGCTAAAATATTTTGGGTT | 348 |
| Hu.DMD.Exon51.20.004 | AGTAGGAGCTAAAATATTTT | 349 |
| Hu.DMD.Exon51.20.005 | GTCTGAGTAGGAGCTAAAAT | 350 |
| Hu.DMD.Exon51.20.006 | TAACAGTCTGAGTAGGAGCT | 351 |
| Hu.DMD.Exon51.20.007 | CAGAGTAACAGTCTGAGTAG | 352 |
| Hu.DMD.Exon51.20.008 | CACAGGTTGTGTCACCAGAG | 353 |
| Hu.DMD.Exon51.20.009 | AGTTTCCTTAGTAACCACAG | 354 |
| Hu.DMD.Exon51.20.010 | TAGTTTGGAGATGGCAGTTT | 355 |
| Hu.DMD.Exon51.20.011 | GGAAGATGGCATTTCTAGTT | 356 |
| Hu.DMD.Exon51.20.012 | TACCTCCAACATCAAGGAAG | 357 |
| Hu.DMD.Exon51.20.013 | ATCTGCCAGAGCAGGTACCT | 358 |
| Hu.DMD.Exon51.20.014 | CCAAGCCCGGTTGAAATCTG | 359 |
| Hu.DMD.Exon51.20.015 | GTCGGTAAGTTCTGTCCAAG | 360 |
| Hu.DMD.Exon51.20.016 | AAGCAGAGAAAGCCAGTCGG | 361 |
| Hu.DMD.Exon51.20.017 | TTTTATAACTTGATCAAGCA | 362 |
| Hu.DMD.Exon51.20.018 | CATCACCCTCTGTGATTTTA | 363 |
| Hu.DMD.Exon51.20.019 | CTCAAGGTCACCCACCATCA | 364 |
| Hu.DMD.Exon51.20.020 | CATCTCGTTGATATCCTCAA | 365 |
| Hu.DMD.Exon51.20.021 | CTTCTGCTTGATGATCATCT | 366 |
| Hu.DMD.Exon51.20.022 | CATACCTTCTGCTTGATGAT | 367 |
| Hu.DMD.Exon51.20.023 | TTTCTCATACCTTCTGCTTG | 368 |
| Hu.DMD.Exon51.20.024 | CATTTTTTCTCATACCTTCT | 369 |
| Hu.DMD.Exon51.20.025 | TTTATCATTTTTTCTCATAC | 370 |
| Hu.DMD.Exon51.20.026 | CAACTTTTATCATTTTTTCT | 371 |
| Hu.DMD.Exon52.25.001 | CTGTAAGAACAAATATCCCTTAGTA | 372 |
| Hu.DMD.Exon52.25.002 | TGCCTGTAAGAACAAATATCCCTTA | 373 |
| Hu.DMD.Exon52.25.002.2 | GTTGCCTGTAAGAACAAATATCCCT | 374 |
| Hu.DMD.Exon52.25.003 | ATTGTTGCCTGTAAGAACAAATATC | 375 |
| Hu.DMD.Exon52.25.003.2 | GCATTGTTGCCTGTAAGAACAAATA | 376 |
| Hu.DMD.Exon52.25.004 | CCTGCATTGTTGCCTGTAAGAACAA | 377 |
| Hu.DMD.Exon52.25.004.2 | ATCCTGCATTGTTGCCTGTAAGAAC | 378 |
| Hu.DMD.Exon52.25.005 | CAAATCCTGCATTGTTGCCTGTAAG | 379 |
| Hu.DMD.Exon52.25.005.2 | TCCAAATCCTGCATTGTTGCCTGTA | 380 |
| Hu.DMD.Exon52.25.006 | TGTTCCAAATCCTGCATTGTTGCCT | 381 |
| Hu.DMD.Exon52.25.006.2 | TCTGTTCCAAATCCTGCATTGTTGC | 382 |

-continued

| Name | Sequences | SEQ ID NO. |
|---|---|---|
| Hu.DMD.Exon52.25.007 | AACTGGGGACGCCTCTGTTCCAAAT | 383 |
| Hu.DMD.Exon52.25.007.2 | GCCTCTGTTCCAAATCCTGCATTGT | 384 |
| Hu.DMD.Exon52.25.008 | CAGCGGTAATGAGTTCTTCCAACTG | 385 |
| Hu.DMD.Exon52.25.008.2 | CTTCCAACTGGGGACGCCTCTGTTC | 386 |
| Hu.DMD.Exon52.25.009 | CTTGTTTTTCAAATTTTGGGCAGCG | 387 |
| Hu.DMD.Exon52.25.010 | CTAGCCTCTTGATTGCTGGTCTTGT | 388 |
| Hu.DMD.Exon52.25.010.2 | TTTTCAAATTTTGGGCAGCGGTAAT | 389 |
| Hu.DMD.Exon52.25.011 | TTCGATCCGTAATGATTGTTCTAGC | 390 |
| Hu.DMD.Exon52.25.011.2 | GATTGCTGGTCTTGTTTTTCAAATT | 391 |
| Hu.DMD.Exon52.25.012 | CTTACTTCGATCCGTAATGATTGTT | 392 |
| Hu.DMD.Exon52.25.012.2 | TTGTTCTAGCCTCTTGATTGCTGGT | 393 |
| Hu.DMD.Exon52.25.013 | AAAAACTTACTTCGATCCGTAATGA | 394 |
| Hu.DMD.Exon52.25.014 | TGTTAAAAACTTACTTCGATCCGT | 395 |
| Hu.DMD.Exon52.25.015 | ATGCTTGTTAAAAACTTACTTCGA | 396 |
| Hu.DMD.Exon52.25.016 | GTCCCATGCTTGTTAAAAACTTAC | 397 |
| Hu.DMD.Exon52.20.001 | AGAACAAATATCCCTTAGTA | 398 |
| Hu.DMD.Exon52.20.002 | GTAAGAACAAATATCCCTTA | 399 |
| Hu.DMD.Exon52.20.003 | TGCCTGTAAGAACAAATATC | 400 |
| Hu.DMD.Exon52.20.004 | ATTGTTGCCTGTAAGAACAA | 401 |
| Hu.DMD.Exon52.20.005 | CCTGCATTGTTGCCTGTAAG | 402 |
| Hu.DMD.Exon52.20.006 | CAAATCCTGCATTGTTGCCT | 403 |
| Hu.DMD.Exon52.20.007 | GCCTCTGTTCCAAATCCTGC | 404 |
| Hu.DMD.Exon52.20.008 | CTTCCAACTGGGGACGCCTC | 405 |
| Hu.DMD.Exon52.20.009 | CAGCGGTAATGAGTTCTTCC | 406 |
| Hu.DMD.Exon52.20.010 | TTTTCAAATTTTGGGCAGCG | 407 |
| Hu.DMD.Exon52.20.011 | GATTGCTGGTCTTGTTTTTC | 408 |
| Hu.DMD.Exon52.20.012 | TTGTTCTAGCCTCTTGATTG | 409 |
| Hu.DMD.Exon52.20.013 | TTCGATCCGTAATGATTGTT | 410 |
| Hu.DMD.Exon52.20.014 | CTTACTTCGATCCGTAATGA | 411 |
| Hu.DMD.Exon52.20.015 | AAAAACTTACTTCGATCCGT | 412 |
| Hu.DMD.Exon52.20.016 | TGTTAAAAACTTACTTCGA | 413 |
| Hu.DMD.Exon52.20.017 | ATGCTTGTTAAAAACTTAC | 414 |
| Hu.DMD.Exon52.20.018 | GTCCCATGCTTGTTAAAAA | 415 |
| Hu.DMD.Exon53.25.001 | CTAGAATAAAGGAAAAATAAATAT | 416 |
| Hu.DMD.Exon53.25.002 | AACTAGAATAAAGGAAAAATAAAT | 417 |
| Hu.DMD.Exon53.25.002.2 | TTCAACTAGAATAAAGGAAAAATA | 418 |
| Hu.DMD.Exon53.25.003 | CTTTCAACTAGAATAAAGGAAAAA | 419 |
| Hu.DMD.Exon53.25.003.2 | ATTCTTTCAACTAGAATAAAGGAA | 420 |
| Hu.DMD.Exon53.25.004 | GAATTCTTTCAACTAGAATAAAGG | 421 |

-continued

| Name | Sequences | SEQ ID NO. |
|---|---|---|
| Hu.DMD.Exon53.25.004.2 | TCTGAATTCTTTCAACTAGAATAAA | 422 |
| Hu.DMD.Exon53.25.005 | ATTCTGAATTCTTTCAACTAGAATA | 423 |
| Hu.DMD.Exon53.25.005.2 | CTGATTCTGAATTCTTTCAACTAGA | 424 |
| Hu.DMD.Exon53.25.006 | CACTGATTCTGAATTCTTTCAACTA | 425 |
| Hu.DMD.Exon53.25.006.2 | TCCCACTGATTCTGAATTCTTTCAA | 426 |
| Hu.DMD.Exon53.25.007 | CATCCCACTGATTCTGAATTCTTTC | 427 |
| Hu.DMD.Exon53.25.008 | TACTTCATCCCACTGATTCTGAATT | 428 |
| Hu.DMD.Exon53.25.008.2 | CTGAAGGTGTTCTTGTACTTCATCC | 429 |
| Hu.DMD.Exon53.25.009 | CGGTTCTGAAGGTGTTCTTGTACT | 430 |
| Hu.DMD.Exon53.25.009.2 | CTGTTGCCTCCGGTTCTGAAGGTGT | 431 |
| Hu.DMD.Exon53.25.010 | TTTCATTCAACTGTTGCCTCCGGTT | 432 |
| Hu.DMD.Exon53.25.010.2 | TAACATTTCATTCAACTGTTGCCTC | 433 |
| Hu.DMD.Exon53.25.011 | TTGTGTTGAATCCTTTAACATTTCA | 434 |
| Hu.DMD.Exon53.25.012 | TCTTCCTTAGCTTCCAGCCATTGTG | 435 |
| Hu.DMD.Exon53.25.012.2 | CTTAGCTTCCAGCCATTGTGTTGAA | 436 |
| Hu.DMD.Exon53.25.013 | GTCCTAAGACCTGCTCAGCTTCTTC | 437 |
| Hu.DMD.Exon53.25.013.2 | CTGCTCAGCTTCTTCCTTAGCTTCC | 438 |
| Hu.DMD.Exon53.25.014 | CTCAAGCTTGGCTCTGGCCTGTCCT | 439 |
| Hu.DMD.Exon53.25.014.2 | GGCCTGTCCTAAGACCTGCTCAGCT | 440 |
| Hu.DMD.Exon53.25.015 | TAGGGACCCTCCTTCCATGACTCAA | 441 |
| Hu.DMD.Exon53.25.016 | TTTGGATTGCATCTACTGTATAGGG | 442 |
| Hu.DMD.Exon53.25.016.2 | ACCCTCCTTCCATGACTCAAGCTTG | 443 |
| Hu.DMD.Exon53.25.017 | CTTGGTTTCTGTGATTTTCTTTTGG | 444 |
| Hu.DMD.Exon53.25.017.2 | ATCTACTGTATAGGGACCCTCCTTC | 445 |
| Hu.DMD.Exon53.25.018 | CTAACCTTGGTTTCTGTGATTTTCT | 446 |
| Hu.DMD.Exon53.25.018.2 | TTTCTTTTGGATTGCATCTACTGTA | 447 |
| Hu.DMD.Exon53.25.019 | TGATACTAACCTTGGTTTCTGTGAT | 448 |
| Hu.DMD.Exon53.25.020 | ATCTTTGATACTAACCTTGGTTTCT | 449 |
| Hu.DMD.Exon53.25.021 | AAGGTATCTTTGATACTAACCTTGG | 450 |
| Hu.DMD.Exon53.25.022 | TTAAAAGGTATCTTTGATACTAAC | 451 |
| Hu.DMD.Exon53.20.001 | ATAAAAGGAAAAATAAATAT | 452 |
| Hu.DMD.Exon53.20.002 | GAATAAAAGGAAAAATAAAT | 453 |
| Hu.DMD.Exon53.20.003 | AACTAGAATAAAAGGAAAAA | 454 |
| Hu.DMD.Exon53.20.004 | CTTTCAACTAGAATAAAAGG | 455 |
| Hu.DMD.Exon53.20.005 | GAATTCTTTCAACTAGAATA | 456 |
| Hu.DMD.Exon53.20.006 | ATTCTGAATTCTTTCAACTA | 457 |
| Hu.DMD.Exon53.20.007 | TACTTCATCCCACTGATTCT | 458 |
| Hu.DMD.Exon53.20.008 | CTGAAGGTGTTCTTGTACT | 459 |

-continued

| Name | Sequences | SEQ ID NO. |
|---|---|---|
| Hu.DMD.Exon53.20.009 | CTGTTGCCTCCGGTTCTGAA | 460 |
| Hu.DMD.Exon53.20.010 | TAACATTTCATTCAACTGTT | 461 |
| Hu.DMD.Exon53.20.011 | TTGTGTTGAATCCTTTAACA | 462 |
| Hu.DMD.Exon53.20.012 | CTTAGCTTCCAGCCATTGTG | 463 |
| Hu.DMD.Exon53.20.013 | CTGCTCAGCTTCTTCCTTAG | 464 |
| Hu.DMD.Exon53.20.014 | GGCCTGTCCTAAGACCTGCT | 465 |
| Hu.DMD.Exon53.20.015 | CTCAAGCTTGGCTCTGGCCT | 466 |
| Hu.DMD.Exon53.20.016 | ACCCTCCTTCCATGACTCAA | 467 |
| Hu.DMD.Exon53.20.017 | ATCTACTGTATAGGGACCCT | 468 |
| Hu.DMD.Exon53.20.018 | TTTCTTTTGGATTGCATCTA | 469 |
| Hu.DMD.Exon53.20.019 | CTTGGTTTCTGTGATTTTCT | 470 |
| Hu.DMD.Exon53.20.020 | CTAACCTTGGTTTCTGTGAT | 471 |
| Hu.DMD.Exon53.20.021 | TGATACTAACCTTGGTTTCT | 472 |
| Hu.DMD.Exon53.20.022 | ATCTTTGATACTAACCTTGG | 473 |
| Hu.DMD.Exon53.20.023 | AAGGTATCTTTGATACTAAC | 474 |
| Hu.DMD.Exon53.20.024 | TTAAAAGGTATCTTTGATA | 475 |
| Hu.DMD.Exon54.25.001 | CTATAGATTTTTATGAGAAAGAGA | 476 |
| Hu.DMD.Exon54.25.002 | AACTGCTATAGATTTTTATGAGAAA | 477 |
| Hu.DMD.Exon54.25.003 | TGGCCAACTGCTATAGATTTTTATG | 478 |
| Hu.DMD.Exon54.25.004 | GTCTTTGGCCAACTGCTATAGATTT | 479 |
| Hu.DMD.Exon54.25.005 | CGGAGGTCTTTGGCCAACTGCTATA | 480 |
| Hu.DMD.Exon54.25.006 | ACTGGCGGAGGTCTTTGGCCAACTG | 481 |
| Hu.DMD.Exon54.25.007 | TTTGTCTGCCACTGGCGGAGGTCTT | 482 |
| Hu.DMD.Exon54.25.008 | AGTCATTTGCCACATCTACATTTGT | 483 |
| Hu.DMD.Exon54.25.008.2 | TTTGCCACATCTACATTTGTCTGCC | 484 |
| Hu.DMD.Exon54.25.009 | CCGGAGAAGTTTCAGGGCCAAGTCA | 485 |
| Hu.DMD.Exon54.25.010 | GTATCATCTGCAGAATAATCCCGGA | 486 |
| Hu.DMD.Exon54.25.010.2 | TAATCCCGGAGAAGTTTCAGGGCCA | 487 |
| Hu.DMD.Exon54.25.011 | TTATCATGTGGACTTTTCTGGTATC | 488 |
| Hu.DMD.Exon54.25.012 | AGAGGCATTGATATTCTCTGTTATC | 489 |
| Hu.DMD.Exon54.25.012.2 | ATGTGGACTTTTCTGGTATCATCTG | 490 |
| Hu.DMD.Exon54.25.013 | CTTTTATGAATGCTTCTCCAAGAGG | 491 |
| Hu.DMD.Exon54.25.013.2 | ATATTCTCTGTTATCATGTGGACTT | 492 |
| Hu.DMD.Exon54.25.014 | CATACCTTTTATGAATGCTTCTCCA | 493 |
| Hu.DMD.Exon54.25.014.2 | CTCCAAGAGGCATTGATATTCTCTG | 494 |
| Hu.DMD.Exon54.25.015 | TAATTCATACCTTTTATGAATGCTT | 495 |
| Hu.DMD.Exon54.25.015.2 | CTTTTATGAATGCTTCTCCAAGAGG | 496 |
| Hu.DMD.Exon54.25.016 | TAATGTAATTCATACCTTTTATGAA | 497 |
| Hu.DMD.Exon54.25.017 | AGAAATAATGTAATTCATACCTTTT | 498 |

-continued

| Name | Sequences | SEQ ID NO. |
| --- | --- | --- |
| Hu.DMD.Exon54.25.018 | GTTTTAGAAATAATGTAATTCATAC | 499 |
| Hu.DMD.Exon54.20.001 | GATTTTTATGAGAAAGAGA | 500 |
| Hu.DMD.Exon54.20.002 | CTATAGATTTTTATGAGAAA | 501 |
| Hu.DMD.Exon54.20.003 | AACTGCTATAGATTTTTATG | 502 |
| Hu.DMD.Exon54.20.004 | TGGCCAACTGCTATAGATTT | 503 |
| Hu.DMD.Exon54.20.005 | GTCTTTGGCCAACTGCTATA | 504 |
| Hu.DMD.Exon54.20.006 | CGGAGGTCTTTGGCCAACTG | 505 |
| Hu.DMD.Exon54.20.007 | TTTGTCTGCCACTGGCGGAG | 506 |
| Hu.DMD.Exon54.20.008 | TTTGCCACATCTACATTTGT | 507 |
| Hu.DMD.Exon54.20.009 | TTCAGGGCCAAGTCATTTGC | 508 |
| Hu.DMD.Exon54.20.010 | TAATCCCGGAGAAGTTTCAG | 509 |
| Hu.DMD.Exon54.20.011 | GTATCATCTGCAGAATAATC | 510 |
| Hu.DMD.Exon54.20.012 | ATGTGGACTTTTCTGGTATC | 511 |
| Hu.DMD.Exon54.20.013 | ATATTCTCTGTTATCATGTG | 512 |
| Hu.DMD.Exon54.20.014 | CTCCAAGAGGCATTGATATT | 513 |
| Hu.DMD.Exon54.20.015 | CTTTTATGAATGCTTCTCCA | 514 |
| Hu.DMD.Exon54.20.016 | CATACCTTTTATGAATGCTT | 515 |
| Hu.DMD.Exon54.20.017 | TAATTCATACCTTTTATGAA | 516 |
| Hu.DMD.Exon54.20.018 | TAATGTAATTCATACCTTTT | 517 |
| Hu.DMD.Exon54.20.019 | AGAAATAATGTAATTCATAC | 518 |
| Hu.DMD.Exon54.20.020 | GTTTTAGAAATAATGTAATT | 519 |
| Hu.DMD.Exon55.25.001 | CTGCAAAGGACCAAATGTTCAGATG | 520 |
| Hu.DMD.Exon55.25.002 | TCACCCTGCAAAGGACCAAATGTTC | 521 |
| Hu.DMD.Exon55.25.003 | CTCACTCACCCTGCAAAGGACCAAA | 522 |
| Hu.DMD.Exon55.25.004 | TCTCGCTCACTCACCCTGCAAAGGA | 523 |
| Hu.DMD.Exon55.25.005 | CAGCCTCTCGCTCACTCACCCTGCA | 524 |
| Hu.DMD.Exon55.25.006 | CAAAGCAGCCTCTCGCTCACTCACC | 525 |
| Hu.DMD.Exon55.25.007 | TCTTCCAAAGCAGCCTCTCGCTCAC | 526 |
| Hu.DMD.Exon55.25.007.2 | TCTATGAGTTTCTTCCAAAGCAGCC | 527 |
| Hu.DMD.Exon55.25.008 | GTTGCAGTAATCTATGAGTTTCTTC | 528 |
| Hu.DMD.Exon55.25.008.2 | GAACTGTTGCAGTAATCTATGAGTT | 529 |
| Hu.DMD.Exon55.25.009 | TTCCAGGTCCAGGGGAACTGTTGC | 530 |
| Hu.DMD.Exon55.25.010 | GTAAGCCAGGCAAGAAACTTTTCCA | 531 |
| Hu.DMD.Exon55.25.010.2 | CCAGGCAAGAAACTTTTCCAGGTCC | 532 |
| Hu.DMD.Exon55.25.011 | TGGCAGTTGTTTCAGCTTCTGTAAG | 533 |
| Hu.DMD.Exon55.25.011.2 | TTCAGCTTCTGTAAGCCAGGCAAGA | 635 |
| Hu.DMD.Exon55.25.012 | GGTAGCATCCTGTAGGACATTGGCA | 534 |
| Hu.DMD.Exon55.25.012.2 | GACATTGGCAGTTGTTTCAGCTTCT | 535 |

-continued

| Name | Sequences | SEQ ID NO. |
|---|---|---|
| Hu.DMD.Exon55.25.013 | TCTAGGAGCCTTTCCTTACGGGTAG | 536 |
| Hu.DMD.Exon55.25.014 | CTTTTACTCCCTTGGAGTCTTCTAG | 537 |
| Hu.DMD.Exon55.25.014.2 | GAGCCTTTCCTTACGGGTAGCATCC | 538 |
| Hu.DMD.Exon55.25.015 | TTGCCATTGTTTCATCAGCTCTTTT | 539 |
| Hu.DMD.Exon55.25.015.2 | CTTGGAGTCTTCTAGGAGCCTTTCC | 540 |
| Hu.DMD.Exon55.25.016 | CTTACTTGCCATTGTTTCATCAGCT | 541 |
| Hu.DMD.Exon55.25.016.2 | CAGCTCTTTTACTCCCTTGGAGTCT | 542 |
| Hu.DMD.Exon55.25.017 | CCTGACTTACTTGCCATTGTTTCAT | 543 |
| Hu.DMD.Exon55.25.018 | AAATGCCTGACTTACTTGCCATTGT | 544 |
| Hu.DMD.Exon55.25.019 | AGCGGAAATGCCTGACTTACTTGCC | 545 |
| Hu.DMD.Exon55.25.020 | GCTAAAGCGGAAATGCCTGACTTAC | 546 |
| Hu.DMD.Exon55.20.001 | AAGGACCAAATGTTCAGATG | 547 |
| Hu.DMD.Exon55.20.002 | CTGCAAAGGACCAAATGTTC | 548 |
| Hu.DMD.Exon55.20.003 | TCACCCTGCAAAGGACCAAA | 549 |
| Hu.DMD.Exon55.20.004 | CTCACTCACCCTGCAAAGGA | 550 |
| Hu.DMD.Exon55.20.005 | TCTCGCTCACTCACCCTGCA | 551 |
| Hu.DMD.Exon55.20.006 | CAGCCTCTCGCTCACTCACC | 552 |
| Hu.DMD.Exon55.20.007 | CAAAGCAGCCTCTCGCTCAC | 553 |
| Hu.DMD.Exon55.20.008 | TCTATGAGTTTCTTCCAAAG | 554 |
| Hu.DMD.Exon55.20.009 | GAACTGTTGCAGTAATCTAT | 555 |
| Hu.DMD.Exon55.20.010 | TTCCAGGTCCAGGGGGAACT | 556 |
| Hu.DMD.Exon55.20.011 | CCAGGCAAGAAACTTTTCCA | 557 |
| Hu.DMD.Exon55.20.012 | TTCAGCTTCTGTAAGCCAGG | 558 |
| Hu.DMD.Exon55.20.013 | GACATTGGCAGTTGTTTCAG | 559 |
| Hu.DMD.Exon55.20.014 | GGTAGCATCCTGTAGGACAT | 560 |
| Hu.DMD.Exon55.20.015 | GAGCCTTTCCTTACGGGTAG | 561 |
| Hu.DMD.Exon55.20.016 | CTTGGAGTCTTCTAGGAGCC | 562 |
| Hu.DMD.Exon55.20.017 | CAGCTCTTTTACTCCCTTGG | 563 |
| Hu.DMD.Exon55.20.018 | TTGCCATTGTTTCATCAGCT | 564 |
| Hu.DMD.Exon55.20.019 | CTTACTTGCCATTGTTTCAT | 565 |
| Hu.DMD.Exon55.20.020 | CCTGACTTACTTGCCATTGT | 566 |
| Hu.DMD.Exon55.20.021 | AAATGCCTGACTTACTTGCC | 567 |
| Hu.DMD.Exon55.20.022 | AGCGGAAATGCCTGACTTAC | 568 |
| Hu.DMD.Exon55.20.023 | GCTAAAGCGGAAATGCCTGA | 569 |
| H50A(+02+30)-AVI-5656 | CCACTCAGAGCTCAGATCTTCTAACTTCC | 584 |
| H50D(+07-18)-AVI-5915 | GGGATCCAGTATACTTACAGGCTCC | 585 |
| H50A(+07+33) | CTTCCACTCAGAGCTCAGATCTTCTAA | 586 |
| H51A(+61+90)-AVI-4657 | ACATCAAGGAAGATGGCATTTCTAGTTTGG | 587 |

-continued

| Name | Sequences | SEQ ID NO. |
| --- | --- | --- |
| H51A(+66+95)-AVI-4658 | CTCCAACATCAAGGAAGATGGCATTTCTAG | 588 |
| H51A(+111+134) | TTCTGTCCAAGCCCGGTTGAAATC | 589 |
| H51A(+175+195) | CACCCACCATCACCCTCYGTG | 590 |
| H51A(+199+220) | ATCATCTCGTTGATATCCTCAA | 591 |
| H51A(+66+90) | ACATCAAGGAAGATGGCATTTCTAG | 592 |
| H51A(-01+25) | ACCAGAGTAACAGTCTGAGTAGGAGC | 593 |
| h51AON1 | TCAAGGAAGATGGCATTTCT | 594 |
| h51AON2 | CCTCTGTGATTTTATAACTTGAT | 595 |
| H51D(+08-17) | ATCATTTTTTCTCATACCTTCTGCT | 596 |
| H51D(+16-07) | CTCATACCTTCTGCTTGATGATC | 597 |
| hAON#23 | TGGCATTTCTAGTTTGG | 598 |
| hAON#24 | CCAGAGCAGGTACCTCCAACATC | 599 |
| H44A(+61+84) | TGTTCAGCTTCTGTTAGCCACTGA | 600 |
| H44A(+85+104) | TTTGTGTCTTTCTGAGAAAC | 601 |
| h44AON1 | CGCCGCCATTTCTCAACAG | 602 |
| H44A(-06+14) | ATCTGTCAAATCGCCTGCAG | 603 |
| H45A(+71+90) | TGTTTTTGAGGATTGCTGAA | 604 |
| h45AON1 | GCTGAATTATTTCTTCCCC | 605 |
| h45AON5 | GCCCAATGCCATCCTGG | 606 |
| H45A(-06+20) | CCAATGCCATCCTGGAGTTCCTGTAA | 607 |
| H53A(+39+69) | CATTCAACTGTTGCCTCCGGTTCTGAAGGTG | 608 |
| H53A(+23+47) | CTGAAGGTGTTCTTGTACTTCATCC | 609 |
| h53AON1 | CTGTTGCCTCCGGTTCTG | 610 |
| H53A(-12+10) | ATTCTTTCAACTAGAATAAAAG | 611 |
| huEx45.30.66 | GCCATCCTGGAGTTCCTGTAAGATACCAAA | 612 |
| huEx45.30.71 | CCAATGCCATCCTGGAGTTCCTGTAAGATA | 613 |
| huEx45.30.79 | GCCGCTGCCCAATGCCATCCTGGAGTTCCT | 614 |
| huEx45.30.83 | GTTTGCCGCTGCCCAATGCCATCCTGGAGT | 615 |
| huEx45.30.88 | CAACAGTTTGCCGCTGCCCAATGCCATCCT | 616 |
| huEx45.30.92 | CTGACAACAGTTTGCCGCTGCCCAATGCCA | 617 |
| huEx45.30.96 | TGTTCTGACAACAGTTTGCCGCTGCCCAAT | 618 |
| huEx45.30.99 | CAATGTTCTGACAACAGTTTGCCGCTGCCC | 619 |
| huEx45.30.103 | CATTCAATGTTCTGACAACAGTTTGCCGCT | 620 |

-continued

| Name | Sequences | SEQ ID NO. |
|---|---|---|
| huEx45.30.120 | TATTTCTTCCCCAGTTGCATTCAATGTTCT | 621 |
| huEx45.30.127 | GCTGAATTATTTCTTCCCCAGTTGCATTCA | 622 |
| huEx45.30.132 | GGATTGCTGAATTATTTCTTCCCCAGTTGC | 623 |
| huEx45.30.137 | TTTGAGGATTGCTGAATTATTTCTTCCCCA | 624 |
| huEx53.30.84 | GTACTTCATCCCACTGATTCTGAATTCTTT | 625 |
| huEx53.30.88 | TCTTGTACTTCATCCCACTGATTCTGAATT | 626 |
| huEx53.30.91 | TGTTCTTGTACTTCATCCCACTGATTCTGA | 627 |
| huEx53.30.103 | CGGTTCTGAAGGTGTTCTTGTACTTCATCC | 628 |
| huEx53.30.106 | CTCCGGTTCTGAAGGTGTTCTTGTACTTCA | 629 |
| huEx53.30.109 | TGCCTCCGGTTCTGAAGGTGTTCTTGTACT | 630 |
| huEx53.30.112 | TGTTGCCTCCGGTTCTGAAGGTGTTCTTGT | 631 |
| huEx53.30.115 | AACTGTTGCCTCCGGTTCTGAAGGTGTTCT | 632 |
| huEx53.30.118 | TTCAACTGTTGCCTCCGGTTCTGAAGGTGT | 633 |
| h50AON1 | | |
| h50AON2 | | |

| Peptide Transporters (NH₂ to COOH)*: | | |
|---|---|---|
| rTAT | RRRQRRKKRC | 570 |
| R₉F₂ | RRRRRRRRRFFC | 571 |
| (RRAhx)₄B | RRAhxRRAhxRRAhxRRAhxB | 572 |
| (RAhxR)₄AhxB; (P007) | RAhxRRAhxRRAhxRRAhxRAhxB | 573 |
| (AhxRR)₄AhxB | AhxRRAhxRRAhxRRAhxRRAhxB | 574 |
| (RAhx)₆B | RAhxRAhxRAhxRAhxRAhxRAhxB | 575 |
| (RAhx)₈B | RAhxRAhxRAhxRAhxRAhxRAhxRAhxRAhxB | 576 |
| (RAhxR)₅AhxB | RAhxRRAhxRRAhxRRAhxRRAhxRAhxB | 577 |
| (RAhxRRBR)₂AhxB; (CP06062) | RAhxRRBRRAhxRRBRAhxB | 578 |
| MSP | ASSLNIA | 579 |

| Cell Penetrating Peptide/Homing Peptide/PMO Conjugates (NH₂ to COOH and 5' to 3') | | |
|---|---|---|
| MSP-PMO | ASSLNIA-XB-GGCCAAACCTCGGCTTACCTGAAAT | 580 636 |
| CP06062-MSP-PMO | RXRRBRRXRRBR-XB-ASSLNIA-X-GGCCAAACCTCGGCTTACCTGAAAT | 581 636 |

-continued

| Name | Sequences | SEQ ID NO. |
|---|---|---|
| MSP-CP06062-PMO | ASSLNIA-X-RXRRBRRXRRBR-B-<br>GGCCAAACCTCGGCTTACCTGAAAT | 582<br>636 |
| CP06062-PMO | RXRRBRRXRRBR-XB-<br>GGCCAAACCTCGGCTTACCTGAAAT | 583<br>636 |

*Ahx is 6-aminohexanoic acid and B is beta-alanine.

It is claimed:

1. An antisense oligonucleotide of 22 bases comprising a base sequence that is 100% complementary to 22 consecutive bases of exon 52 of the human dystrophin pre-mRNA, wherein the base sequence comprises 21 consecutive bases of CAGCGGTAATGAGTTCTTCCAACTG (SEQ ID NO:385), in which thymine bases are uracil bases, wherein the antisense oligonucleotide is a 2'-O-methyl oligonucleotide, and wherein the antisense oligonucleotide induces exon 52 skipping; or a pharmaceutically acceptable salt thereof.

2. An antisense oligonucleotide of 22 bases comprising a base sequence that is 100% complementary to 22 consecutive bases of exon 52 of the human dystrophin pre-mRNA, wherein the base sequence comprises 21 consecutive bases of CAGCGGTAATGAGTTCTTCCAACTG (SEQ ID NO:385), in which: (i) thymine bases are uracil bases and (ii) cytosine bases are 5-methylcytosine bases, wherein the antisense oligonucleotide is a 2'-O-methyl oligonucleotide, and wherein the antisense oligonucleotide induces exon 52 skipping; or a pharmaceutically acceptable salt thereof.

3. An antisense oligonucleotide of 22 bases comprising a base sequence that is 100% complementary to 22 consecutive bases of exon 52 of the human dystrophin pre-mRNA, wherein the base sequence comprises 21 consecutive bases of CAGCGGTAATGAGTTCTTCCAACTG (SEQ ID NO:385), in which: (i) thymine bases are uracil bases and (ii) one or more of the bases are hypoxanthine, wherein the antisense oligonucleotide is a 2'-O-methyl oligonucleotide, and wherein the antisense oligonucleotide induces exon 52 skipping; or a pharmaceutically acceptable salt thereof.

4. An antisense oligonucleotide of 22 bases comprising a base sequence that is 100% complementary to 22 consecutive bases of exon 52 of the human dystrophin pre-mRNA, wherein the base sequence comprises 21 consecutive bases of CAGCGGTAATGAGTTCTTCCAACTG (SEQ ID NO:385), in which: (i) thymine bases are uracil bases, (ii) one or more of the bases are hypoxanthine, and (iii) cytosine bases are 5-methylcytosine bases, wherein the antisense oligonucleotide is a 2'-O-methyl oligonucleotide, and wherein the antisense oligonucleotide induces exon 52 skipping; or a pharmaceutically acceptable salt thereof.

5. A pharmaceutical composition comprising an antisense oligonucleotide of 22 bases comprising a base sequence that is 100% complementary to 22 consecutive bases of exon 52 of the human dystrophin pre-mRNA, wherein the base sequence comprises 21 consecutive bases of CAGCGGTAATGAGT-TCTTCCAACTG (SEQ ID NO:385), in which thymine bases are uracil bases, wherein the antisense oligonucleotide is a 2'-O-methyl oligonucleotide, and wherein the antisense oligonucleotide induces exon 52 skipping; or a pharmaceutically acceptable salt thereof, and a pharmaceutically acceptable carrier.

6. A pharmaceutical composition comprising an antisense oligonucleotide of 22 bases comprising a base sequence that is 100% complementary to 22 consecutive bases of exon 52 of the human dystrophin pre-mRNA, wherein the base sequence comprises 21 consecutive bases of CAGCGGTAATGAGT-TCTTCCAACTG (SEQ ID NO:385), in which: (i) thymine bases are uracil bases and (ii) cytosine bases are 5-methylcytosine bases, wherein the antisense oligonucleotide is a 2'-O-methyl oligonucleotide, and wherein the antisense oligonucleotide induces exon 52 skipping; or a pharmaceutically acceptable salt thereof, and a pharmaceutically acceptable carrier.

7. A pharmaceutical composition comprising an antisense oligonucleotide of 22 bases comprising a base sequence that is 100% complementary to 22 consecutive bases of exon 52 of the human dystrophin pre-mRNA, wherein the base sequence comprises 21 consecutive bases of CAGCGGTAATGAGT-TCTTCCAACTG (SEQ ID NO:385), in which: (i) thymine bases are uracil bases and (ii) one or more of the bases are hypoxanthine, wherein the antisense oligonucleotide is a 2'-O-methyl oligonucleotide, and wherein the antisense oligonucleotide induces exon 52 skipping; or a pharmaceutically acceptable salt thereof, and a pharmaceutically acceptable carrier.

8. A pharmaceutical composition comprising an antisense oligonucleotide of 22 bases comprising a base sequence that is 100% complementary to 22 consecutive bases of exon 52 of the human dystrophin pre-mRNA, wherein the base sequence comprises 21 consecutive bases of CAGCGGTAATGAGT-TCTTCCAACTG (SEQ ID NO:385), in which: (i) thymine bases are uracil bases, (ii) one or more of the bases are hypoxanthine, and (iii) cytosine bases are 5-methylcytosine bases, wherein the antisense oligonucleotide is a 2'-O-methyl oligonucleotide, and wherein the antisense oligonucleotide induces exon 52 skipping; or a pharmaceutically acceptable salt thereof, and a pharmaceutically acceptable carrier.

\* \* \* \* \*